US011930703B2

United States Patent
Takeda et al.

(10) Patent No.: US 11,930,703 B2
(45) Date of Patent: Mar. 12, 2024

(54) ORGANIC COMPOUND, LIGHT-EMITTING ELEMENT, LIGHT-EMITTING DEVICE, ELECTRONIC DEVICE, DISPLAY DEVICE, AND LIGHTING DEVICE

(71) Applicant: SEMICONDUCTOR ENERGY LABORATORY CO., LTD., Atsugi (JP)

(72) Inventors: Kyoko Takeda, Kanagawa (JP); Harue Osaka, Kanagawa (JP); Satoshi Seo, Kanagawa (JP); Tsunenori Suzuki, Kanagawa (JP); Naoaki Hashimoto, Kanagawa (JP); Yusuke Takita, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 212 days.

(21) Appl. No.: 16/486,181

(22) PCT Filed: Mar. 8, 2018

(86) PCT No.: PCT/IB2018/051496
§ 371 (c)(1),
(2) Date: Aug. 15, 2019

(87) PCT Pub. No.: WO2018/167612
PCT Pub. Date: Sep. 20, 2019

(65) Prior Publication Data
US 2019/0393420 A1    Dec. 26, 2019

(30) Foreign Application Priority Data

Mar. 17, 2017  (JP) .................................. 2017-053054

(51) Int. Cl.
*H10K 85/60* (2023.01)
*C07D 493/04* (2006.01)
(Continued)

(52) U.S. Cl.
CPC ......... *H10K 85/636* (2023.02); *C07D 493/04* (2013.01); *C09K 11/06* (2013.01);
(Continued)

(58) Field of Classification Search
CPC ... C07D 493/04; C07D 495/04; C07F 7/0812; C09K 11/06; C09K 2211/1018;
(Continued)

(56) References Cited

U.S. PATENT DOCUMENTS 9,112,157 B2    8/2015  Brown et al.
9,412,953 B2    8/2016  Inoue et al.
(Continued)

FOREIGN PATENT DOCUMENTS

CN    101659593 A    3/2010
CN    102924217 A    2/2013
(Continued)

OTHER PUBLICATIONS

Machine translation for JP 2010-087408 A (publication date: Apr. 2010). (Year: 2010).*

(Continued)

*Primary Examiner* — Dawn L Garrett
(74) *Attorney, Agent, or Firm* — Fish & Richardson P.C.

(57) ABSTRACT

A novel organic compound is provided. An organic compound that emits light with high chromaticity is provided. An organic compound that emits blue light with high chromaticity is provided. An organic compound with high emission efficiency is provided. An organic compound having an excellent hole-transport property is provided. An organic compound having high reliability is provided. An organic compound that has a naphtho[2,3-b;7,6-b']bisbenzofuran skeleton or a naphtho[2,3-b;7,6-b']bisbenzothiophene skeleton and has a molecular weight of less than or equal to 5000 is provided. The present inventors have found that the (Continued)

organic compound is a significantly effective skeleton as a luminophor of a light-emitting element. The organic compound has high emission efficiency and exhibits favorable blue light emission; thus, a light-emitting element using the organic compound can be a blue light-emitting element with high emission efficiency.

9 Claims, 62 Drawing Sheets

(51) Int. Cl.
   *C09K 11/06* (2006.01)
   *H10K 50/11* (2023.01)
   *H10K 101/10* (2023.01)

(52) U.S. Cl.
   CPC ......... *H10K 85/615* (2023.02); *H10K 85/626* (2023.02); *H10K 85/633* (2023.02); *H10K 85/6574* (2023.02); *C09K 2211/1018* (2013.01); *H10K 50/11* (2023.02); *H10K 2101/10* (2023.02)

(58) Field of Classification Search
   CPC ............ H01L 51/0052; H01L 51/0058; H01L 51/006; H01L 51/0061; H01L 51/0073; H01L 51/5012; H01L 51/5016; H01L 85/615; H01L 85/626; H01L 85/633; H01L 85/6574; H01L 50/11; H01L 2101/10; H10K 85/636
   See application file for complete search history.

(56) References Cited

U.S. PATENT DOCUMENTS

| | | | |
|---|---|---|---|
| 9,447,111 | B2 | 9/2016 | Kitamura et al. |
| 9,496,503 | B2 | 11/2016 | Takeda et al. |
| 9,586,972 | B2 | 3/2017 | Kitamura et al. |
| 9,627,623 | B2 | 4/2017 | Takaku et al. |
| 9,634,263 | B2 | 4/2017 | Ogita et al. |
| 9,818,952 | B2 | 11/2017 | Jung et al. |
| 10,003,031 | B2 | 6/2018 | Jang et al. |
| 10,428,084 | B2 | 10/2019 | Park et al. |
| 11,239,426 | B2 | 2/2022 | Skulason et al. |
| 2010/0032658 | A1 | 2/2010 | Lee et al. |
| 2011/0248246 | A1 | 10/2011 | Ogita et al. |
| 2013/0324716 | A1* | 12/2013 | Brown ................. H01L 51/006 544/35 |
| 2015/0031896 | A1* | 1/2015 | Vestweber ........ C07F 9/657163 564/429 |
| 2015/0108440 | A1 | 4/2015 | Jung et al. |
| 2015/0166560 | A1 | 6/2015 | Kitamura et al. |
| 2015/0171334 | A1* | 6/2015 | Kato .................... C07D 307/91 548/440 |
| 2015/0218184 | A1* | 8/2015 | Kitamura ............ H01L 51/0074 549/60 |
| 2018/0251473 | A1 | 9/2018 | Mun et al. |
| 2018/0282276 | A1 | 10/2018 | Mun et al. |
| 2019/0378992 | A1* | 12/2019 | Skulason ............. C07D 493/14 |
| 2019/0389877 | A1* | 12/2019 | Uno ..................... C07D 495/04 |
| 2022/0093872 | A1 | 3/2022 | Skulason et al. |

FOREIGN PATENT DOCUMENTS

| | | | |
|---|---|---|---|
| EP | 2145936 | A | 1/2010 |
| JP | 2010-059147 | A | 3/2010 |
| JP | 2010-087408 | A * | 4/2010 |
| JP | 2012-169550 | A | 9/2012 |
| JP | 2013-045811 | A | 3/2013 |
| JP | 2013-232521 | A | 11/2013 |
| JP | 2013-234151 | A | 11/2013 |
| JP | 2014-082247 | A | 5/2014 |
| JP | 2014-237682 | A | 12/2014 |
| JP | 2016-122729 | A | 7/2016 |
| JP | 2020-512277 | | 4/2020 |
| JP | 2021-046407 | A | 3/2021 |
| KR | 2010-0007780 | A | 1/2010 |
| KR | 2014-0023407 | A | 2/2014 |
| KR | 2014-0023408 | A | 2/2014 |
| KR | 2014-0024438 | A | 2/2014 |
| KR | 2014-0024439 | A | 2/2014 |
| KR | 2014-0024440 | A | 2/2014 |
| KR | 2017-0077806 | A | 7/2017 |
| KR | 2019-0059448 | A | 5/2019 |
| TW | 201009046 | | 3/2010 |
| WO | WO-2013/173396 | | 11/2013 |
| WO | WO-2018/097937 | | 5/2018 |
| WO | WO-2018/185571 | | 10/2018 |
| WO | WO-2018/194035 | | 10/2018 |

OTHER PUBLICATIONS

Nakanishi, K., Sasamori, T., Kuramochi, K., Tokitoh, N., Kawabata, T., & Tsubaki, K. (2014). Synthesis and properties of butterfly-shaped expanded naphthofuran derivatives. The Journal of Organic Chemistry, 79(6), 2625-2631. (Year: 2014).*

Serevičius, T et al., (2013). Photophysical properties of 2-phenylanthracene and its conformationally-stabilized derivatives. Dyes and Pigments, 98(2), 304-315. (Year: 2013).*

Yamamoto.K et al., "Synthesis and properties of naphthobisbenzo[b]thiophenes: structural curvature of higher acene frameworks for solubility enhancement and high-order orientation in crystalline states", Tetrahedron Letters, Apr. 4, 2012, vol. 53, No. 14, pp. 1786-1789.

International Search Report (Application No. PCT/IB2018/051496) dated Jun. 12, 2018.

Written Opinion (Application No. PCT/IB2018/051496) dated Jun. 12, 2018.

* cited by examiner

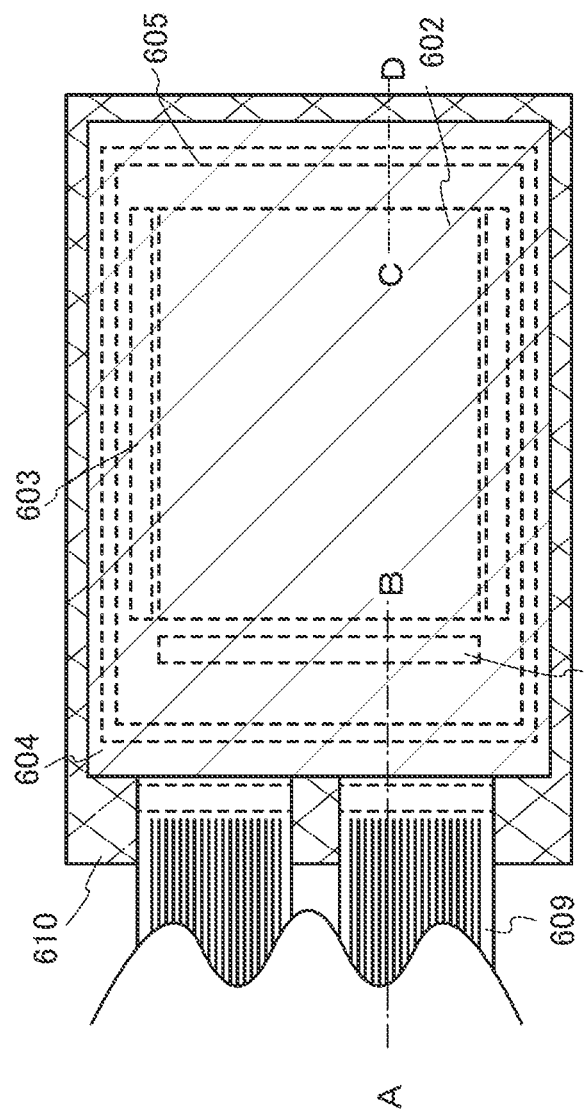
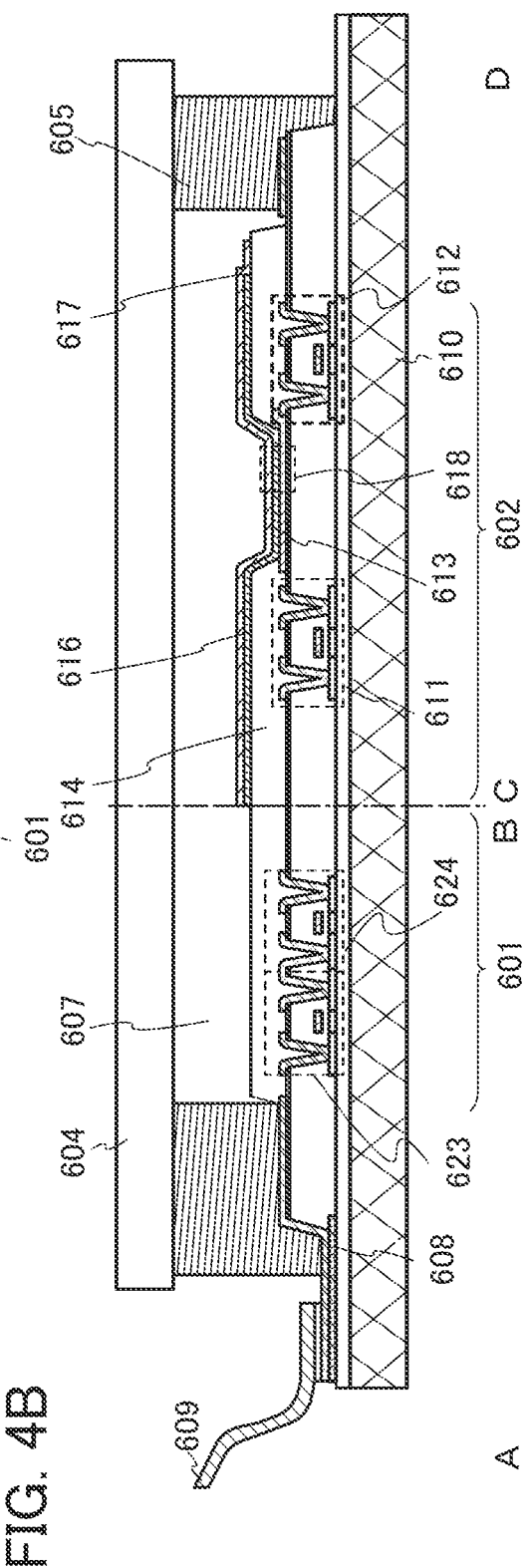
FIG. 4A
FIG. 4B

ORGANIC COMPOUND, LIGHT-EMITTING ELEMENT, LIGHT-EMITTING DEVICE, ELECTRONIC DEVICE, DISPLAY DEVICE, AND LIGHTING DEVICE

CROSS REFERENCE TO RELATED APPLICATIONS

This application is a U.S. National Phase Application under 35 U.S.C. § 371 of International Application PCT/IB2018/051496, filed on Mar. 8, 2018, which claims the benefit of a foreign priority application filed in Japan as Application No. 2017-053054 on Mar. 17, 2017, both of which are incorporated by reference.

TECHNICAL FIELD

Embodiments of the present invention relate to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a storage device, an imaging device, a method for driving any of them, and a method for manufacturing any of them.

BACKGROUND ART

Some display devices and light-emitting devices including organic EL elements are practically used and are increasingly finding diverse applications. In recent years, liquid crystal displays have greatly progressed; thus, it is natural that organic EL displays, next-generation displays, need to have high quality.

Although a variety of substances have been developed as materials for organic EL displays, not so many of them have high resistance enough for practical use. In consideration of diversity, affinity, and the like of combinations, it is needless to say that the number of options is preferably larger.

Organic EL elements have a function-separated-type structure in which a plurality of substances have different functions. Demands for light-emitting materials among the substances, in particular, emission efficiency, which affects power consumption, and emission colors, which can improve display quality, are high.

Patent Document 1 discloses an organic compound having a naphthobisbenzofuran skeleton.

REFERENCE

[Patent Document 1] Japanese Published Patent Application No. 2014-237682

DISCLOSURE OF INVENTION

An object of one embodiment of the present invention is to provide a novel organic compound. Another object of one embodiment of the present invention is to provide an organic compound that emits light with high chromaticity. Another object of one embodiment of the present invention is to provide an organic compound that emits blue light with high chromaticity. Another object of one embodiment of the present invention is to provide an organic compound with high emission efficiency. Another object of one embodiment of the present invention is to provide an organic compound having an excellent carrier-transport property. Another object of one embodiment of the present invention is to provide an organic compound with high reliability.

Another object of one embodiment of the present invention is to provide a novel light-emitting element. Another object of one embodiment of the present invention is to provide a light-emitting element with high emission efficiency. Another object of one embodiment of the present invention is to provide a light-emitting element with high chromaticity. Another object of one embodiment of the present invention is to provide a light-emitting element that emits blue light with high chromaticity. Another object of one embodiment of the present invention is to provide a light-emitting element with a long lifetime. Another object of one embodiment of the present invention is to provide a light-emitting element with low driving voltage.

Another object of one embodiment of the present invention is to provide a light-emitting device, an electronic device, and a display device each with low power consumption. Another object of one embodiment of the present invention is to provide a light-emitting device, an electronic device, and a display device each having high reliability. Another object of one embodiment of the present invention is to provide a light-emitting device, an electronic device, and a display device each having high display quality.

It is only necessary that at least one of the above-described objects be achieved in the present invention.

One embodiment of the present invention is a light-emitting element including an organic compound that is represented by General Formula (G1) shown below and has a molecular weight of less than or equal to 5000.

[Chemical Formula 1]

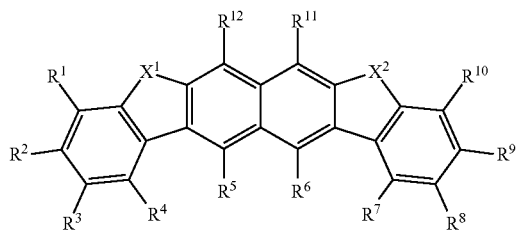

(G1)

In General Formula (G1), $X^1$ and $X^2$ independently represent an oxygen atom or a sulfur atom, and $R^1$ to $R^{12}$ independently represent hydrogen or a substituent.

Another embodiment of the present invention is the light-emitting element having the above structure in which the substituent is a substituted or unsubstituted aliphatic hydrocarbon group having 1 to 100 carbon atoms, a substituted or unsubstituted alicyclic hydrocarbon group having 3 to 100 carbon atoms, a substituted or unsubstituted aromatic hydrocarbon group having 6 to 100 carbon atoms, a substituted or unsubstituted heterocyclic group having 1 to 100 carbon atoms, or a substituted or unsubstituted diarylamino group having 12 to 100 carbon atoms.

Another embodiment of the present invention is a light-emitting element including an organic compound that is represented by General Formula (G1) shown below and has a molecular weight of less than or equal to 5000.

[Chemical Formula 2]

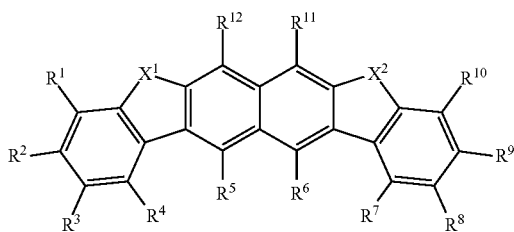

(G1)

In General Formula (G1), $X^1$ and $X^2$ independently represent an oxygen atom or a sulfur atom. In the formula, at least one of $R^1$ to $R^{12}$ represents a substituent having 6 to 100 carbon atoms, and the other or others independently represent hydrogen or a substituent having 1 to 25 carbon atoms.

Another embodiment of the present invention is a light-emitting element including an organic compound that is represented by General Formula (G1) shown below and has a molecular weight of less than or equal to 5000.

[Chemical Formula 3]

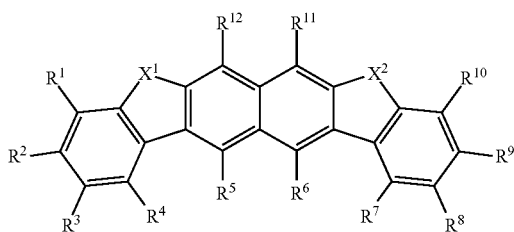

(G1)

In General Formula (G1), $X^1$ and $X^2$ independently represent an oxygen atom or a sulfur atom. In the formula, one or two of $R^1$ to $R^{12}$ independently represent a substituent having 6 to 100 carbon atoms, and the others independently represent hydrogen or a substituent having 1 to 25 carbon atoms.

Another embodiment of the present invention is a light-emitting element including an organic compound that is represented by General Formula (G1) shown below and has a molecular weight of less than or equal to 5000.

[Chemical Formula 4]

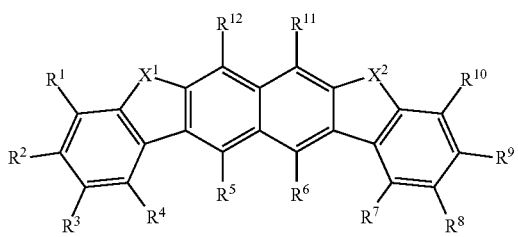

(G1)

In General Formula (G1), $X^1$ and $X^2$ independently represent an oxygen atom or a sulfur atom. In the formula, one or both of $R^2$ and $R^9$ among $R^1$ to $R^{12}$ independently represent a substituent having 6 to 100 carbon atoms, and the others independently represent hydrogen or a substituent having 1 to 25 carbon atoms.

Another embodiment of the present invention is a light-emitting element including an organic compound that is represented by General Formula (G1) shown below and has a molecular weight of less than or equal to 5000.

[Chemical Formula 5]

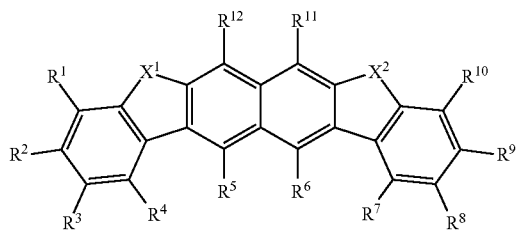

(G1)

In General Formula (G1), $X^1$ and $X^2$ independently represent an oxygen atom or a sulfur atom. In the formula, one or both of $R^3$ and $R^8$ among $R^1$ to $R^{12}$ independently represent a substituent having 6 to 100 carbon atoms, and the others independently represent hydrogen or a substituent having 1 to 25 carbon atoms.

Another embodiment of the present invention is the light-emitting element having the above structure in which the substituent having 6 to 100 carbon atoms is a substituted or unsubstituted aliphatic hydrocarbon group, a substituted or unsubstituted alicyclic hydrocarbon group, a substituted or unsubstituted aromatic hydrocarbon group, a substituted or unsubstituted heterocyclic group, or a substituted or unsubstituted diarylamino group. Note that examples of an aryl group included in the diarylamino group include a heteroaryl group.

Another embodiment of the present invention is the light-emitting element having the above structure in which the substituent having 6 to 100 carbon atoms is a substituent having 12 to 100 carbon atoms.

Another embodiment of the present invention is the light-emitting element having the above structure in which the substituent having 6 to 100 carbon atoms is a substituent represented by General Formula (g1) or (g2) shown below.

[Chemical Formula 6]

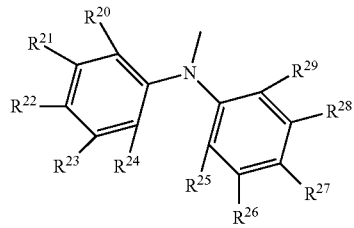

(g1)

(g2)
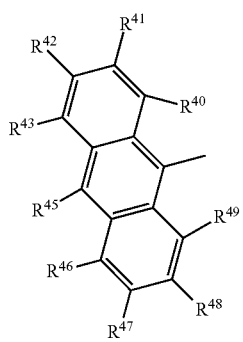
Another embodiment of the present invention is the light-emitting element having the above structure in which the substituent having 6 to 100 carbon atoms is a substituent selected from substituents represented by Structural Formulae (Ar-100) to (Ar-109) and (Ar-29) shown below.
[Chemical Formula 7]
(Ar-100)
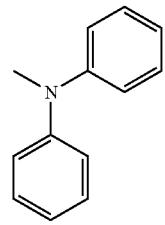
(Ar-101)
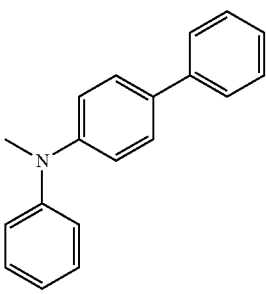
(Ar-102)
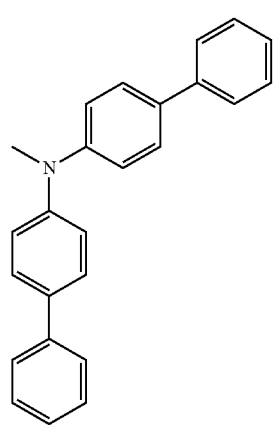
(Ar-103)
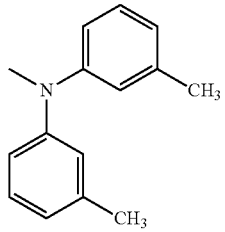
(Ar-104)
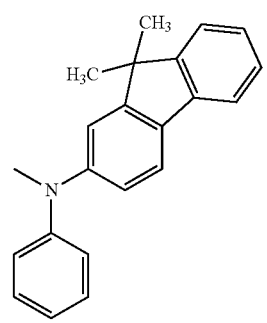
(Ar-105)
(Ar-106)
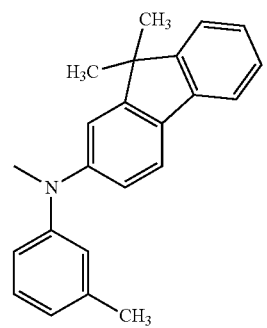

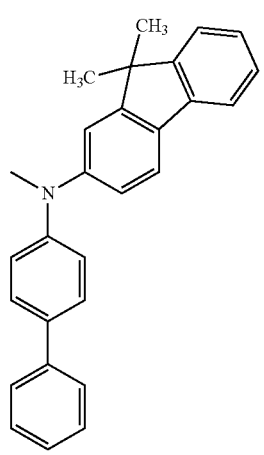
(Ar-107)

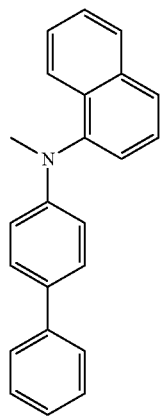
(Ar-108)

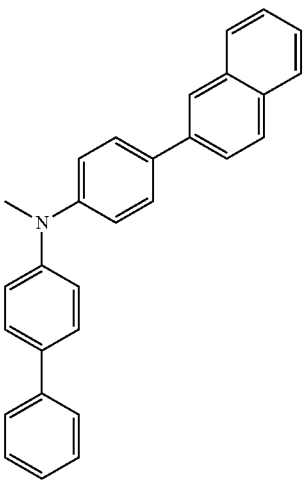
(Ar-109)

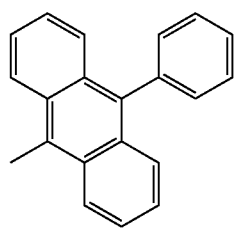
(Ar-29)

Another embodiment of the present invention is the light-emitting element having the above structure in which the substituent having 1 to 25 carbon atoms is a substituted or unsubstituted aliphatic hydrocarbon group, a substituted or unsubstituted alicyclic hydrocarbon group, a substituted or unsubstituted aromatic hydrocarbon group, or a substituted or unsubstituted heterocyclic group.

Another embodiment of the present invention is a light-emitting element including an organic compound represented by General Formula (G2) shown below.

[Chemical Formula 8]

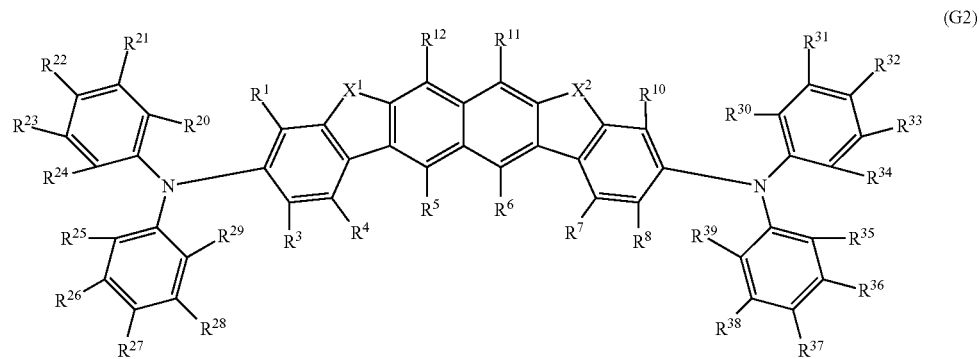
(G2)

In General Formula (G2), $X^1$ and $X^2$ independently represent an oxygen atom or a sulfur atom. In the formula, $R^1$, $R^3$ to $R^8$, $R^{10}$ to $R^{12}$, $R^{20}$ to $R^{29}$, and $R^{30}$ to $R^{39}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is a light-emitting element including an organic compound represented by General Formula (G3) shown below.

[Chemical Formula 9]

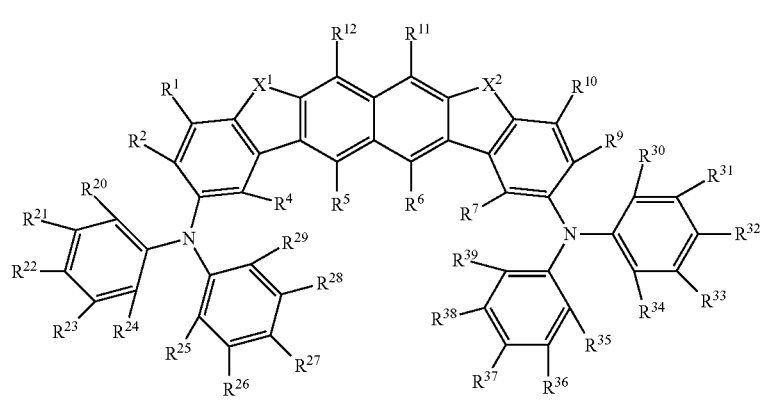

(G3)

In General Formula (G3), $X^1$ and $X^2$ independently represent an oxygen atom or a sulfur atom. In the formula, $R^1$, $R^2$, $R^4$ to $R^7$, $R^9$ to $R^{12}$, $R^{20}$ to $R^{29}$, and $R^{30}$ to $R^{39}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is a light-emitting element including an organic compound represented by General Formula (G4) shown below.

In General Formula (G4), $X^1$ and $X^2$ independently represent an oxygen atom or a sulfur atom. In the formula, $R^1$, $R^3$ to $R^8$, $R^{10}$ to $R^{12}$, $R^{40}$ to $R^{49}$, and $R^{50}$ to $R^{59}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is the light-emitting element having the above structure in which $X^1$ and $X^2$ are the same atoms.

Another embodiment of the present invention is the light-emitting element having the above structure in which $X^1$ and $X^2$ are oxygen atoms.

Another embodiment of the present invention is the light-emitting element in which the organic compound has a molecular weight of less than or equal to 3000.

Another embodiment of the present invention is the light-emitting element in which the organic compound has a molecular weight of less than or equal to 1500.

[Chemical Formula 10]

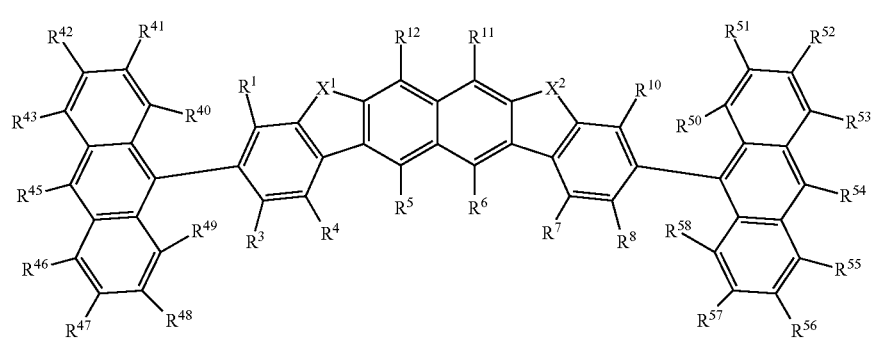

(G4)

Another embodiment of the present invention is an organic compound that is represented by General Formula (G1) shown below and has a molecular weight of less than or equal to 5000.

[Chemical Formula 11]

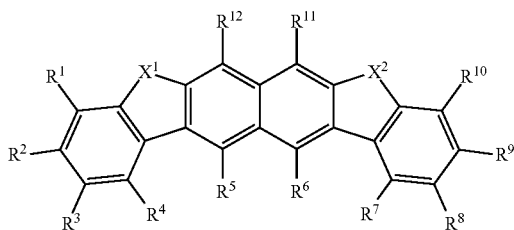

(G1)

In General Formula (G1), $X^1$ and $X^2$ independently represent an oxygen atom or a sulfur atom. In the formula, at least one of $R^1$ to $R^{12}$ represents a substituent having 6 to 100 carbon atoms, and the other or others independently represent hydrogen or a substituent having 1 to 25 carbon atoms.

Another embodiment of the present invention is an organic compound that is represented by General Formula (G1) shown below and has a molecular weight of less than or equal to 5000.

[Chemical Formula 12]

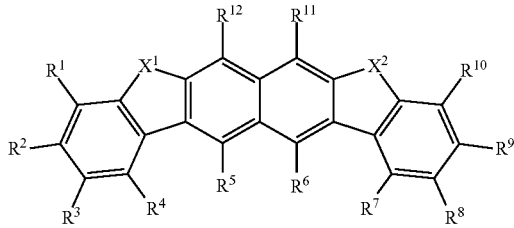

(G1)

In General Formula (G1), $X^1$ and $X^2$ independently represent an oxygen atom or a sulfur atom. In the formula, one or two of $R^1$ to $R^{12}$ independently represent a substituent having 6 to 100 carbon atoms, and the others independently represent hydrogen or a substituent having 1 to 25 carbon atoms.

Another embodiment of the present invention is an organic compound that is represented by General Formula (G1) shown below and has a molecular weight of less than or equal to 5000.

[Chemical Formula 13]

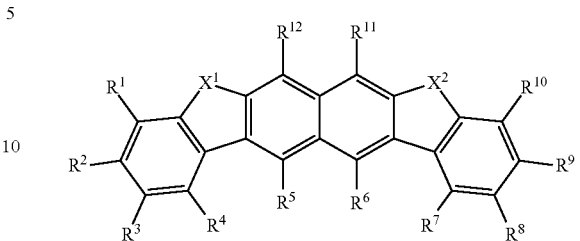

(G1)

In General Formula (G1), $X^1$ and $X^2$ independently represent an oxygen atom or a sulfur atom. In the formula, one or both of $R^2$ and $R^9$ among $R^1$ to $R^{12}$ independently represent a substituent having 6 to 100 carbon atoms, and the others independently represent hydrogen or a substituent having 1 to 25 carbon atoms.

Another embodiment of the present invention is an organic compound that is represented by General Formula (G1) shown below and has a molecular weight of less than or equal to 5000.

[Chemical Formula 14]

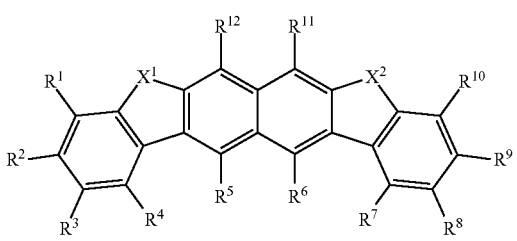

(G1)

In General Formula (G1), $X^1$ and $X^2$ independently represent an oxygen atom or a sulfur atom. In the formula, one or both of $R^3$ and $R^8$ among $R^1$ to $R^{12}$ independently represent a substituent having 6 to 100 carbon atoms, and the others independently represent hydrogen or a substituent having 1 to 25 carbon atoms.

Another embodiment of the present invention is the organic compound having the above structure in which the substituent having 6 to 100 carbon atoms is a substituted or unsubstituted aliphatic hydrocarbon group, a substituted or unsubstituted alicyclic hydrocarbon group, a substituted or unsubstituted aromatic hydrocarbon group, a substituted or unsubstituted heterocyclic group, or a substituted or unsubstituted diarylamino group. Note that examples of an aryl group included in the diarylamino group include a heteroaryl group.

Another embodiment of the present invention is the organic compound having the above structure in which the substituent having 6 to 100 carbon atoms is a substituent having 12 to 100 carbon atoms.

Another embodiment of the present invention is the organic compound having the above structure in which the substituent having 6 to 100 carbon atoms is a substituent represented by General Formula (g1) or (g2) shown below.

[Chemical Formula 15]
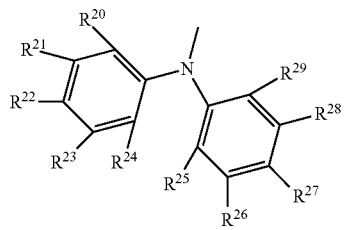
(g1)
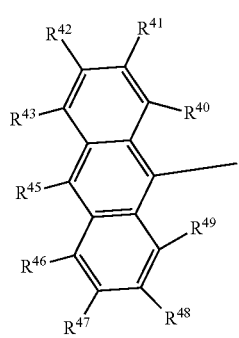
(g2)
Another embodiment of the present invention is the organic compound having the above structure in which the substituent having 6 to 100 carbon atoms is a substituent selected from substituents represented by Structural Formulae (Ar-100) to (Ar-109) and (Ar-29) shown below.
[Chemical Formula 16]
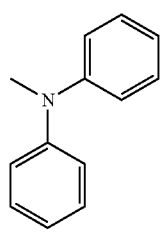
(Ar-100)
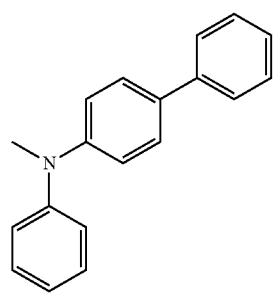
(Ar-101)
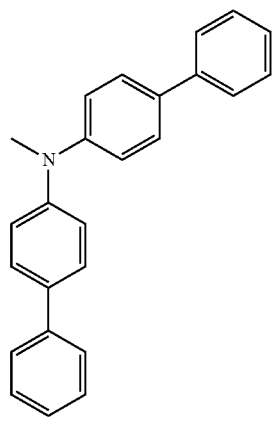
(Ar-102)
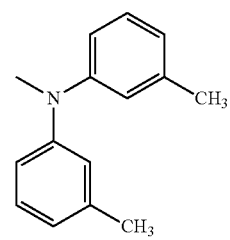
(Ar-103)
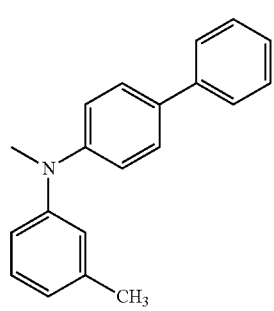
(Ar-104)
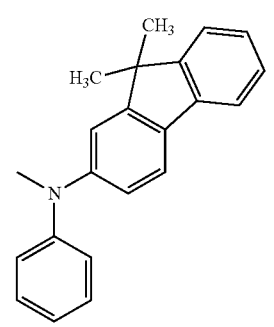
(Ar-105)
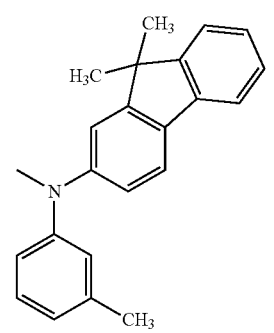
(Ar-106)

(Ar-107)

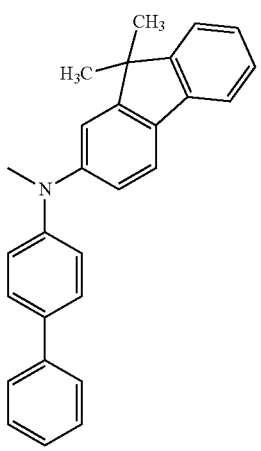

(Ar-108)

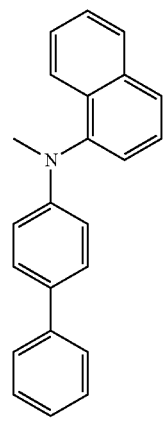

(Ar-109)

(Ar-29)

Another embodiment of the present invention is the organic compound having the above structure in which the substituent having 1 to 25 carbon atoms is a substituted or unsubstituted aliphatic hydrocarbon group, a substituted or unsubstituted alicyclic hydrocarbon group, a substituted or unsubstituted aromatic hydrocarbon group, or a substituted or unsubstituted heterocyclic group.

Another embodiment of the present invention is an organic compound represented by General Formula (G2) shown below.

[Chemical Formula 17]

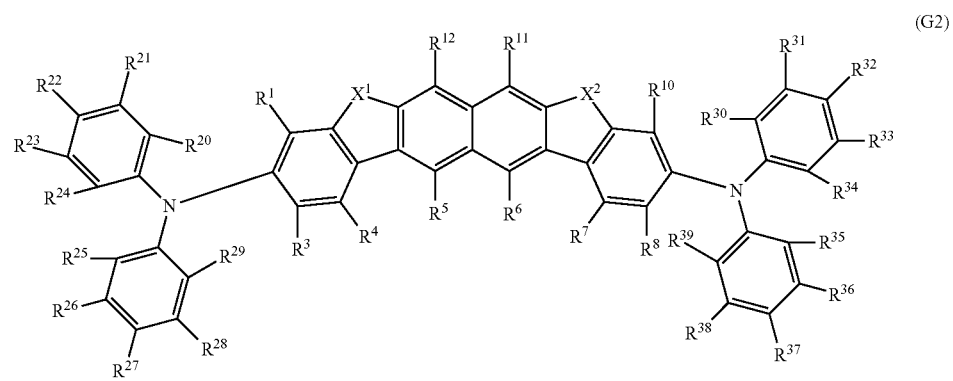

(G2)

In General Formula (G2), $X^1$ and $X^2$ independently represent an oxygen atom or a sulfur atom. In the formula, $R^1$, $R^3$ to $R^8$, $R^{10}$ to $R^{12}$, $R^{20}$ to $R^{29}$, and $R^{30}$ to $R^{39}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is an organic compound represented by General Formula (G3) shown below.

[Chemical Formula 18]

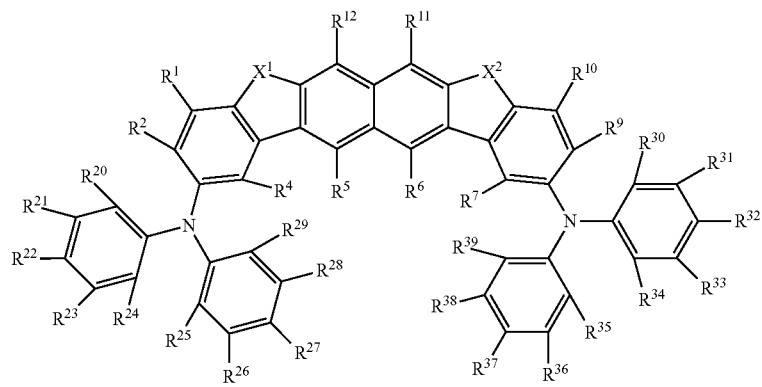

(G3)

In General Formula (G3), $X^1$ and $X^2$ independently represent an oxygen atom or a sulfur atom. In the formula, $R^1$, $R^2$, $R^4$ to $R^7$, $R^9$ to $R^{12}$, $R^{20}$ to $R^{29}$, and $R^{30}$ to $R^{39}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is an organic compound represented by General Formula (G4) shown below.

Another embodiment of the present invention is the organic compound having the above structure in which the molecular weight is less than or equal to 3000.

Another embodiment of the present invention is the organic compound having the above structure in which the molecular weight is less than or equal to 1500.

Another embodiment of the present invention is an organic compound represented by Structural Formula (100) shown below.

[Chemical Formula 19]

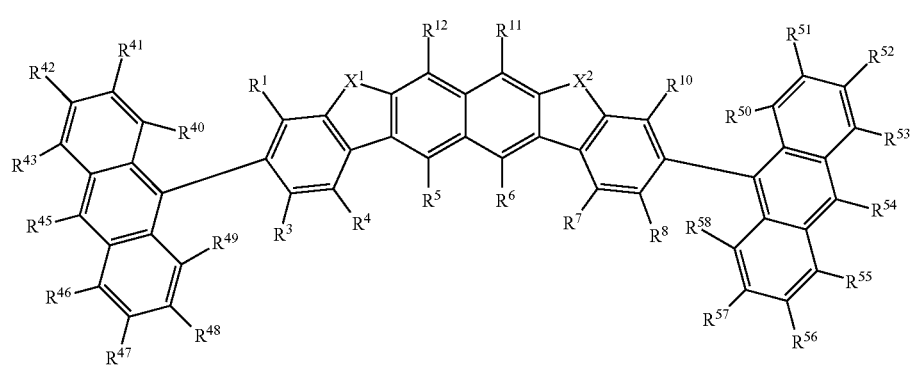

(G4)

In General Formula (G4), $X^1$ and $X^2$ independently represent an oxygen atom or a sulfur atom. In the formula, $R^1$, $R^3$ to $R^8$, $R^{10}$ to $R^{12}$, $R^{40}$ to $R^{49}$, and $R^{50}$ to $R^{59}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is the organic compound having the above structure in which $X^1$ and $X^2$ are the same atoms.

Another embodiment of the present invention is the organic compound having the above structure in which $X^1$ and $X^2$ are oxygen atoms.

[Chemical Formula 20]

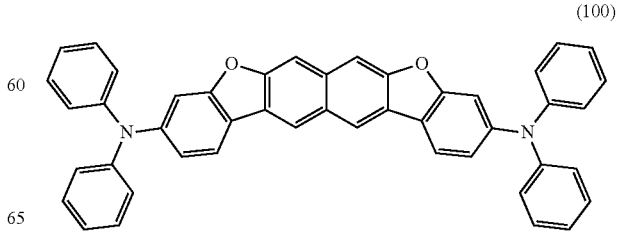

(100)

Another embodiment of the present invention is an organic compound represented by Structural Formula (300) shown below.

[Chemical Formula 21]

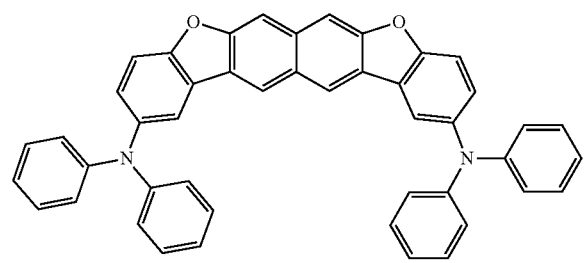

(300)

Another embodiment of the present invention is an organic compound represented by Structural Formula (118) shown below.

[Chemical Formula 22]

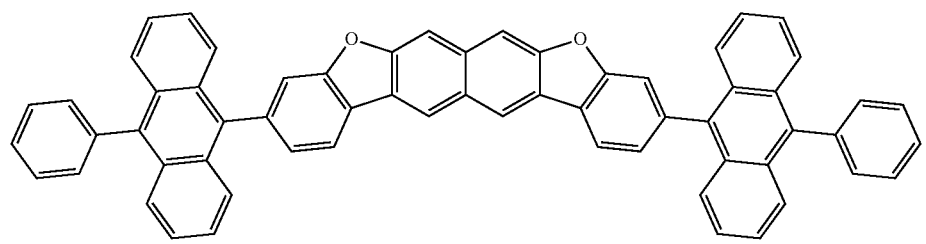

(118)

Another embodiment of the present invention is a light-emitting element including the organic compound having the above structure.

Another embodiment of the present invention is a light-emitting device including the light-emitting element having the above structure, and a transistor or a substrate.

Another embodiment of the present invention is a display device including the light-emitting element having the above structure, and a transistor or a substrate.

Another embodiment of the present invention is an electronic device including the light-emitting device having the above structure, and a sensor, an operation button, a speaker, or a microphone.

Another embodiment of the present invention is a lighting device including the light-emitting device having the above structure and a housing.

Another embodiment of the present invention is an organic compound represented by General Formula ($G_o1$) shown below.

[Chemical Formula 23]

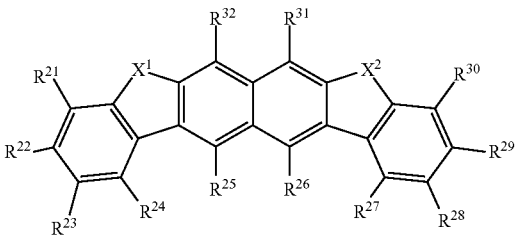

($G_o1$)

In General Formula ($G_o1$), $X^1$ and $X^2$ independently represent an oxygen atom or a sulfur atom. In the formula, one or two of $R^{21}$ to $R^{32}$ represent halogen, and the others independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is an organic compound represented by General Formula ($G_o2$) shown below.

[Chemical Formula 23]

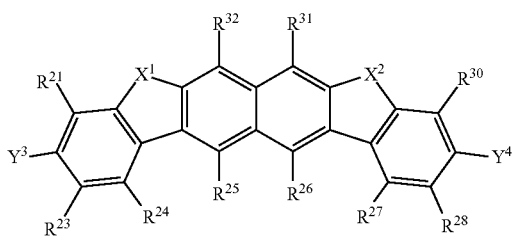

($G_o2$)

In General Formula ($G_o2$), $X^1$ and $X^2$ independently represent an oxygen atom or a sulfur atom. In the formula, $Y^3$ and $Y^4$ independently represent halogen, and $R^{21}$, $R^{23}$ to $R^{28}$, and $R^{30}$ to $R^{32}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Another embodiment of the present invention is an organic compound represented by General Formula (G₀3) shown below.

[Chemical Formula 25]

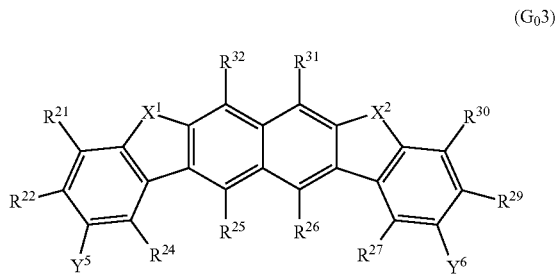

(G₀3)

In General Formula (G₀3), $X^1$ and $X^2$ independently represent an oxygen atom or a sulfur atom. In the formula, $Y^5$ and $Y^6$ independently represent halogen, and $R^{21}$, $R^{22}$, $R^{24}$ to $R^{27}$, and $R^{29}$ to $R^{32}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

Note that the light-emitting device in this specification includes, in its category, an image display device that uses a light-emitting element. The light-emitting device may also include a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may be included in a lighting device or the like.

According to one embodiment of the present invention, a novel organic compound can be provided. An organic compound that emits light with high chromaticity can be provided. An organic compound that emits blue light with high chromaticity can be provided. An organic compound with high emission efficiency can be provided. An organic compound having an excellent hole-transport property can be provided. An organic compound having high reliability can be provided.

According to another embodiment of the present invention, a novel light-emitting element can be provided. A light-emitting element with high emission efficiency can be provided. A light-emitting element with high chromaticity can be provided. A light-emitting element that emits blue light with high chromaticity can be provided. A light-emitting element with a long lifetime can be provided. A light-emitting element with low driving voltage can be provided.

According to another embodiment of the present invention, a light-emitting device, an electronic device, and a display device each with low power consumption can be provided. A light-emitting device, an electronic device, and a display device each having high reliability can be provided. A light-emitting device, an electronic device, and a display device each having high display quality can be provided.

Note that the description of these effects does not preclude the existence of other effects. One embodiment of the present invention does not necessarily have all the effects listed above. Other effects will be apparent from and can be derived from the description of the specification, the drawings, the claims, and the like.

BRIEF DESCRIPTION OF DRAWINGS

FIGS. 4A and 4B are conceptual diagrams of an active matrix light-emitting device.

FIGS. 9A, 9B1, 9B2, 9C, and 9D illustrate electronic devices.

BEST MODE FOR CARRYING OUT THE INVENTION

Figure 1A:
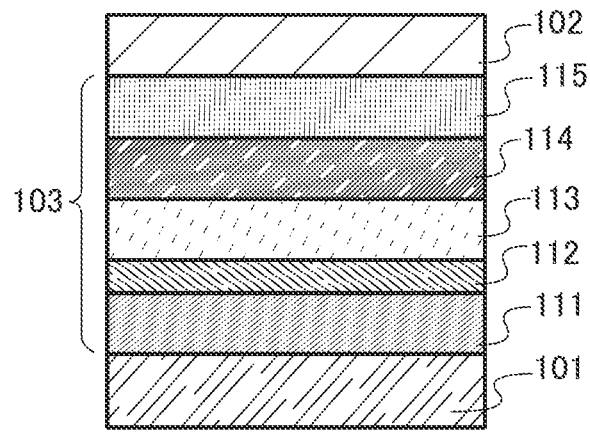
FIGS. 1A to 1C are schematic diagrams of light-emitting elements.

Embodiments and examples of the present invention will be described below with reference to the drawings. It will be readily appreciated by those skilled in the art that modes and details of the present invention can be modified in various ways without departing from the spirit and scope of the present invention. Thus, the present invention should not be construed as being limited to the description in the following embodiments and examples.

Embodiment 1

One embodiment of the present invention is an organic compound that has a naphtho[2,3-b;7,6-b']bisbenzofuran skeleton or a naphtho[2,3-b;7,6-b']bisbenzothiophene skeleton and has a molecular weight of less than or equal to 5000 and a light-emitting element including the organic compound. The present inventors have found that the organic compound is a significantly effective skeleton as a luminophor of a light-emitting element. The organic compound has high emission efficiency and exhibits favorable blue light emission; thus, a light-emitting element using the organic compound can be a blue light-emitting element with high emission efficiency. A variety of substances have been developed as blue fluorescent materials, and among them, this organic compound is a highly promising material as a blue light-emitting material for expressing a color gamut covering the BT2020 color gamut, because of its significantly high chromaticity of blue light emission.

The organic compound that has a naphtho[2,3-b;7,6-b'] bisbenzofuran skeleton or a naphtho[2,3-b;7,6-b']bisbenzothiophene skeleton and has a molecular weight of less than or equal to 5000 preferably has a substituent. The substituent is preferably a substituent having 1 to 100 carbon atoms. Specific examples of the substituent having 1 to 100 carbon atoms include a substituted or unsubstituted aliphatic hydrocarbon group having 1 to 100 carbon atoms, a substituted or unsubstituted alicyclic hydrocarbon group having 3 to 100 carbon atoms, a substituted or unsubstituted aromatic hydrocarbon group having 6 to 100 carbon atoms, a substituted or unsubstituted heterocyclic group having 1 to 100 carbon atoms, and a substituted or unsubstituted diarylamino group having 12 to 100 carbon atoms.

Note that the organic compound preferably has one or two substituents having 6 to 100 carbon atoms, more preferably one or two relatively large first substituents having 12 to 100 carbon atoms. The organic compound may also have a relatively small second substituent, and the second substituent is preferably a substituent having 1 to 25 carbon atoms, more preferably a substituent having 1 to 6 carbon atoms. The organic compound of one embodiment of the present invention, which has the first substituent and no second substituent, is easy to synthesize and preparing raw materials for the organic compound is also easy, so that the organic compound can be manufactured at low cost. Accordingly, the organic compound is preferred.

Note that the organic compound preferably has a molecular weight of less than or equal to 3000 in terms of easy synthesis, more preferably has a molecular weight of less than or equal to 1500 in terms of easy evaporation.

The organic compound of one embodiment of the present invention that has a molecular weight of less than or equal to 5000 can be represented by General Formula (G1) shown below.

[Chemical Formula 26]

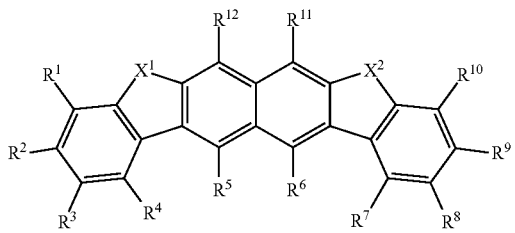

(G1)

In General Formula (G1), $X^1$ and $X^2$ independently represent an oxygen atom or a sulfur atom. Note that both of $X^1$ and $X^2$ are preferably the same atoms in terms of simple synthesis. More preferably, both of $X^1$ and $X^2$ are oxygen atoms, in which case the following effects are obtained, for example: synthesis is easy, light with a shorter wavelength can be emitted owing to a high singlet excitation level, and a high emission quantum yield can be achieved. Note that when the number of oxygen atoms is larger in $X^1$ and $X^2$, light with a shorter wavelength is emitted, whereas when the number of sulfur atoms is larger in $X^1$ and $X^2$, light with a longer wavelength is emitted. Thus, $X^1$ and $X^2$ can be appropriately determined depending on the target singlet excitation level and emission wavelength. In the formula, $R^1$ to $R^{12}$ independently represent hydrogen or a substituent.

It is preferred that the substituents independently have 1 to 100 carbon atoms. Examples of the substituent include a substituted or unsubstituted aliphatic hydrocarbon group having 1 to 100 carbon atoms, a substituted or unsubstituted alicyclic hydrocarbon group having 3 to 100 carbon atoms, a substituted or unsubstituted aromatic hydrocarbon group having 6 to 100 carbon atoms, a substituted or unsubstituted heterocyclic group having 1 to 100 carbon atoms, and a substituted or unsubstituted diarylamino group having 12 to 100 carbon atoms.

It is preferred that at least one of $R^1$ to $R^{12}$ represents a substituent having 6 to 100 carbon atoms, in which case the other or others independently represent hydrogen or a substituent having 1 to 25 carbon atoms. The number of substituents having 6 to 100 carbon atoms in $R^1$ to $R^{12}$ is preferably 1 or 2 in terms of simple synthesis and easy evaporation; it is preferably 1 for easy evaporation, in which case the molecular weight is small. Meanwhile, the molecular weight is preferably large for high heat resistance, in which case the number of substituents is preferably large because the molecular weight can easily be increased without much extension of conjugation.

In the case where the organic compound represented by General Formula (G1) has a substituent having 6 to 100 carbon atoms, one or both of $R^2$ and $R^9$ or one or both of $R^3$ and $R^8$ are preferably the substituent in terms of simple synthesis. It is particularly preferred that one or both of $R^2$ and $R^9$ are a substituent having 6 to 100 carbon atoms, in which case the emission quantum yield is high.

In the case where the organic compound represented by General Formula (G1) has a substituent having 6 to 100 carbon atoms, one of substituents in the meta-positions (e.g., $R^1$ or $R^2$ and $R^5$ or $R^6$) is preferably hydrogen in terms of simple synthesis because the steric hindrance of the substituents can be small. That is to say, hydrogen is preferably bonded to carbon adjacent to carbon to which the substituent having 6 to 100 carbon atoms is bonded.

In the case where the organic compound represented by General Formula (G1) has a substituent having 6 to 100 carbon atoms, one or a plurality of $R^1$ to $R^3$ and $R^8$ to $R^{12}$ are preferably the substituent in terms of simple synthesis because the steric hindrance of the substituents can be small.

Note that examples of the substituent having 6 to 100 carbon atoms include a substituted or unsubstituted aliphatic hydrocarbon group, a substituted or unsubstituted alicyclic hydrocarbon group, a substituted or unsubstituted aromatic hydrocarbon group, a substituted or unsubstituted heterocyclic group, and a substituted or unsubstituted diarylamino group. Note that examples of an aryl group included in the diarylamino group include a heteroaryl group. The diarylamino group is preferably selected to increase an emission quantum yield.

In the case where the organic compound represented by General Formula (G1) has a substituted or unsubstituted diarylamino group having 12 to 100 carbon atoms as the substituent having 6 to 100 carbon atoms, one or both of $R^2$ and $R^9$ are preferably the diarylamino group, in which case the reliability of the organic compound as a light-emitting material is high. The organic compound in which both of $R^2$ and $R^9$ are a substituted or unsubstituted diarylamino group having 12 to 100 carbon atoms is more preferred because of its high quantum yield. Furthermore, the organic compound in which both of $R^2$ and $R^9$ are a substituted or unsubstituted diarylamino group having 12 to 100 carbon atoms has a short emission wavelength and a sharp spectrum; thus, the organic compound is preferably used for displays and the like, where monochromatic light needs to be obtained.

In the case where the substituent having 6 to 100 carbon atoms is a substituted or unsubstituted diarylamino group having 12 to 100 carbon atoms, one or both of $R^3$ and $R^8$ are preferably the diarylamino group, in which case the hole-transport property is good; more preferably, both of $R^3$ and $R^8$ are the diarylamino group, in which case the hole-transport property is better. The organic compound in which one or both of $R^3$ and $R^8$ are the diarylamino group has a longer emission wavelength and a slightly broader spectrum than an organic compound in which one or both of $R^2$ and $R^9$ are the substituent.

Specific examples of the substituent having 6 to 100 carbon atoms include aromatic hydrocarbon groups such as a phenyl group, a biphenyl group, a terphenyl group, a naphthyl group, a fluorenyl group, a spirofluorenyl group, a phenanthryl group, an anthryl group, a dihydroanthryl group, a triphenylenyl group, and a pyrenyl group, and heterocyclic groups such as a pyridyl group, a bipyridyl group, a pyrimidyl group, a bipyrimidyl group, a pyrazyl group, a bipyrazyl group, a triazyl group, a quinolyl group, an isoquinolyl group, a phenanthryl group, a quinoxalinyl group, an azofluorenyl group, a diazofluorenyl group, a carbazolyl group, a benzocarbazolyl group, a dibenzocarbazolyl group, a dibenzofuranyl group, a benzonaphthofuranyl group, a dinaphthofuranyl group, a dibenzothiophenyl group, a benzonaphthothiophenyl group, a dinaphthothiophenyl group, a benzofuropyridyl group, a benzofuropyrimidyl group, a benzothiopyridyl group, a benzothiopyrimidyl group, a naphthofuropyridyl group, a naphthofuropyrimidyl group, a naphthothiopyridyl group, a naphthothiopyrimidyl group, a dibenzoquinoxalinyl group, an acridinyl group, a xanthenyl group, a phenothiazinyl group, a phenoxazinyl group, and a phenazyl group. Another example is a diarylamino group. The diarylamino group has a structure in which a phenyl group, a biphenyl group, a terphenyl group, a naphthyl group, a fluorenyl group, a spirofluorenyl group, a phenanthryl group, an anthryl group, a triphenylenyl group, or a pyrenyl group is bonded to nitrogen of an amine, as an aryl group. The substituent having 6 to 100 carbon atoms is preferably the diarylamino group.

Note that each of these substituents may further have an aliphatic hydrocarbon group having 1 to 6 carbon atoms, an alicyclic hydrocarbon group having 3 to 6 carbon atoms, or the like as a substituent. This structure is preferred in that the solubility in an organic solvent is high.

The structural formulae of examples of the substituent having 6 to 100 carbon atoms are shown below. As described above, each of the substituents may further have an aliphatic hydrocarbon group having 1 to 6 carbon atoms or an alicyclic hydrocarbon group having 3 to 6 carbon atoms as a substituent, for example.

[Chemical Formula 27]

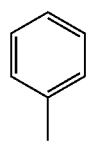
(Ar-1)

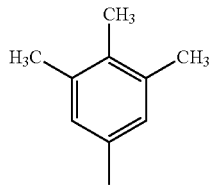
(Ar-2)

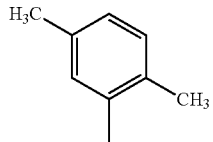
(Ar-3)

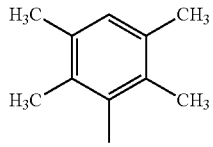
(Ar-4)

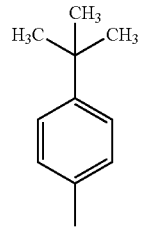
(Ar-5)

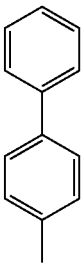
(Ar-6)

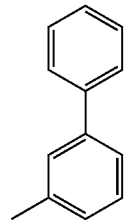
(Ar-7)

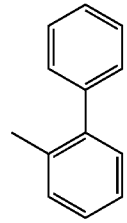
(Ar-8)

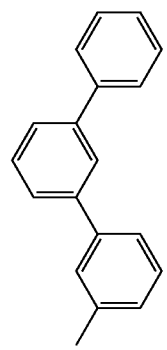 (Ar-9)
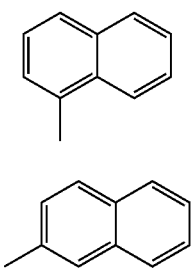 (Ar-10)
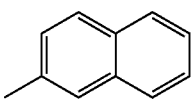 (Ar-11)
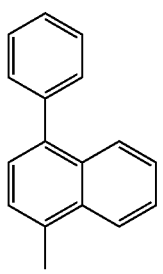 (Ar-12)
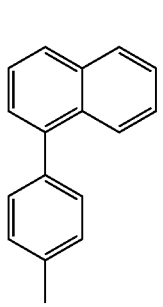 (Ar-13)
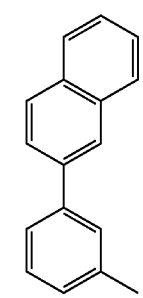 (Ar-14)
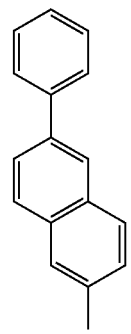 (Ar-15)
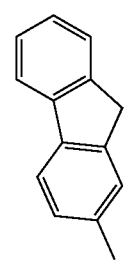 (Ar-16)
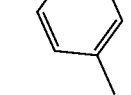 (Ar-17)
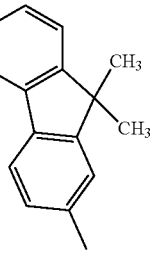 (Ar-17)
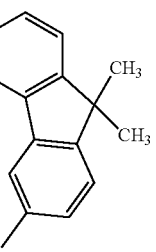 (Ar-18)
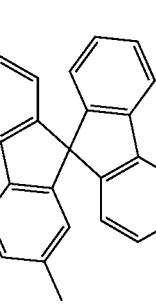 (Ar-19)

(Ar-20)
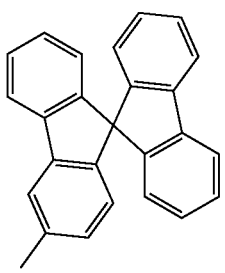
(Ar-21)
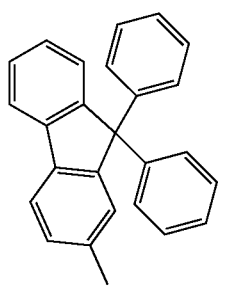
(Ar-22)
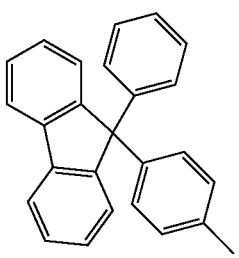
(Ar-23)
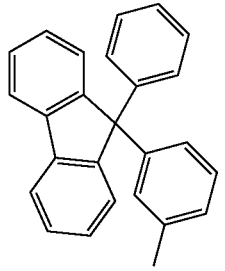
[Chemical Formula 28]
(Ar-24)
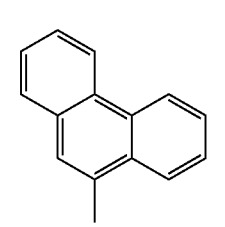
(Ar-25)
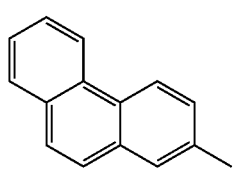
(Ar-26)
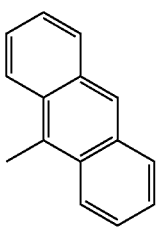
(Ar-27)
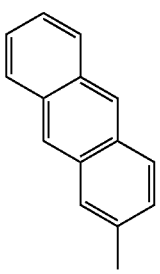
(Ar-28)
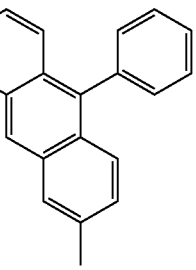
(Ar-29)
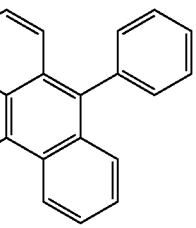
(Ar-30)
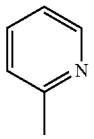
(Ar-31)
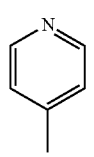
(Ar-32)
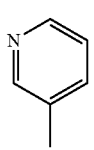

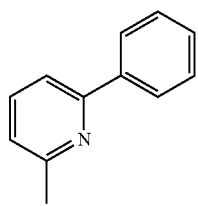 (Ar-33)
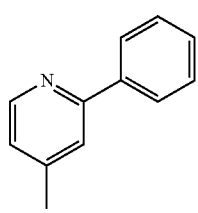 (Ar-34)
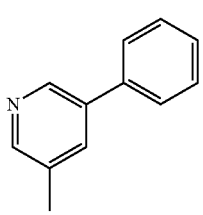 (Ar-35)
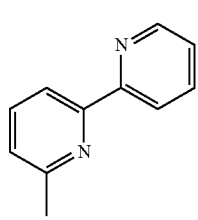 (Ar-36)
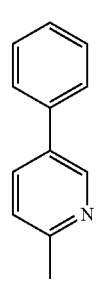 (Ar-37)
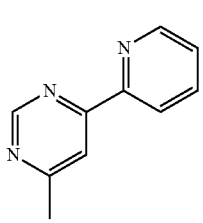 (Ar-38)
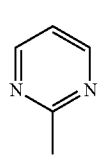 (Ar-39)
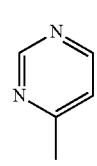 (Ar-40)
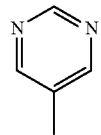 (Ar-41)
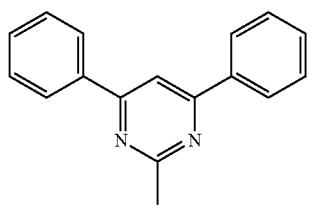 (Ar-42)
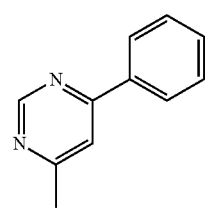 (Ar-43)
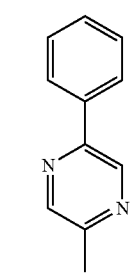 (Ar-44)
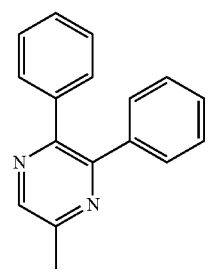 (Ar-45)
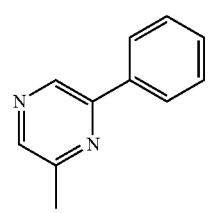 (Ar-46)
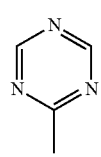 (Ar-47)

(Ar-48) 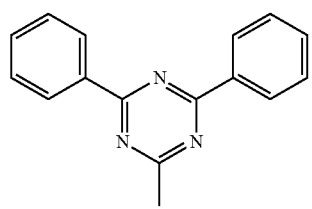
(Ar-49) 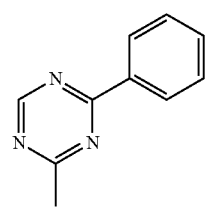
(Ar-50) 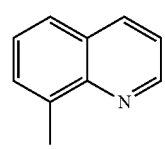
(Ar-51) 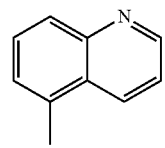
(Ar-52) 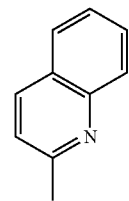
(Ar-53) 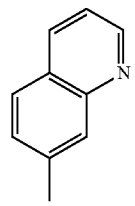
(Ar-54) 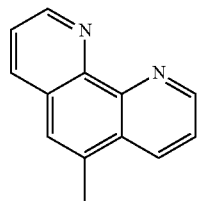
(Ar-55) 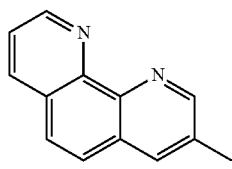
(Ar-56) 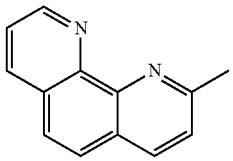
[Chemical Formula 29]
(Ar-57) 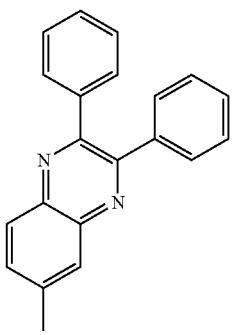
(Ar-58) 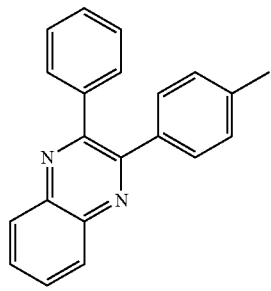
(Ar-59) 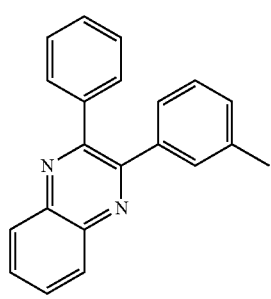
(Ar-60) 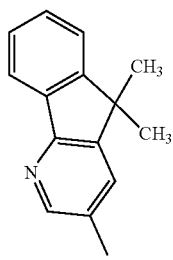

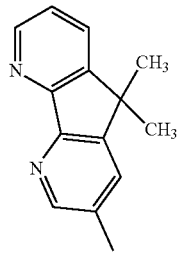 (Ar-61)
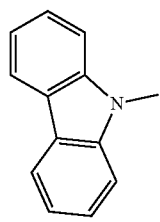 (Ar-62)
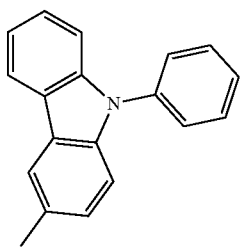 (Ar-63)
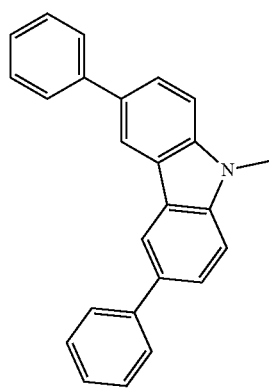 (Ar-64)
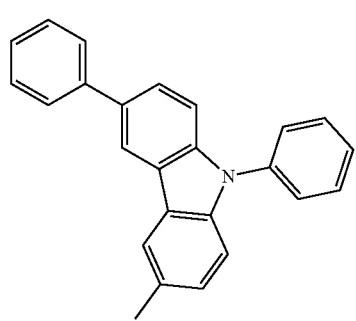 (Ar-65)
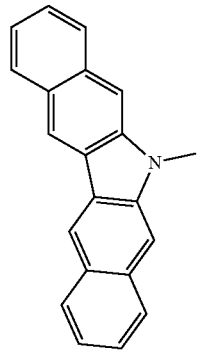 (Ar-66)
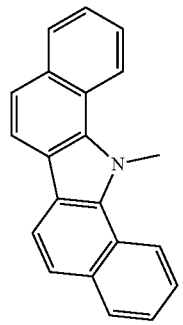 (Ar-67)
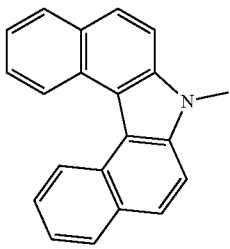 (Ar-68)
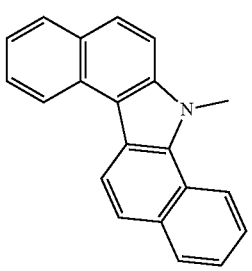 (Ar-69)
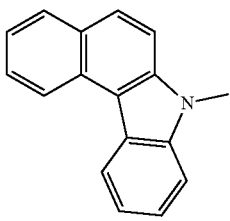 (Ar-70)

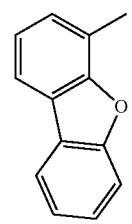 (Ar-71)
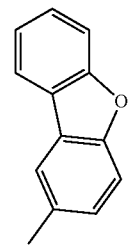 (Ar-72)
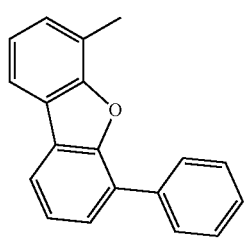 (Ar-73)
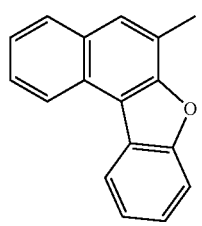 (Ar-74)
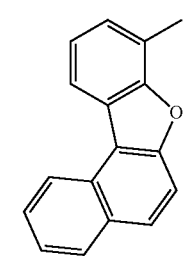 (Ar-75)
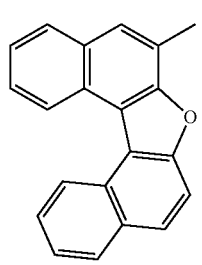 (Ar-76)
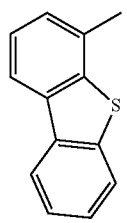 (Ar-77)
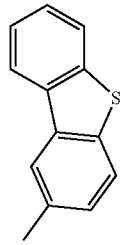 (Ar-78)
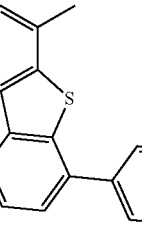 (Ar-79)
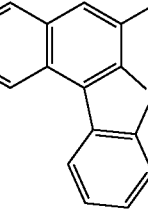 (Ar-80)
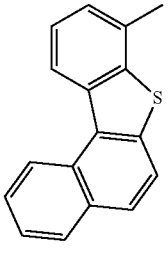 (Ar-81)
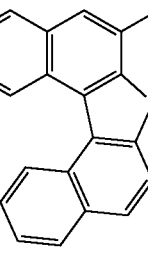 (Ar-82)

[Chemical Formula 30]
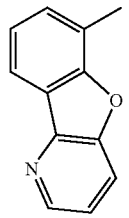 (Ar-83)
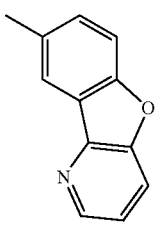 (Ar-84)
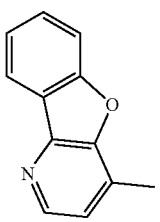 (Ar-85)
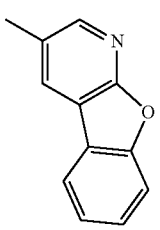 (Ar-86)
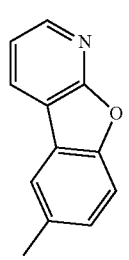 (Ar-87)
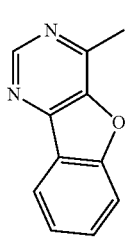 (Ar-88)
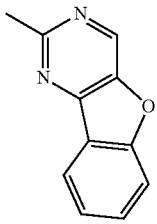 (Ar-89)
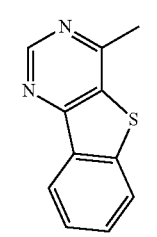 (Ar-90)
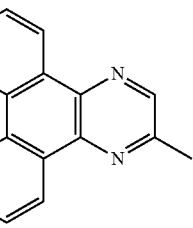 (Ar-91)
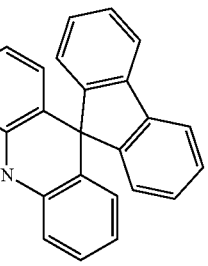 (Ar-92)
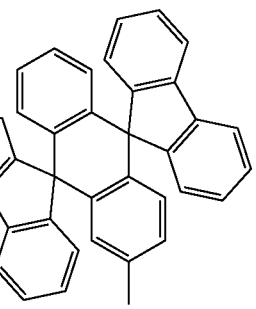 (Ar-93)
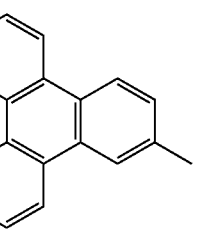 (Ar-94)

(Ar-95)
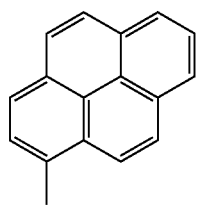
[Chemical Formula 31]
(Ar-96)
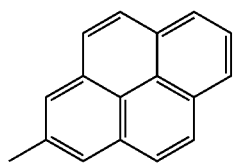
(Ar-100)
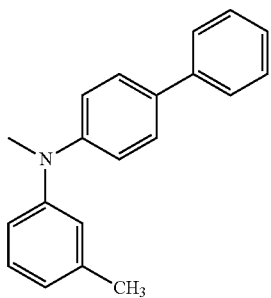
(Ar-101)
(Ar-102)
(Ar-103)
(Ar-104)
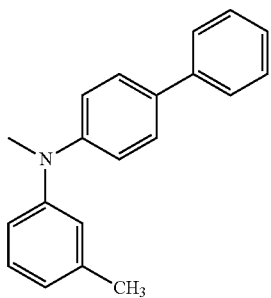
(Ar-105)
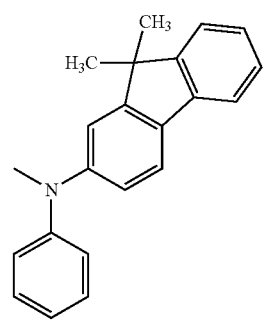
(Ar-106)
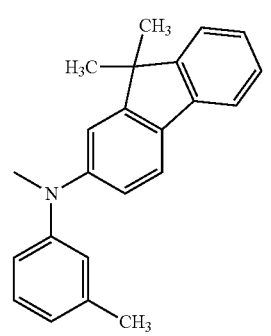
(Ar-107)
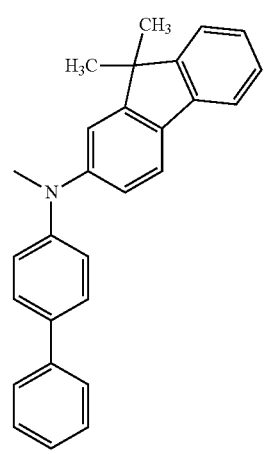

(Ar-108)
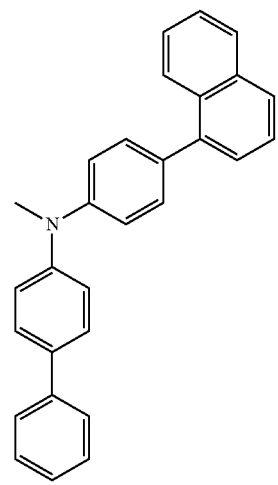
(Ar-121)
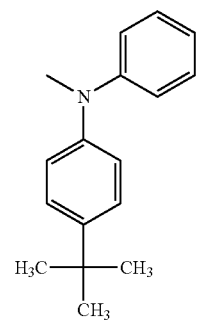
(Ar-122)
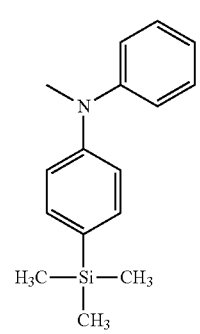
(Ar-109)
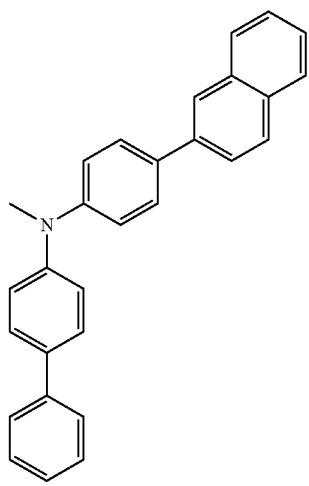
[Chemical Formula 32]
(Ar-123)
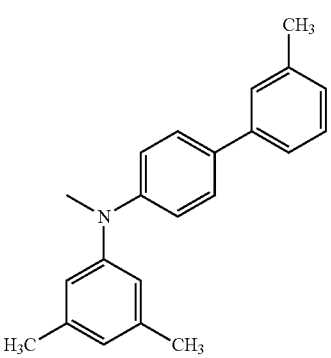
(Ar-120)
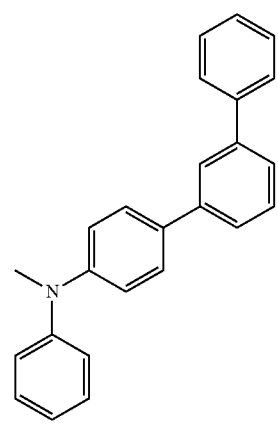
(Ar-124)
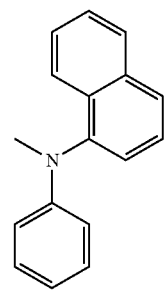
(Ar-125)
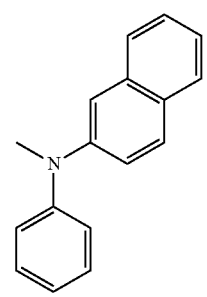

(Ar-126)
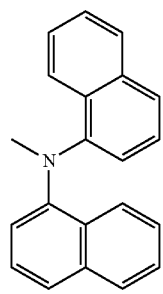
(Ar-127)
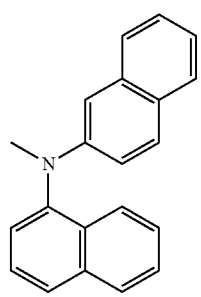
(Ar-128)
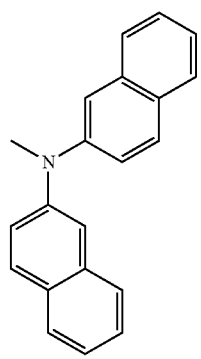
(Ar-129)
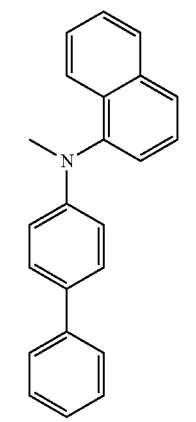
(Ar-130)
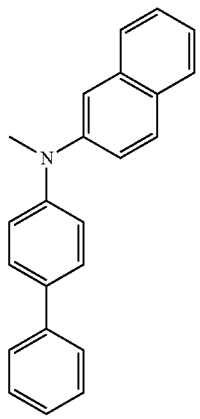
(Ar-131)
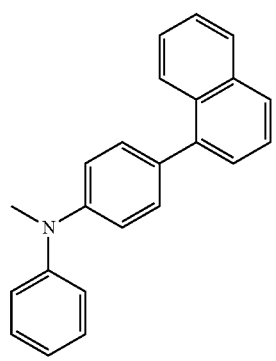
(Ar-132)
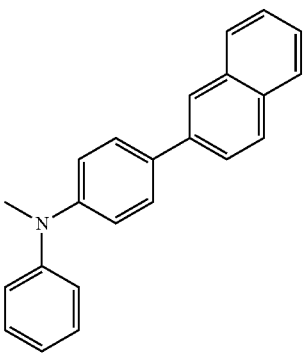
(Ar-133)
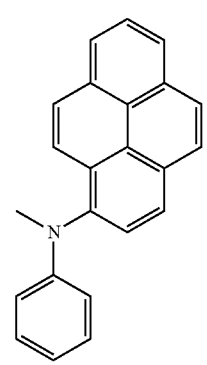

-continued

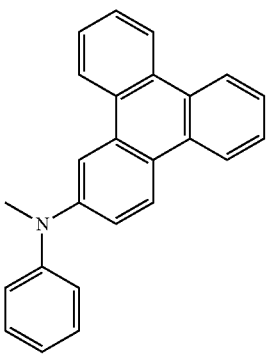
(Ar-134)

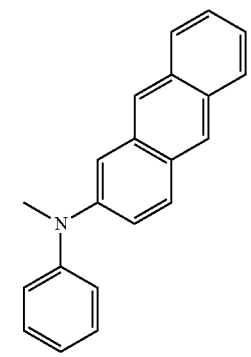
(Ar-135)

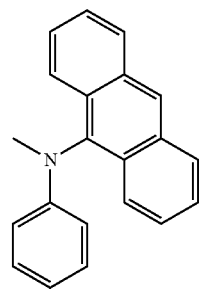
(Ar-136)

[Chemical Formula 33]

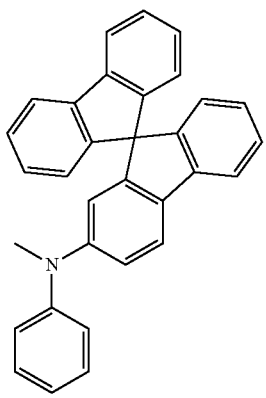
(Ar-137)

-continued

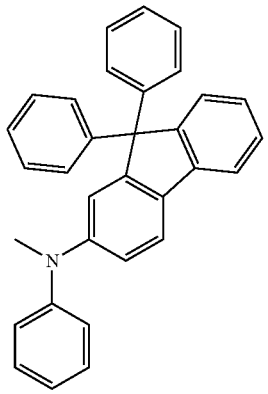
(Ar-138)

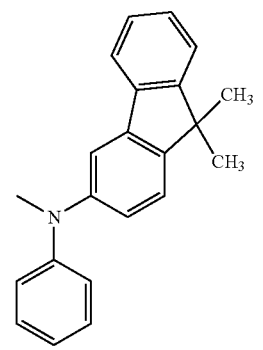
(Ar-139)

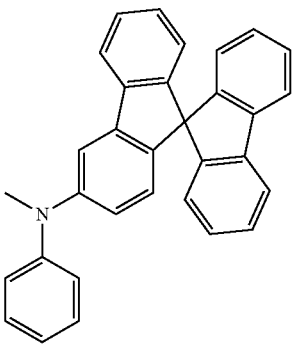
(Ar-140)

Note that the structure of a substituent in which two or more substituents are bonded to each other, such as (Ar-2) to (Ar-9), (Ar-12) to (Ar-15), (Ar-17) to (Ar-23), (Ar-28), (Ar-29), (Ar-33) to (Ar-38), (Ar-42) to (Ar-46), (Ar-48), (Ar-49), (Ar-57) to (Ar-61), (Ar-63) to (Ar-65), (Ar-79), (Ar-92), and (Ar-93), is sterical; thus, a film including an organic compound having such a substituent is not easily crystallized and stable film quality is obtained.

When a substituent is bonded to another substituent via a phenylene group as in the structures of (Ar-13), (Ar-14), (Ar-22), and (Ar-23), conjugation does not easily extend to the substituent and thus the singlet excitation level can be kept high. A structure in which a substituent is bonded to another substituent via a metaphenylene group has a noticeable effect and thus is particularly preferred. A structure in which a substituent is bonded to another substituent via a paraphenylene group has high reliability and thus is preferred.

Furthermore, a substituent having two or more condensed rings, such as (Ar-10) to (Ar-96) and a heterocyclic compound are preferred because of their excellent carrier-transport properties. The anthryl groups of (Ar-26) to (Ar-29) are preferred because of their excellent hole and electron transport properties.

The substituents of (Ar-100) to (Ar-140) are examples of arylamino groups. When an arylamino group has a structure in which two or more substituents bonded to each other are bonded to nitrogen, like (Ar-101), (Ar-102), (Ar-104), (Ar-107) to (Ar-120), (Ar-123), and (Ar-129) to (Ar-132), the structure is sterical; thus, a film including an organic compound having such an arylamino group is not easily crystallized and stable film quality is obtained. Note that such an arylamino group is preferably selected as the substituent having 6 to 100 carbon atoms, in which case the emission quantum yield of an organic compound increases.

The structures of (Ar-108), (Ar-109), (Ar-129), and (Ar-132), in which an aryl group is bonded to nitrogen of an amine via a phenylene group, are preferred in that conjugation does not easily extend to the aryl group and thus the singlet excitation level can be kept high. The structure in which a different substituent is bonded to an amine via a phenylene group is preferred in that conjugation does not easily extend and thus the singlet excitation level can be kept high. It is particularly preferred that the phenylene group is a metaphenylene group, in which case a significant effect can be obtained.

The substituents such as (Ar-101) to (Ar-120), (Ar-123), (Ar-129) to (Ar-132), (Ar-137), and (Ar-138), in which a parabiphenyl structure is bonded to an amine, are preferred in that the reliability of a light-emitting material is increased.

The structures of (Ar-103) to (Ar-107), (Ar-121) to (Ar-123), and (Ar-139), which include an alkyl group or an alkylsilyl group, are preferred in that solubility in an organic solvent is high. Furthermore, inhibiting the interaction between molecules can help lower the sublimation temperature, and thus, an alkyl group or an alkylsilyl group is preferably bonded to a plurality of substituents as in the structures of (Ar-103) and (Ar-123).

Note that when the organic compound has two or more diarylamino groups as substituents, an emission center skeleton in the organic compound can be a naphtho[2,3-b;7,6-b']bisbenzofuran skeleton or a naphtho[2,3-b;7,6-b']bisbenzothiophene skeleton, resulting in a high quantum yield.

The structures of (Ar-19) to (Ar-23), (Ar-92), (Ar-93), and (Ar-137) to (Ar-140), in which substituents are bonded via carbon having a sigma bond at, for example, the 9-position of fluorine, are preferred in that conjugation does not easily extend, the S1 level is high, and the emission wavelength is shorter.

Note that the groups represented by structural formulae shown below are particularly preferred among the groups shown above.

[Chemical Formula 34]

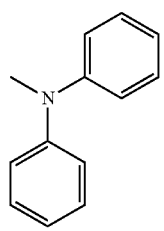
(Ar-100)

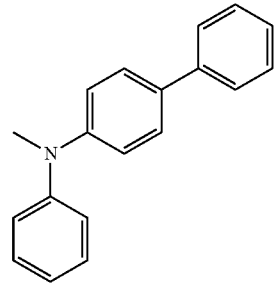
(Ar-101)

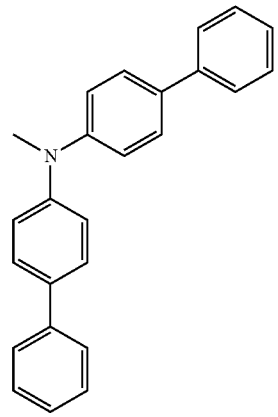
(Ar-102)

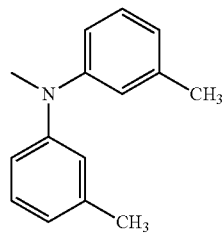
(Ar-103)

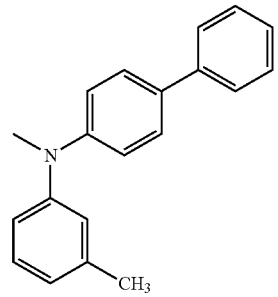
(Ar-104)

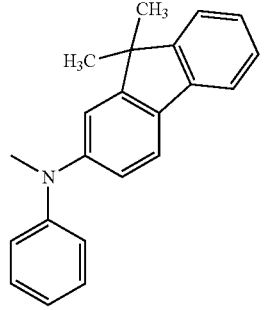
(Ar-105)

(Ar-105)
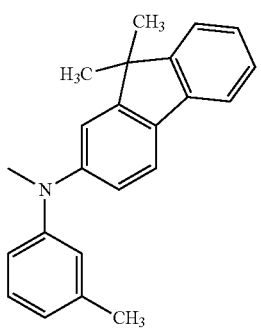

(Ar-106)
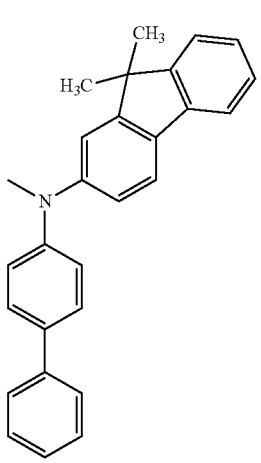

(Ar-108)
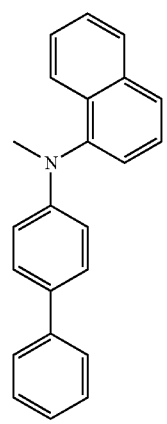

(Ar-109)
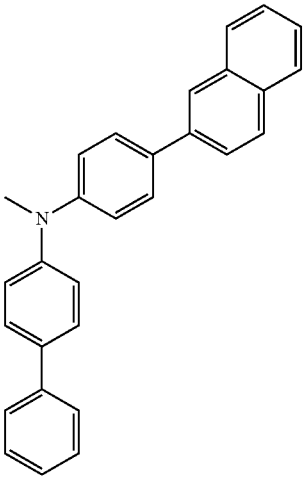

(Ar-29)
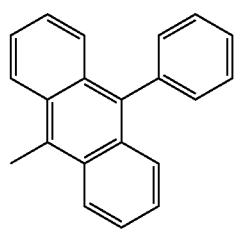

The groups represented by General Formulas (g1) and (g2) shown below are also preferred as the substituent having 6 to 100 carbon atoms.

[Chemical Formula 35]

(g1)
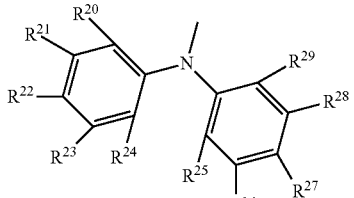

(g2)
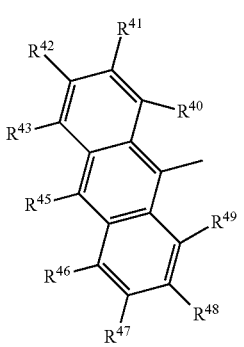

The organic compound represented by General Formula (G1) that has the group represented by General Formula (g1) among the above substituents is preferred because of its high emission efficiency. The organic compound represented by General Formula (G1) that has the group represented by General Formula (g2) among the above substituents is preferred because of its excellent carrier-transport property. That is, organic compounds represented by General Formulas (G2) to (G4) shown below are preferred.

[Chemical Formula 36]

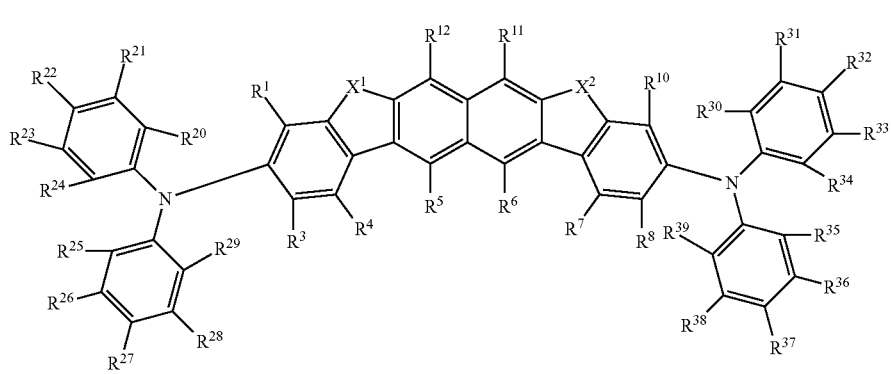

(G2)

[Chemical Formula 37]

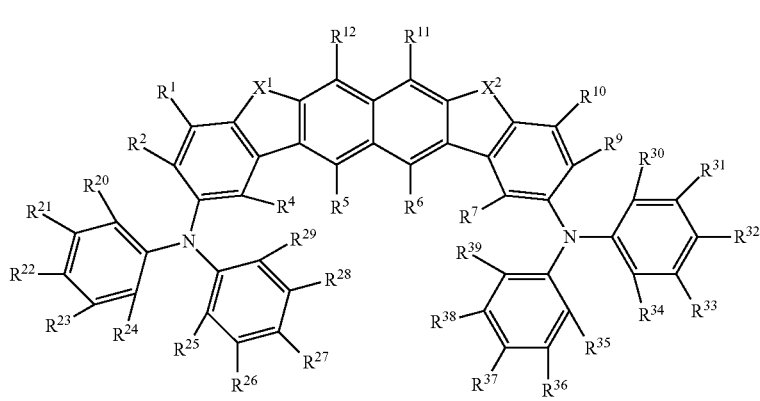

(G3)

[Chemical Formula 38]

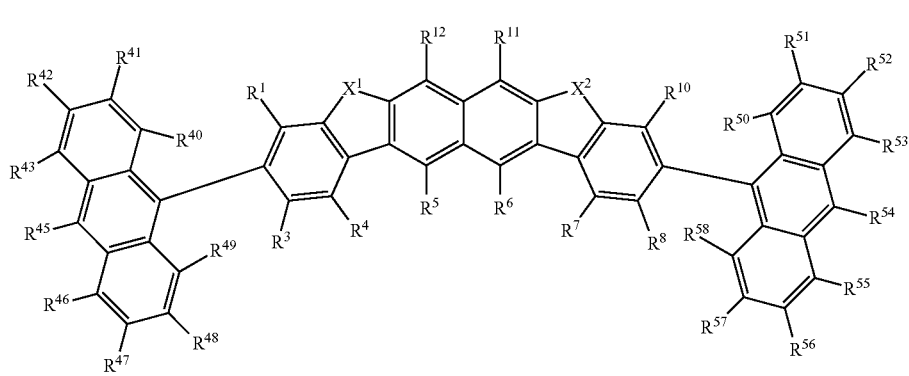

(G4)

In General Formulas (G2) to (G4), $X^1$ and $X^2$ independently represent an oxygen atom or a sulfur atom. In addition, $R^1$, $R^3$ to $R^8$, $R^{10}$ to $R^{12}$, $R^{20}$ to $R^{29}$, and $R^{30}$ to $R^{39}$ in General Formula (G2), $R^1$, $R^2$, $R^4$ to $R^7$, $R^9$ to $R^{12}$, $R^{20}$ to $R^{29}$, and $R^{30}$ to $R^{39}$ in General Formula (G3), and $R^1$, $R^3$ to $R^8$, $R^{10}$ to $R^{12}$, $R^{40}$ to $R^{49}$, and $R^{50}$ to $R^{59}$ in General Formula (G4) independently represent hydrogen or a substituent having 1 to 25 carbon atoms.

Examples of the substituent having 1 to 25 carbon atoms include an aliphatic hydrocarbon group having 1 to 10 carbon atoms, an alicyclic hydrocarbon group having 3 to 20 carbon atoms, an aromatic hydrocarbon group having 6 to 25 carbon atoms, a heterocyclic group having 1 to 25 carbon atoms, and an alkylsilyl group.

Examples of the aliphatic hydrocarbon group having 1 to 10 carbon atoms include a methyl group, an ethyl group, a propyl group, an isopropyl group, a butyl group, a tert-butyl group, a pentyl group, a hexyl group, a heptyl group, an octyl group, a nonyl group, a decyl group, and an icosyl group. Examples of the alicyclic hydrocarbon group having 3 to 20 carbon atoms include a cyclopropyl group, a cyclohexyl group, an adamantyl group, and a norbornyl group. Examples of the aromatic hydrocarbon group having 6 to 25 carbon atoms include a phenyl group, a biphenyl group, a naphthyl group, a phenanthryl group, an anthryl group, a fluorenyl group, a fluorenyl group whose 9-position is substituted by two alkyl groups, a spirofluorenyl group, a pyrenyl group, and a triphenylenyl group. Examples of the heterocyclic group having 1 to 25 carbon atoms include a carbazolyl group, a dibenzofuranyl group, and a dibenzothiophenyl group.

Each of these substituents may further have an aliphatic hydrocarbon group having 1 to 6 carbon atoms, an alicyclic hydrocarbon group having 3 to 6 carbon atoms, or the like as a substituent.
Examples of the organic compounds of embodiments of the present invention with the above-described structure are shown below.
[Chemical Formula 39]
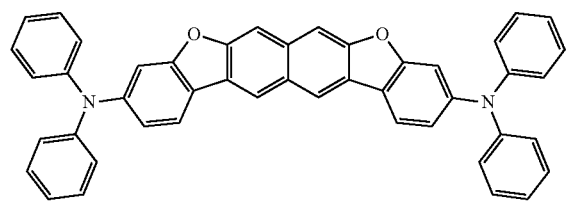
(100)
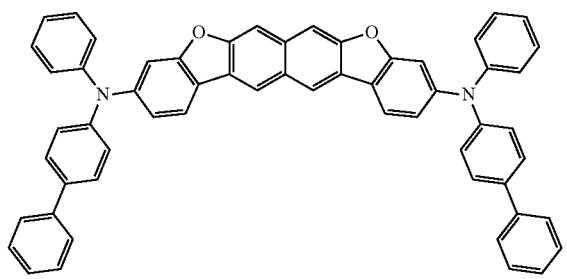
(101)
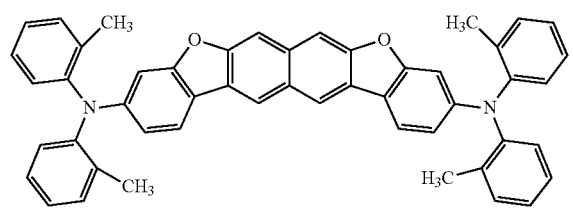
(102)
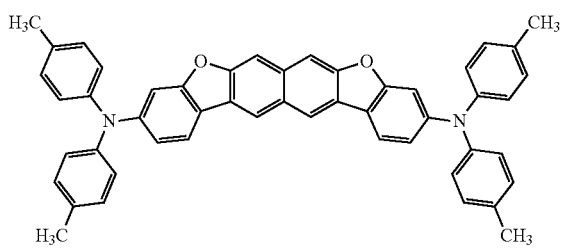
(103)
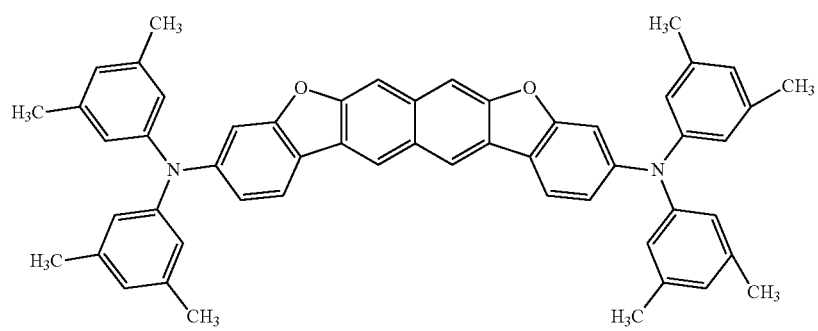
(104)
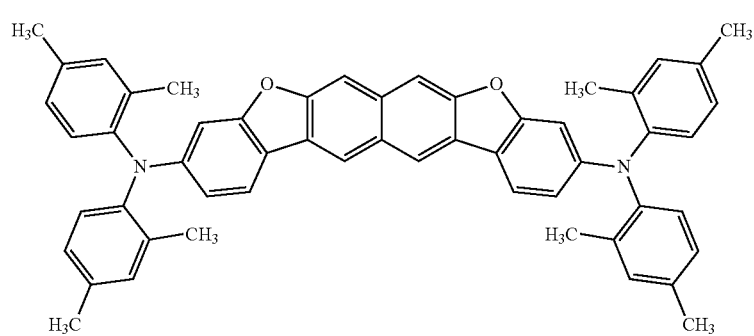
(105)

-continued
[Chemical Formula 40]
(106)
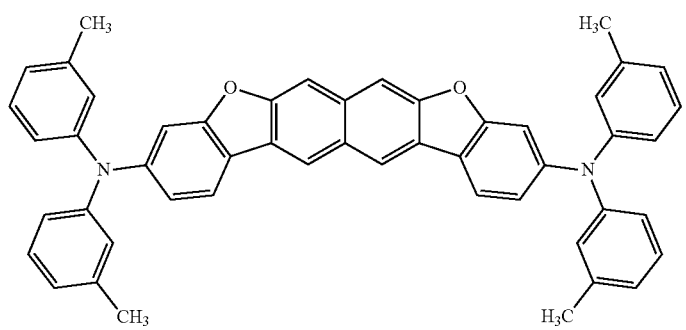
(107)
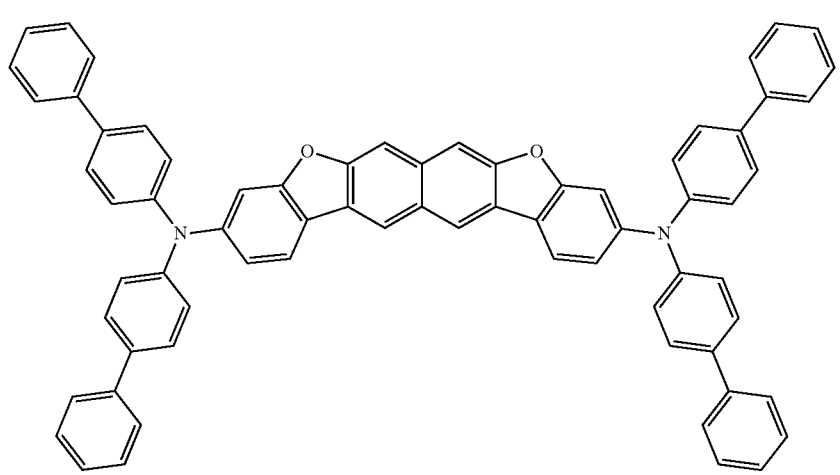
(108)
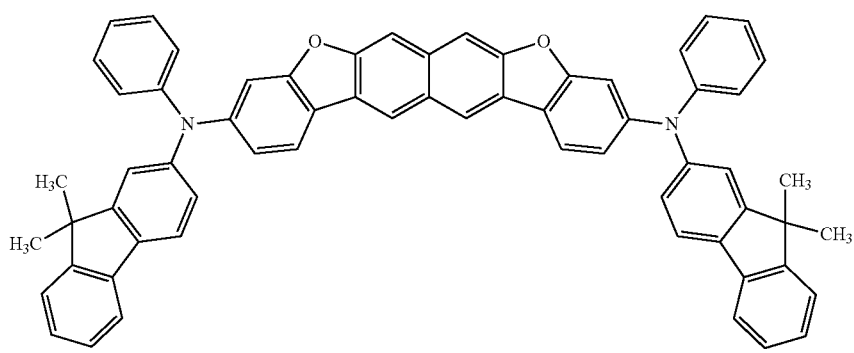
(109)
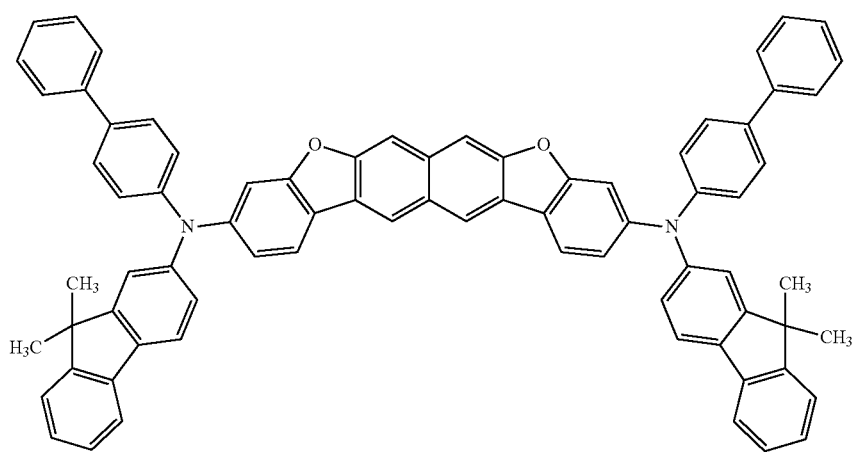

(110)
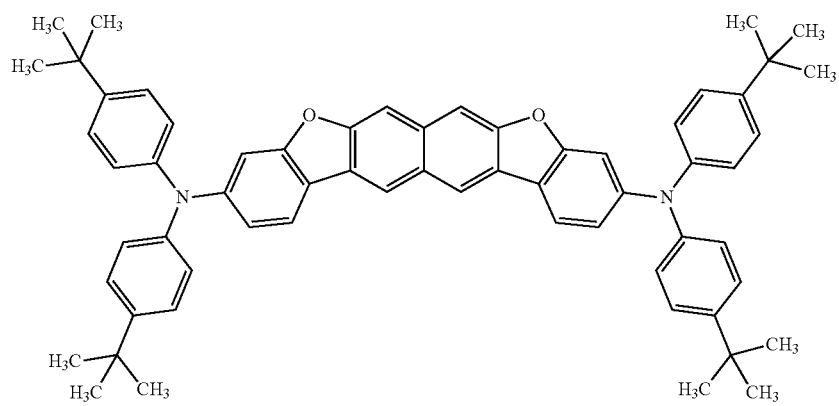
[Chemical Formula 41]
(111)
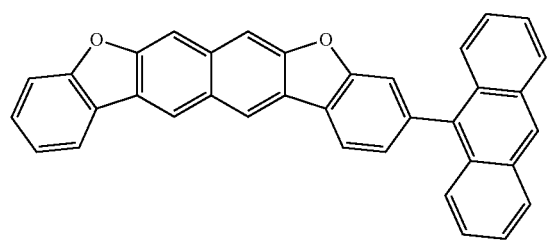
(112)
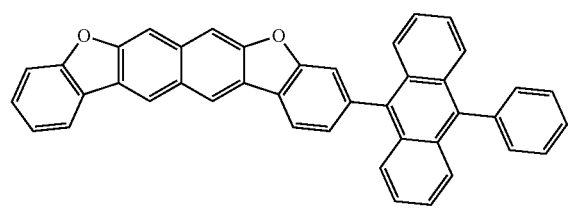
(113)
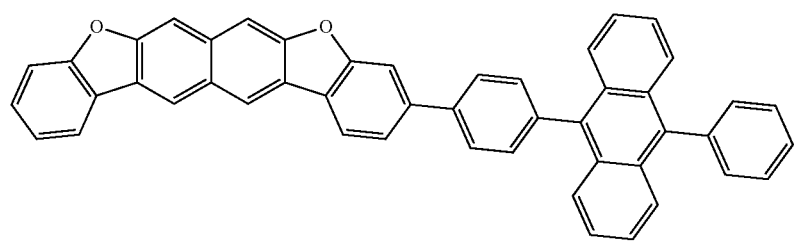
(114)
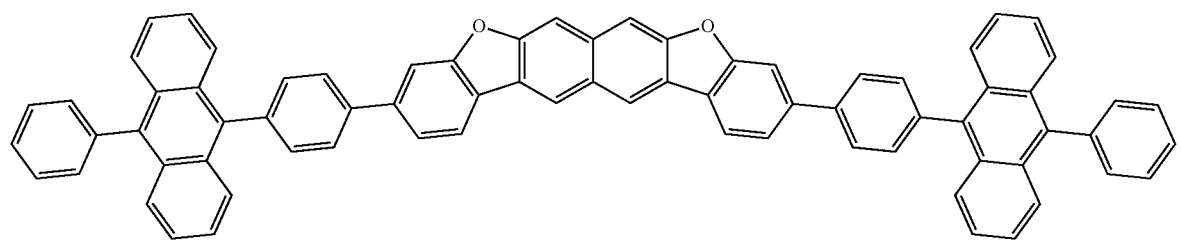
(115)
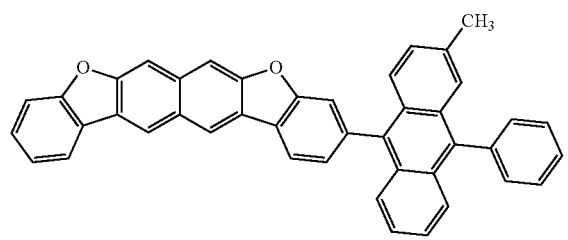
(116)
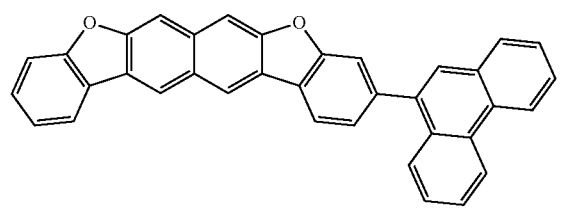

[Chemical Formula 42]
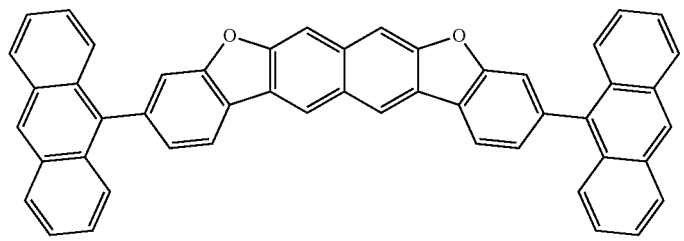
(117)
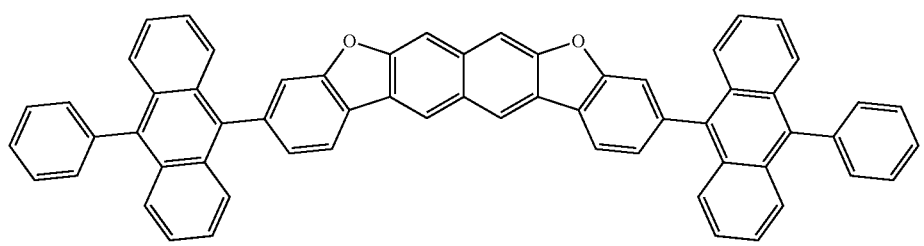
(118)
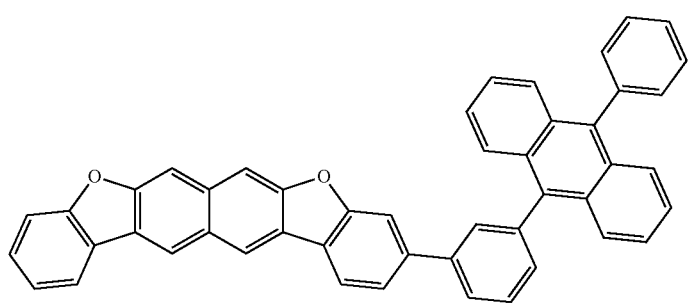
(119)
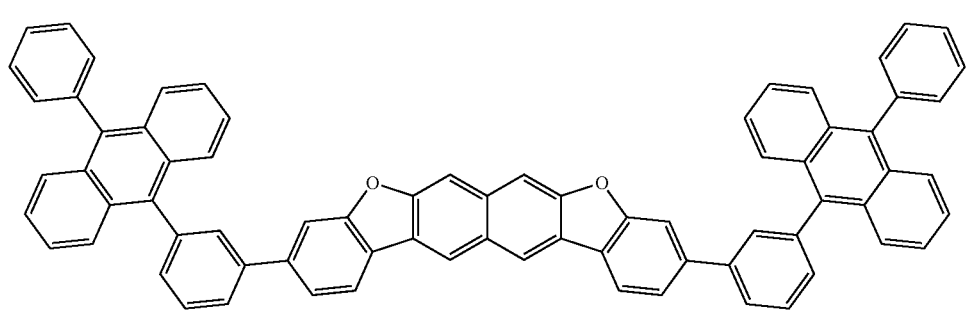
(120)
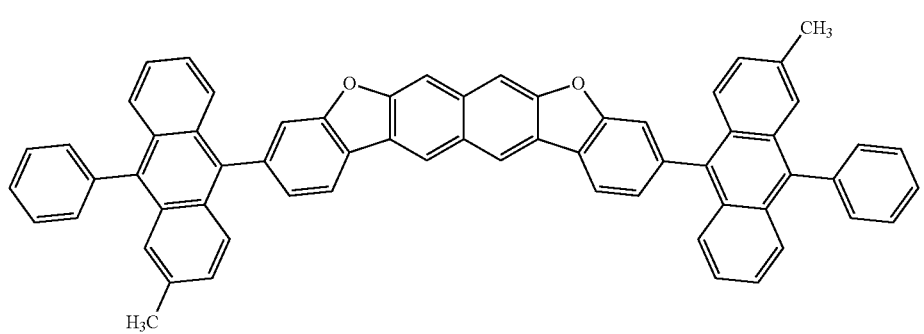
(121)

(122)
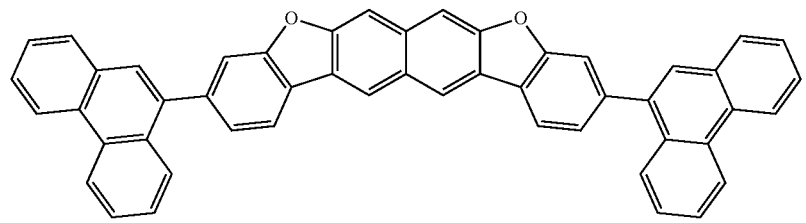
[Chemical Formula 43]
(123)
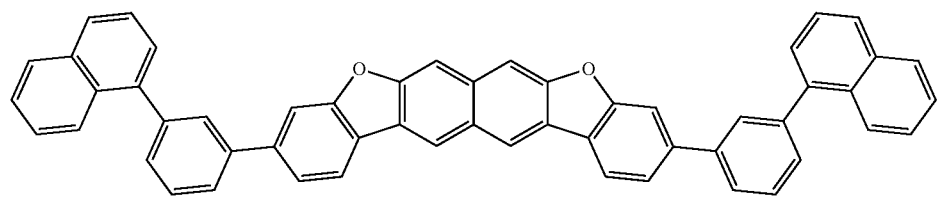
(124)
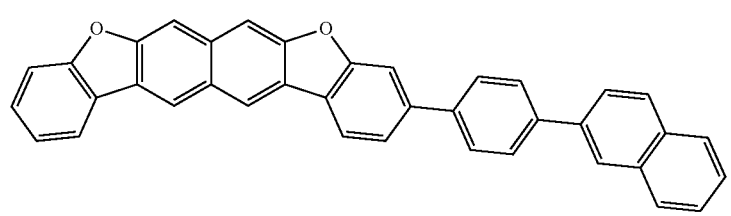
(125)
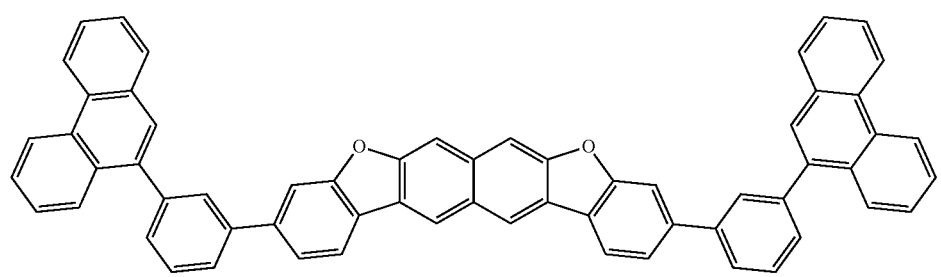
(126)
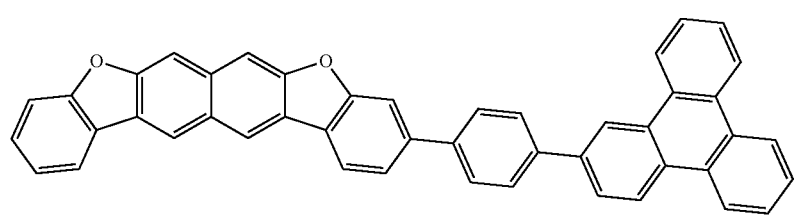
(127)
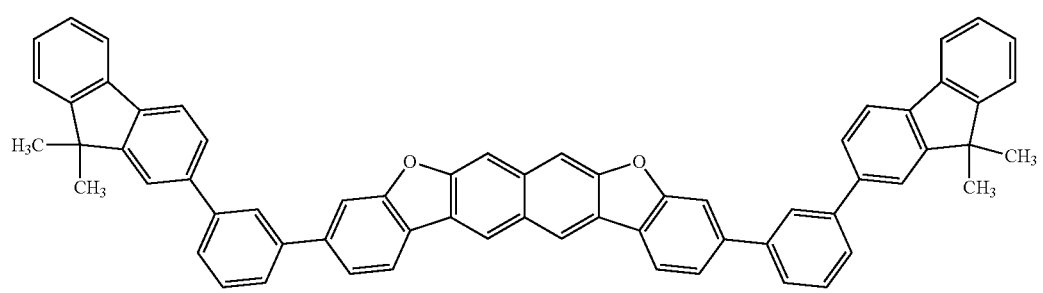

-continued
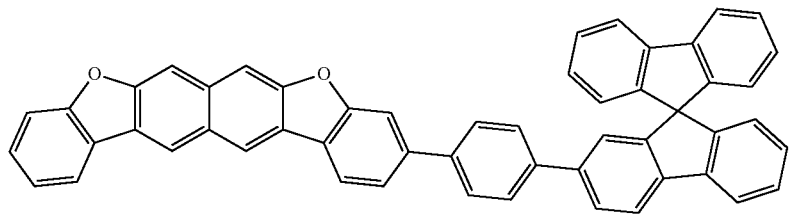
(128)
[Chemical Formula 44]
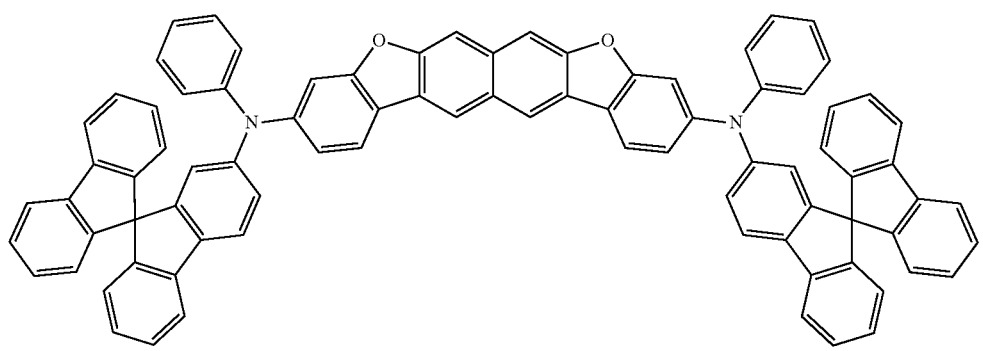
(129)
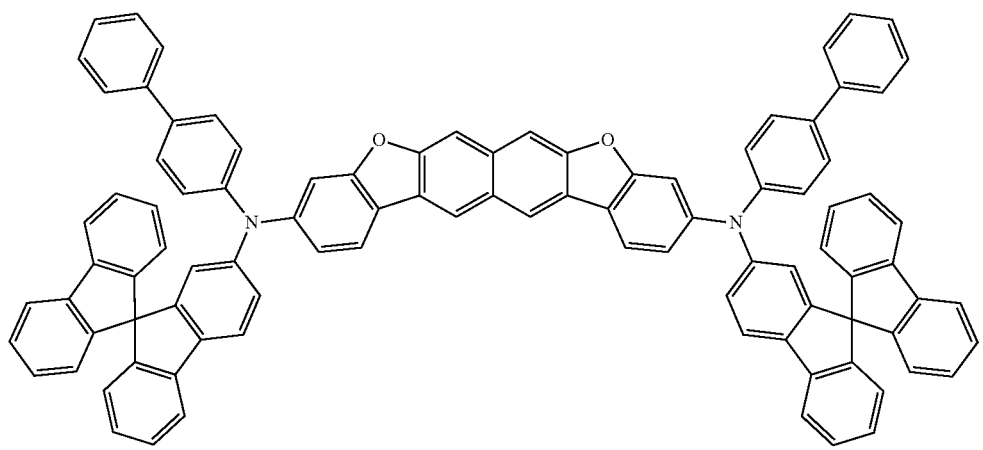
(130)
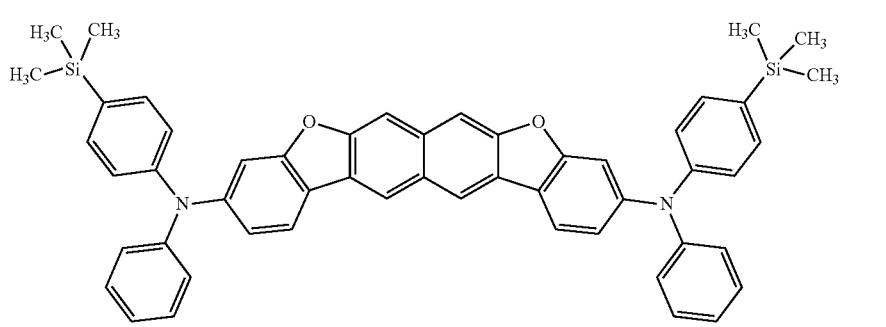
(131)

-continued
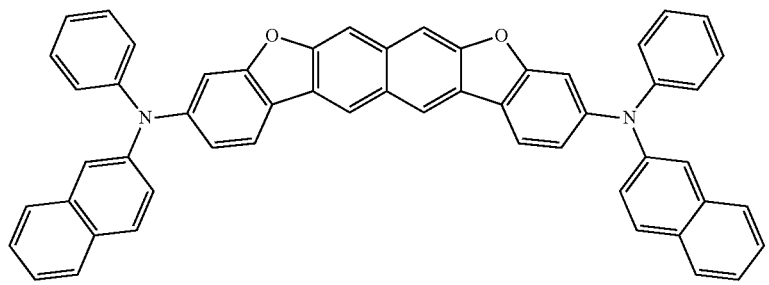
(132)
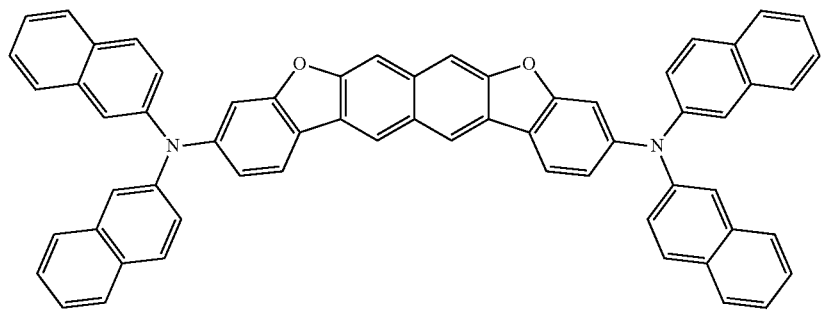
(133)
[Chemical Formula 45]
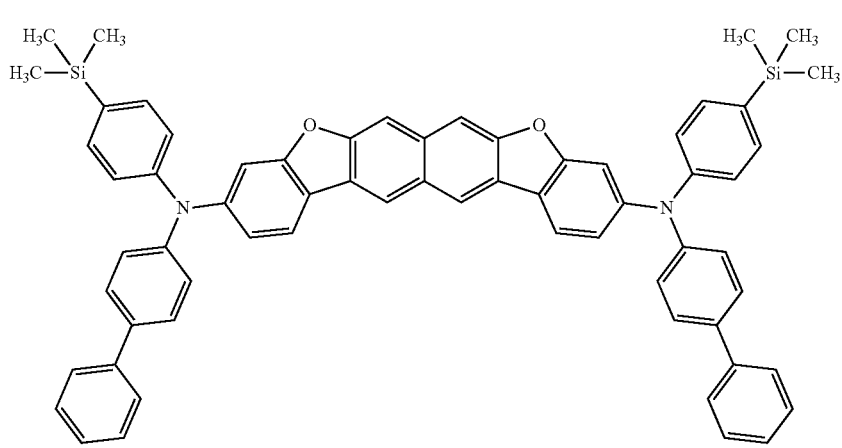
(134)
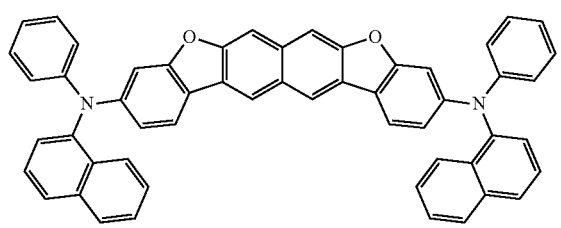
(135)
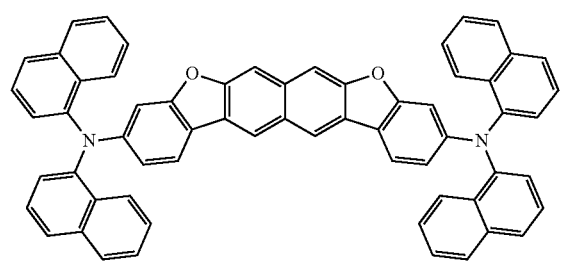
(136)
[Chemical Formula 46]
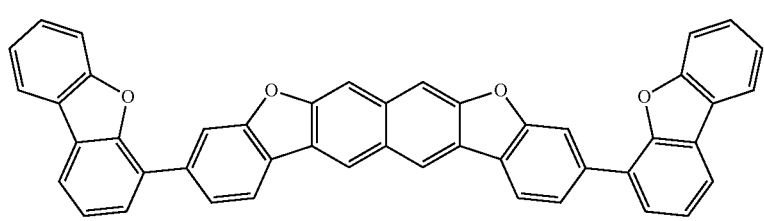
(137)

-continued
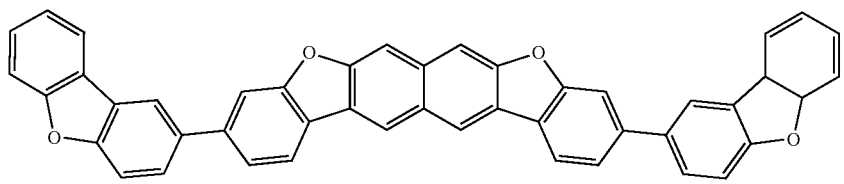
(138)
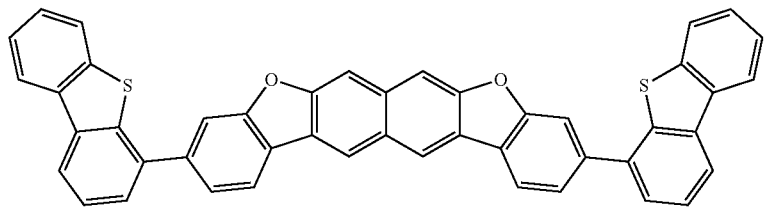
(139)
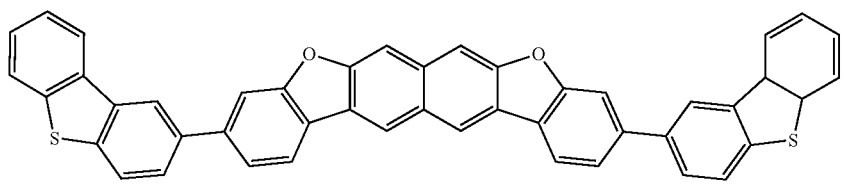
(140)
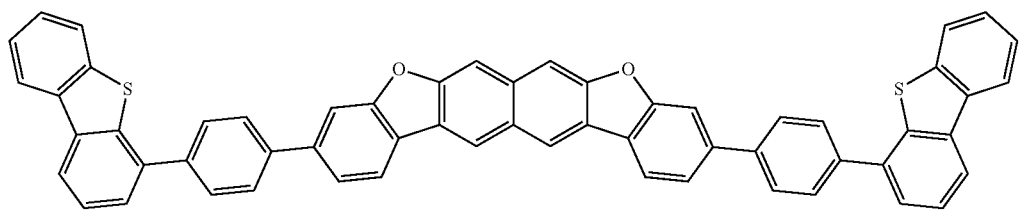
(141)
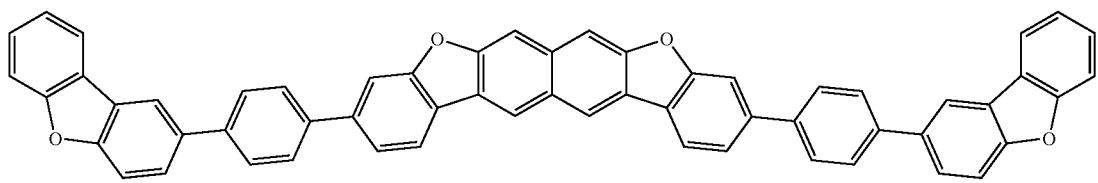
(142)
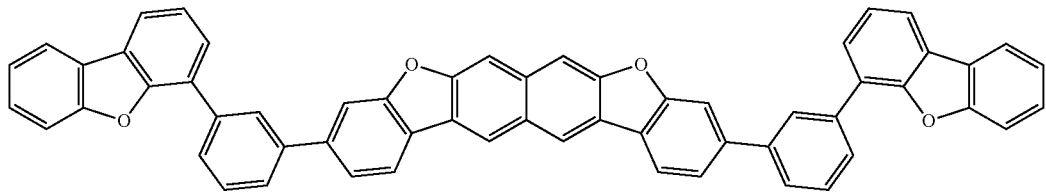
(143)
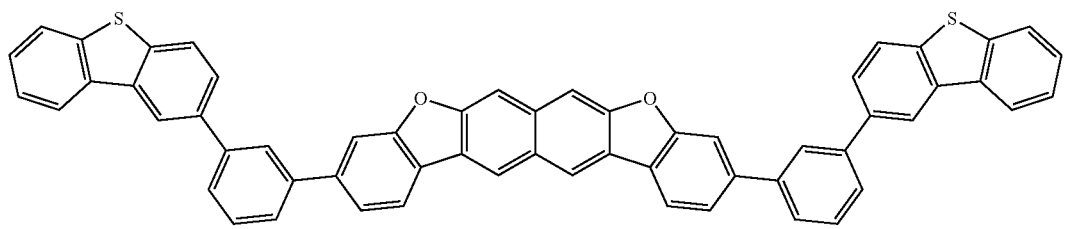
(144)

-continued
[Chemical Formula 47]
(145)
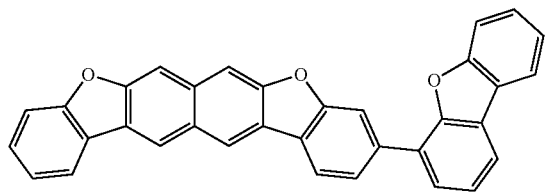
(146)
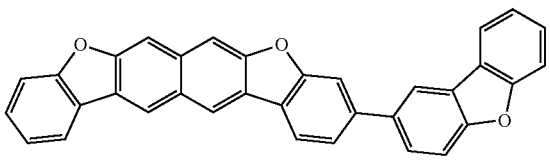
(147)
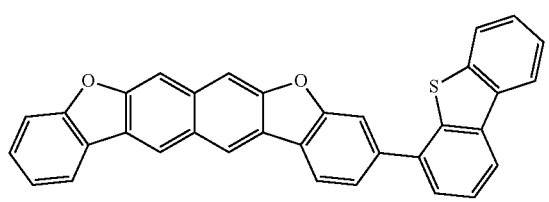
(148)
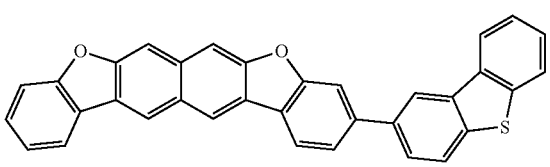
(149)
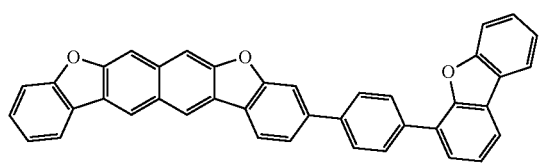
(150)
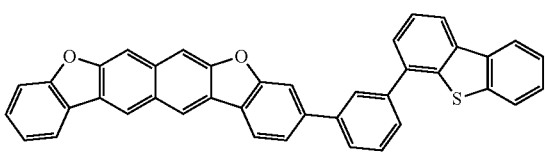
[Chemical Formula 48]
(151)
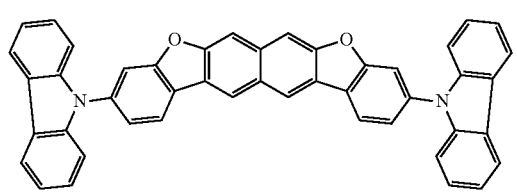
(152)
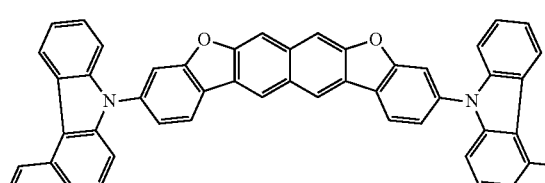
(153)
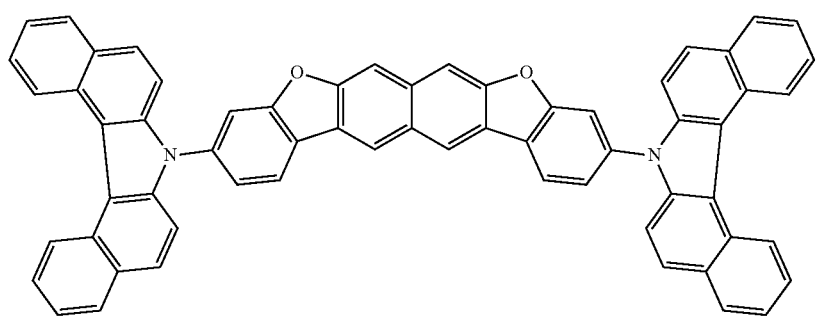
(154)
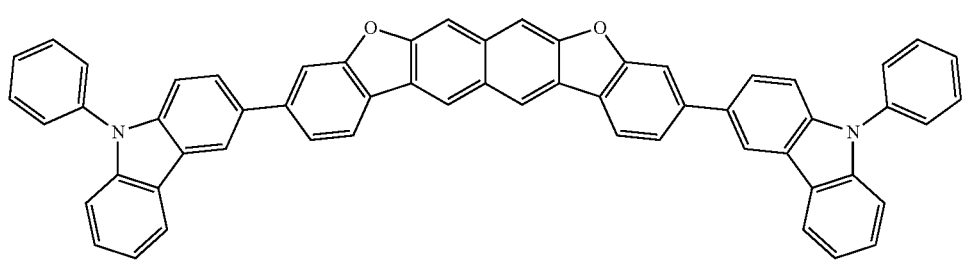

(155)
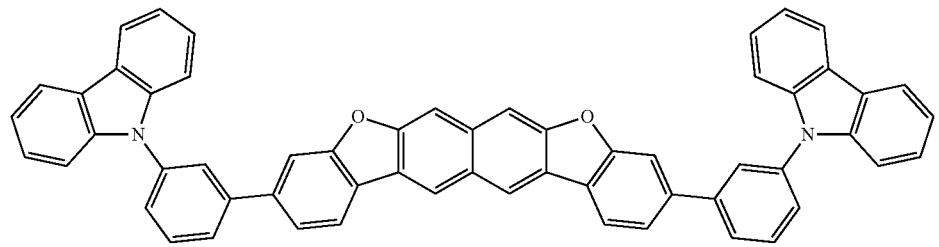
[Chemical Formula 49]
(156)
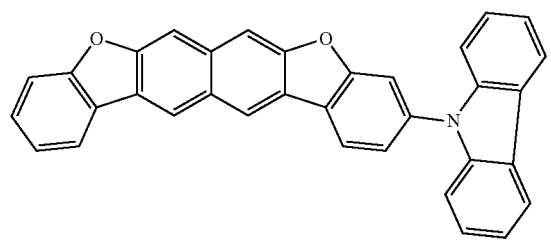
(157)
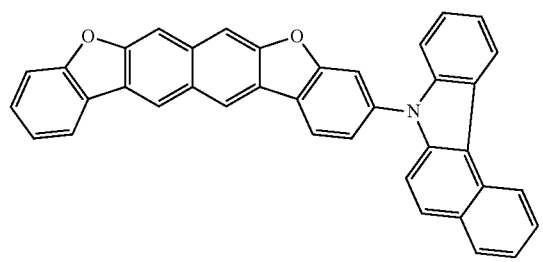
(158)
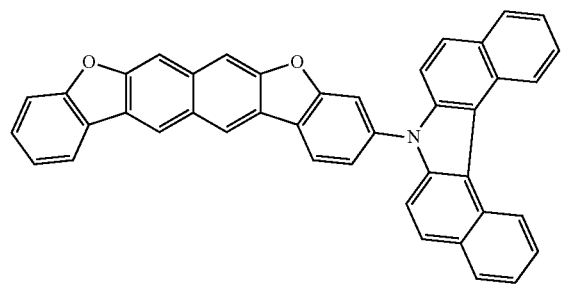
(159)
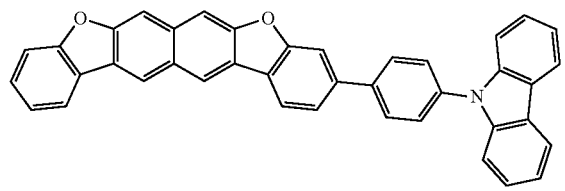
(160)
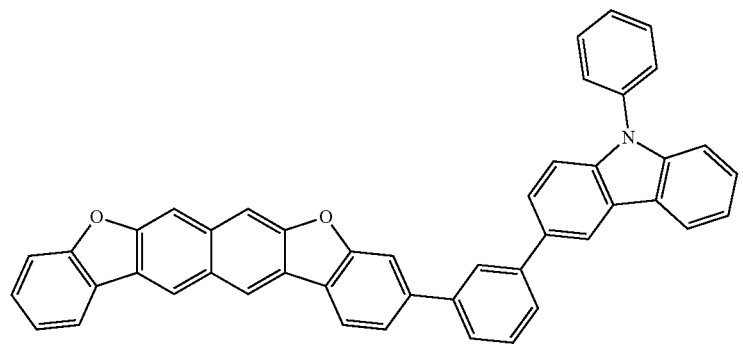

[Chemical Formula 50]
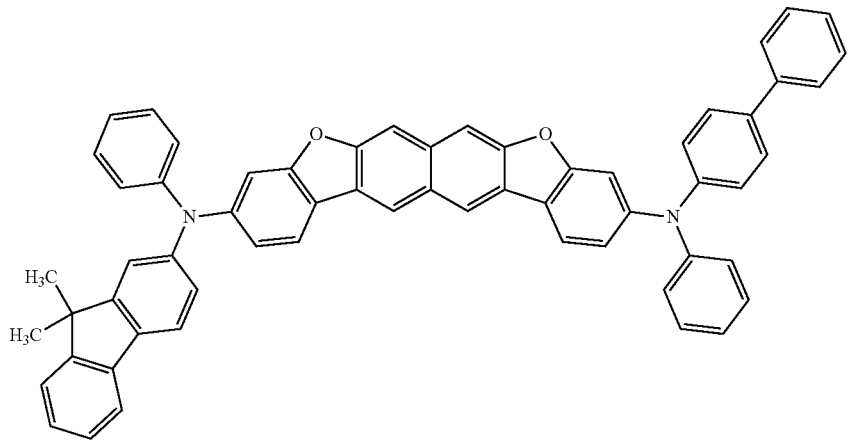
(161)
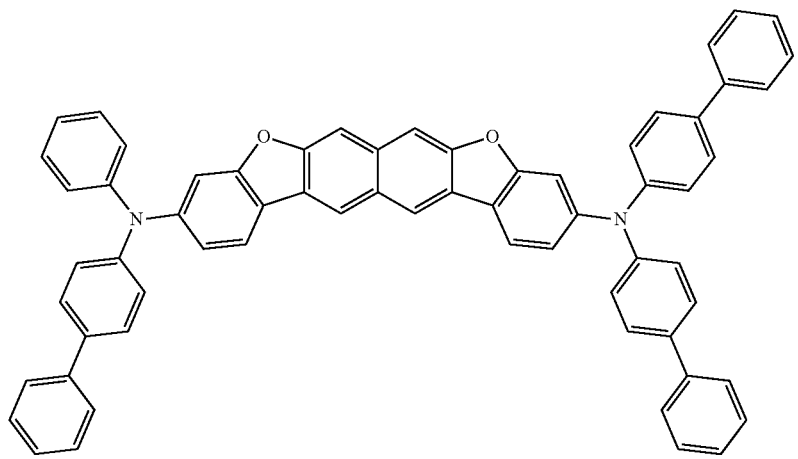
(162)
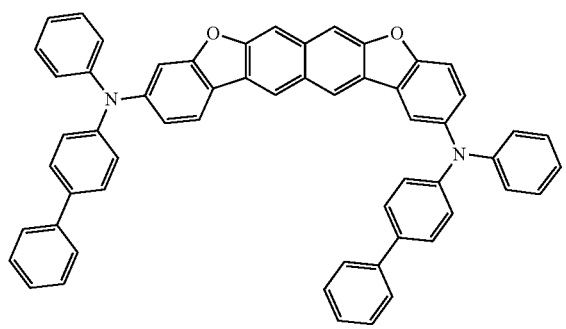
(163)
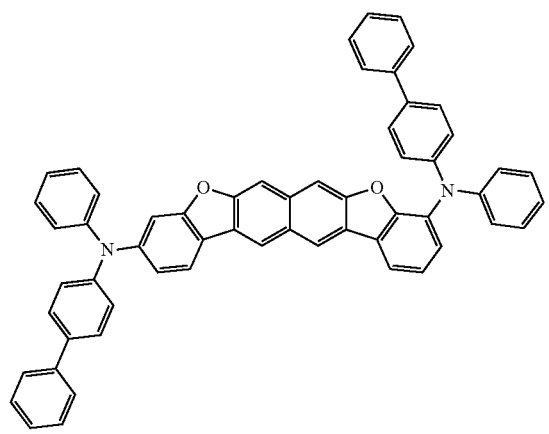
(164)

(165)
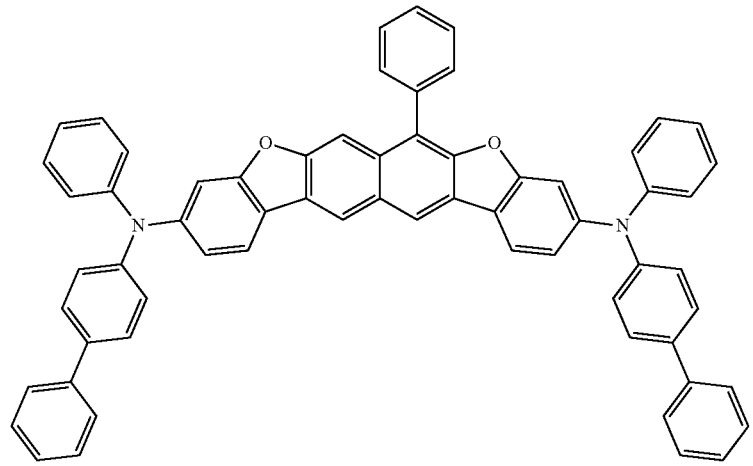
[Chemical Formula 51]
(166)
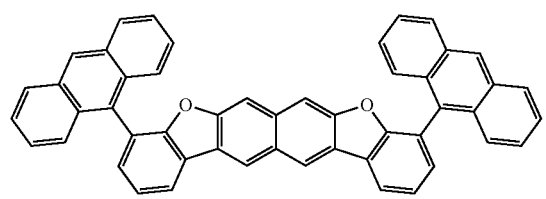
(167)
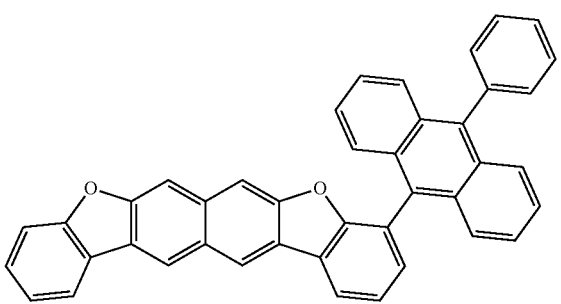
(168)
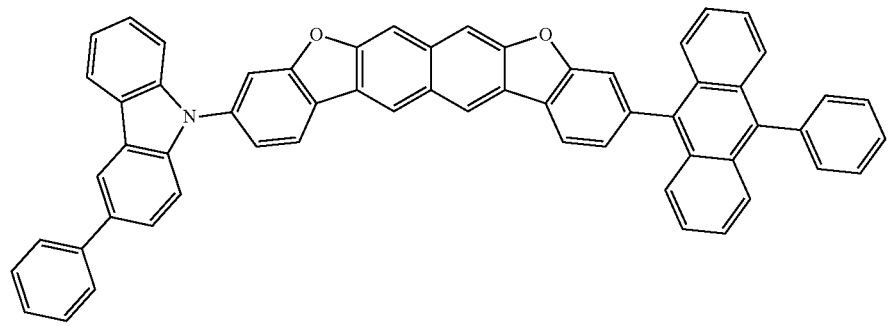
(169)
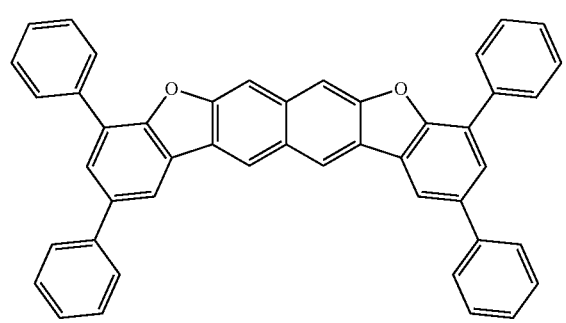

(170)
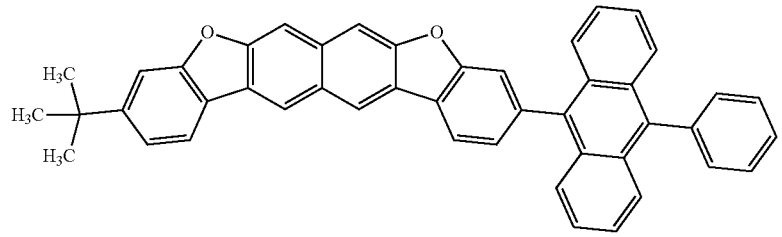
[Chemical Formula 52]
(200)
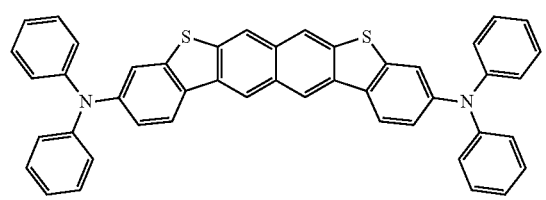
(201)
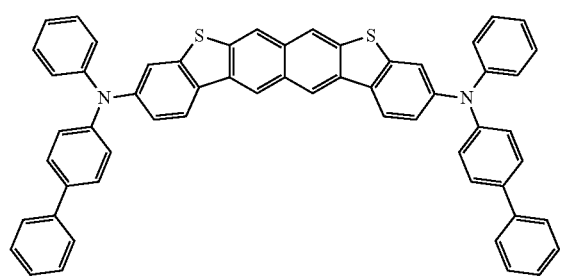
(202)
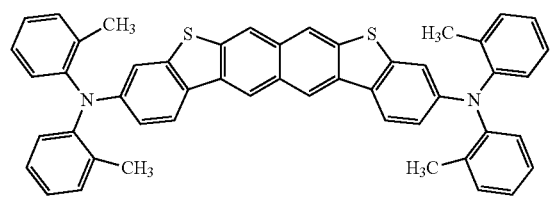
(203)
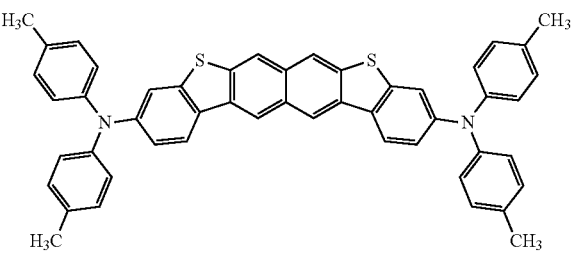
(204)
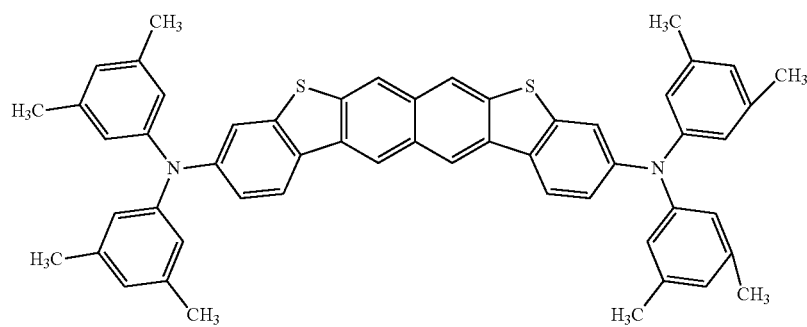
(205)
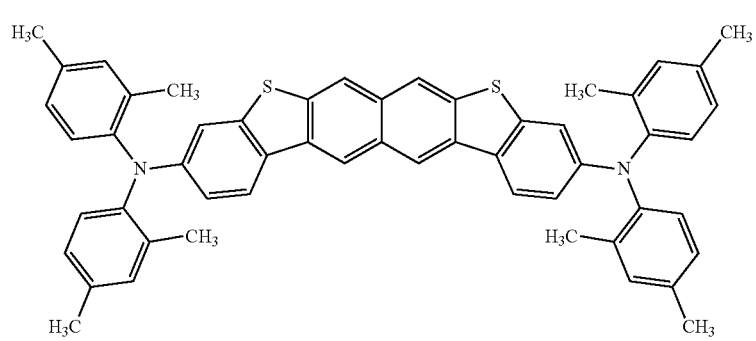

[Chemical Formula 53]
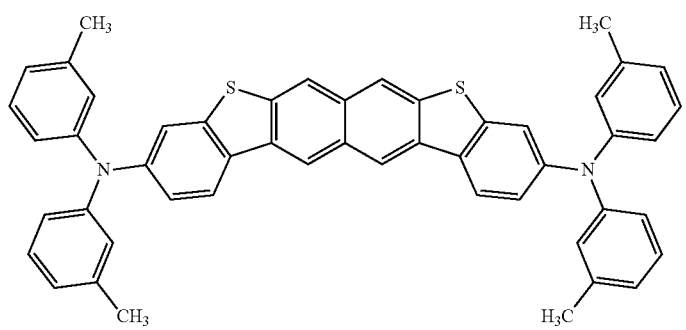
(206)
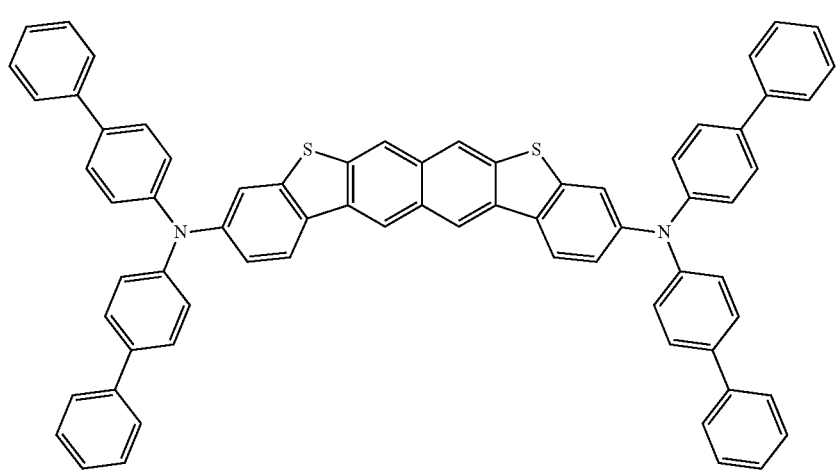
(207)
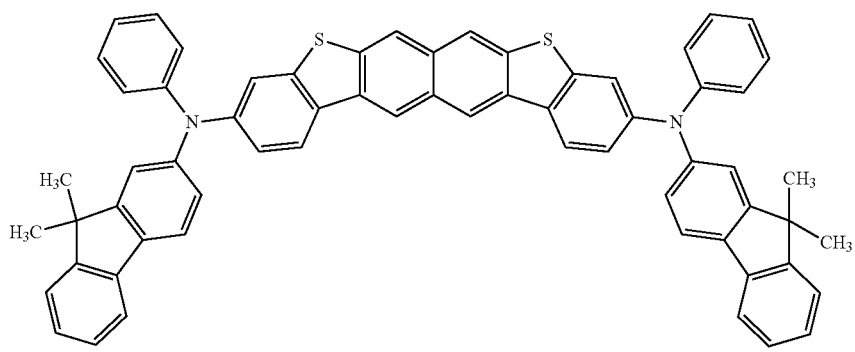
(208)
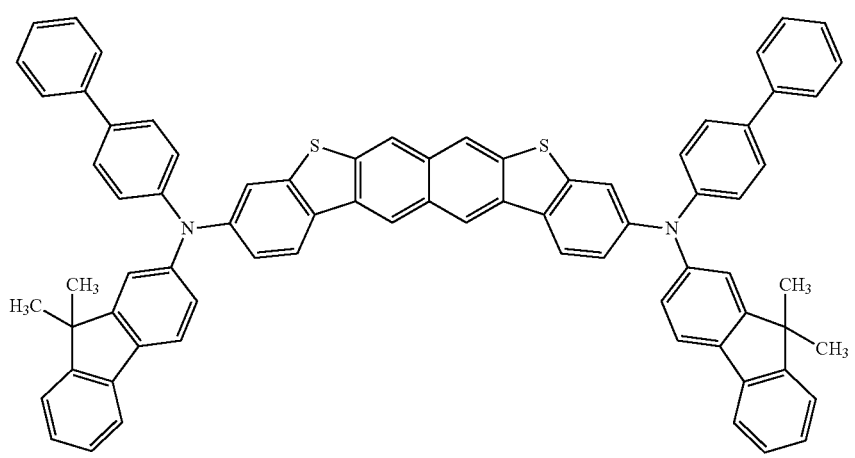
(209)

-continued
(210)
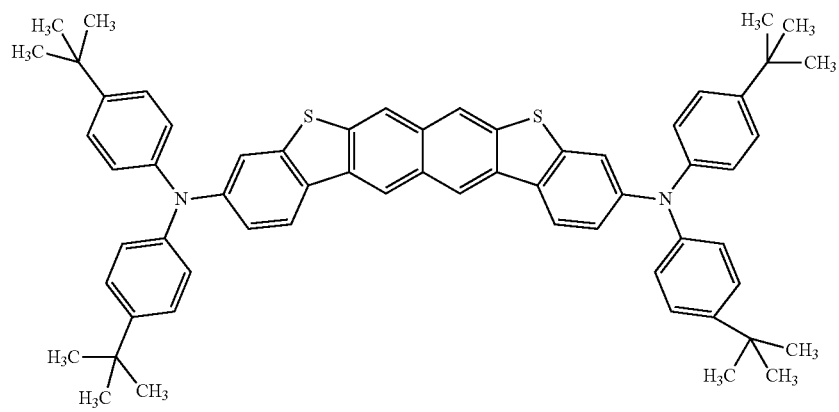
[Chemical Formula 54]
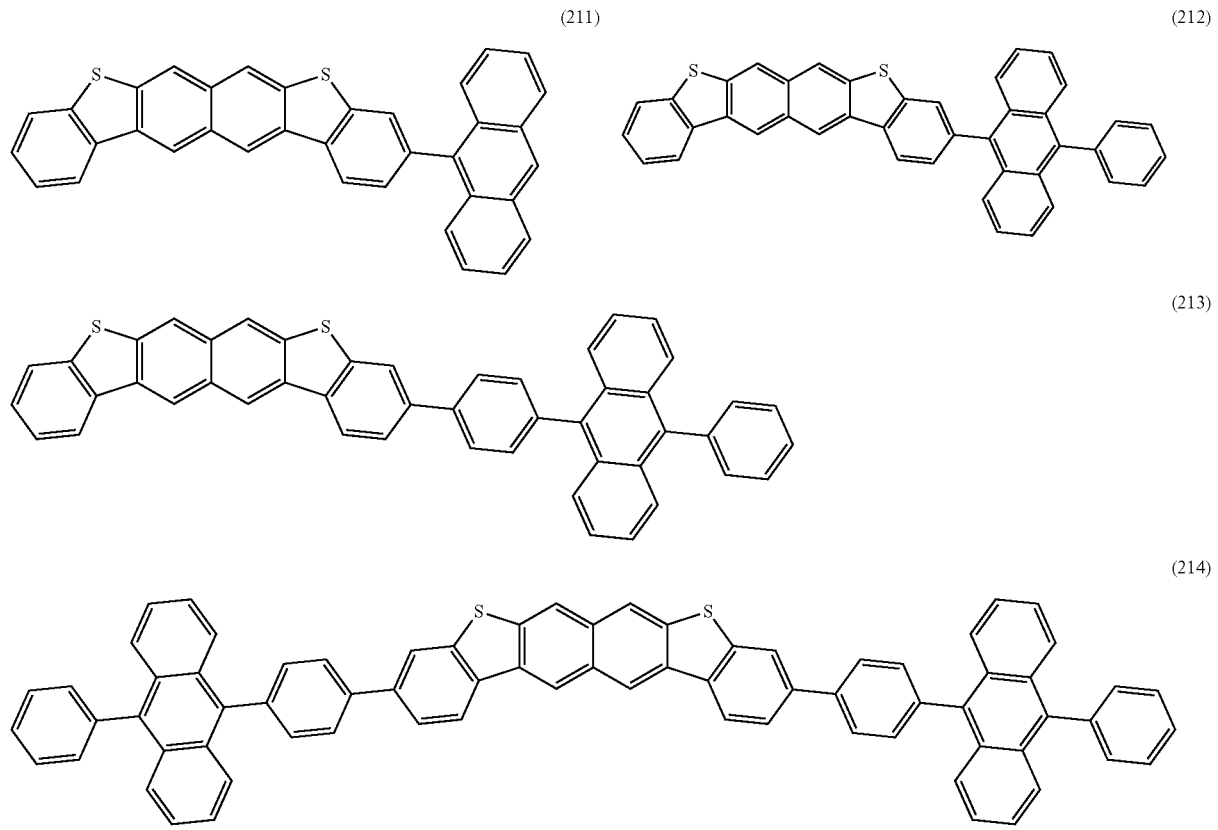
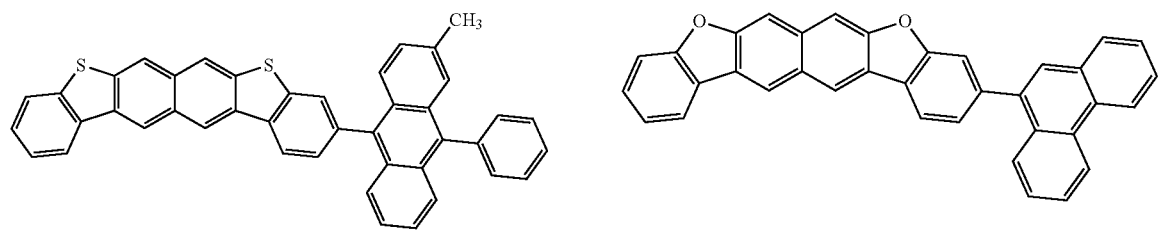

[Chemical Formula 55]
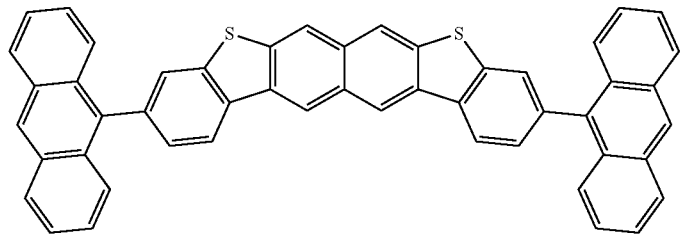
(217)
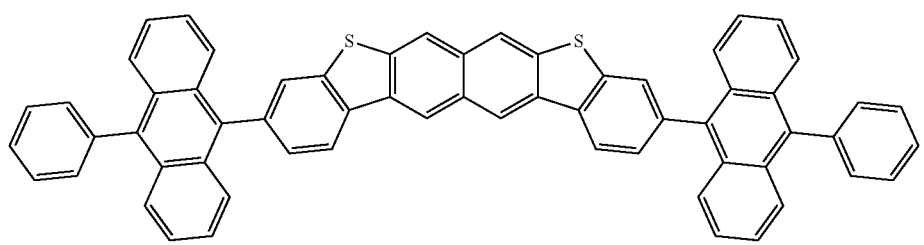
(218)
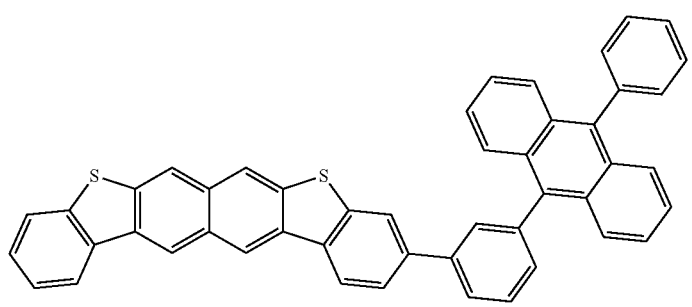
(219)
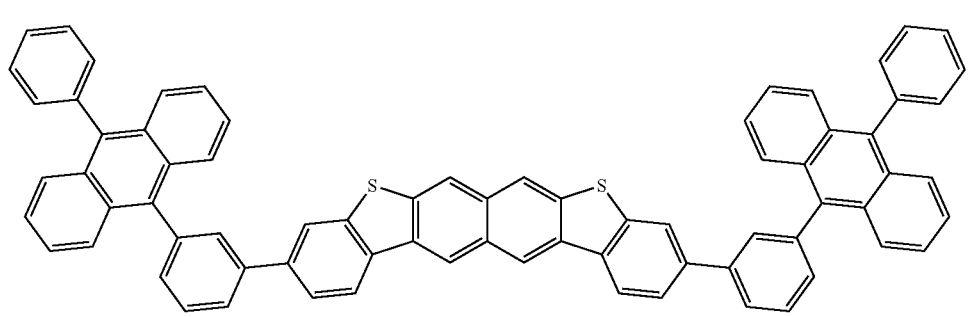
(220)
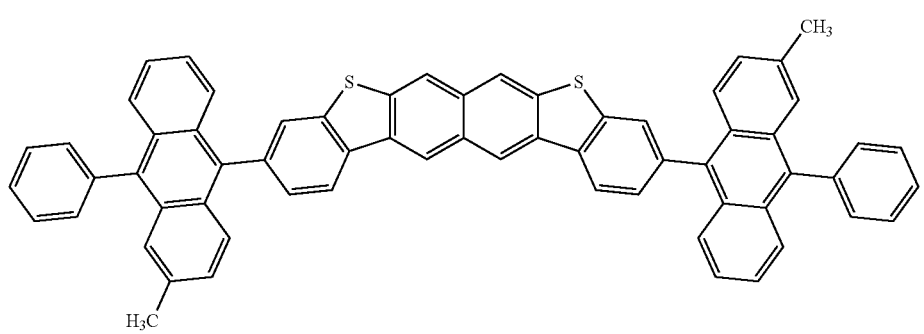
(221)

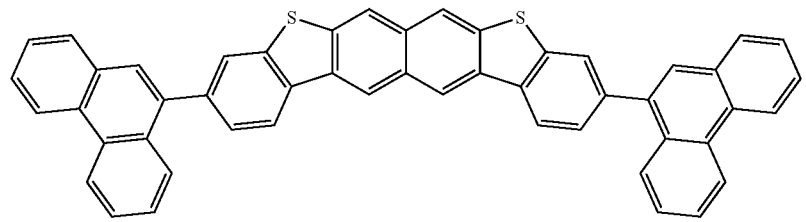
(222)
[Chemical Formula 56]
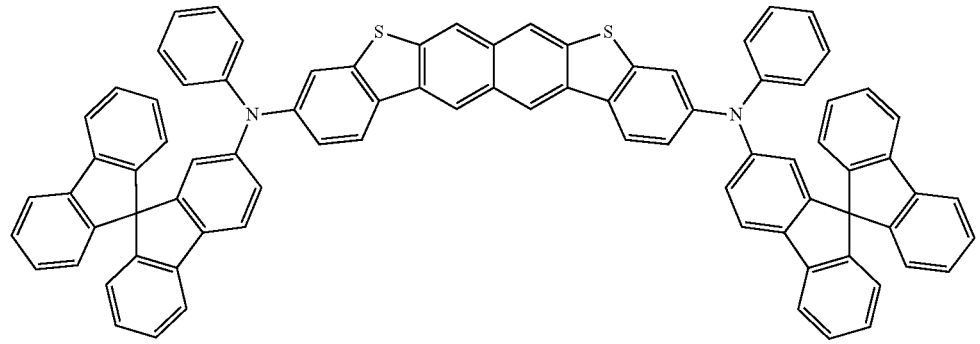
(223)
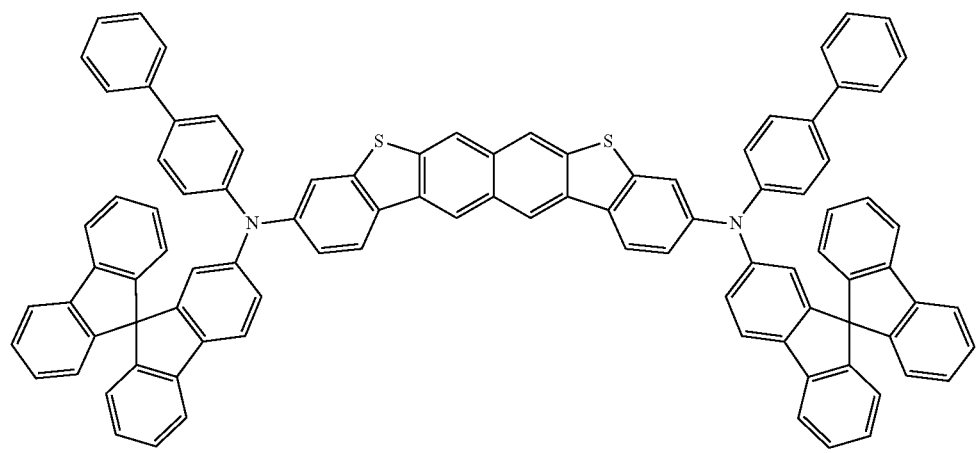
(224)
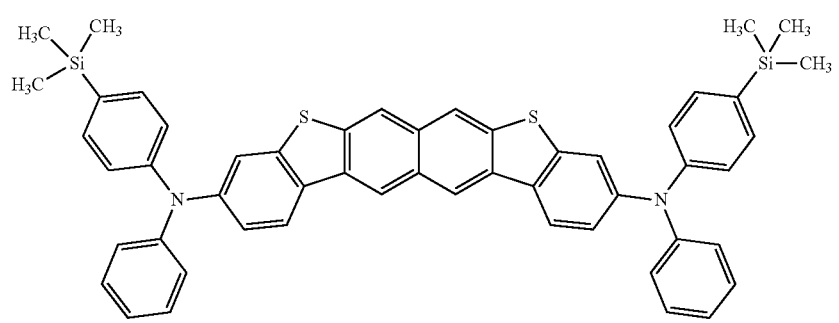
(225)

-continued
(226)
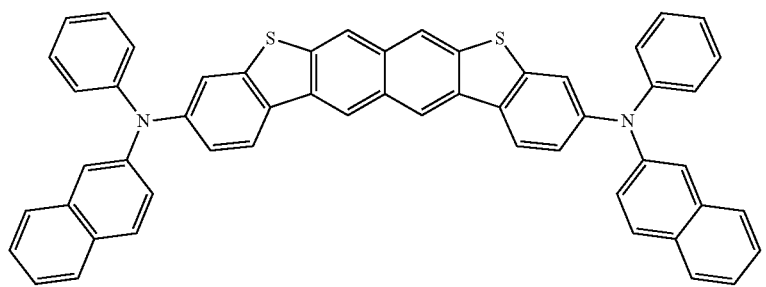
(227)
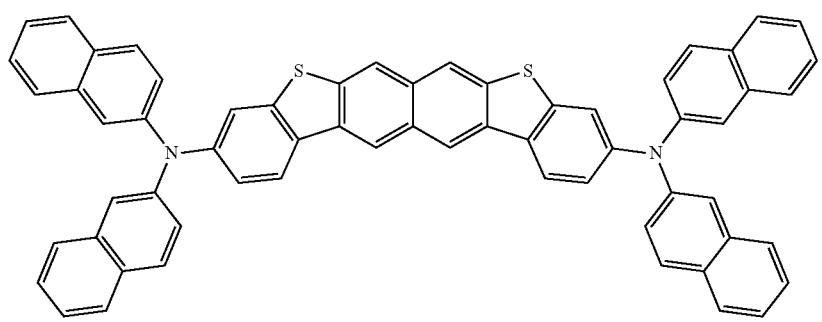
[Chemical Formula 57]
(228)
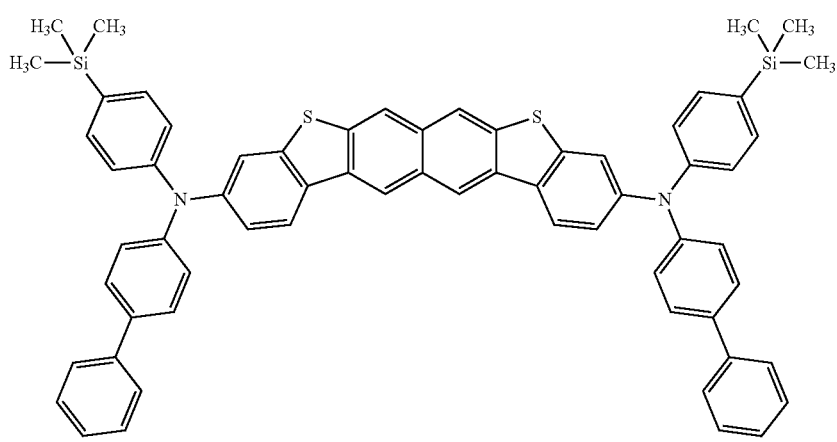
(229)
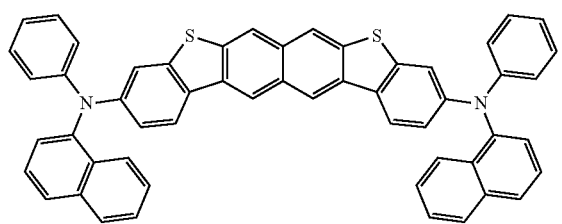
(230)
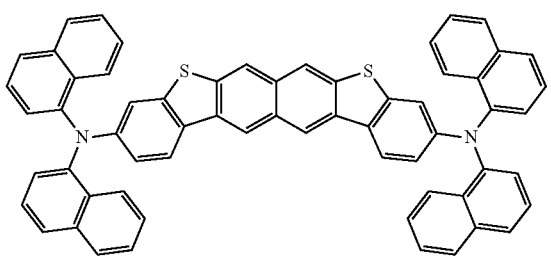

[Chemical Formula 58]
(300)
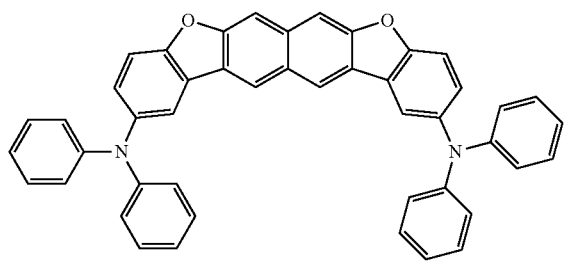
(301)
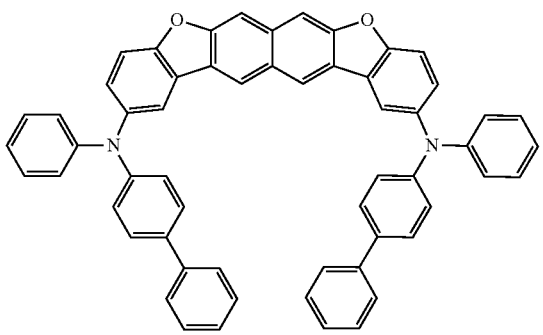
(302)
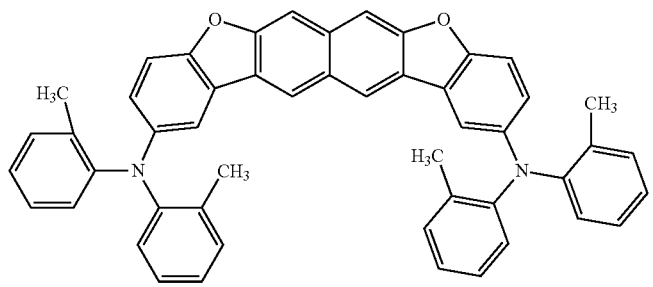
(303)
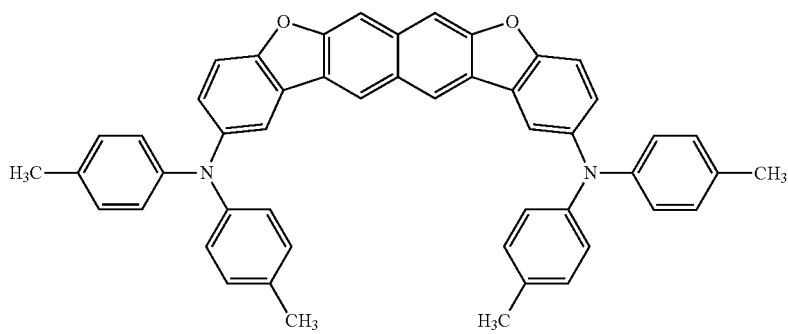
(304)
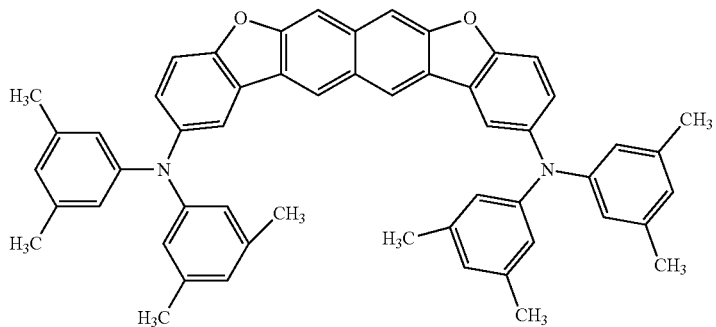

(305)
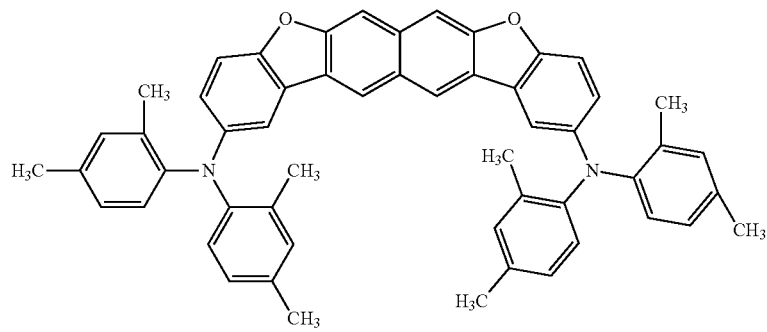
[Chemical Formula 59]
(306)
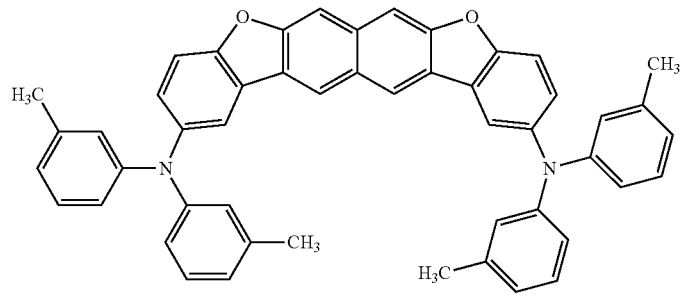
(307)
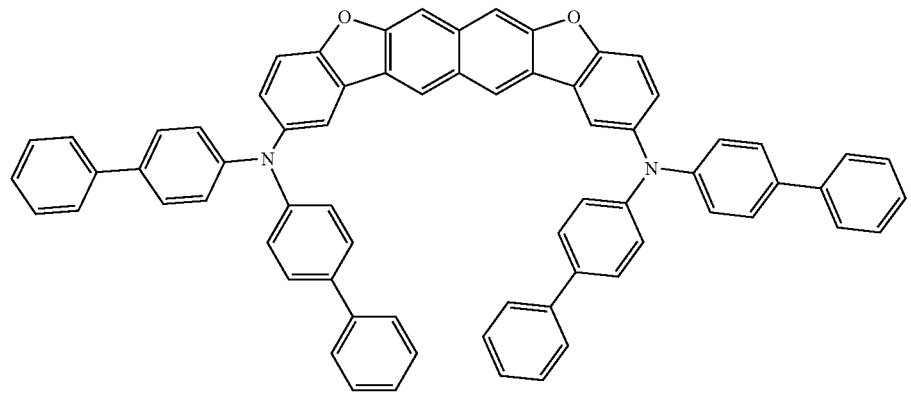
(308)
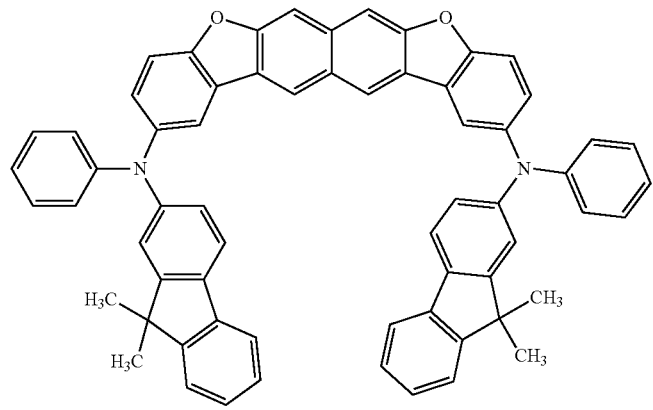

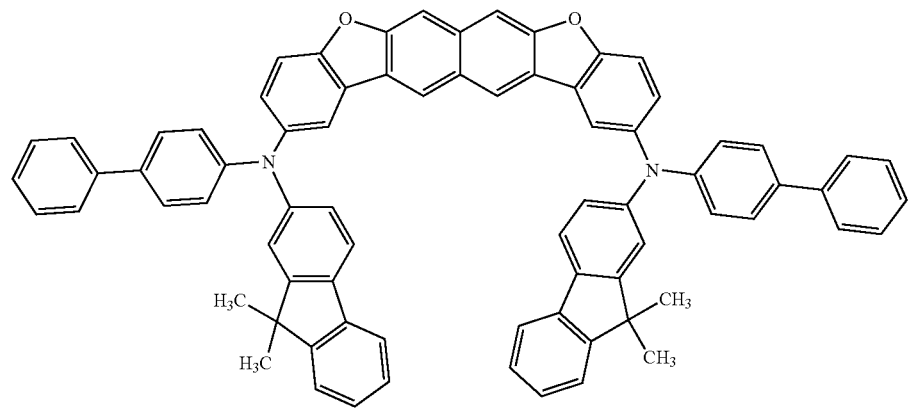
(309)
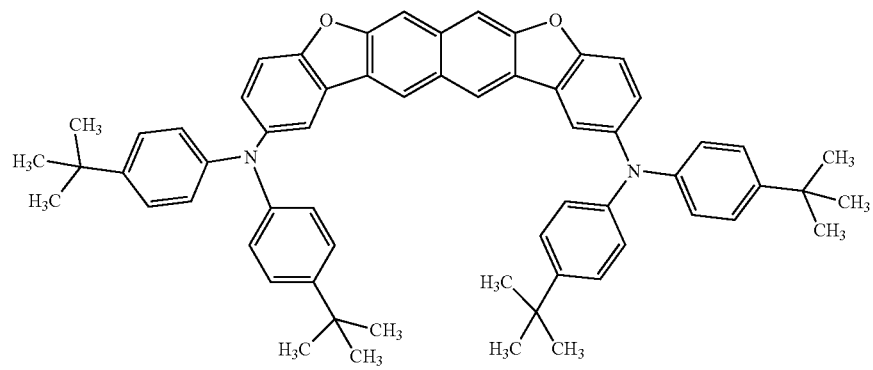
(310)
[Chemical Formula 60]
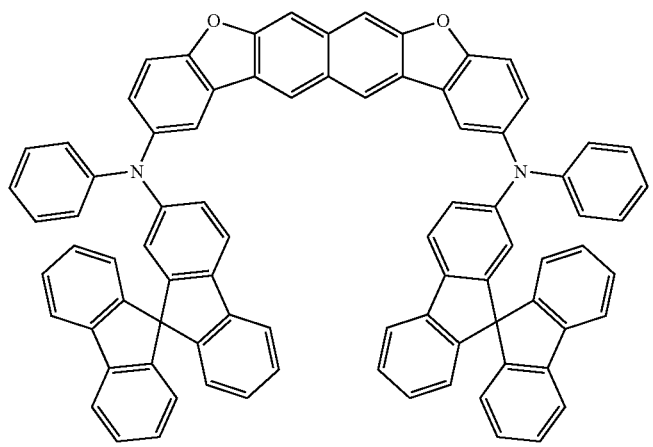
(311)
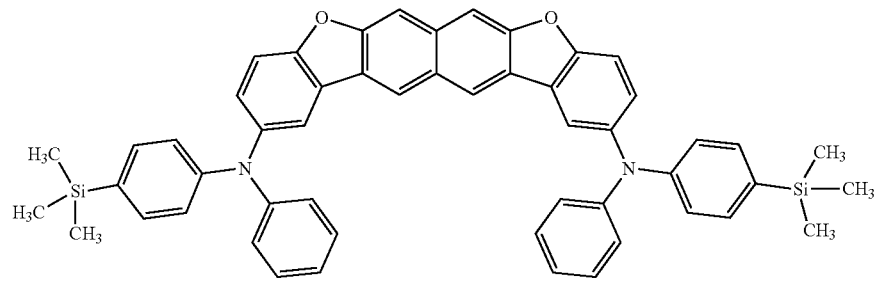
(312)

-continued
(313)
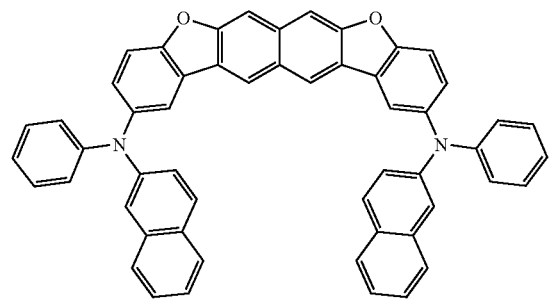
(314)
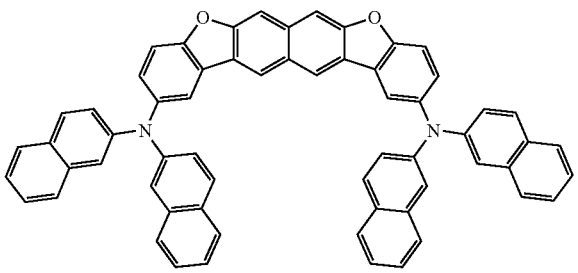
(315)
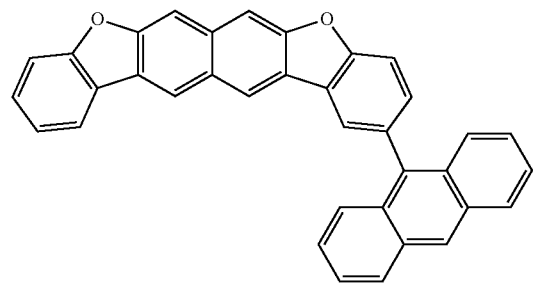
[Chemical Formula 61]
(316)
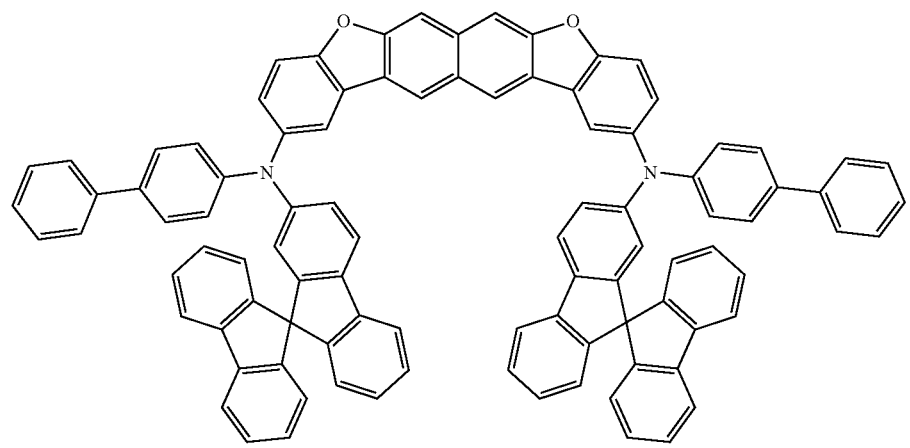
(317)
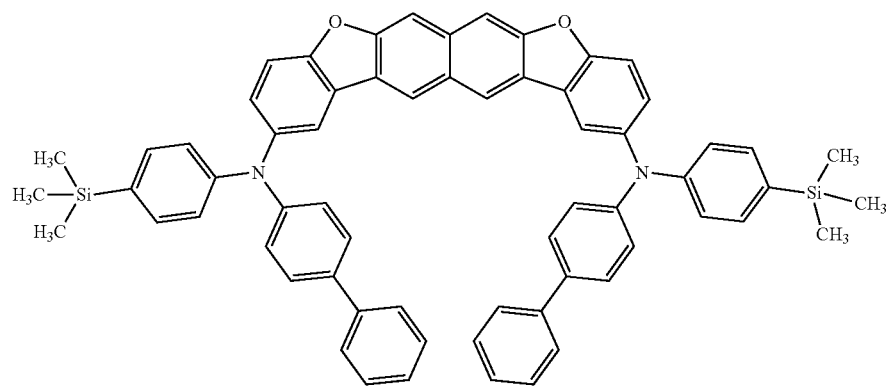

-continued
(318)
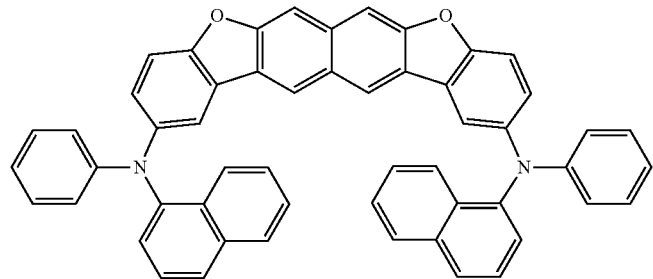
(319)
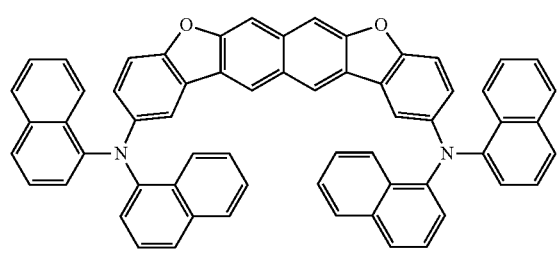
(320)
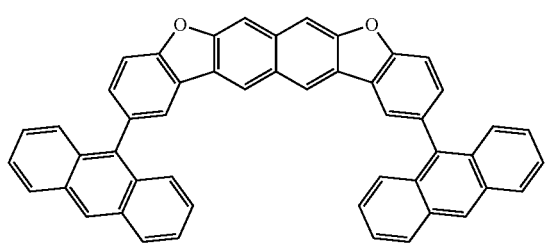
[Chemical Formula 62]
(321)
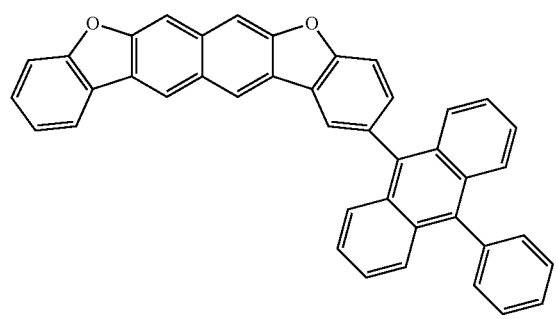
(322)
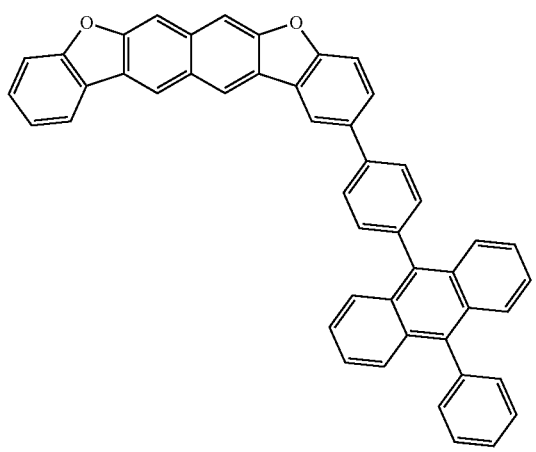
(323)
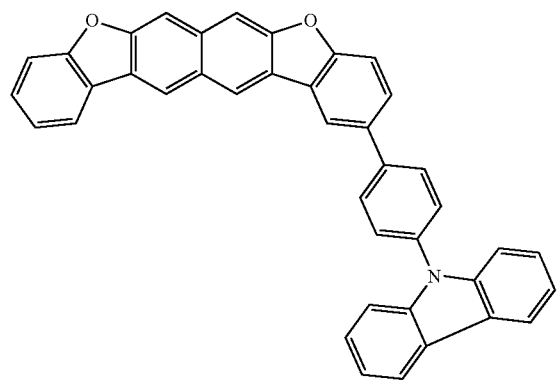
(324)
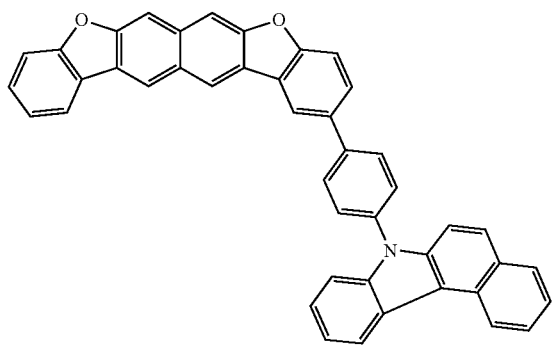

(325)
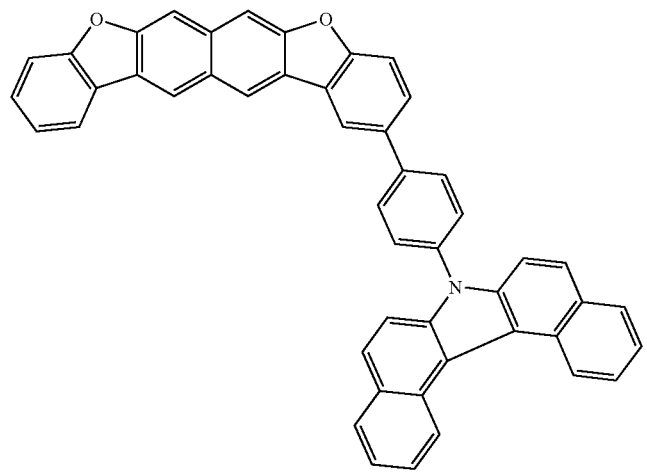
[Chemical Formula 63]
(326)
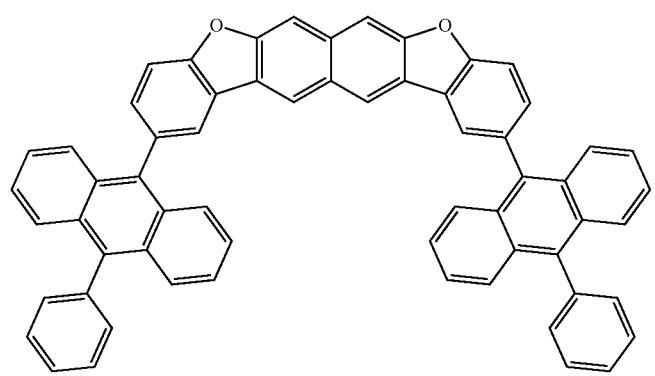
(327)
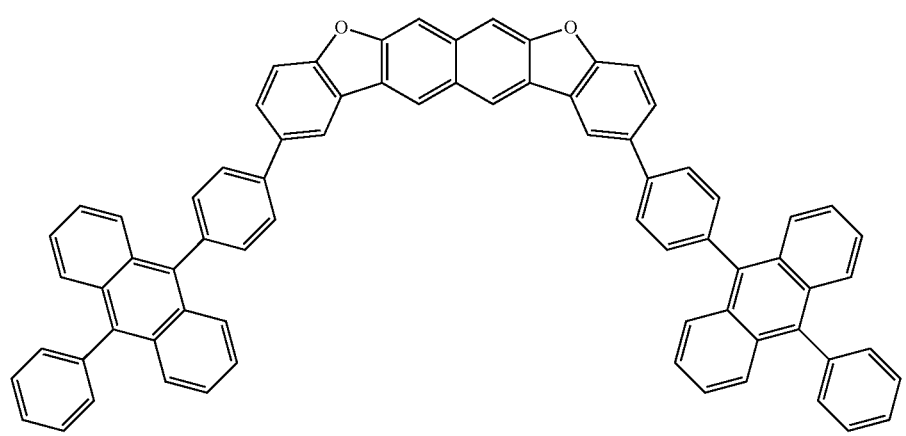
(328) (329)
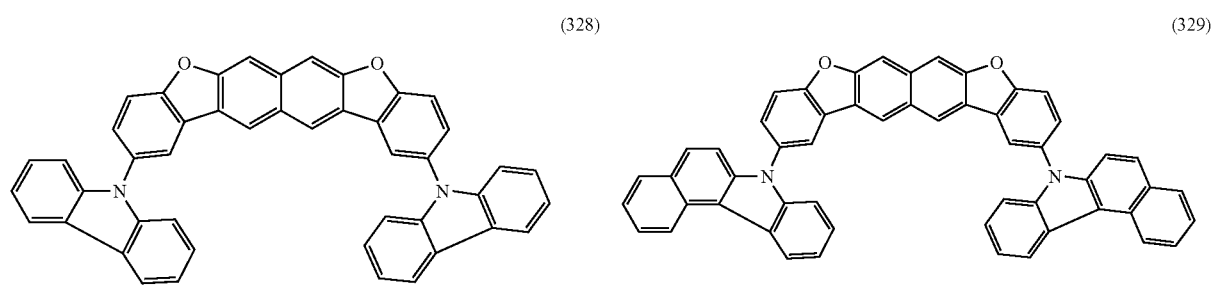

-continued
(330)
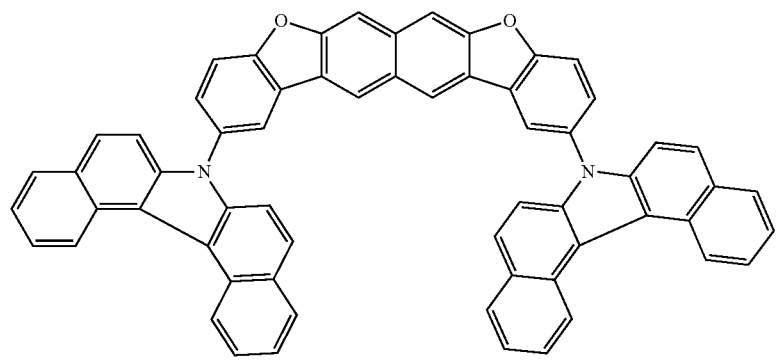
[Chemical Formula 64]
(400) (401)
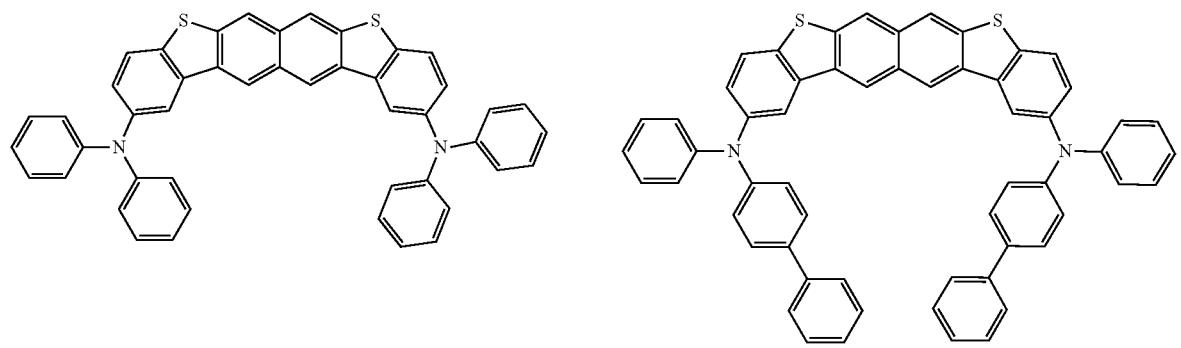
(402)
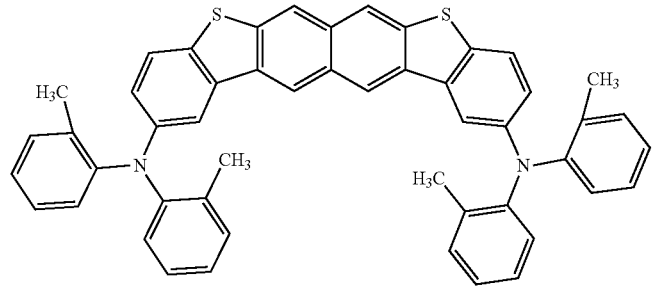
(403)
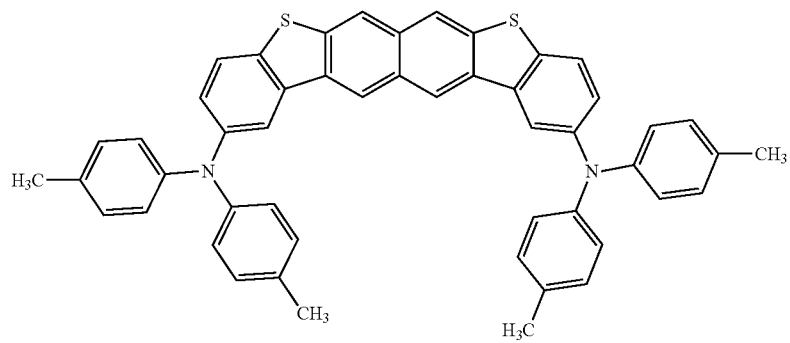

-continued
(404)
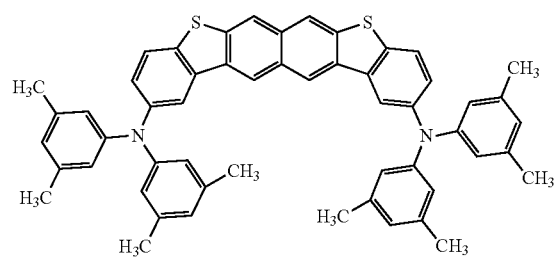
(405)
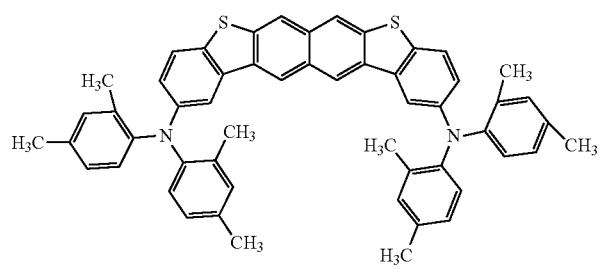
[Chemical Formula 65]
(406)
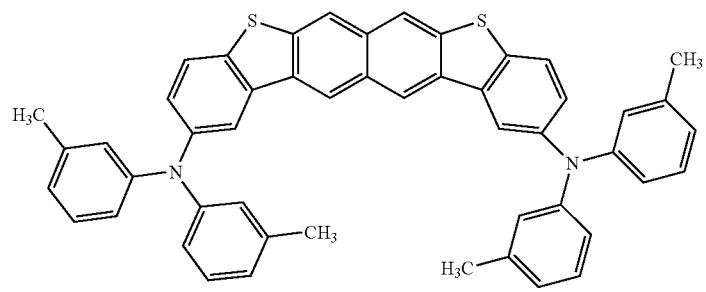
(407)
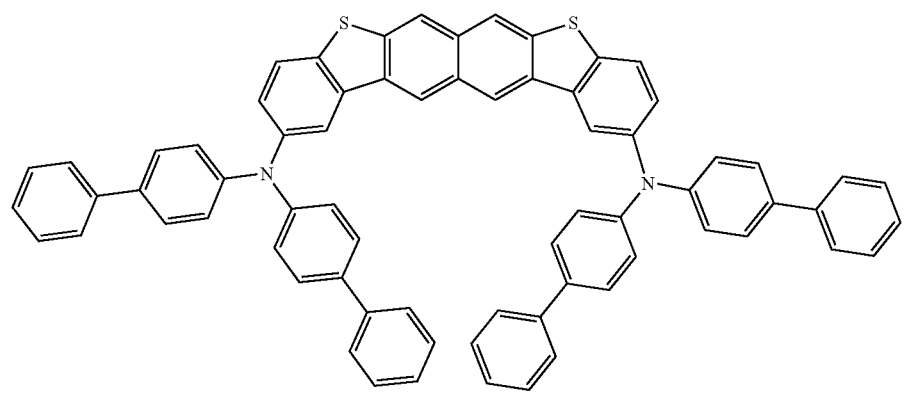
(408)
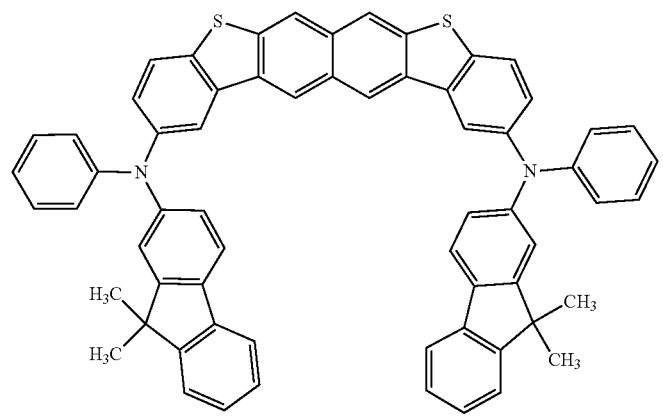

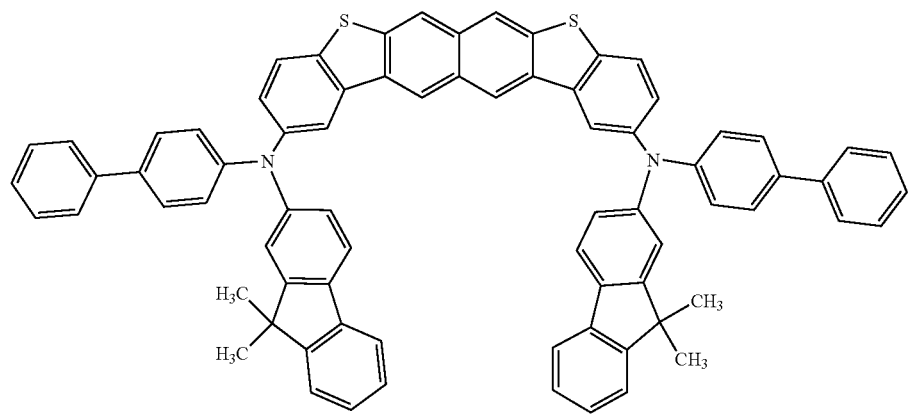
(409)
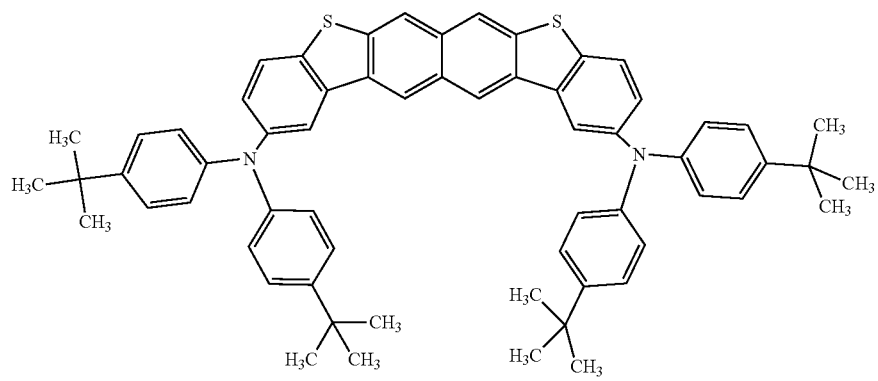
(410)
[Chemical Formula 66]
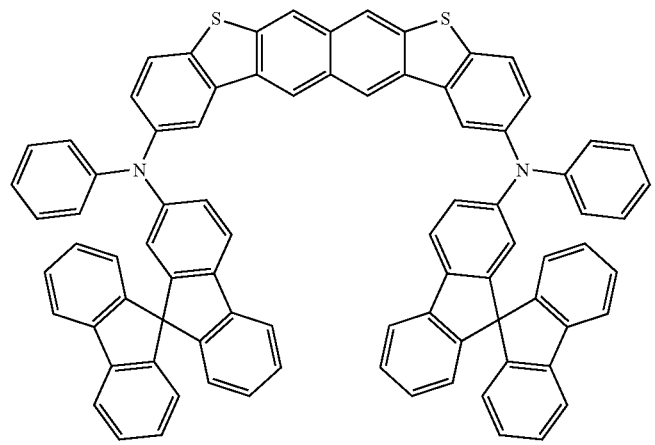
(411)
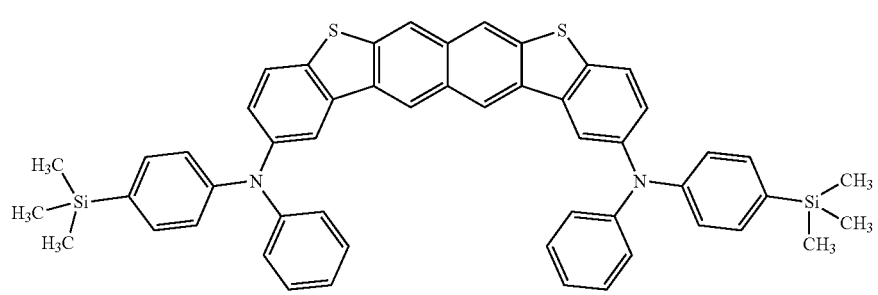
(412)

-continued
(413)
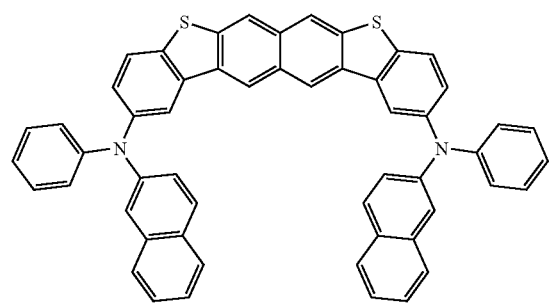
(414)
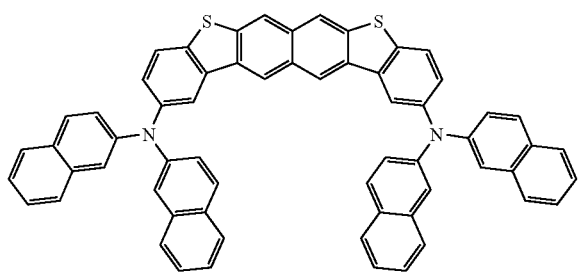
(415)
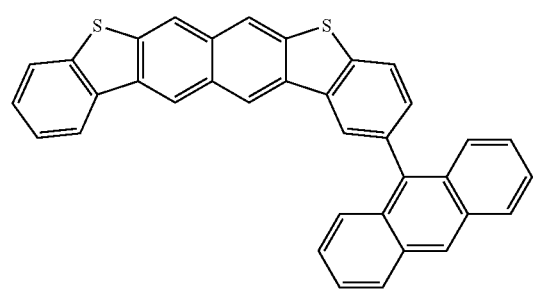
[Chemical Formula 67]
(416)
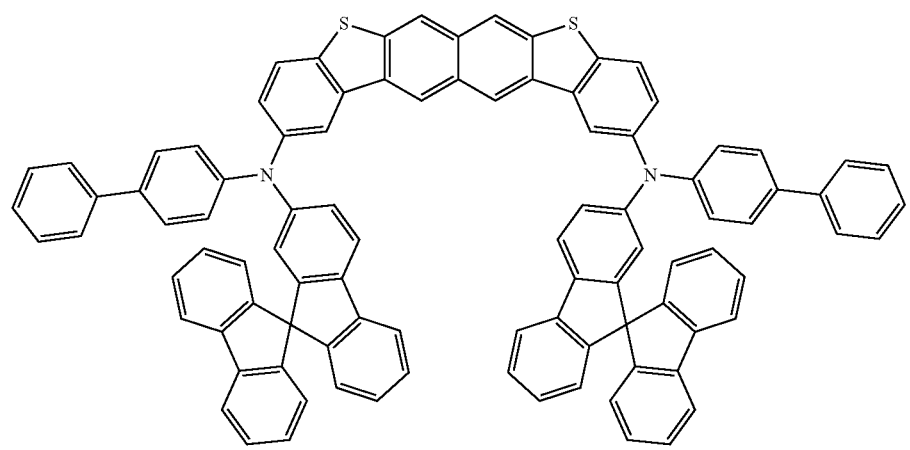
(417)
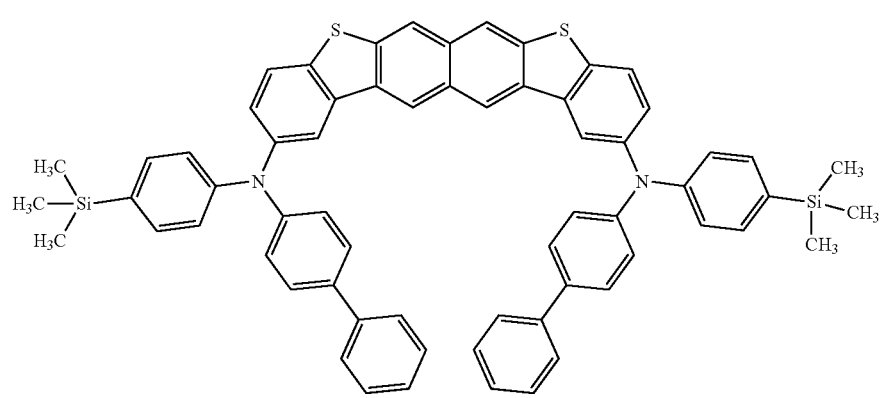

-continued
(418)
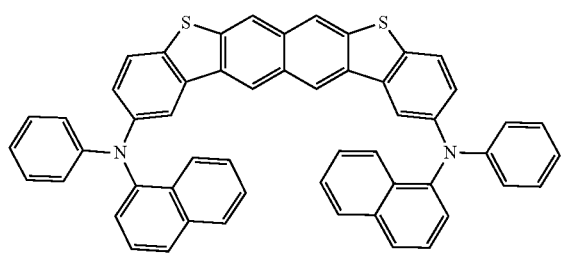
(419)
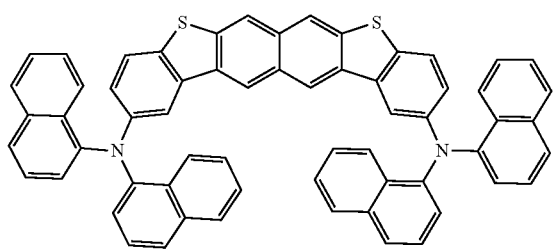
(420)
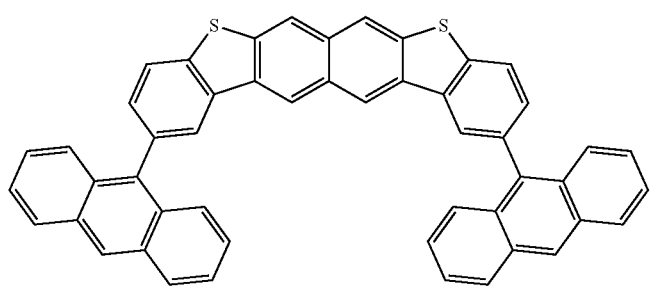
[Chemical Formula 68]
(421)
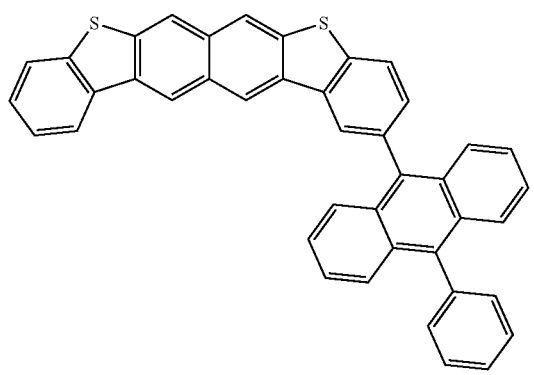
(422)
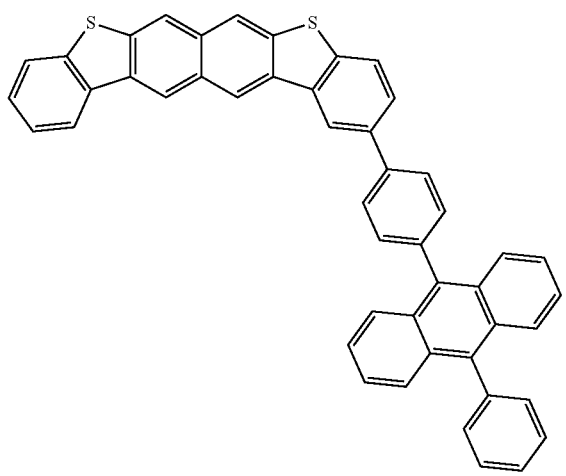
(423)
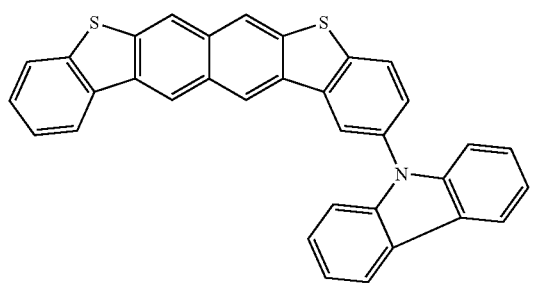
(424)
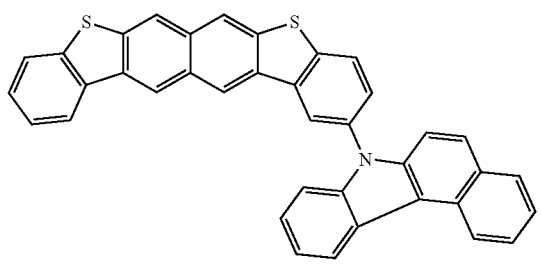

-continued
(425)
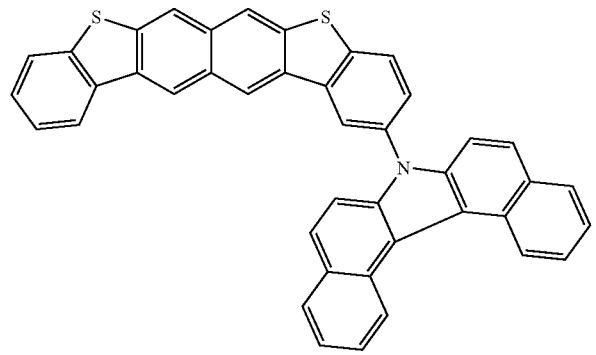
[Chemical Formula 69]
(426)
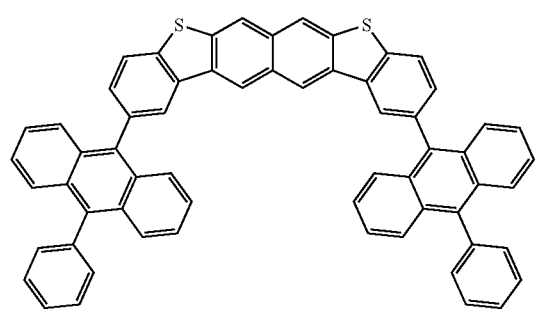
(427)
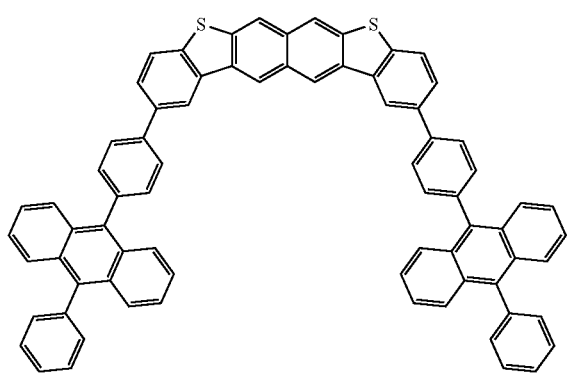
(428)
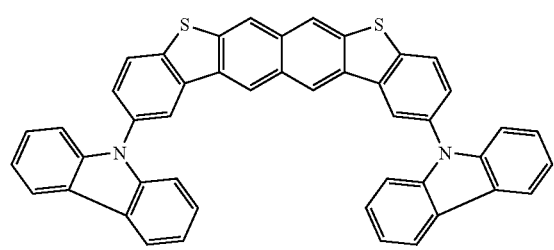
(429)
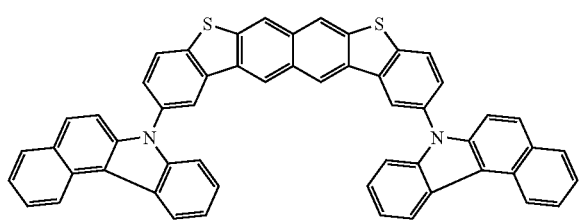
(430)
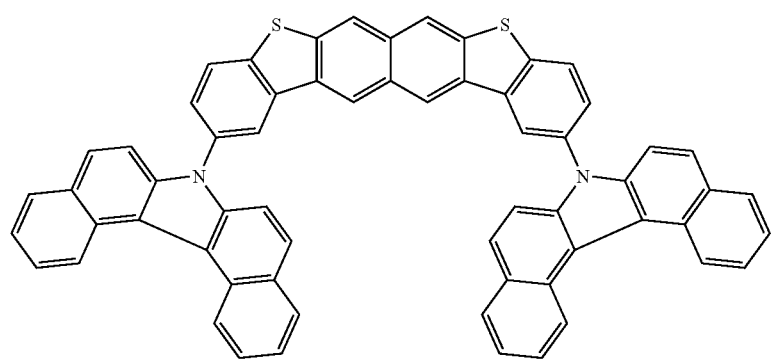

Next, a method for synthesizing the organic compound represented by General Formula (G1) will be described as an example of a synthesis method for the organic compound of one embodiment of the present invention described above. The organic compound represented by General Formula (G1) is shown below.

[Chemical Formula 70]

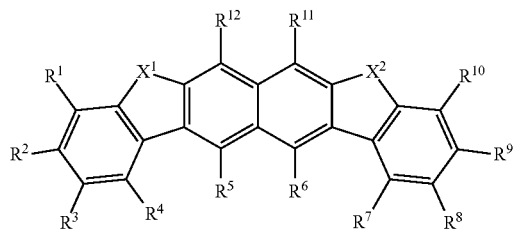

(G1)

Note that the organic compound represented by General Formula (G1) has a molecular weight of less than or equal to 5000. In the formula, $X^1$ and $X^2$ independently represent an oxygen atom or a sulfur atom, and $R^1$ to $R^{12}$ independently represent hydrogen or a substituent. Note that at least one of $R^1$ to $R^{12}$ is preferably a substituent; thus, a synthesis method for an organic compound having a substituent will be described below.

First, a synthesis method for a naphthobisbenzofuran skeleton or a naphthobisbenzothiophene skeleton will be described. A cross coupling reaction of a naphthalene compound (a1), an aryl compound (a2), and an aryl compound (a3) is caused as shown in a scheme shown below, whereby a naphthalene compound represented by (a4) can be obtained. In the scheme, $R^{100}$ and $R^{101}$ each represent an alkyl group such as a methyl group, and $B^1$ and $B^2$ each represent boronic acid or dialkoxyboronic acid, for example. At least one of $Y^3$ and $Y^4$ represents a halogen group such as chlorine or bromine, or a sulfonyl group, for example, and substituents can be introduced into the site(s) of $Y^3$ and/or $Y^4$ later. Note that the sites of $Y^3$ and $Y^4$ are only an example and the sites may be changed; thus, substituents can be introduced into various sites. In the case where one of $Y^3$ and $Y^4$ represents a halogen group such as chlorine or bromine, or a sulfonyl group, the other may represent hydrogen or any other substituent. In the scheme, $Y^1$ and $Y^2$ each represent a halogen group such as bromine or iodine, or a sulfonyl group. Note that $Y^1$ and $Y^2$ each preferably represent a leaving group with high reactivity compared with $Y^3$ and $Y^4$.

[Chemical Formula 71]

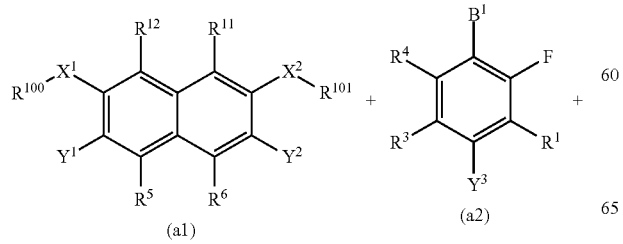

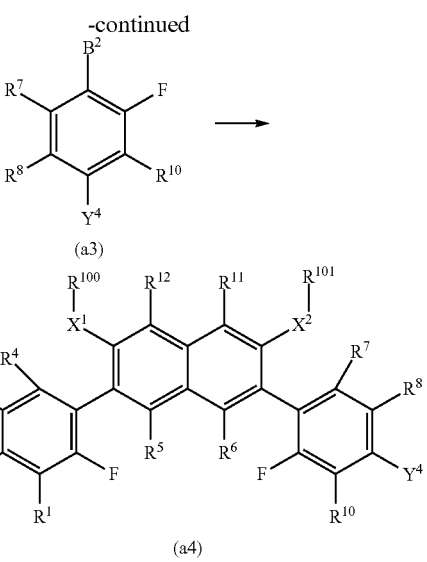

A variety of conditions can be employed to cause the reaction shown in the above scheme. As an example, a synthesis method using a metal catalyst in the presence of a base, such as a Suzuki-Miyaura reaction, can be employed.

Here, the compound (a2) and the compound (a3) are made to react with the compound (a1) at the same time, but in the case where the compound (a2) and the compound (a3) have different substituents, the reaction is preferably performed in such a manner that the compound (a2) and the compound (a1) are made to react with each other and then the product is made to react with the compound (a3). In this case, high yield and high purity of an objective substance can be achieved.

Then, a dealkylation reaction of the naphthalene compound (a4) is caused as in a scheme shown below, whereby a naphthalene compound represented by (a5) can be obtained.

[Chemical Formula 72]

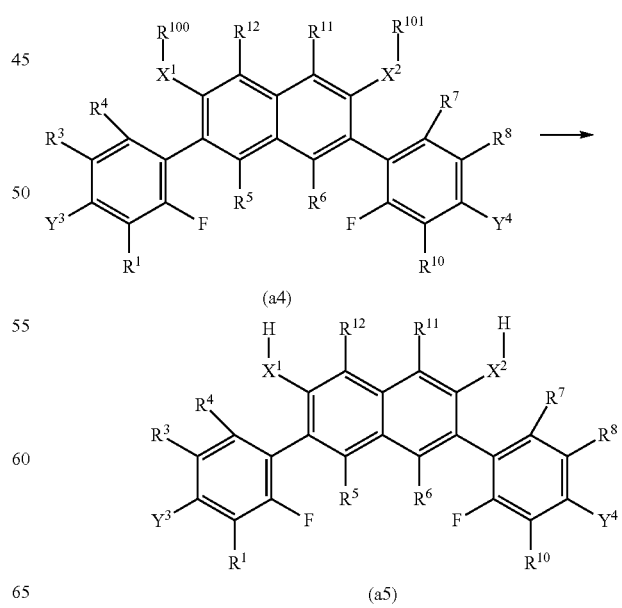

A variety of conditions can be employed to cause this reaction; for example, Lewis acid such as boron tribromide is used in a solvent such as dichloromethane.

After that, as shown in the following scheme, a halogenated naphtho[2,3-b;7,6-b']bisbenzofuran compound or halogenated naphtho[2,3-b;7,6-b']bisbenzothiophene compound represented by (a6) can be obtained from the naphthalene compound (a5).

[Chemical Formula 73]

(a5)

(a6)

A variety of conditions can be employed to cause this reaction; for example, the compound (a5) is dissolved in N-methylpyrrolidone (abbreviation: NMP), dimethyl sulfoxide (abbreviation: DMSO), or the like, potassium carbonate or cesium carbonate is added to the solution, and heating is performed.

Subsequently, a cross coupling reaction of the halogenated naphtho[2,3-b;7,6-b']bisbenzofuran compound or halogenated naphtho[2,3-b;7,6-b']bisbenzothiophene compound (a6), an aryl compound (a7), and an aryl compound (a8), is caused as shown in the following scheme, whereby a naphtho[2,3-b;7,6-b']bisbenzofuran compound or naphtho[2,3-b;7,6-b']bisbenzothiophene compound represented by General Formula (G1) can be obtained. Note that $B^3$ and $B^4$ can be independently boronic acid, dialkoxyboronic acid, aluminum, zirconium, zinc, or tin, for example. When the aryl compound (a7) and the aryl compound (a8) are secondary amines, $B^3$ and $B^4$ represent hydrogen.

[Chemical Formula 74]

(a6)

+

(a7)   (a8)

⟶

(G1)

A variety of conditions can be employed to cause this reaction. As an example, a synthesis method using a metal catalyst in the presence of a base, such as a Suzuki-Miyaura reaction, can be employed. When the aryl compound (a7) and the aryl compound (a8) are secondary amines, Ullmann coupling or the Buchwald-Hartwig reaction can be employed.

Here, the compound (a7) and the compound (a8) are made to react with the compound (a6) at the same time, but in the case where the compound (a7) and the compound (a8) have different substituents, that is, $R^2$ and $R^9$ are different substituents, the reaction is preferably performed in the following two steps: the compound (a7) and the compound (a6) are made to react with each other and then the product is made to react with the compound (a8). Thus, high yield and high purity of an objective substance can be achieved.

The reaction in which $Y^3$ and $Y^4$ of the compound (a6) are substituted by $R^2$ of the compound (a7) and $R^9$ of the compound (a8), respectively, is shown here. To change the sites or number of substituents to be introduced, raw materials in which a halogen group or a sulfonyl group is introduced into a substitution site (sites) of the compound (a2) and/or the compound (a3) are used.

Thus, the compound (a6) is a raw material that is valuable for synthesizing the organic compound represented by General Formula (G1). Similarly, the compound (a5) and the compound (a4) are also valuable raw materials.

At least one of $Y^3$ and $Y^4$ of the compound (a6) represents a halogen group such as chlorine or bromine, or a sulfonyl group, and a substituent can be introduced into the site of $Y^3$ and/or $Y^4$ later. Note that the sites of $Y^3$ and $Y^4$ are only an example and the sites may be changed to any of $R^1$, $R^3$ to $R^8$, and $R^{10}$ to $R^{12}$; thus, substituents can be introduced into various sites. In the case where one of $Y^3$ and $Y^4$ represents a halogen group such as chlorine or bromine, or a sulfonyl group, the other may represent hydrogen or any other substituent.

That is, the compound (a6) can be represented by General Formula ($G_0$1).

121

[Chemical Formula 75]

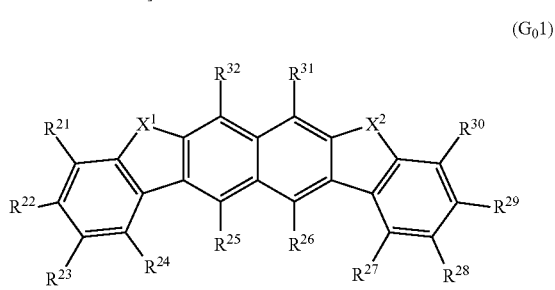

(G₀1)

In General Formula (G₀1), $X^1$ and $X^2$ independently represent an oxygen atom or a sulfur atom. In the formula, one or two of $R^{21}$ to $R^{32}$ represent a halogen group or a sulfonyl group, and the others independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

The organic compound represented by General Formula (G1) preferably has substituents at $R^2$ and $R^9$. That is, the organic compound represented by General Formula (G₀1) preferably has a halogen group and a sulfonyl group at $R^{22}$ and $R^{29}$, and the organic compound represented by General Formula (G₀2) shown below is of greater value.

[Chemical Formula 76]

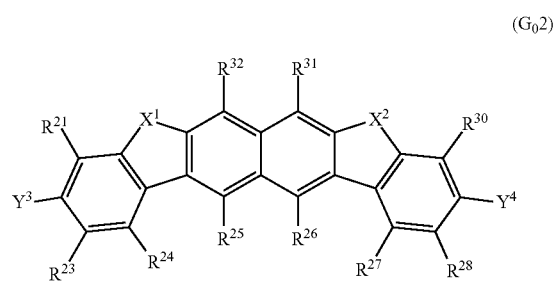

(G₀2)

The organic compound represented by General Formula (G1) preferably has substituents at $R^3$ and $R^8$. That is, the organic compound represented by General Formula (G₀1) preferably has a halogen group and a sulfonyl group at $R^{23}$ and $R^{28}$, and the organic compound represented by General Formula (G₀3) shown below is of greater value.

[Chemical Formula 77]

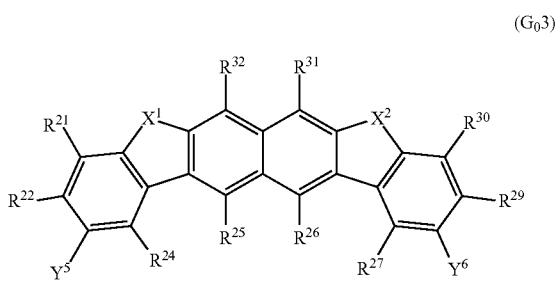

(G₀3)

122

Embodiment 2

An example of a light-emitting element which is one embodiment of the present invention will be described in detail below with reference to FIG. 1A.

In this embodiment, the light-emitting element includes a pair of electrodes (an anode 101 and a cathode 102), and an EL layer 103 provided between the anode 101 and the cathode 102.

The anode 101 is preferably formed using any of metals, alloys, conductive compounds each with a high work function (specifically, a work function of 4.0 eV or more), any of mixtures thereof, or the like. Specific examples are indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like. Films of these conductive metal oxides are usually formed by a sputtering method but may be formed by application of a sol-gel method or the like. In an example of the formation method, indium oxide-zinc oxide can be deposited by a sputtering method using a target in which zinc oxide is added to indium oxide at greater than or equal to 1 wt % and less than or equal to 20 wt %. Furthermore, indium oxide containing tungsten oxide and zinc oxide (IWZO) can be deposited by a sputtering method using a target in which, to indium oxide, tungsten oxide is added at greater than or equal to 0.5 wt % and less than or equal to 5 wt % and zinc oxide is added at greater than or equal to 0.1 wt % and less than or equal to 1 wt %. Other examples include gold (Au), platinum (Pt), nickel (Ni), tungsten (W), chromium (Cr), molybdenum (Mo), iron (Fe), cobalt (Co), copper (Cu), palladium (Pd), aluminum (Al), and nitrides of metal materials (e.g., titanium nitride). Graphene can also be used. In the case where the hole-injection layer 111 includes a composite material including a first substance and a second substance, an electrode material other than the above can be selected regardless of the work function.

The hole-injection layer 111 is formed using the first substance having a relatively excellent acceptor property. Preferably, the hole-injection layer 111 is formed using a composite material of the first substance having an acceptor property and the second substance having a hole-transport property. In the case where the composite material is used as a material of the hole-injection layer 111, a substance having an acceptor property with respect to the second substance is used as the first substance. The first substance draws electrons from the second substance, so that electrons are generated in the first substance. In the second substance from which electrons are drawn, holes are generated. By an electric field, the drawn electrons flow to the anode 101 and the generated holes are injected into a light-emitting layer 113 through a hole-transport layer 112. Thus, a light-emitting element having a low driving voltage can be provided.

The first substance is preferably a transition metal oxide, an oxide of a metal belonging to any of Groups 4 to 8 of the periodic table, an organic compound having an electron-withdrawing group (a halogen group or a cyano group), or the like.

As the transition metal oxide or the oxide of a metal belonging to any of Groups 4 to 8 of the periodic table, vanadium oxide, niobium oxide, tantalum oxide, chromium oxide, molybdenum oxide, tungsten oxide, manganese oxide, rhenium oxide, titanium oxide, ruthenium oxide, zirconium oxide, hafnium oxide, or silver oxide is preferable because of its excellent acceptor property. Molybdenum oxide is particularly preferable because of its high stability in the air, low hygroscopicity, and high handiness.

Examples of the organic compound having an electron-withdrawing group (a halogen group or a cyano group) include 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). A compound in which electron-withdrawing groups are bonded to a condensed aromatic ring having a plurality of hetero atoms, such as HAT-CN, is particularly preferable because it is thermally stable.

The second substance has a hole-transport property and preferably has a hole mobility of $10^{-6}$ cm$^2$/Vs or higher. Examples of a material that can be used as the second substance include aromatic amines such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B); carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, pentacene, coronene, rubrene, perylene, and 2,5,8,11-tetra(tert-butyl) perylene. The aromatic hydrocarbon may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl] anthracene (abbreviation: DPVPA). Alternatively, the following compound can be used: a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino] biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]-fluoren-2-amine (abbreviation: PCBAF), or N-phenyl-N-[4-(9-phenyl-9H-carbazol-3-yl)phenyl]-spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl] dibenzothiophene (abbreviation: DBTFLP-III), or 4-[4-(9-phenyl-9H-fluoren-9-yl)phenyl]-6-phenyldibenzothiophene (abbreviation: DBTFLP-IV); or a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds are highly reliable, have high hole-transport properties, and contribute to a reduction in drive voltage.

The organic compound of one embodiment of the present invention is also a substance having a hole-transport property and thus can be used as the second substance. Particularly preferred is the organic compound having a diarylamino group, an electron-rich heterocyclic group, or an aromatic hydrocarbon group as a substituent.

A wet process can be used to form the hole-injection layer 111. In this case, a conductive high molecular compound to which an acid is added, such as a poly(ethylenedioxythiophene)/poly(styrenesulfonic acid) aqueous solution (PEDOT/PSS), a polyaniline/camphor sulfonic acid aqueous solution (PANI/CSA), PTPDES, Et-PTPDEK, PPBA, or polyaniline/poly(styrenesulfonic acid) (PANI/PSS), can be used, for example.

The hole-transport layer 112 is a layer containing a material having a hole-transport property. Any of the materials for the second substance, which is a substance contained in the hole-injection layer 111, can be used as the material having a hole-transport property. The hole-transport layer 112 can be formed of either a single layer or a plurality of layers. In the case where the hole-transport layer 112 is formed of a plurality of layers, for easy hole injection, the HOMO level of the hole-transport layer 112 preferably becomes deeper stepwise from a layer on the hole-injection layer 111 side to a layer on the light-emitting layer 113 side. Such a structure is highly suitable for a blue fluorescence-emitting element in which a host material in the light-emitting layer 113 has a deep HOMO level.

The structure of the hole-transport layer 112 including a plurality of layers to have a HOMO level which becomes deeper stepwise toward the light-emitting layer 113 is particularly suitable for an element in which the hole-injection layer 111 is formed using an organic acceptor (an organic compound having the above-mentioned electron-withdrawing group (a halogen group or a cyano group)). The use of such a structure allows formation of a highly favorable element with an excellent carrier-injection property and a low drive voltage can be obtained.

The organic compound of one embodiment of the present invention is also a substance having a hole-transport property and thus can be used as the material having a hole-transport property. In particular, the organic compound having a diarylamino group, an electron-rich heterocyclic group, or an aromatic hydrocarbon group as a substituent is preferred.

Note that a wet process can be used to form the hole-transport layer 112. In the case where the hole-transport layer 112 is formed by a wet process, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can be used.

The light-emitting layer 113 may contain any light-emitting substance such as a fluorescent substance, a phosphorescent substance, a substance that emits thermally activated delayed fluorescence (TADF), quantum dots, or a metal halide perovskite; however, the light-emitting layer 113 preferably contains the organic compound of one embodiment of the present invention described in Embodiment 1, as a light-emitting substance. The use of the organic compound of one embodiment of the present invention as a light-emitting substance facilitates formation of a light-emitting element having high efficiency and significantly high chromaticity.

Furthermore, the light-emitting layer 113 may be a single layer or include a plurality of layers. In the case where a light-emitting layer including a plurality of layers is formed, a layer containing a phosphorescent substance and a layer containing a fluorescent substance may be stacked. In this case, an exciplex described later is preferably utilized in the layer containing a phosphorescent substance.

The organic compound of one embodiment of the present invention is a substance having a favorable quantum yield and thus can be used as a light-emitting substance. In particular, a substance having a naphtho[2,3-b;7,6-b']bisbenzofuran skeleton or a naphtho[2,3-b;7,6-b']bisbenzothiophene skeleton is easy to design as a material that exhibits light with a short wavelength, such as blue light. Furthermore, the organic compound has a high singlet excitation level and is also suitable for a fluorescent host material.

Examples of a fluorescent substance that can be used include, but are not limited to, the following substances: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine, N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). In particular, condensed aromatic diamine compounds typified by pyrenediamine compounds such as 1,6FLPAPrn and 1,6mMemFLPAPrn are preferable because of their high hole-trapping properties, high emission efficiency, and high reliability.

Examples of a material that can be used as a phosphorescent substance in the light-emitting layer 113 are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex a having imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C']iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation:

FIr(acac)). These compounds emit blue phosphorescence having an emission peak at 440 nm to 520 nm.

Other examples include an organometallic iridium complex having pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$(Phen)]). These compounds mainly emit green phosphorescence having an emission peak at 500 nm to 600 nm. Note that an organometallic iridium complex having a pyrimidine skeleton has distinctively high reliability and emission efficiency and thus is especially preferable.

Other examples include an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato) (dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); an organometallic iridium complex having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); a platinum complex such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). These compounds emit red phosphorescence having an emission peak at 600 nm to 700 nm. Furthermore, an organometallic iridium complex having a pyrazine skeleton can emit red light with high chromaticity.

Besides the above phosphorescent compounds, a variety of phosphorescent materials may be selected and used.

Examples of the TADF material include a fullerene, a derivative thereof, an acridine, a derivative thereof, and an eosin derivative. Furthermore, porphyrin containing a metal such as magnesium (Mg), zinc (Zn), cadmium (Cd), tin (Sn), platinum (Pt), indium (In), or palladium (Pd) can be used. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are represented by the following structural formulae.

[Chemical Formula 78]

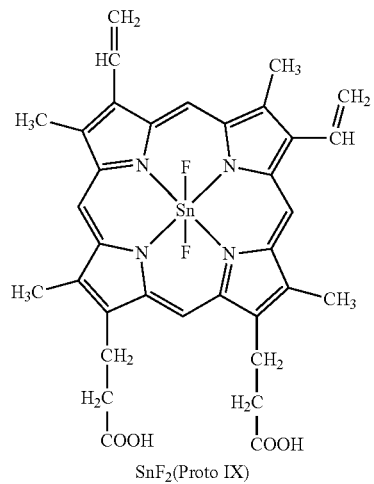

SnF$_2$(Proto IX)

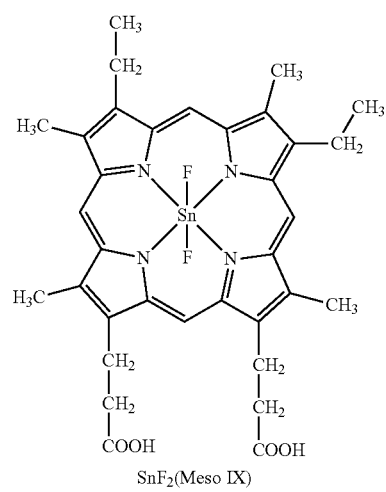

SnF$_2$(Meso IX)

-continued

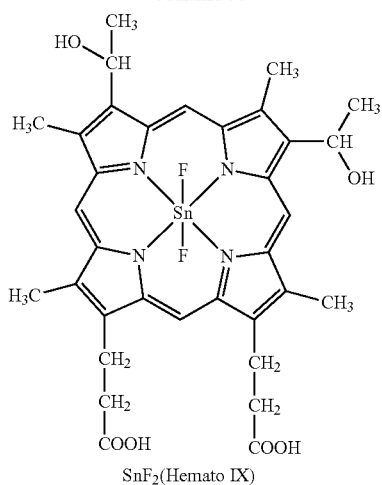

SnF₂(Hemato IX)

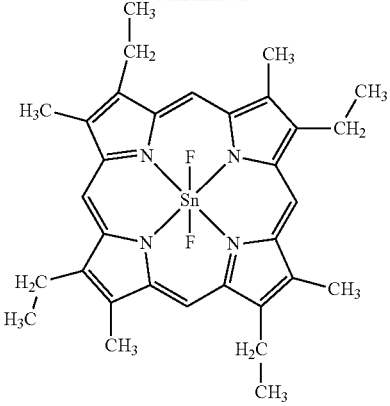

SnF₂(Etio I)

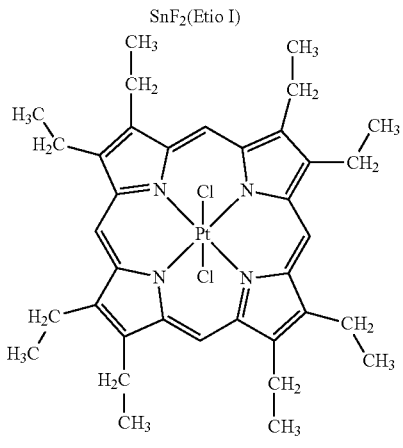

PtCl₂OEP)

SnF₂(Copro III-4Me)

SnF₂(OEP)

Alternatively, a heterocyclic compound having both a π-electron rich heteroaromatic ring and a π-electron deficient heteroaromatic ring, such as 2-(biphenyl-4-yl)-4,6-bis (12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4, 6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA), which are represented by the following structural formulae, can be used. Such a heterocyclic compound is preferable because of having excellent electron-transport and hole-transport properties owing to a π-electron rich heteroaromatic ring and a π-electron deficient heteroaromatic ring. Note that a substance in which the π-electron rich heteroaromatic ring is directly bonded to the π-electron deficient heteroaromatic ring is particularly preferable because the donor property of the π-electron rich heteroaromatic ring and the acceptor property of the π-electron deficient heteroaromatic ring are both improved and the energy difference between the S₁ level and the T₁ level becomes small, so that thermally activated delayed fluorescence can be obtained with high efficiency. Note that an aromatic ring to which an electron-withdrawing group such as a cyano group is bonded may be used instead of the π-electron deficient heteroaromatic ring.
[Chemical Formula 79]
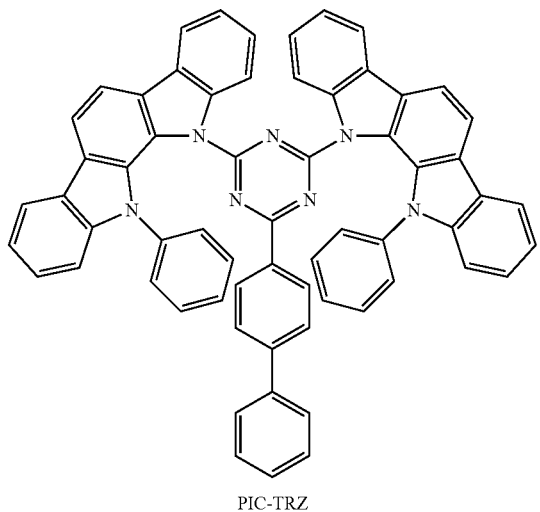
PIC-TRZ
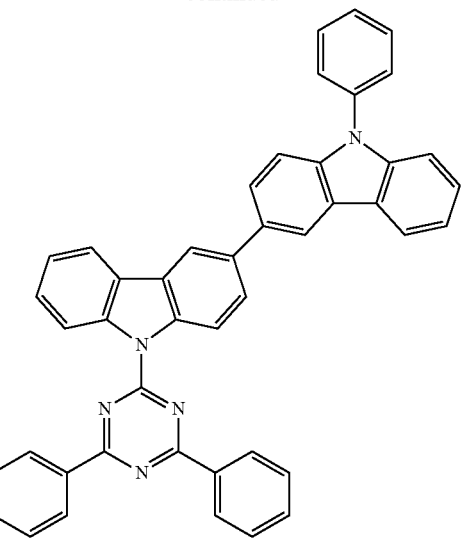
PCCzTzn
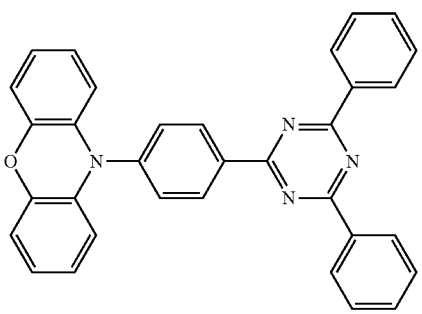
PXZ-TRZ
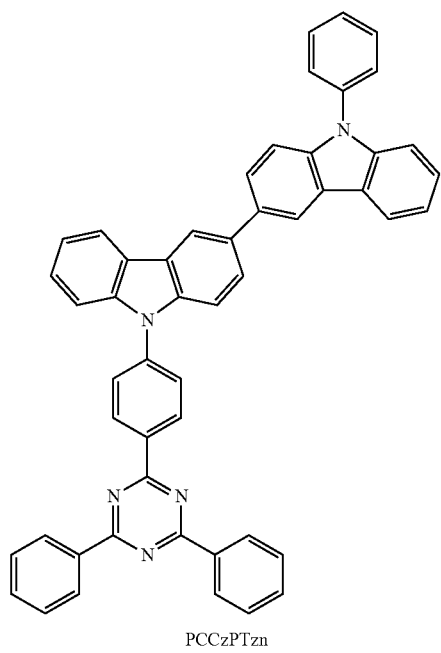
PCCzPTzn
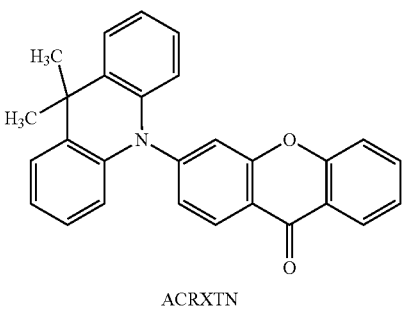
PPZ-3TPT
ACRXTN

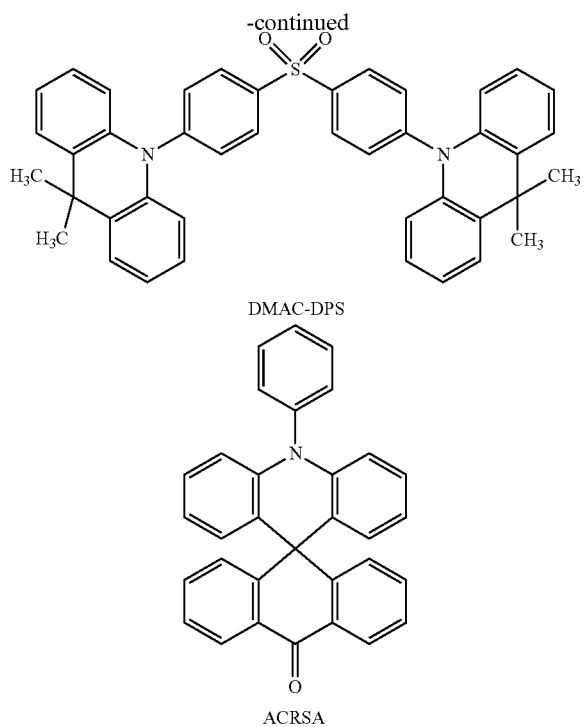

DMAC-DPS

ACRSA

Examples of the quantum dot include nano-sized particles of a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, semiconductor clusters, metal halide perovskites, and the like.

Specific examples include, but are not limited to, cadmium selenide (CdSe), cadmium sulfide (CdS), cadmium telluride (CdTe), zinc selenide (ZnSe), zinc oxide (ZnO), zinc sulfide (ZnS), zinc telluride (ZnTe), mercury sulfide (HgS), mercury selenide (HgSe), mercury telluride (HgTe), indium arsenide (InAs), indium phosphide (InP), gallium arsenide (GaAs), gallium phosphide (GaP), indium nitride (InN), gallium nitride (GaN), indium antimonide (InSb), gallium antimonide (GaSb), aluminum phosphide (AlP), aluminum arsenide (AlAs), aluminum antimonide (AlSb), lead(II) selenide (PbSe), lead(II) telluride (PbTe), lead(II) sulfide (PbS), indium selenide ($In_2Se_3$), indium telluride ($In_2Te_3$), indium sulfide ($In_2S_3$), gallium selenide ($Ga_2Se_3$), arsenic(III) sulfide ($As_2S_3$), arsenic(III) selenide ($As_2Se_3$), arsenic(III) telluride ($As_2Te_3$), antimony(III) sulfide ($Sb_2S_3$), antimony(III) selenide ($Sb_2Se_3$), antimony(III) telluride ($Sb_2Te_3$), bismuth(III) sulfide ($Bi_2S_3$), bismuth(III) selenide ($Bi_2Se_3$), bismuth(III) telluride ($Bi_2Te_3$), silicon (Si), silicon carbide (SiC), germanium (Ge), tin (Sn), selenium (Se), tellurium (Te), boron (B), carbon (C), phosphorus (P), boron nitride (BN), boron phosphide (BP), boron arsenide (BAs), aluminum nitride (AlN), aluminum sulfide ($Al_2S_3$), barium sulfide (BaS), barium selenide (BaSe), barium telluride (BaTe), calcium sulfide (CaS), calcium selenide (CaSe), calcium telluride (CaTe), beryllium sulfide (BeS), beryllium selenide (BeSe), beryllium telluride (BeTe), magnesium sulfide (MgS), magnesium selenide (MgSe), germanium sulfide (GeS), germanium selenide (GeSe), germanium telluride (GeTe), tin(IV) sulfide ($SnS_2$), tin(II) sulfide (SnS), tin(II) selenide (SnSe), tin(II) telluride (SnTe), lead(II) oxide (PbO), copper(I) fluoride (CuF), copper(I) chloride (CuCl), copper(I) bromide (CuBr), copper(I) iodide (CuI), copper(I) oxide ($Cu_2O$), copper(I) selenide ($Cu_2Se$), nickel(II) oxide (NiO), cobalt(II) oxide (CoO), cobalt(II) sulfide (CoS), triiron tetraoxide ($Fe_3O_4$), iron(II) sulfide (FeS), manganese(II) oxide (MnO), molybdenum (IV) sulfide ($MoS_2$), vanadium(II) oxide (VO), vanadium (IV) oxide ($VO_2$), tungsten(IV) oxide ($WO_2$), tantalum(V) oxide ($Ta_2O_5$), titanium oxide (e.g., $TiO_2$, $Ti_2O_5$, $Ti_2O_3$, and $Ti_5O_9$), zirconium oxide ($ZrO_2$), silicon nitride ($Si_3N_4$), germanium nitride ($Ge_3N_4$), aluminum oxide ($Al_2O_3$), barium titanate ($BaTiO_3$), a compound of selenium, zinc, and cadmium (CdZnSe), a compound of indium, arsenic, phosphorus (InAsP), a compound of cadmium, selenium, and sulfur (CdSeS), a compound of cadmium, selenium, and tellurium (CdSeTe), a compound of indium, gallium, and arsenic (InGaAs), a compound of indium, gallium, and selenium (InGaSe), a compound of indium, selenium, and sulfur (InSeS), a compound of copper, indium, and sulfur (e.g., $CuInS_2$), and combinations thereof. What is called an alloyed quantum dot, whose composition is represented by a given ratio, may be used. For example, an alloyed quantum dot represented by $CdS_xSe_{1-x}$ (x is a given number between 0 and 1 inclusive) is an effective means for obtaining blue light emission because the emission wavelength can be changed by changing x.

As the quantum dot, a core-type quantum dot, a core-shell quantum dot, a core-multishell quantum dot, or the like may be used. When a core is covered with a shell formed of another inorganic material having a wider band gap, the influence of a defect or a dangling bond existing at the surface of a nanocrystal can be reduced. Since such a structure can significantly improve the quantum efficiency of light emission, it is preferable to use a core-shell or core-multishell quantum dot. Examples of the material of a shell include zinc sulfide (ZnS) and zinc oxide (ZnO).

Quantum dots have a high proportion of surface atoms and thus have high reactivity and easily cohere together. For this reason, it is preferable that a protective agent be attached to or a protective group be provided on the surfaces of the quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

The quantum dots may be quantum rods with rod-like shapes. A quantum rod emits directional light polarized in the c-axis direction; thus, quantum rods can be used as a light-emitting material to obtain a light-emitting element with higher external quantum efficiency.

A light-emitting layer in which the quantum dots are dispersed as a light-emitting material in a host material may be formed as follows: the quantum dots are dispersed in the host material or the host material and the quantum dots are dissolved or dispersed in an appropriate liquid medium, a wet process (e.g., a spin coating method, a casting method, a die coating method, a blade coating method, a roll coating method, an inkjet method, a printing method, a spray coating method, a curtain coating method, and a Langmuir-Blodgett method) is performed to form a layer, and then, the solvent is removed or baking is performed.

Examples of the liquid medium used for the wet process include the following organic solvents: ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); and dimethyl sulfoxide (DMSO).

In the case where a fluorescent substance is used, a host material suitable for the light-emitting layer is a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthryl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). The use of a substance having an anthracene skeleton as a host material for a fluorescent substance makes it possible to obtain a light-emitting layer with high emission efficiency and high durability. Note that CzPA, cgDBCzPA, 2mBnfPPA, and PCzPA have excellent characteristics and thus are particularly preferably selected.

In the case where a material other than the above materials is used as a host material, various carrier-transport materials, such as a material having an electron-transport property and a material having a hole-transport property, can be used.

Examples of the material with an electron-transport property are a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl) tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and a heterocyclic compound having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton and the heterocyclic compound having a pyridine skeleton have high reliability and thus are preferable. In particular, the heterocyclic compound having a diazine (pyrimidine or pyrazine) skeleton has an excellent electron-transport property and contributes to a reduction in drive voltage.

Examples of a material having a hole-transport property include a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); a compound having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and a compound having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds are highly reliable, have high hole-transport properties, and contribute to a reduction in drive voltage. The hole-transport material may be selected from a variety of substances as well as from the hole-transport materials given above.

In the case where a fluorescent substance is used as a light-emitting substance, a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)-biphenyl-4'-yl}-anthracene (abbreviation: FLPPA), is preferably used. The use of a substance having an anthracene skeleton as a host material for a fluorescent substance makes it possible to obtain a light-emitting layer with high emission efficiency and high durability. Note that CzPA, cgDBCzPA, 2mBnfPPA, and PCzPA have excellent characteristics and thus are particularly preferably selected.

Note that a host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

Substances in such a mixed host material may form an exciplex. When a combination of materials is selected so as to form an exciplex that exhibits light emission whose wavelength overlaps with the wavelength of a lowest-energy-side absorption band of a fluorescent substance, a phosphorescent substance, or a TADF material, energy can be transferred smoothly and light emission can be efficiently obtained. Such a structure is preferred to reduce the drive voltage.

The light-emitting layer 113 having the above-described structure can be formed by co-evaporation by a vacuum evaporation method, or a gravure printing method, an offset printing method, an inkjet method, a spin coating method, a dip coating method, or the like using a mixed solution.

An electron-transport layer 114 contains a substance having an electron-transport property. As the substance having an electron-transport property, any of the materials having electron-transport properties and the materials having anthracene skeletons, which can be used as a host material, can be used.

The organic compound of one embodiment of the present invention is also a substance having a hole-transport property and thus can be used as the material having a hole-transport property. The organic compound having an electron-deficient heterocyclic group or an aromatic hydrocarbon group as a substituent is particularly preferred.

Between the electron-transport layer and the light-emitting layer, a layer that controls transport of electron carriers may be provided. This layer is formed by addition of a small amount of a substance having an excellent electron-trapping property to the aforementioned material having an excellent electron-transport property and is capable of adjusting the carrier balance by retarding transport of electron carriers. Such a structure is very effective in preventing a problem (such as a reduction in element lifetime) caused when electrons pass through the light-emitting layer.

An electron-injection layer 115 may be provided between the electron-transport layer 114 and the cathode 102 and in contact with the cathode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. In addition, an electride may be used for the electron-injection layer 115. Examples of the electride include a substance in which electrons are added at high concentration to calcium oxide-aluminum oxide. Note that a layer that is formed using a substance having an electron-transport property and contains an alkali metal or an alkaline earth metal is preferably used as the electron-injection layer 115, in which case electron injection from the cathode 102 is efficiently performed.

Figure 1B:
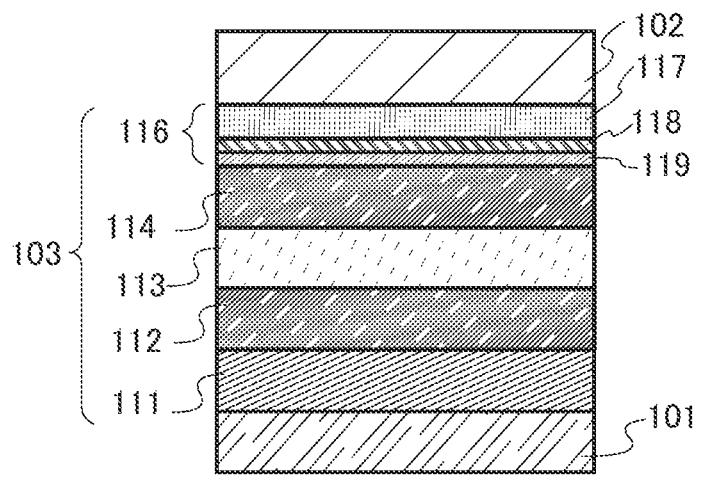

Instead of the electron-injection layer 115, a charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of the material that can be used for the hole-injection layer 111. The p-type layer 117 may be formed by stacking a film containing the above acceptor material as a material included in the composite material and a film containing the above hole-transport material. When a potential is applied to the p-type layer 117, electrons are injected into the electron-transport layer 114 and holes are injected into the cathode 102; thus, the light-emitting element operates. When a layer containing the organic compound of one embodiment of the present invention exists in the electron-transport layer 114 to be in contact with the charge-generation layer 116, a luminance decrease over driving time of the light-emitting element can be suppressed, and thus, the light-emitting element can have a long lifetime.

Note that the charge-generation layer 116 preferably includes an electron-relay layer 118 and/or an electron-injection buffer layer 119 in addition to the p-type layer 117.

The electron-relay layer 118 contains at least a substance with an electron-transport property and has a function of preventing an interaction between the electron-injection buffer layer 119 and the p-type layer 117 to transfer electrons smoothly. The LUMO level of the substance with an electron-transport property contained in the electron-relay layer 118 is preferably between the LUMO level of an acceptor substance in the p-type layer 117 and the LUMO level of a substance contained in a layer of the electron-transport layer 114 in contact with the charge-generation layer 116. Specifically, the LUMO energy level of the substance with an electron-transport property used for the electron-relay layer 118 is preferably higher than or equal to −5.0 eV, more preferably higher than or equal to −5.0 eV and lower than or equal to −3.0 eV. As the substance with an electron-transport property used for the electron-relay layer 118, a phthalocyanine-based material or a metal complex having a metal-oxygen bond and an aromatic ligand is preferably used.

A substance having an excellent electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the cathode 102, a metal, an alloy, an electrically conductive compound, or a mixture thereof each having a low work function (specifically, 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the cathode 102 and the electron-transport layer, for the cathode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an inkjet method, a spin coating method, or the like. Alternatively, a wet process using a sol-gel method or a wet process using a paste of a metal material may be employed.

A variety of methods, either a dry process or a wet process, can be used to form the EL layer 103. For example, a vacuum evaporation method or a wet process (such as a spin coating method, a casting method, a die coating method, a blade coating method, a roll coating method, an inkjet method, a printing method (e.g., a gravure printing method, an offset printing method, and a screen printing method), a spray coating method, a curtain coating method, and a Langmuir-Blodgett method) may be used.

Different methods may be used to form the electrodes or the layers described above.

Here, a method for forming a layer 786 containing a light-emitting substance by a droplet discharge method will be described with reference to FIGS. 2A to 2D. FIGS. 2A to 2D are cross-sectional views illustrating a method for forming the layer 786 containing a light-emitting substance.

Figure 2A:
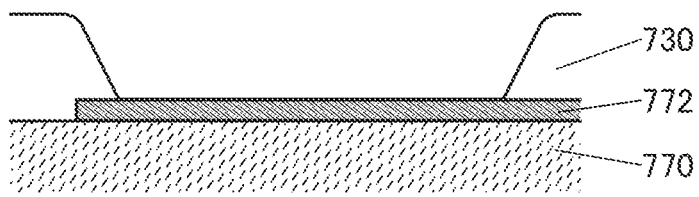
FIGS. 2A to 2D illustrate an example of a method for manufacturing a light-emitting element.
Figure 2B:
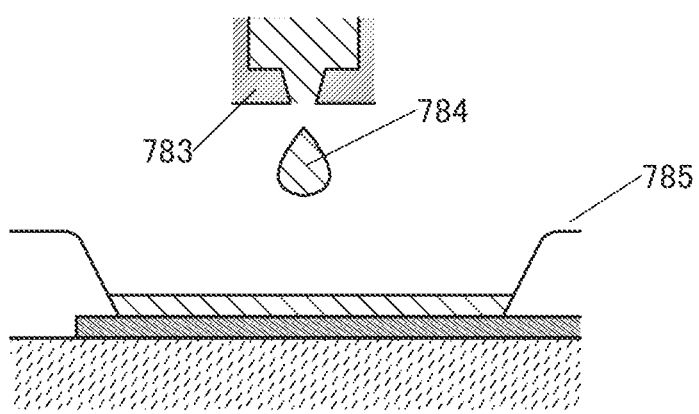

First, a conductive film 772 is formed over a planarization insulating film 770, and an insulating film 730 is formed to cover part of the conductive film 772 (see FIG. 2A).

Then, a droplet 784 is discharged from a droplet discharge apparatus 783 to the conductive film 772 exposed in an opening of the insulating film 730, so that a layer 785 containing a composition is formed. The droplet 784 is a composition containing a solvent and is attached to the conductive film 772 (see FIG. 2B).

Note that the step of discharging the droplet 784 may be performed under reduced pressure.

Figure 2C:
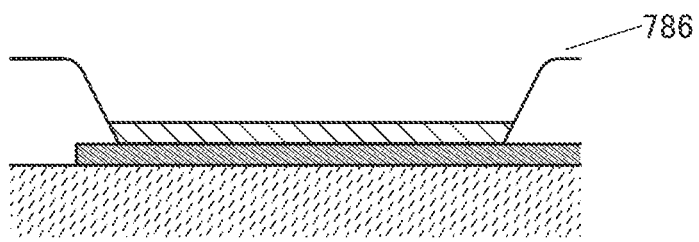

Next, the solvent is removed from the layer 785 containing a composition, and the resulting layer is solidified to form the layer 786 containing a light-emitting substance (see FIG. 2C).

The solvent may be removed by drying or heating.

Figure 2D:
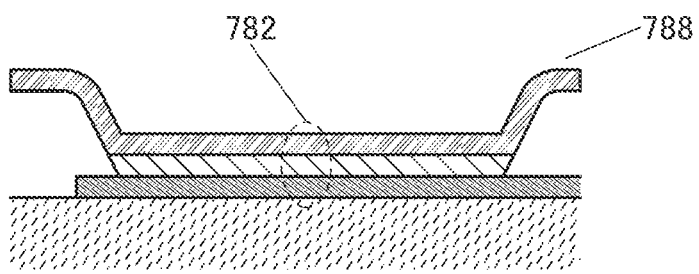

Next, a conductive film 788 is formed over the layer 786 containing a light-emitting substance; thus, a light-emitting element 782 is formed (see FIG. 2D).

When the layer 786 containing a light-emitting substance is formed by a droplet discharge method in this manner, the composition can be selectively discharged; accordingly, waste of material can be reduced. Furthermore, a lithography process or the like for shaping is not needed, and thus, the process can be simplified and cost reduction can be achieved.

The droplet discharge method mentioned above is a general term for a method with a droplet discharge means such as a nozzle having a composition discharge outlet or a head having one or a plurality of nozzles.

Figure 3:
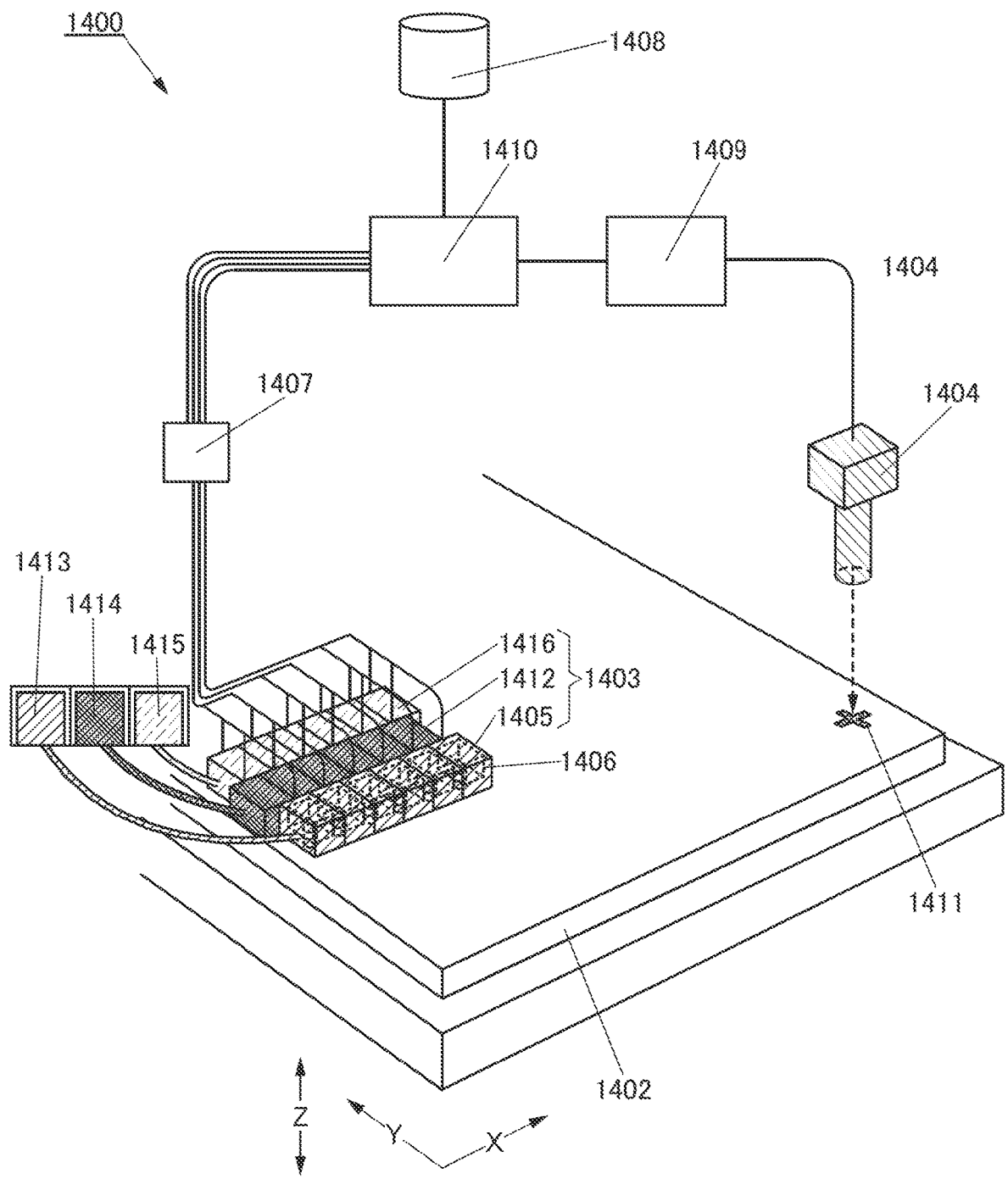
FIG. 3 illustrates an example of a method for manufacturing a light-emitting element.

Next, a droplet discharge apparatus used for the droplet discharge method will be described with reference to FIG. 3. FIG. 3 is a conceptual diagram illustrating a droplet discharge apparatus 1400.

The droplet discharge apparatus 1400 includes a droplet discharge means 1403. The droplet discharge means 1403 includes a head 1405, a head 1412, and a head 1416.

The heads 1405 and 1412 are connected to a control means 1407 which is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The computer 1410 recognizes the digital signal, generates a control signal, and transmits it to the control means 1407.

An image sensor or the like including a charge coupled device (CCD) or a complementary metal oxide semiconductor (CMOS) can be used as the imaging means 1404. Note that information on a pattern to be formed on the substrate 1402 is stored in a storage medium 1408, and a control signal is transmitted to the control means 1407 on the basis of the information, so that the heads 1405, 1412, and 1416 of the droplet discharge means 1403 can be individually controlled. Materials to be discharged are supplied to the heads 1405, 1412, and 1416 from material supply sources 1413, 1414, and 1415, respectively, through pipes.

Inside each of the heads 1405, 1412, and 1416, a space indicated by a dotted line 1406 to be filled with a liquid material and a nozzle serving as a discharge outlet are provided. Although not illustrated, the inside structure of the head 1412 is similar to that of the head 1405. When the nozzle sizes of the heads 1405 and 1412 are different from each other, different materials with different widths can be discharged simultaneously. Each head can discharge a plurality of light-emitting materials or the like to draw a pattern. In the case of drawing a pattern over a large area, the same material can be simultaneously discharged from a plurality of nozzles in order to improve throughput. When a large substrate is used, the heads 1405, 1412, and 1416 can freely scan the substrate in the directions of arrows X, Y, and Z in FIG. 3, and a region in which a pattern is drawn can be freely set. Thus, the same patterns can be drawn on one substrate.

Furthermore, the step of discharging the composition may be performed under reduced pressure. The substrate may be heated when the composition is discharged. The discharge of the composition is followed by drying and/or baking. Both the drying and baking are heat treatments but different in purpose, temperature, and time. The drying and baking are performed under normal pressure or reduced pressure by laser irradiation, rapid thermal annealing, heating in a heating furnace, or the like. Note that there is no particular limitation on the timing of the heat treatment and the number of times of the heat treatment. The temperature for adequately performing the drying and baking depends on the material of the substrate and the properties of the composition.

In the above-described manner, the layer 786 containing a light-emitting substance can be formed with the droplet discharge apparatus.

The layer 786 containing a light-emitting substance can be formed with the droplet discharge apparatus by a wet process using a composition in which any of a variety of organic materials and organic-inorganic halide perovskite materials is dissolved or dispersed in a solvent. In this case, the following various organic solvents can be used to form a coating composition: benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, and cyclohexane. In particular, a less polar benzene derivative such as benzene, toluene, xylene, or mesitylene is preferably used because a solution with a suitable concentration can be obtained and a material contained in ink can be prevented from deteriorating due to oxidation or the like. Furthermore, to form a uniform film or a film with a uniform thickness, a solvent with a boiling point of 100° C. or higher is preferably used, and more preferably, toluene, xylene, or mesitylene is used.

Note that the above-described structure can be combined with any of the structures in this embodiment and the other embodiments.

Next, an embodiment of a light-emitting element in which a plurality of light-emitting units are stacked (also referred to as a stacked element) will be described with reference to FIG. 1C. This light-emitting element includes a plurality of light-emitting units between an anode and a cathode. Each light-emitting unit has a structure similar to that of the EL layer 103 illustrated in FIG. 1A. In other words, the light-emitting element illustrated in FIG. 1A or 1B includes a single light-emitting unit, and the light-emitting element illustrated in FIG. 1C includes a plurality of light-emitting units.

Figure 1C:
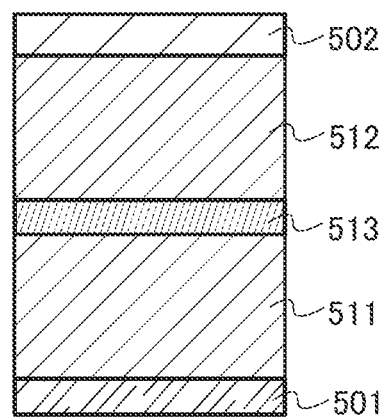

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond to the anode 101 and the cathode 102, respectively, illustrated in FIG. 1A, and the description of FIG. 1A can be applied thereto. Furthermore, the first light-emitting unit 511 and the second light-emitting unit 512 may have the same structure or different structures.

The charge-generation layer 513 has a function of injecting electrons into one of the light-emitting units and injecting holes into the other light-emitting unit when a voltage is applied between the first electrode 501 and the second electrode 502. That is, in FIG. 1C, the charge-generation layer 513 injects electrons into the first light-emitting unit 511 and holes into the second light-emitting unit 512 when a voltage is applied such that the potential of the first electrode is higher than the potential of the second electrode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 serves as an electron-injection layer in the light-emitting unit on the anode side; therefore, the light-emitting unit is not necessarily provided with an additional electron-injection layer.

The light-emitting element having two light-emitting units is described with reference to FIG. 1C; however, one embodiment of the present invention can also be applied to a light-emitting element in which three or more light-emitting units are stacked. With a plurality of light-emitting units partitioned by the charge-generation layer 513 between a pair of electrodes as in the light-emitting element of this embodiment, it is possible to provide a long-life element which can emit light with high luminance at a low current density. A light-emitting device which can be driven at a low voltage and has low power consumption can be provided.

Furthermore, when emission colors of the light-emitting units are different, light emission of a desired color can be obtained from the light-emitting element as a whole.

Embodiment 3

In this embodiment, a light-emitting device including the light-emitting element described in Embodiment 1 will be described.

A light-emitting device of one embodiment of the present invention will be described with reference to FIGS. 4A and 4B. FIG. 4A is a top view of the light-emitting device, and FIG. 4B is a cross-sectional view taken along the lines A-B and C-D in FIG. 4A. The light-emitting device includes a driver circuit portion (source line driver circuit) 601, a pixel portion 602, and a driver circuit portion (gate line driver circuit) 603, which control light emission of a light-emitting element and are illustrated with dotted lines. A reference numeral 604 denotes a sealing substrate; 605, a sealant; and 607, a space surrounded by the sealant 605.

Note that a lead wiring 608 is a wiring for transmitting signals to be input to the source line driver circuit 601 and the gate line driver circuit 603 and receiving a video signal, a clock signal, a start signal, a reset signal, and the like from a flexible printed circuit (FPC) 609 serving as an external input terminal. Although only the FPC is illustrated here, a printed wiring board (PWB) may be attached to the FPC. The light-emitting device in this specification includes, in its category, not only the light-emitting device itself but also the device provided with the FPC or the PWB.

Next, a cross-sectional structure will be described with reference to FIG. 4B. The driver circuit portion and the pixel portion are formed over an element substrate 610. Here, the source line driver circuit 601, which is the driver circuit portion, and one pixel of the pixel portion 602 are illustrated.

As the source line driver circuit 601, a CMOS circuit in which an n-channel FET 623 and a p-channel FET 624 are combined is formed. The driver circuit may be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and may be formed outside the substrate.

The pixel portion 602 includes a plurality of pixels each including a switching FET 611, a current controlling FET 612, and a first electrode 613 electrically connected to a drain of the current controlling FET 612. One embodiment of the present invention is not limited to this structure. Each pixel of the pixel portion may include three or more FETs and a capacitor in combination.

There is no particular limitation on the kind and crystallinity of a semiconductor used for the FETs; an amorphous semiconductor or a crystalline semiconductor may be used. Examples of the semiconductor used for the FETs include Group 13 semiconductors, Group 14 semiconductors, compound semiconductors, oxide semiconductors, and organic semiconductor materials. Oxide semiconductors are particularly preferable. Examples of the oxide semiconductor include an In—Ga oxide and an In-M-Zn oxide (M is Al, Ga, Y, Zr, La, Ce, or Nd). Note that an oxide semiconductor material that has an energy gap of 2 eV or more, preferably 2.5 eV or more, more preferably 3 eV or more is preferably used, in which case the off-state current of the transistors can be reduced.

Note that an insulator 614 is formed to cover an end portion of the first electrode 613. The insulator 614 can be formed using a positive photosensitive acrylic resin film here.

In order to improve the coverage, the insulator 614 is formed so as to have a curved surface with curvature at its upper or lower end portion. For example, in the case where positive photosensitive acrylic is used as a material of the insulator 614, only the upper end portion of the insulator 614 preferably has a curved surface with a curvature radius (0.2 µm to 3 µm). As the insulator 614, either a negative photosensitive resin or a positive photosensitive resin can be used.

An EL layer 616 and a second electrode 617 are formed over the first electrode 613. The first electrode 613, the EL layer 616, and the second electrode 617 respectively correspond to the anode 101, the EL layer 103, and the cathode 102 in FIGS. 1A and 1B, or to the first electrode 501, an EL layer 503, and the second electrode 502 in FIG. 1C.

The EL layer 616 preferably contains an organometallic complex. The organometallic complex is preferably used as an emission center substance in the light-emitting layer.

The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with a filler and may be filled with an inert gas (e.g., nitrogen or argon) or the sealant 605. It is preferable that the sealing substrate have a recessed portion provided with a desiccant, in which case deterioration due to moisture can be suppressed.

An epoxy-based resin or a glass frit is preferably used as the sealant 605. In this case, it is preferable to use a material that transmits moisture or oxygen as little as possible. As the element substrate 610 and the sealing substrate 604, a glass substrate, a quartz substrate, or a plastic substrate formed of fiber reinforced plastic (FRP), polyvinyl fluoride (PVF), polyester, acrylic, or the like can be used.

In this specification and the like, a transistor or a light-emitting element can be formed using a variety of substrates, for example. The type of the substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used. For the glass substrate, for example, barium borosilicate glass, aluminoborosilicate glass, or soda lime glass can be used. Examples of a material of the flexible substrate, the attachment film, the base material film, or the like are as follows: plastic typified by polyethylene terephthalate (PET), polyethylene naphthalate (PEN), and polyether sulfone (PES). Another example is a synthetic resin such as acrylic. Alternatively, polytetrafluoroethylene (PTFE), polypropylene, polyester, polyvinyl fluoride, polyvinyl chloride, or the like can be used. Alternatively, polyamide, polyimide, aramid, epoxy, an inorganic film formed by evaporation, paper, or the like can be used. Specifically, the use of a semiconductor substrate, a single crystal substrate, an SOI substrate, or the like enables the manufacture of small-sized transistors with high current capability and a small variation in characteristics, size, shape, or the like. A circuit including such transistors achieves lower power consumption or higher integration of the circuit.

Alternatively, a flexible substrate may be used as the substrate, and the transistor or the light-emitting element may be directly formed over the flexible substrate. Alternatively, a separation layer may be provided between a substrate and the transistor or between the substrate and the light-emitting element. The separation layer can be used when part or the whole of a semiconductor device formed over the separation layer is separated from the substrate and transferred to another substrate. In this case, the transistor can be transferred to even a substrate having low heat resistance or a flexible substrate. As the separation layer, a stack of inorganic films, namely a tungsten film and a silicon oxide film, or an organic resin film of polyimide or the like formed over a substrate can be used, for example.

In other words, the transistor or the light-emitting element may be formed using one substrate and then transferred to another substrate. Examples of the substrate to which the transistor or the light-emitting element is transferred include, in addition to the above-described substrates over which the transistor can be formed, a paper substrate, a cellophane substrate, an aramid film substrate, a polyimide film substrate, a stone substrate, a wood substrate, a cloth substrate (including a natural fiber (e.g., silk, cotton, and hemp), a synthetic fiber (e.g., nylon, polyurethane, and polyester), a regenerated fiber (e.g., acetate, cupra, rayon, or regenerated polyester), and the like), a leather substrate, and a rubber substrate. When such a substrate is used, a transistor with excellent properties or a transistor with low power consumption can be formed, a device with high durability and high heat resistance can be provided, and/or a reduction in weight or thickness can be achieved.

Figure 5A:
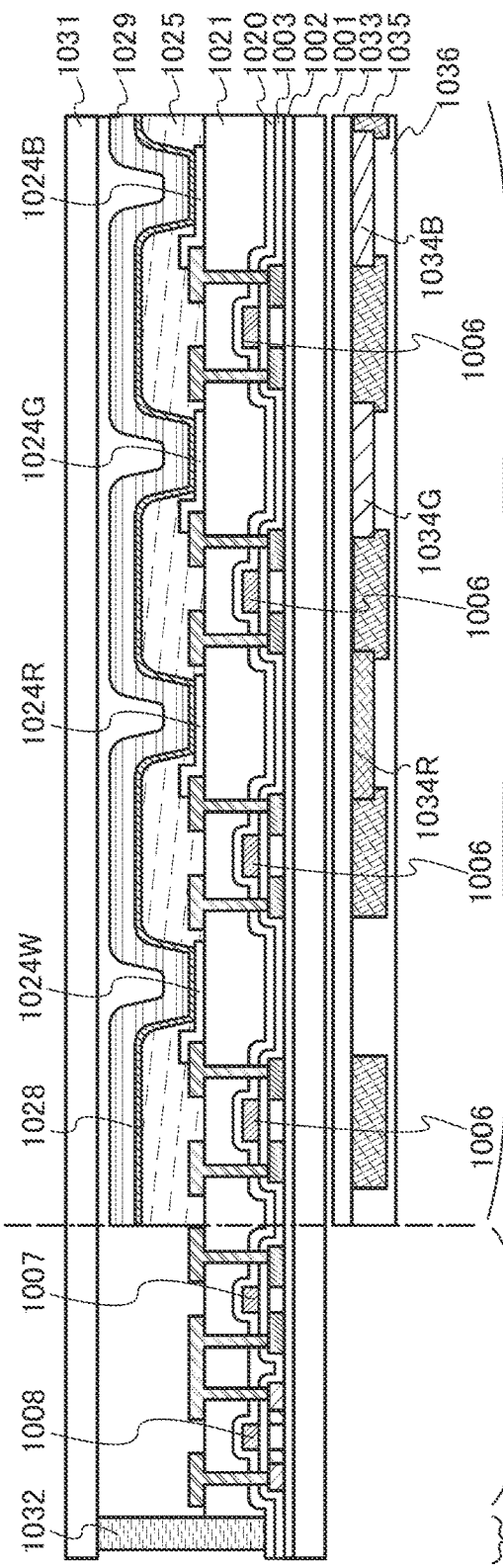
FIGS. 5A and 5B are conceptual diagrams of active matrix light-emitting devices.
Figure 5B:
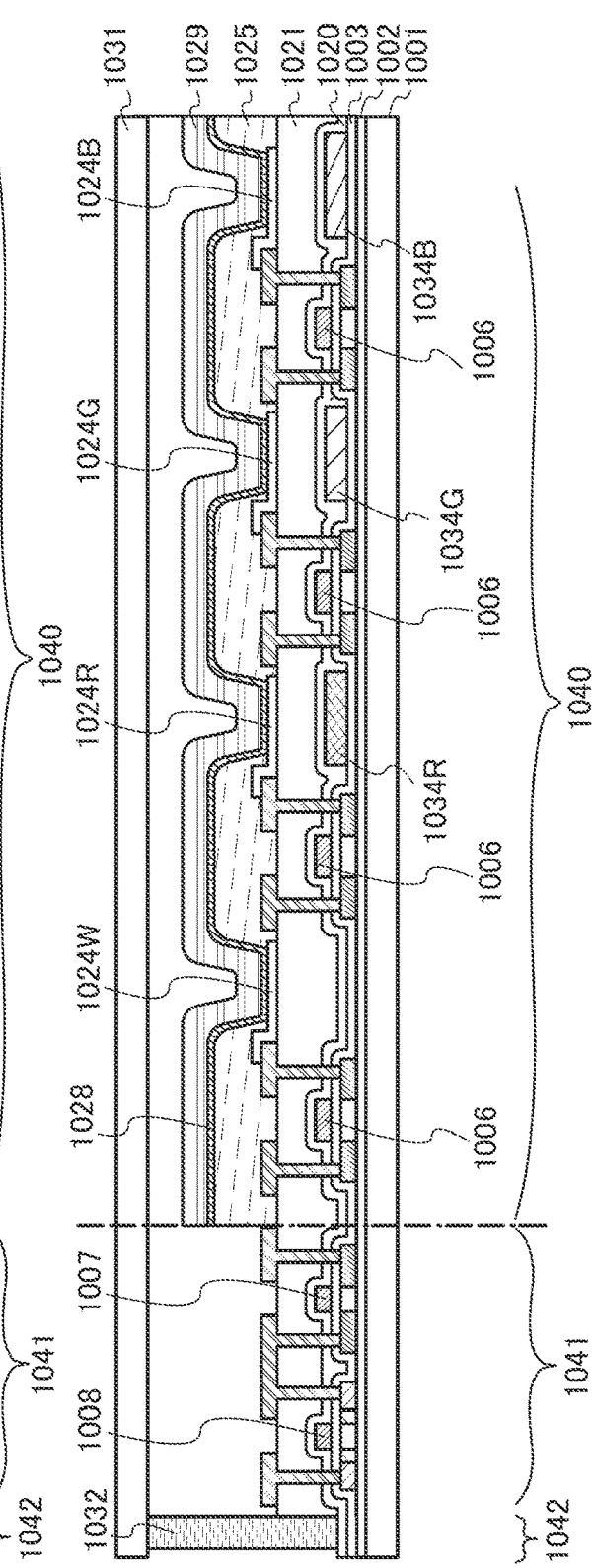

FIGS. 5A and 5B each illustrate an example of a light-emitting device which includes a light-emitting element exhibiting white light emission and coloring layers (color filters) and the like to display a full-color image. FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a cathode 1029 of the light-emitting elements, a sealing substrate 1031, a sealant 1032, and the like.

In FIG. 5A, coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5A, light emitted from some light-emitting layers does not pass through the coloring layers, while light emitted from the other light-emitting layers passes through the respective coloring layers. Since light that does not pass through the coloring layers is white and light that passes through any one of the coloring layers is red, blue, or green, an image can be displayed using pixels of the four colors.

FIG. 5B illustrates an example in which the coloring layers (the red coloring layer 1034R, the green coloring layer 1034G, and the blue coloring layer 1034B) are formed between the gate insulating film 1003 and the first interlayer insulating film 1020. As in this structure, the coloring layers may be provided between the substrate 1001 and the sealing substrate 1031.

Figure 6:
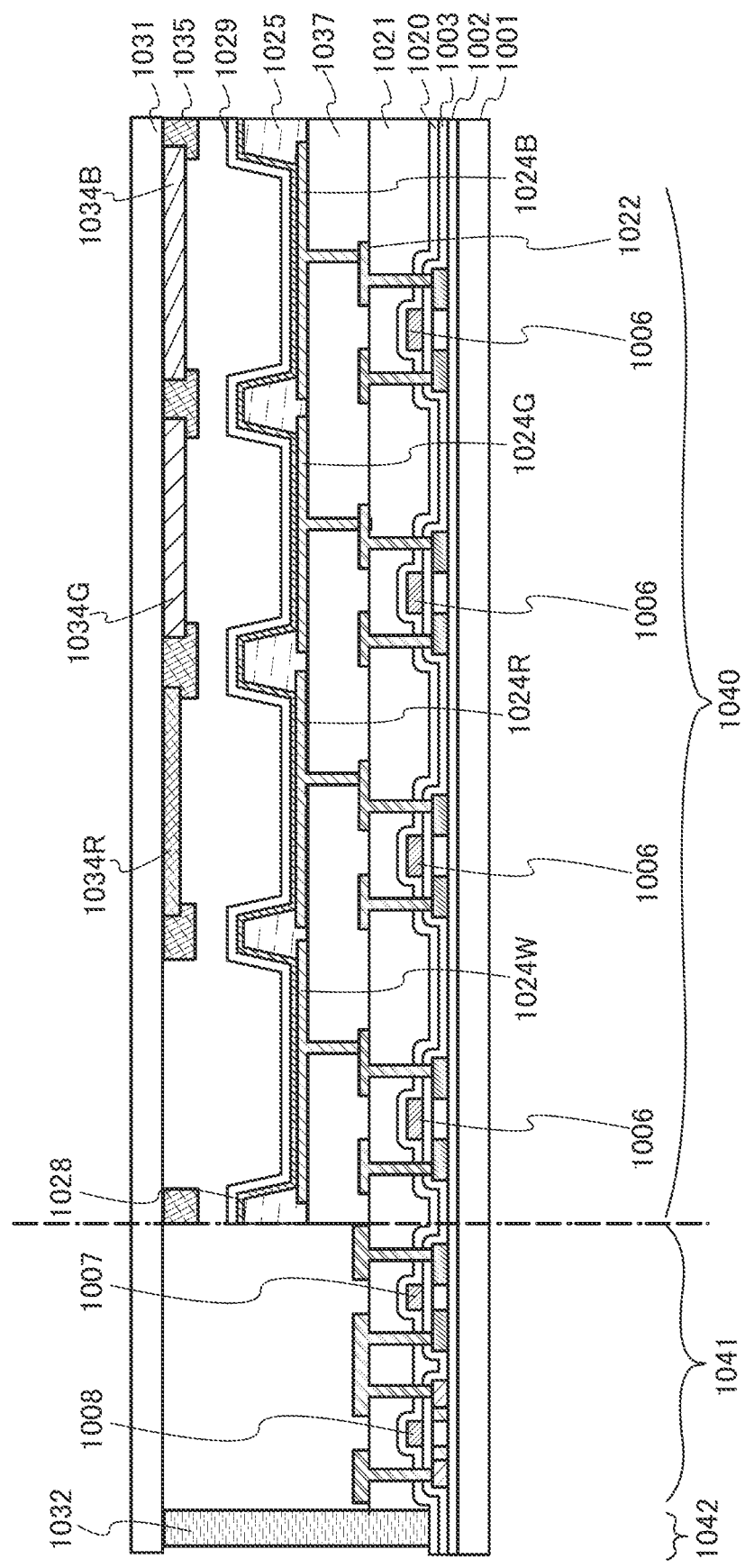
FIG. 6 is a conceptual diagram of an active matrix light-emitting device.

The above-described light-emitting device has a structure in which light is extracted from the substrate 1001 side, over which the FETs are formed (a bottom emission structure), but may have a structure in which light is extracted from the sealing substrate 1031 side (a top emission structure). FIG. 6 is a cross-sectional view of a top-emission light-emitting device. In this case, a substrate that does not transmit light can be used as the substrate 1001. The process up to the step of forming of a connection electrode which connects the FET to the anode of the light-emitting element is performed in a manner similar to that of the bottom-emission light-emitting device. Then, a third interlayer insulating film 1037 is formed to cover an electrode 1022. This insulating film may have a planarization function. The third interlayer insulating film 1037 can be formed using a material similar to that of the second interlayer insulating film or using any of other various materials.

The first electrodes 1024W, 1024R, 1024G, and 1024B of the light-emitting elements each serve as an anode here, but may each serve as a cathode. Furthermore, in the case of the top-emission light-emitting device illustrated in FIG. 6, the first electrodes are preferably reflective electrodes. The EL layer 1028 has a structure similar to the structure of the EL layer 103 in FIG. 1A or 1B or the EL layer 503 in FIG. 1C, with which white light emission can be obtained.

In the case of a top emission structure like that in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 which is positioned between pixels. The coloring layers (the red coloring layer 1034R, the green coloring layer 1034G, and the blue coloring layer 1034B) and the black layer may be covered with an overcoat layer. Note that a light-transmitting substrate is used as the sealing substrate 1031.

One embodiment of the present invention is not particularly limited to the example shown here, in which a full-color image is displayed using four colors of red, green, blue, and white; a full-color image may be displayed using three colors of red, green, and blue or four colors of red, green, blue, and yellow.

Figure 7A:
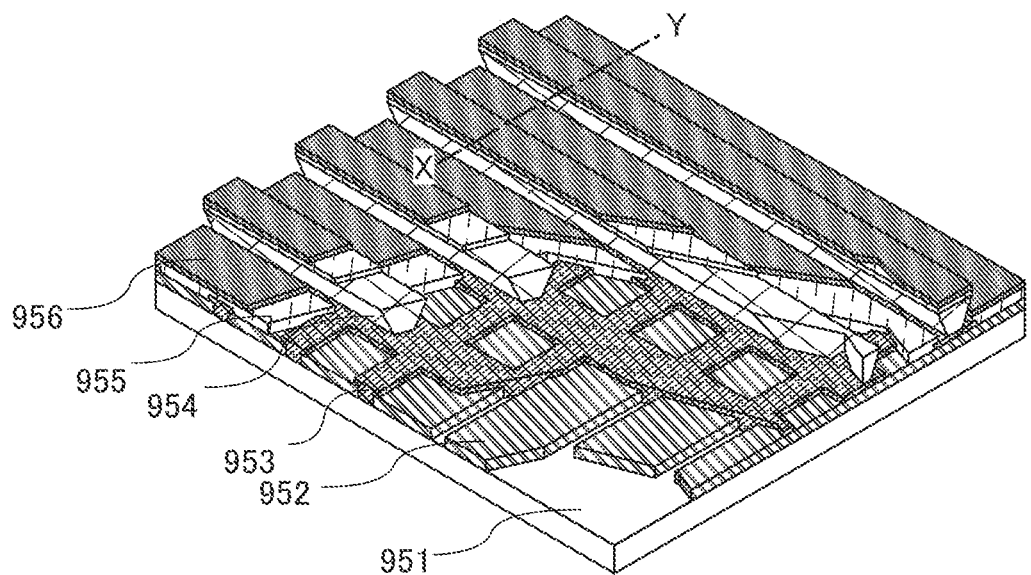
FIGS. 7A and 7B are conceptual diagrams of a passive matrix light-emitting device.
Figure 7B:
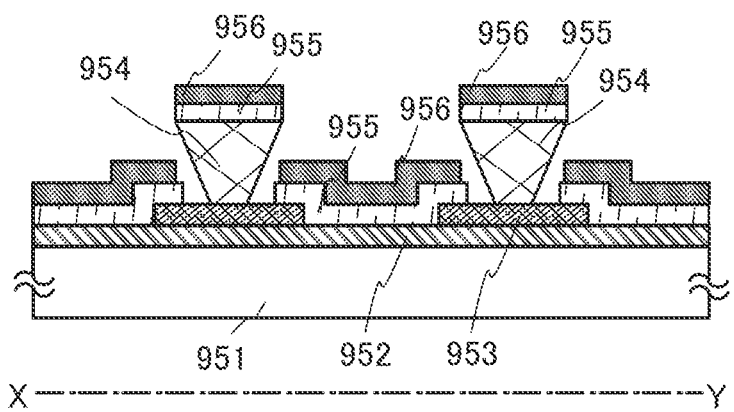

FIGS. 7A and 7B illustrate a passive matrix light-emitting device of one embodiment of the present invention. FIG. 7A is a perspective view of the light-emitting device, and FIG. 7B is a cross-sectional view taken along the line X-Y in FIG. 7A. In FIGS. 7A and 7B, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between the sidewalls is gradually narrowed toward the surface of the substrate. That is, a cross section in the short side direction of the partition layer 954 is a trapezoidal shape, and the lower side (the side which is substantially parallel to the plane direction of the insulating layer 953 and is in contact with the insulating layer 953) is shorter than the upper side (the side which is substantially parallel to the plane direction of the insulating layer 953 and is not in contact with the insulating layer 953). The partition layer 954 provided in this manner can prevent defects of the light-emitting element due to static electricity or the like.

Since many minute light-emitting elements arranged in a matrix can be independently controlled by the FETs formed in the pixel portion, the above-described light-emitting device can be suitably used as an image display device.

<<Lighting Device>>

Figure 8A:
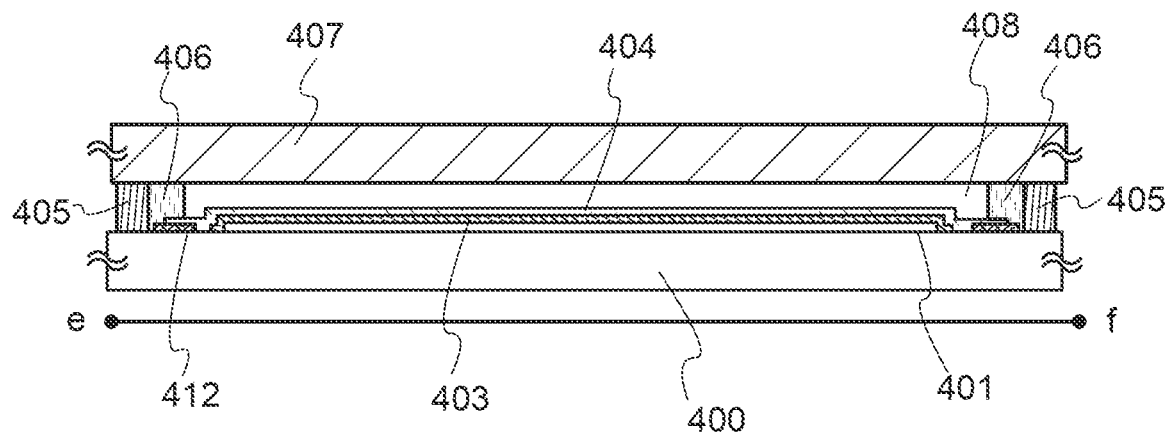
FIGS. 8A and 8B illustrate a lighting device.
Figure 8B:
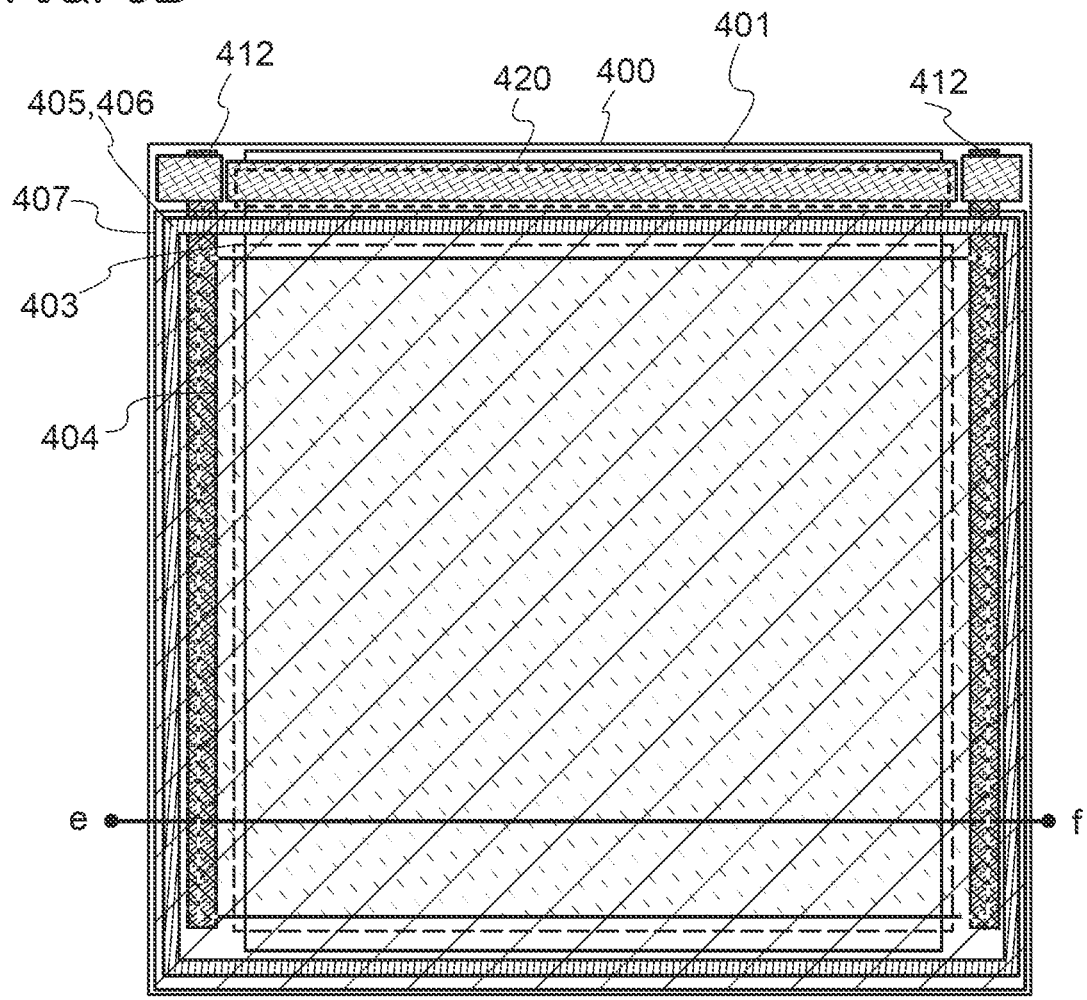

A lighting device of one embodiment of the present invention will be described with reference to FIGS. 8A and 8B. FIG. 8B is a top view of the lighting device, and FIG. 8A is a cross-sectional view taken along the line e-f in FIG. 8B.

In the lighting device, a first electrode 401 is formed over a substrate 400 which is a support and has a light-transmitting property. The first electrode 401 corresponds to the anode 101 in FIGS. 1A and 1B. When light is extracted from the first electrode 401 side, the first electrode 401 is formed using a material having a light-transmitting property.

A pad 412 for applying a voltage to a second electrode 404 is formed over the substrate 400.

An EL layer 403 is formed over the first electrode 401. The EL layer 403 corresponds to, for example, the EL layer 103 in FIGS. 1A and 1B. For these structures, the corresponding description can be referred to.

The second electrode 404 is formed to cover the EL layer 403. The second electrode 404 corresponds to the cathode 102 in FIG. 1A. The second electrode 404 contains a material having high reflectivity when light is extracted from the first electrode 401 side. The second electrode 404 is connected to the pad 412, whereby a voltage is applied thereto.

A light-emitting element is formed with the first electrode 401, the EL layer 403, and the second electrode 404. The light-emitting element is sealed by being fixed to a sealing substrate 407 with sealants 405 and 406, whereby the lighting device is completed. It is possible to omit the sealant 405 or the sealant 406. In addition, the inner sealant 406 can be mixed with a desiccant that enables moisture to be adsorbed, increasing reliability.

When part of the pad 412 and part of the first electrode 401 are extended to the outside of the sealants 405 and 406, the extended parts can serve as external input terminals. An IC chip 420 mounted with a converter or the like may be provided over the external input terminals.

<<Electronic Device>>

Examples of an electronic device of one embodiment of the present invention will be described. Examples of the electronic device include a television device (also referred to as a television or a television receiver), a monitor of a computer or the like, a digital camera, a digital video camera, a digital photo frame, a mobile phone (also referred to as a cellular phone or a mobile phone device), a portable game console, a portable information terminal, an audio reproducing device, and a large-sized game machine such as a pachinko machine. Specific examples of these electronic devices are shown below.

Figure 9A:
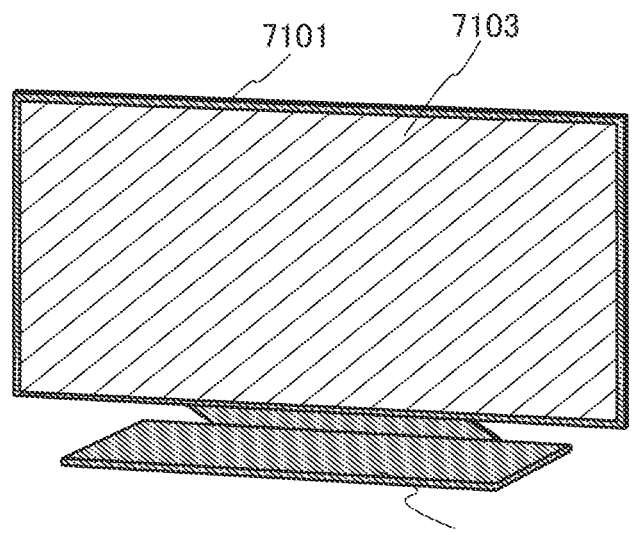
Figure 9A:
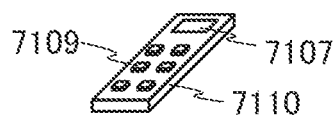
Figure 9A:
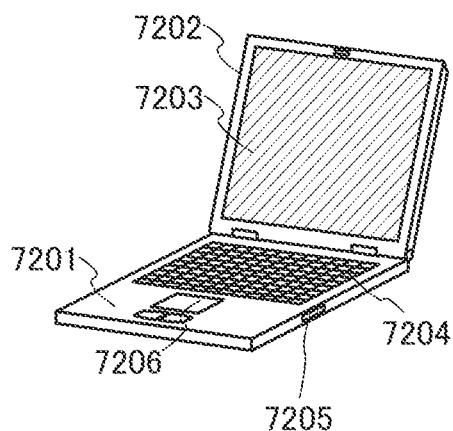
Figure 9A:
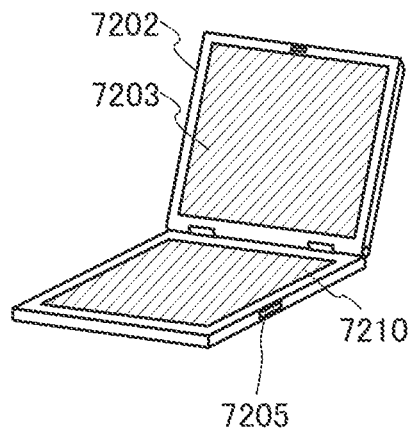

FIG. 9A illustrates an example of a television device. In the television device, a display portion 7103 is incorporated in a housing 7101. Here, the housing 7101 is supported by a stand 7105. Images can be displayed on the display portion 7103 in which light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 9B1 illustrates a computer which includes a main body 7201, a housing 7202, a display portion 7203, a keyboard 7204, an external connection port 7205, a pointing device 7206, and the like. Note that this computer is manufactured by arranging light-emitting elements in a matrix in the display portion 7203. The computer in FIG. 9B1 may have a structure in FIG. 9B2. The computer in FIG. 9B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 9C:
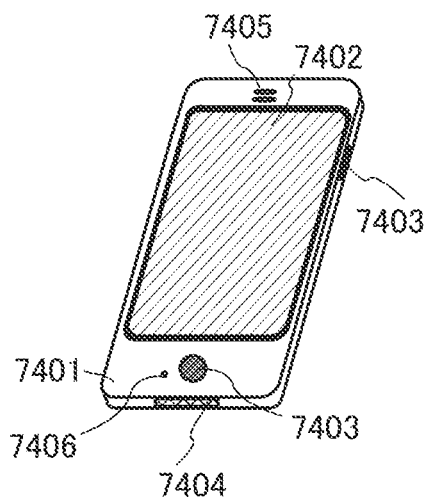
Figure 9D:
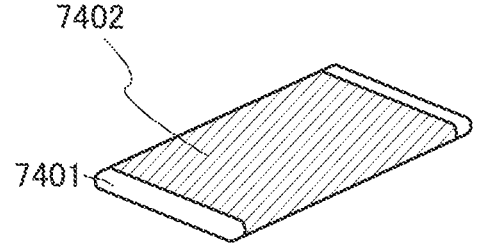

FIGS. 9C and 9D each illustrate an example of a portable information terminal. The portable information terminal is provided with a display portion 7402 incorporated in a housing 7401, operation buttons 7403, an external connection port 7404, a speaker 7405, a microphone 7406, and the like. Note that the portable information terminal includes the display portion 7402 in which light-emitting elements are arranged in a matrix.

Information can be input to each of the portable information terminals illustrated in FIGS. 9C and 9D by touching the display portion 7402 with a finger or the like. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor for sensing inclination, such as a gyroscope sensor or an acceleration sensor, is provided inside the portable information terminal, screen display of the display portion 7402 can be automatically changed by determining the orientation of the portable information terminal (whether the portable information terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Note that in the above electronic devices, any of the structures described in this specification can be combined as appropriate.

The display portion preferably includes the light-emitting element of one embodiment of the present invention. The light-emitting element can have high emission efficiency. In addition, the light-emitting element can be driven at low voltage. Thus, the electronic device including the light-emitting element of one embodiment of the present invention can have low power consumption.

Figure 10:
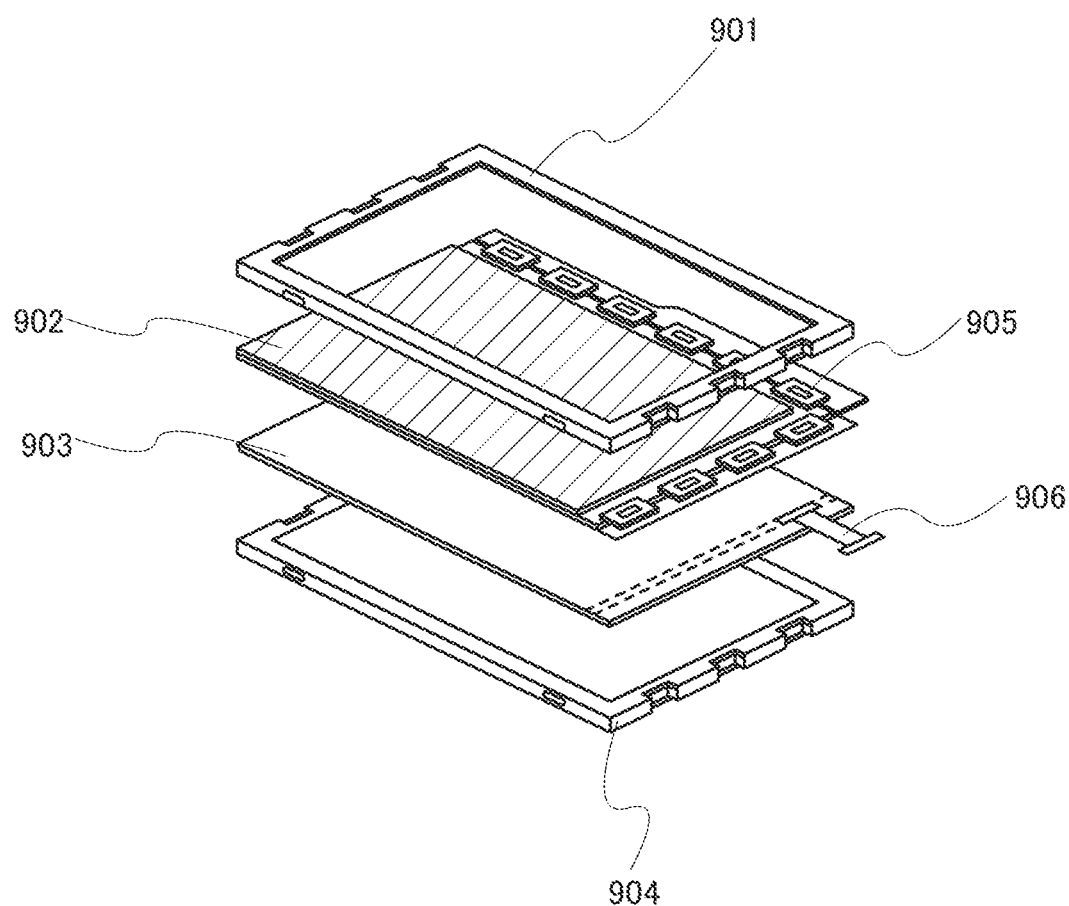
FIG. 10 illustrates a light source device.

FIG. 10 illustrates an example of a liquid crystal display device in which a light-emitting element is used for a backlight. The liquid crystal display device illustrated in FIG. 10 includes a housing 901, a liquid crystal layer 902, a backlight unit 903, and a housing 904. The liquid crystal layer 902 is connected to a driver IC 905. The light-emitting element is used for the backlight unit 903, to which a current is supplied through a terminal 906.

As the light-emitting element, the light-emitting element of one embodiment of the present invention is preferably used. By including the light-emitting element, the backlight of the liquid crystal display device can have low power consumption.

Figure 11:
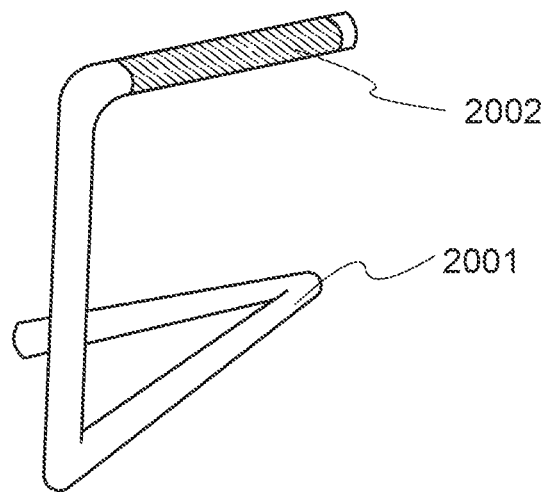
FIG. 11 illustrates a lighting device.

FIG. 11 illustrates an example of a desk lamp of one embodiment of the present invention. The desk lamp illustrated in FIG. 11 includes a housing 2001 and a light source 2002, and a lighting device including a light-emitting element is used as the light source 2002.

Figure 12:
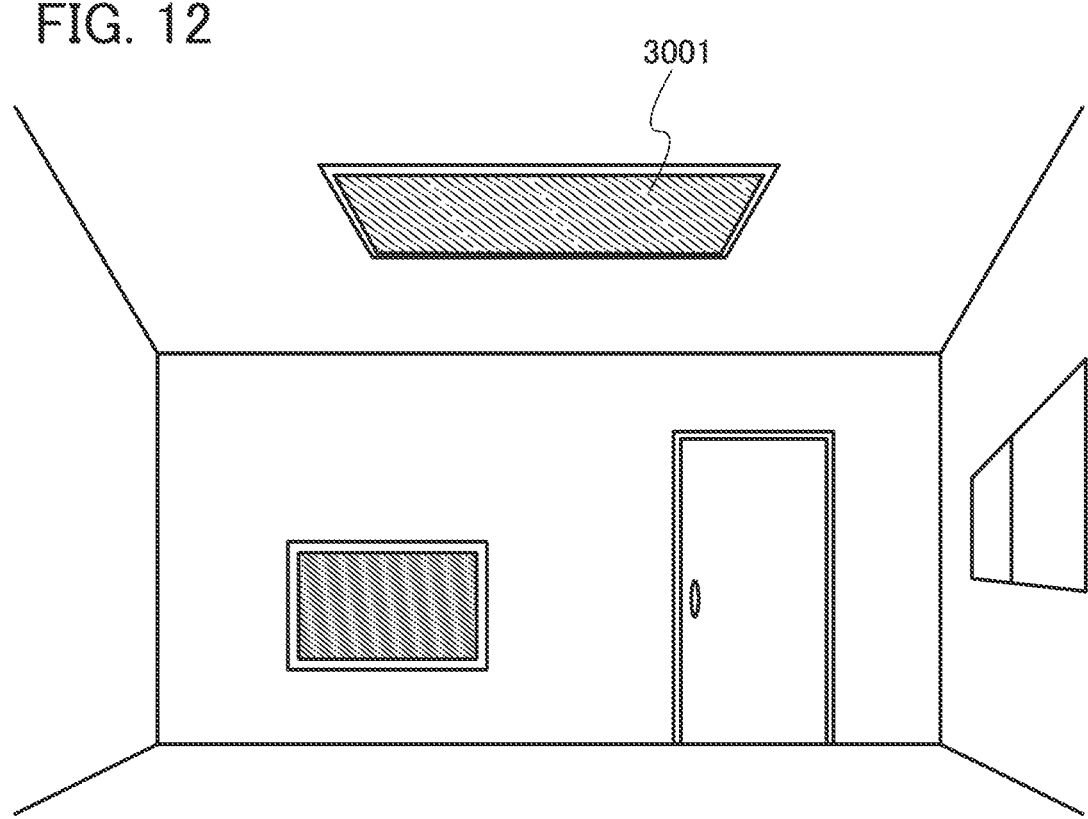
FIG. 12 illustrates a lighting device.

FIG. 12 illustrates an example of an indoor lighting device 3001. The light-emitting element of one embodiment of the present invention is preferably used for the lighting device 3001.

Figure 13:
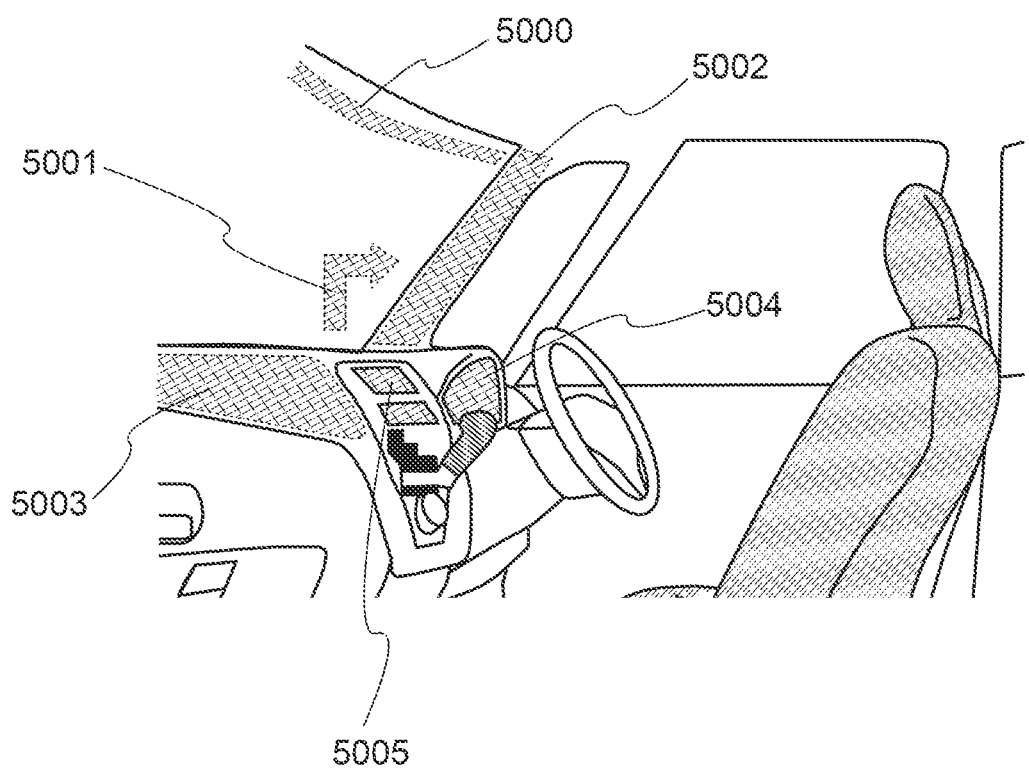
FIG. 13 illustrates an in-vehicle display device and lighting devices.

An automobile of one embodiment of the present invention is illustrated in FIG. 13. In the automobile, light-emitting elements are used for a windshield and a dashboard. Display regions 5000 to 5005 are formed using light-emitting elements, preferably the light-emitting elements of one embodiment of the present invention. This suppresses the power consumption of the display regions 5000 to 5005, showing suitability for use in an automobile.

The display regions 5000 and 5001 are display devices which are provided in the automobile windshield and include the light-emitting elements. When electrodes having light-transmitting properties are used as first electrodes and second electrodes of these light-emitting elements, what is called see-through display devices, through which the opposite side can be seen, can be obtained. Such see-through display devices can be provided even in the automobile windshield without hindering the vision. In the case where a driving transistor or the like is provided, a transistor having a light-transmitting property, such as an organic transistor including an organic semiconductor material or a transistor including an oxide semiconductor, is preferably used.

The display region 5002 is a display device which is provided in a pillar portion and includes the light-emitting element. The display region 5002 can compensate for the view hindered by the pillar by displaying an image taken by an imaging unit provided in the car body. Similarly, the display region 5003 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to ensure safety easily and comfortably.

The display regions 5004 and 5005 can provide a variety of kinds of information such as navigation information, a speedometer, a tachometer, a mileage, a fuel meter, a gear-shift indicator, and air-condition setting. The content or layout of the display can be changed freely by a user as appropriate. Note that such information can also be displayed on the display regions 5000 to 5003. The display regions 5000 to 5005 can also be used as lighting devices.

Figure 14A:
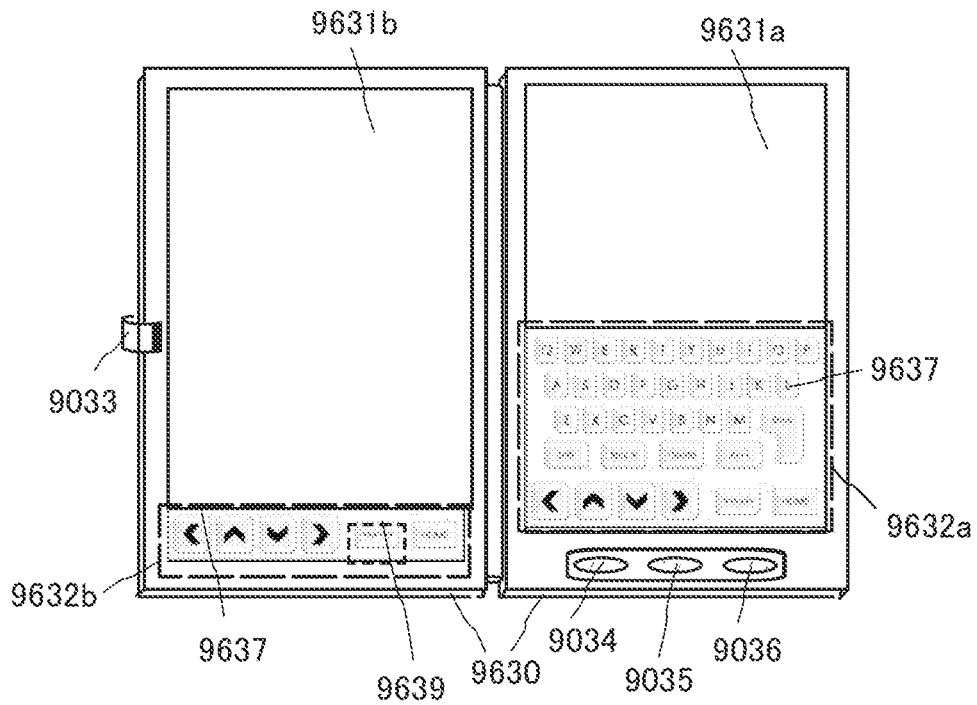
FIGS. 14A to 14C illustrate an electronic device.
Figure 14B:
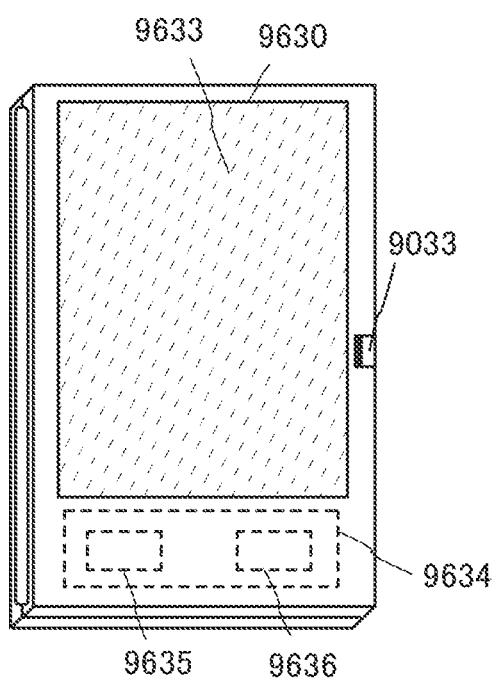

FIGS. 14A and 14B illustrate an example of a foldable tablet terminal. In FIG. 14A, the tablet terminal is opened and includes a housing 9630, a display portion 9631a, a display portion 9631b, a switch 9034 for switching display modes, a power switch 9035, a switch 9036 for switching to power-saving mode, and a clasp 9033. In the tablet terminal, a light-emitting device which includes the light-emitting element of one embodiment of the present invention is used for the display portion 9631a and/or the display portion 9631b.

Part of the display portion 9631a can be a touch panel region 9632a, and data can be input when a displayed operation key 9637 is touched. The structure of the display portion 9631a is not limited to the illustrated structure in which a half region has only a display function and the other half region has a touch panel function. The whole region of the display portion 9631a may have a touch panel function. For example, the whole area of the display portion 9631a can display keyboard buttons to serve as a touch panel, and the display portion 9631b can be used as a display screen.

Like the display portion 9631a, part of the display portion 9631b can be a touch panel region 9632b. When a switching button 9639 for showing/hiding a keyboard on the touch panel is touched with a finger, a stylus, or the like, keyboard buttons can be displayed on the display portion 9631b.

Touch input can be performed in the touch panel region 9632a and the touch panel region 9632b at the same time.

The switch 9034 for switching display modes can switch the display between a portrait mode, a landscape mode, and the like, and between monochrome display and color display, for example. With the switch 9036 for switching to power-saving mode, the luminance of display can be optimized in accordance with the amount of external light in use which is sensed by an optical sensor incorporated in the tablet terminal. In addition to the optical sensor, another sensing device such as a sensor for sensing inclination, e.g., a gyroscope sensor or an acceleration sensor, may be incorporated in the tablet terminal.

One embodiment of the present invention is not particularly limited to the example illustrated in FIG. 14A, in which the display portion 9631a and the display portion 9631b have the same display area. The display portion 9631a and the display portion 9631b may have different areas or different display qualities. For example, one of the display portions 9631a and 9631b may display higher definition images than the other.

The tablet terminal is closed in FIG. 14B. The tablet terminal of this embodiment includes the housing 9630, a solar cell 9633, a charge/discharge control circuit 9634, a battery 9635, and a DCDC converter 9636. Note that FIG. 14B illustrates an example in which the charge/discharge control circuit 9634 includes the battery 9635 and the DCDC converter 9636.

Since the tablet terminal can be folded, the housing 9630 can be closed when the tablet terminal is not used. Thus, the display portion 9631a and the display portion 9631b can be protected; accordingly, a tablet terminal which has high durability and high reliability for long-term use can be provided.

In addition, the tablet terminal illustrated in FIGS. 14A and 14B can have a function of displaying a variety of kinds of information (e.g., a still image, a moving image, and a text image), a function of displaying a calendar, a date, the time, and/or the like on the display portion, a touch-input function of operating or editing information displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 is preferably provided on one or two surfaces of the housing 9630, in which case the battery 9635 can be charged efficiently.

Figure 14C:
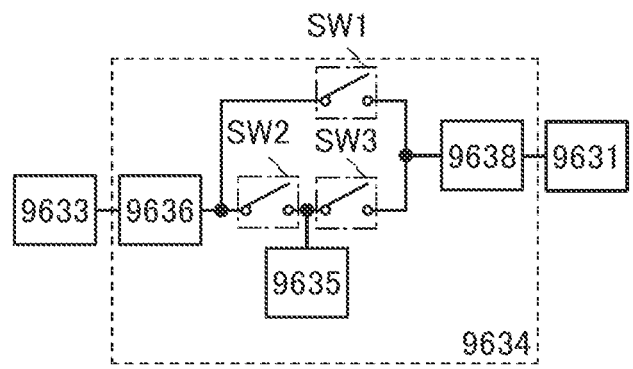

The structure and operation of the charge/discharge control circuit 9634 illustrated in FIG. 14B will be described with reference to a block diagram in FIG. 14C. FIG. 14C illustrates the solar cell 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge/discharge control circuit 9634 illustrated in FIG. 14B.

First, an example of the operation in the case where power is generated by the solar cell 9633 using external light will be described. The voltage of power generated by the solar cell is raised or lowered by the DCDC converter 9636 so as to be a voltage for charging the battery 9635. Then, when the power stored by the solar cell 9633 is used for the operation of the display portion 9631, the switch SW1 is turned on and the voltage of the power is raised or lowered by the converter 9638 so as to be a voltage needed for the display portion 9631. When display on the display portion 9631 is not performed, the switch SW1 is turned off and the switch SW2 is turned on so that the battery 9635 is charged.

Although the solar cell 9633 is described as an example of a power generation means, there is no particular limitation on the power generation means, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or other charge means may be used in combination; the power generation means is not necessarily provided.

One embodiment of the present invention is not limited to the tablet terminal having the shape illustrated in FIGS. 14A to 14C as long as the display portion 9631 is provided.

Figure 15A:
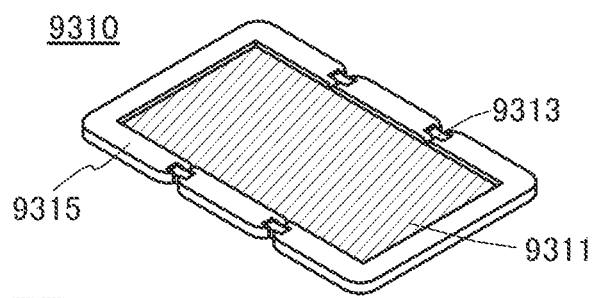
FIGS. 15A to 15C illustrate an electronic device.
Figure 15B:
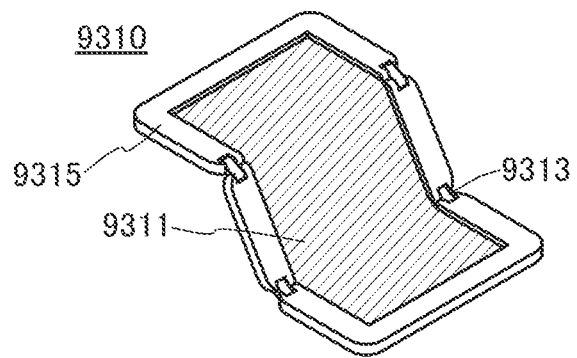
Figure 15C:
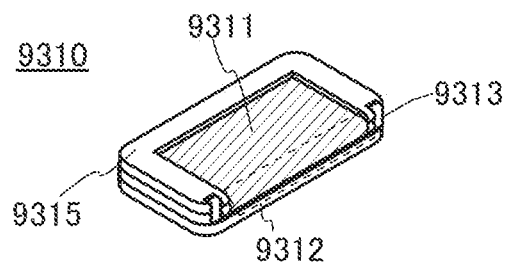

FIGS. 15A to 15C illustrate a foldable portable information terminal 9310. FIG. 15A illustrates the portable information terminal 9310 which is opened. FIG. 15B illustrates the portable information terminal 9310 which is being opened or being folded. FIG. 15C illustrates the portable information terminal 9310 which is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting device of one embodiment of the present invention can be used for the display panel 9311. A display region 9312 of the display panel 9311 is positioned at a side surface of the portable information terminal 9310 which is folded. On the display region 9312, information icons, file shortcuts of frequently used applications or programs, and the like can be displayed; thus, information can be easily checked and an application can be smoothly started.

The organic compound of one embodiment of the present invention can be used for an electronic device such as an organic thin film solar cell. Specifically, the organic compound can be used in a carrier-transport layer or a carrier-injection layer since the organic compound has a carrier-transport property. In addition, a mixed layer of the organic compound and an acceptor substance can be used as a charge generation layer. The organic compound can be photoexcited and hence can be used for a power generation layer.

Example 1

Synthesis Example 1

In this example is shown below a synthesis example of 2,11-bis(diphenylamino)naphtho[2,3-b;7,6-b']bisbenzofuran (abbreviation: 2,11DPhA2Nbf(II)), which is represented by Structural Formula (300) in Embodiment 1, will be described in detail. The structural formula of 2,11DPhA2Nbf(II) is shown below.

[Chemical Formula 80]

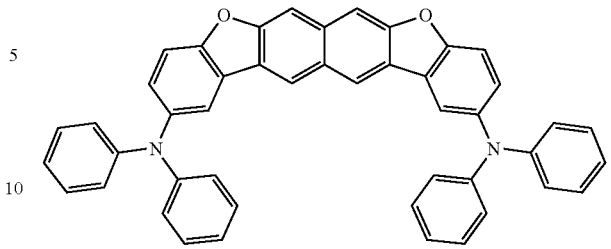

Step 1: Synthesis of 3,6-bis(5-chloro-2-fluorophenyl)-2,7-dimethoxynaphthalene

Into a 200-mL three-neck flask were put 3.8 g (11 mmol) of 3,6-dibromo-2,7-dimethoxynaphthalene, 4.2 g (24 mmol) of 5-chloro-2-fluorophenylboronic acid, 6.7 g (48 mmol) of potassium carbonate, and 0.34 g (1.1 mmol) of tris(2-methylphenyl)phosphine. To this mixture was added 60 mL of toluene. The resulting mixture was degassed by being stirred while the pressure was reduced. To the mixture was added 49 mg (0.22 mmol) of palladium(II) acetate, and stirring was performed under a nitrogen stream at 80° C. for 14 hours. After that, 1.9 g (11 mmol) of 5-chloro-2-fluorophenylboronic acid and 3.0 g (22 mmol) of potassium carbonate were added to the resulting mixture, and stirring was performed under a nitrogen stream at 120° C. for 8 hours. After the stirring, toluene was added to the mixture, and the resulting mixture was suction-filtered through Florisil (manufactured by Wako Pure Chemical Industries, Ltd., Catalog No. 540-00135), Celite (manufactured by Wako Pure Chemical Industries, Ltd., Catalog No. 531-16855), and alumina to give a filtrate. The filtrate was concentrated to give an oily substance.

The obtained oily substance was purified by silica gel column chromatography (as the developing solvent, toluene and hexane in a ratio of 1:2 were used), so that 3.9 g of the objective substance was obtained in a yield of 79%. A synthesis scheme of Step 1 is shown below.

[Chemical Formula 81]

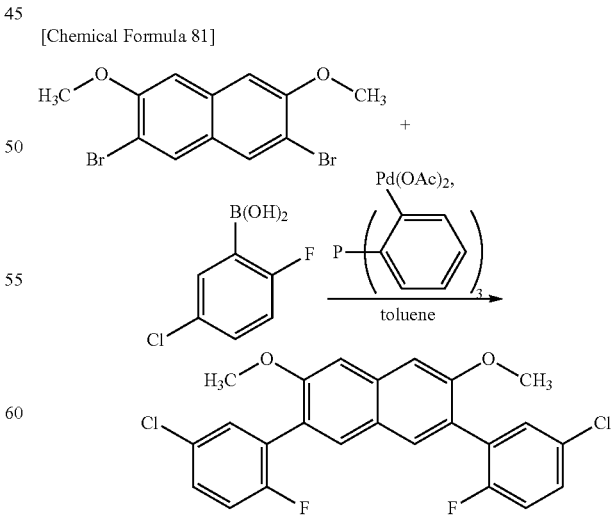

Figure 16A:
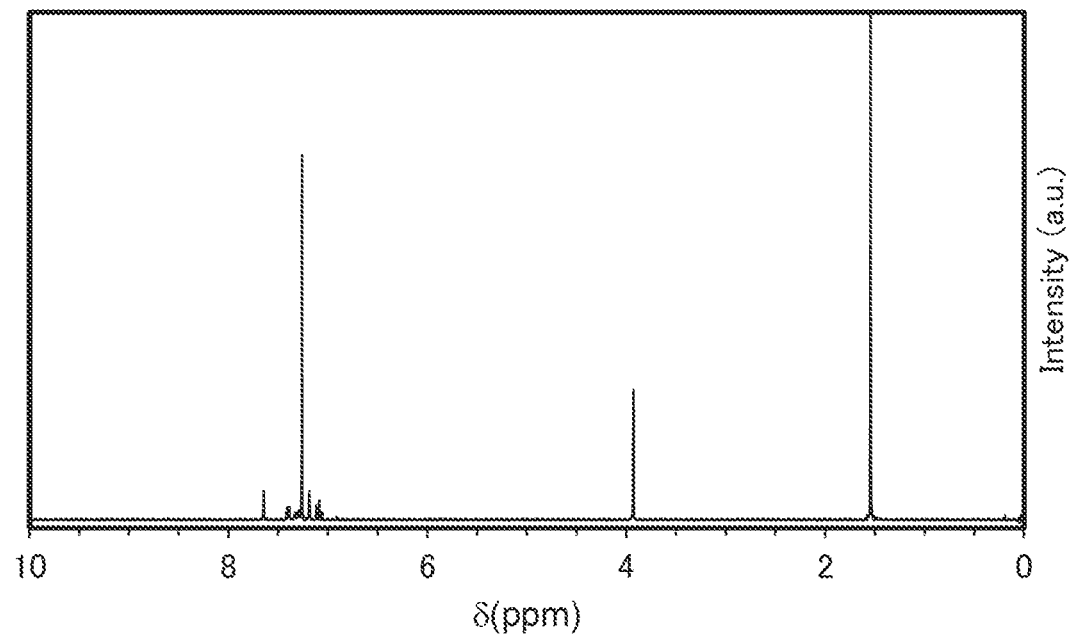
FIGS. 16A and 16B show ¹H NMR spectra of 3,6-bis(5-chloro-2-fluorophenyl)-2,7-dimethoxynaphthalene.
Figure 16B:
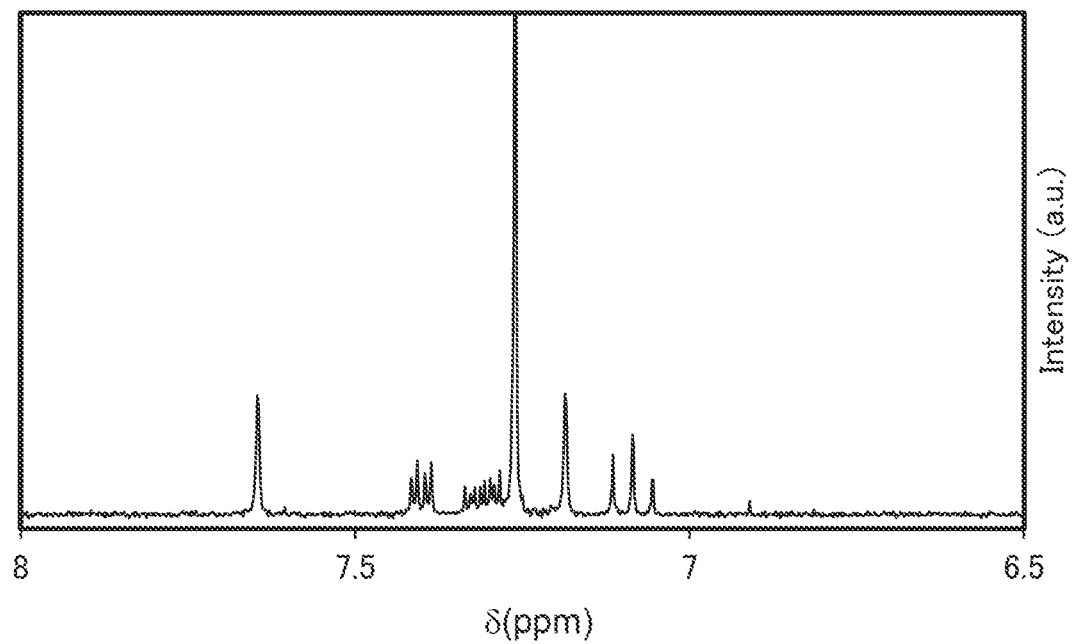

FIGS. 16A and 16B show $^1$H NMR charts of the resulting solid, whose numerical data is shown below. These indicate that 3,6-bis(5-chloro-2-fluorophenyl)-2,7-dimethoxynaphthalene was obtained in this synthesis example.

$^1$H NMR (CDCl$_3$, 300 MHz): δ=3.93 (s, 6H), 7.06 (t, J1=9.0 Hz, 2H), 7.19 (s, 2H), 7.28-7.34 (m, 2H), 7.40 (dd, J1=2.4 Hz, J2=5.7 Hz, 2H), 7.65 (s, 2H).

Step 2: Synthesis of 3,6-bis(5-chloro-2-fluorophenyl)-2,7-dihydroxynaphthalene Into a 200-mL three-neck flask was put 5.0 g (11 mmol) of 3,6-bis(5-chloro-2-fluorophenyl)-2,7-dimethoxynaphthalene. Into the flask was additionally put 30 mL of dichloromethane under a nitrogen stream. To the solution were dripped 25 mL of boron tribromide (approximately 1.0 mol/L dichloromethane solution) and 20 mL of dichloromethane. After the dripping, the resulting solution was stirred at room temperature. After that, approximately 20 mL of water was added to this solution under cooling with ice, and the solution was stirred. Then, the aqueous layer of this mixture was subjected to extraction with dichloromethane, and the extracted solution and the organic layer were combined and washed with water and a saturated aqueous solution of sodium hydrogen carbonate. Magnesium sulfate was added to the obtained organic layer to adsorb moisture, and the resulting mixture was subjected to gravity filtration. The obtained filtrate was concentrated to give 4.8 g of a white solid. A synthesis scheme of Step 2 is shown below.

[Chemical Formula 82]

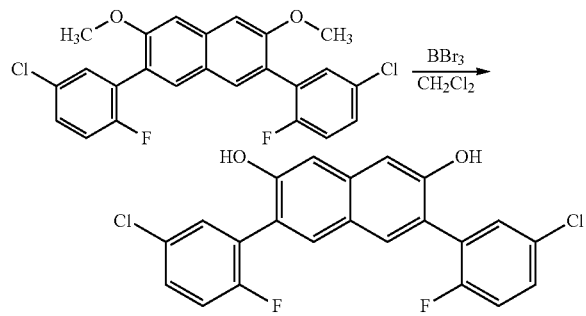

Figure 17A:
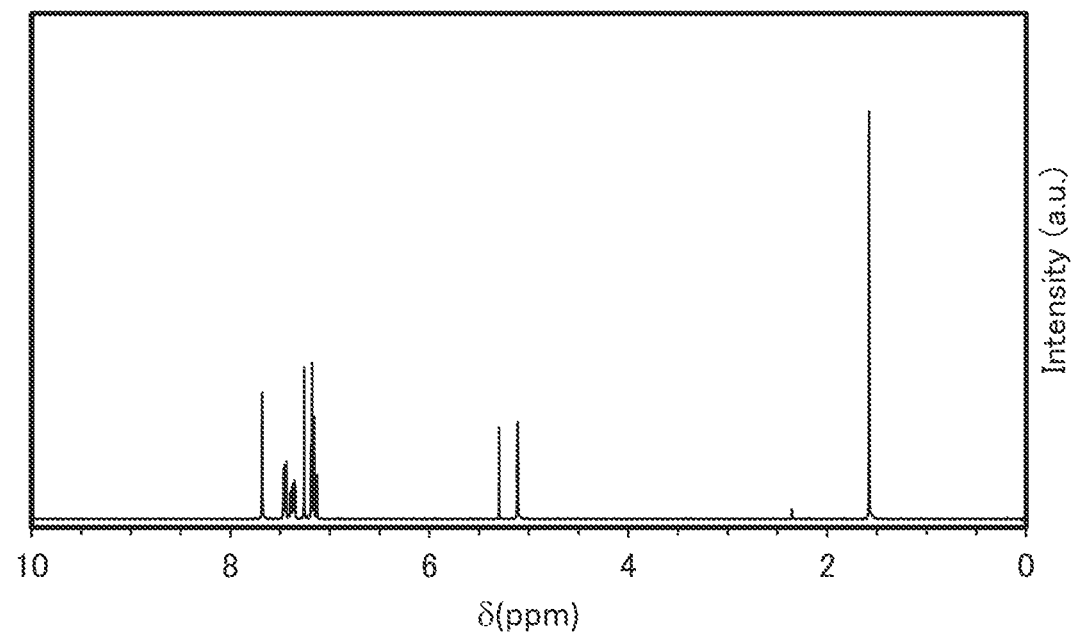
FIGS. 17A and 17B show ¹H NMR spectra of 3,6-bis(5-chloro-2-fluorophenyl)-2,7-dihydroxynaphthalene.
Figure 17B:
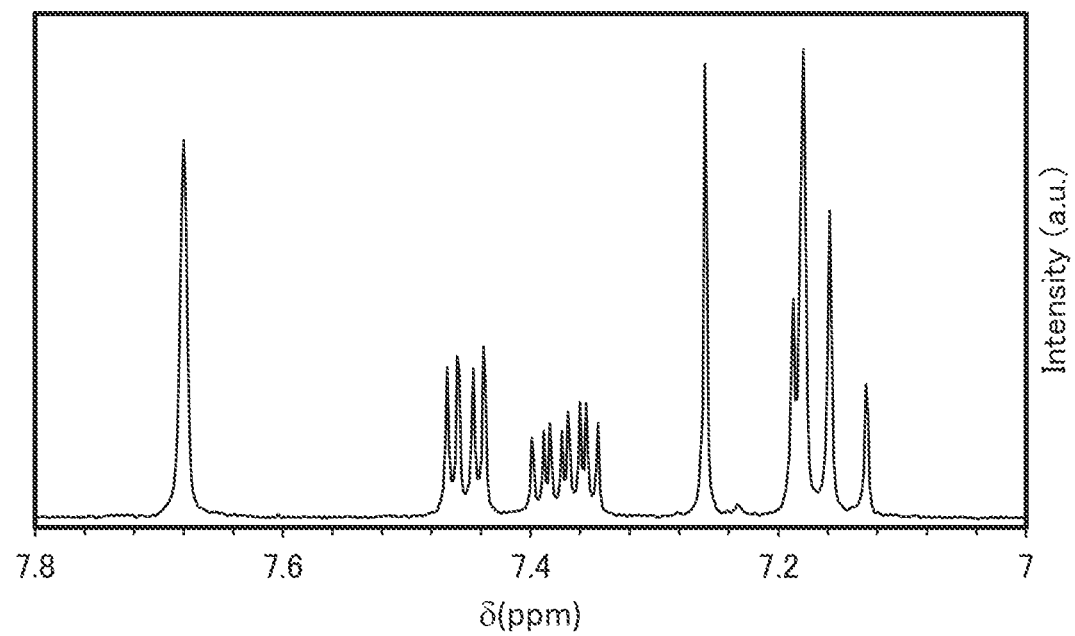

FIGS. 17A and 17B show $^1$H NMR charts of the resulting solid, whose numerical data is shown below. These indicate that 3,6-bis(5-chloro-2-fluorophenyl)-2,7-dihydroxynaphthalene was obtained in this synthesis example.

$^1$H NMR (CDCl$_3$, 300 MHz): δ=5.11 (s, 2H), 7.16 (t, J1=9.0 Hz, 2H), 7.18 (s, 2H), 7.35-7.40 (m, 2H), 7.45 (dd, J1=2.4 Hz, J2=6.3 Hz, 2H), 7.68 (s, 2H).

Step 3: Synthesis of 2,11-dichloronaphtho[2,3-b;7,6-b']bisbenzofuran

Into a 200-mL three-neck flask were put 4.8 g (12 mmol) of 3,6-bis(5-chloro-2-fluorophenyl)-2,7-dihydroxynaphthalene and 6.3 g (46 mmol) of potassium carbonate. To this mixture was added 115 mL of N-methyl-2-pyrrolidone. The resulting mixture was degassed by being stirred while the pressure was reduced. Then, this mixture was stirred under a nitrogen stream at 120° C. for 6.5 hours. After that, water was added to the mixture, and the precipitated solid was collected by filtration. The obtained solid was washed with water and ethanol. Ethanol was added to the resulting solid, heating and stirring were performed, and then the resulting mixture was filtered to give a solid. Toluene was added to the resulting solid, heating and stirring were performed, and then the resulting mixture was filtered to give 3.4 g of a white to light brown solid in a yield of 79%. A synthesis scheme of Step 3 is shown below.

[Chemical Formula 83]

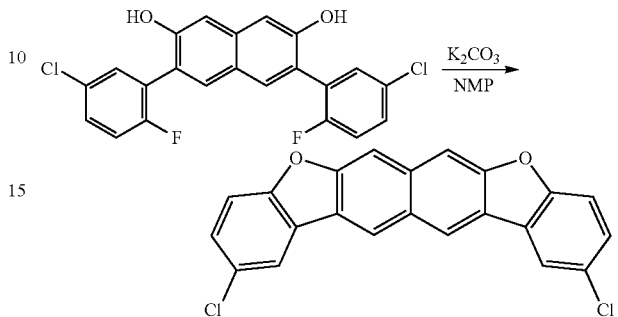

Figure 18A:
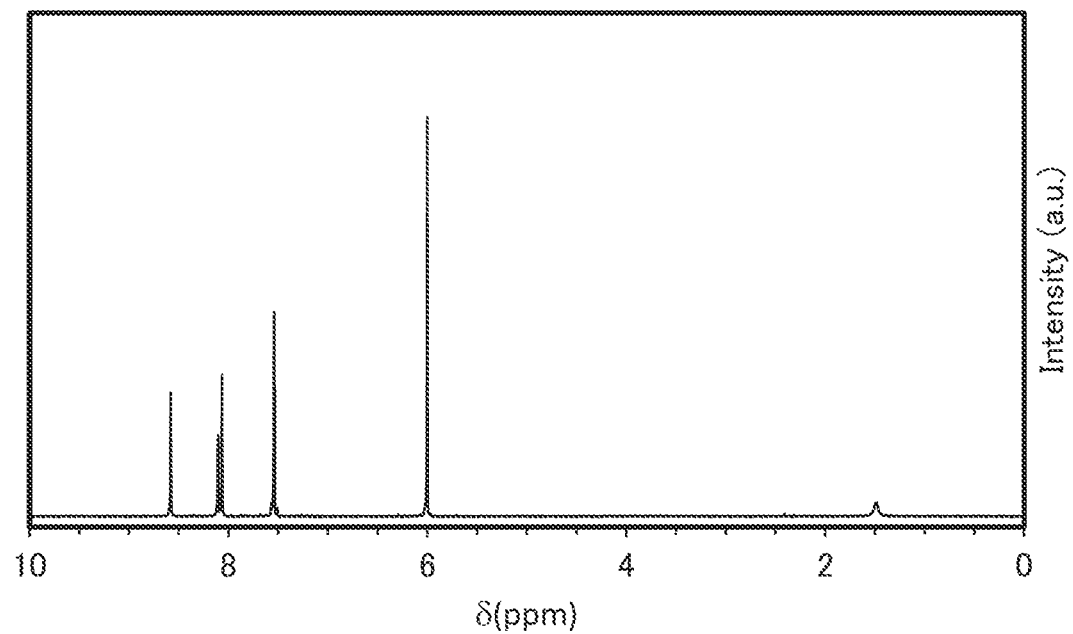
FIGS. 18A and 18B show ¹H NMR spectra of 2,11-dichloronaphtho[2,3-b;7,6-b']bisbenzofuran.
Figure 18B:
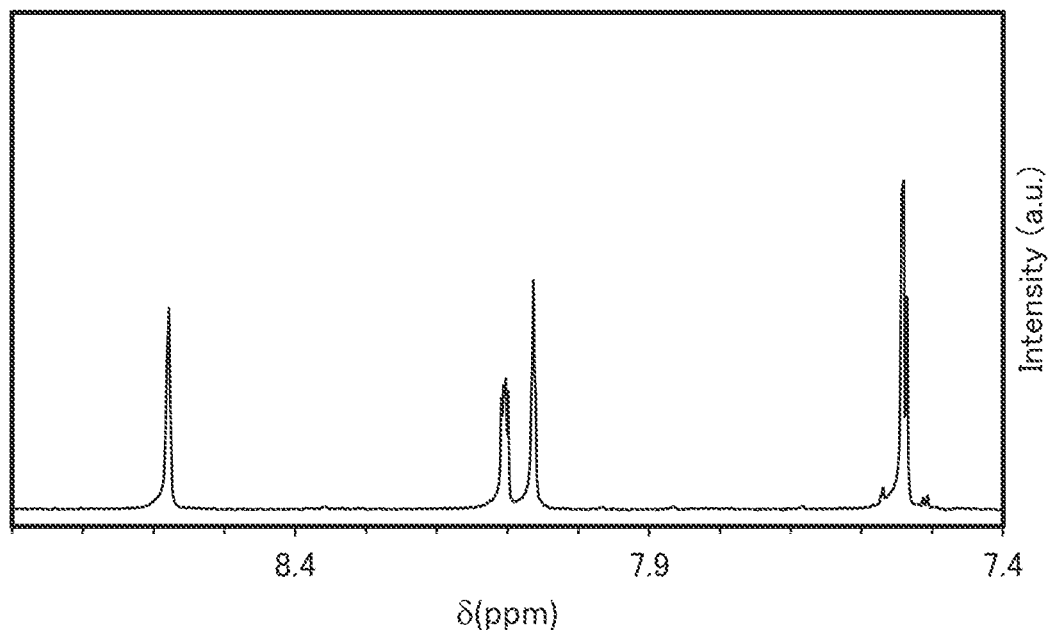

FIGS. 18A and 18B show $^1$H NMR charts of the resulting solid, whose numerical data is shown below. These indicate that 2,11-dichloronaphtho[2,3-b;7,6-b']bisbenzofuran was obtained in this synthesis example.

$^1$H NMR (1,1,2,2-Tetrachloroethane-D2, 300 MHz): δ=7.53-7.54 (m, 4H), 8.06 (s, 2H), 8.10 (dd, J1=0.9 Hz, J1=2.1 Hz, 2H), 8.58 (s, 2H).

Step 4: Synthesis of 2,11-bis(diphenylamino)naphtho[2,3-b;7,6-b']bisbenzofuran (abbreviation: 2,11DPhA2Nbf(II))

Into a 200-mL three-neck flask were put 1.5 g (3.9 mmol) of 2,11-dichloronaphtho[2,3-b;7,6-b']bisbenzofuran, 2.0 g (12 mmol) of diphenylamine, 0.14 g (0.39 mmol) of di(1-adamantyl)-n-butylphosphine, and 2.2 g (23 mmol) of sodium tert-butoxide. To the mixture was added 40 mL of xylene. The resulting mixture was degassed by being stirred while the pressure was reduced. To this mixture was added 45 mg (77 μmol) of bis(dibenzylideneacetone)palladium(0), and stirring was performed under a nitrogen stream at 150° C. for 14 hours. After the stirring, toluene was added to the mixture, and the resulting mixture was suction-filtered through Florisil, Celite, and alumina to give a filtrate. The obtained filtrate was concentrated to give a solid.

This solid was purified by silica gel column chromatography (as the developing solvent, first, toluene and hexane in a ratio of 1:3 were used, and then toluene and hexane in a ratio of 1:2 were used) to give a solid.

The resulting solid was recrystallized with a mixed solvent of toluene and ethanol to give 1.7 g of a pale yellow solid in a yield of 68%. A synthesis scheme of Step 4 is shown below.

[Chemical Formula 84]

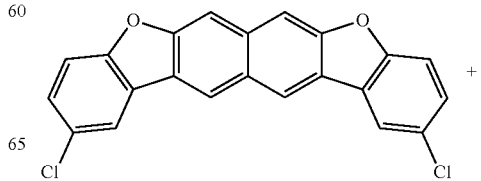

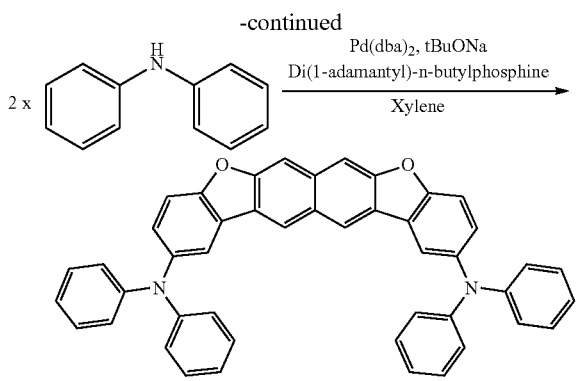

Figure 19A:
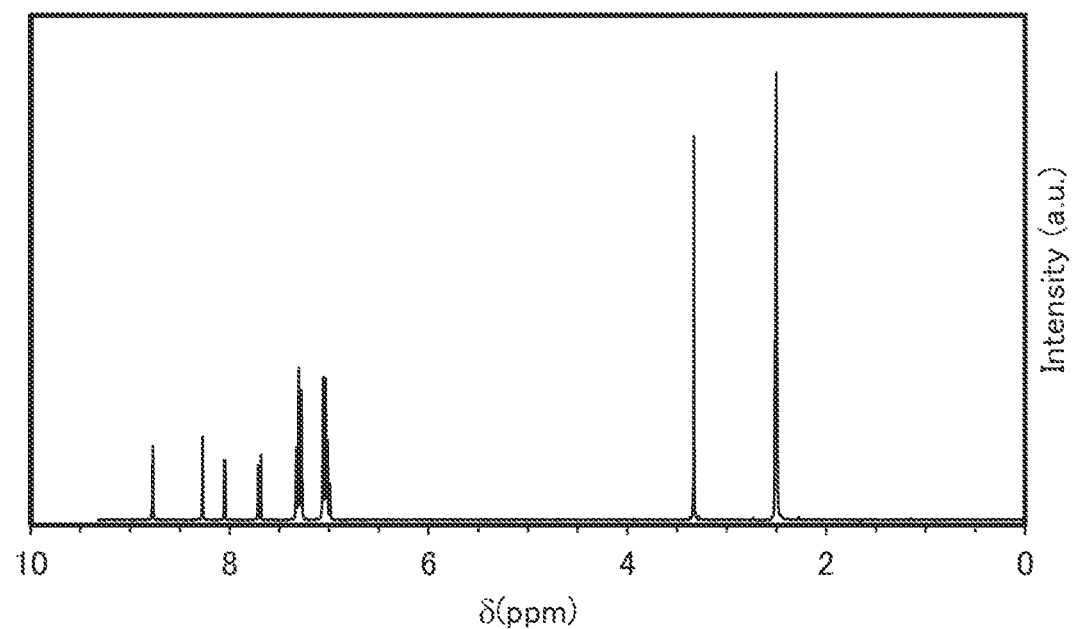
FIGS. 19A and 19B show ¹H NMR spectra of 2,11-bis(diphenylamino)naphtho[2,3-b;7,6-b']bisbenzofuran (abbreviation: 2,11DPhA2Nbf(II)).
Figure 19B:
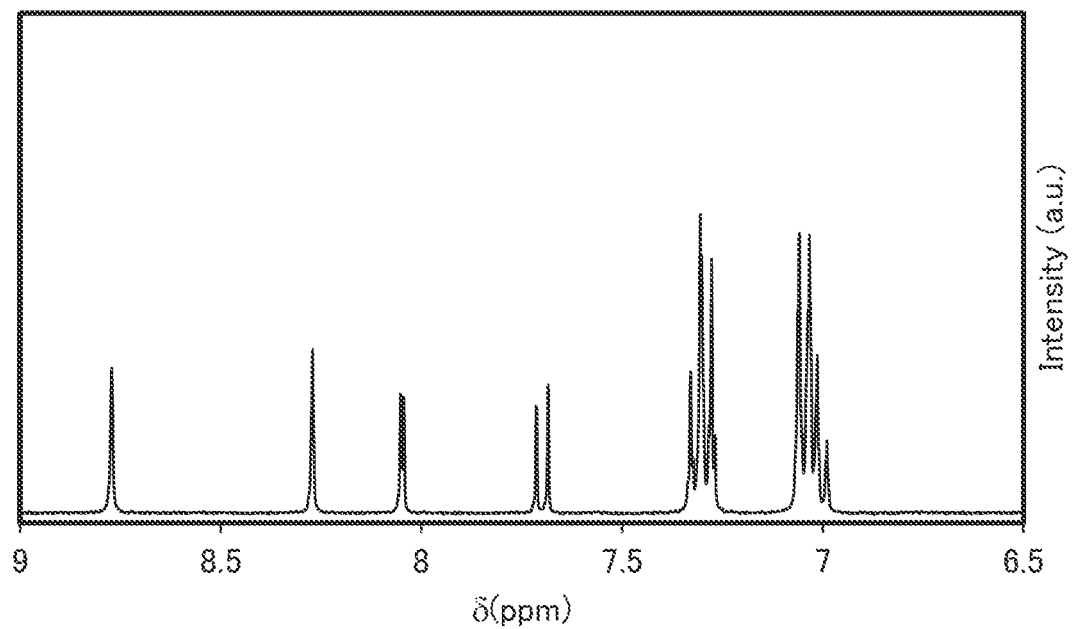

FIGS. 19A and 19B show ¹H NMR charts of the resulting solid, whose numerical data is shown below. These indicate that 2,11DPhA2Nbf(II), which is an organic compound of one embodiment of the present invention, was obtained in this synthesis example.

¹H NMR (DMSO-d₆, 300 MHz): δ=6.99-7.06 (m, 12H), 7.27-7.33 (m, 10H), 7.70 (d, J1=8.4 Hz, 2H), 8.05 (d, J1=2.4 Hz, 2H), 8.27 (s, 2H), 8.77 (s, 2H).

Then, 1.6 g of the resulting solid was purified by a train sublimation method under a pressure of 3.9 Pa with an argon flow rate of 15 mL/min at 295° C. After the purification by sublimation, 1.3 g of a pale yellow solid was obtained at a collection rate of 78%.

Figure 20:
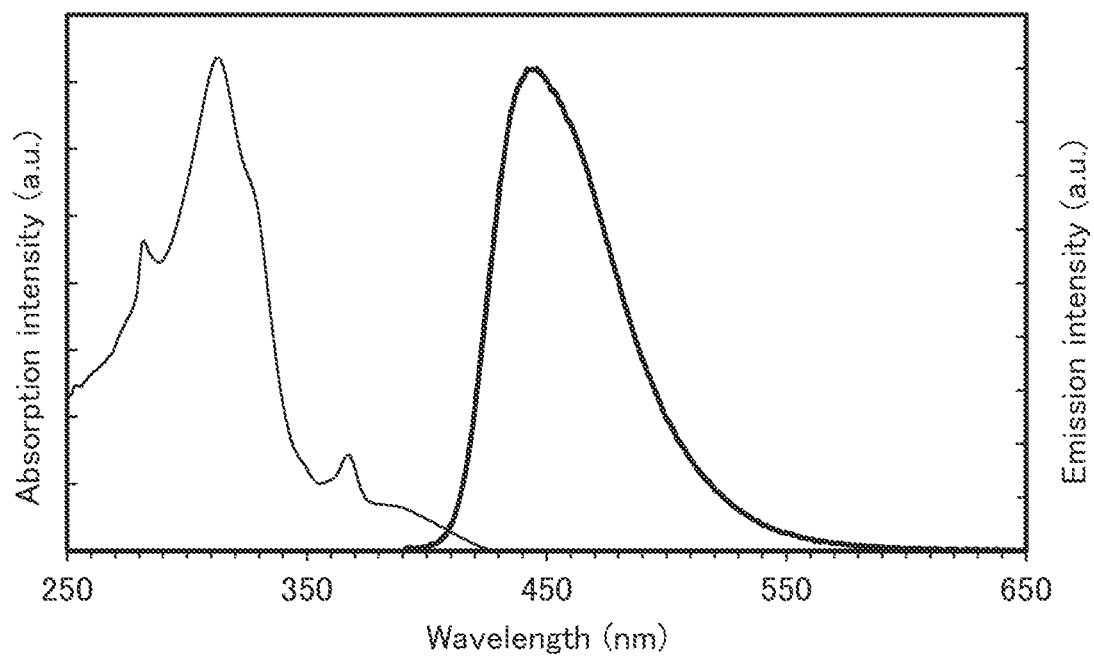
FIG. 20 shows an absorption spectrum and an emission spectrum of 2,11DPhA2Nbf(II) in a toluene solution.
Figure 21:
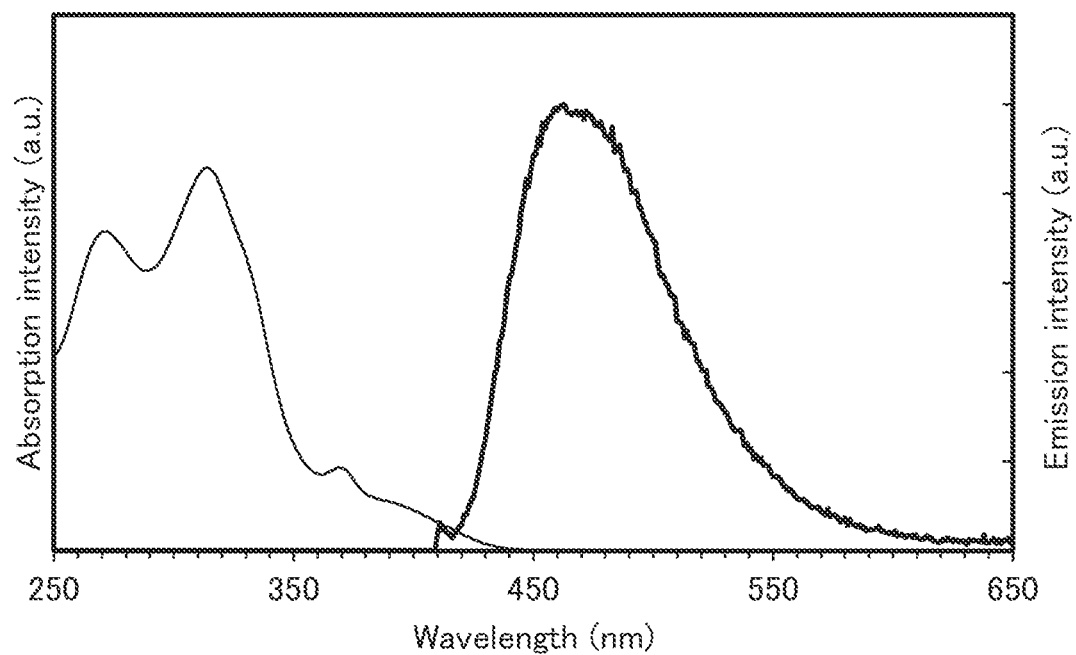
FIG. 21 shows an absorption spectrum and an emission spectrum of a thin film of 2,11DPhA2Nbf(II).

Next, FIG. 20 shows the measurement results of the absorption and emission spectra of 2,11DPhA2Nbf(II) in a toluene solution. FIG. 21 shows the absorption and emission spectra of a thin film of 2,11DPhA2Nbf(II). The solid thin film was formed over a quartz substrate by a vacuum evaporation method. The absorption spectrum of the toluene solution was measured with an ultraviolet-visible light spectrophotometer (V550, manufactured by JASCO Corporation), and FIG. 20 shows a spectrum obtained by subtracting the spectrum of toluene from the spectrum of 2,11DPhA2Nbf(II) in the toluene solution. The absorption spectrum of the thin film was measured with a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.). Quantum yields were measured using an absolute PL quantum yield measurement system (Quantaurus-QY, manufactured by Hamamatsu Photonics K. K.).

As shown in FIG. 20, 2,11DPhA2Nbf(II) in the toluene solution has absorption peaks at around 389 nm, 367 nm, 326 nm, 313 nm, and 282 nm, and an emission wavelength peak at 445 nm (excitation wavelength: 368 nm). As shown in FIG. 21, the thin film of 2,11DPhA2Nbf(II) has absorption peaks at around 390 nm, 373 nm, 333 nm, 313 nm, 272 nm, and 237 nm, and an emission wavelength peak at around 468 nm (excitation wavelength: 400 nm). These results indicate that 2,11DPhA2Nbf(II) emits blue light and can be used as a host for a light-emitting substance or a substance which emits fluorescence in the visible region.

The measured quantum yield of 2,11DPhA2Nbf(II) in the toluene solution was 29%, which is relatively high. This implies that 2,11DPhA2Nbf(II) is suitable for a light-emitting material.

From the above results, it was found that the emission spectrum of the compound of one embodiment of the present invention in which diarylamine is bonded to the 2-position and the 9-position of a naphtho[2,3-b;7,6-b']bisbenzofuran skeleton or a naphtho[2,3-b;7,6-b']bisbenzothiophene skeleton is relatively broad. Thus, the compound is suitable for a light-emitting material for lighting.

Next, 2,11DPhA2Nbf(II) obtained in this example was analyzed by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving 2,11DPhA2Nbf(II) in an organic solvent at a given concentration, and the injection amount was 5.0 μL.

A component with m/z of 642.23, which is an ion derived from 2,11DPhA2Nbf(II), was subjected to the MS² analysis by a Targeted-MS² method. For setting of the Targeted-MS², the mass range of a target ion was set to m/z=642.23±2.0 (isolation window=4) and detection was performed in a positive mode. The analysis was performed with energy (normalized collision energy: NCE) for accelerating a target ion in a collision cell set to 60. The obtained MS spectrum is shown in FIG. 22.

Figure 22:
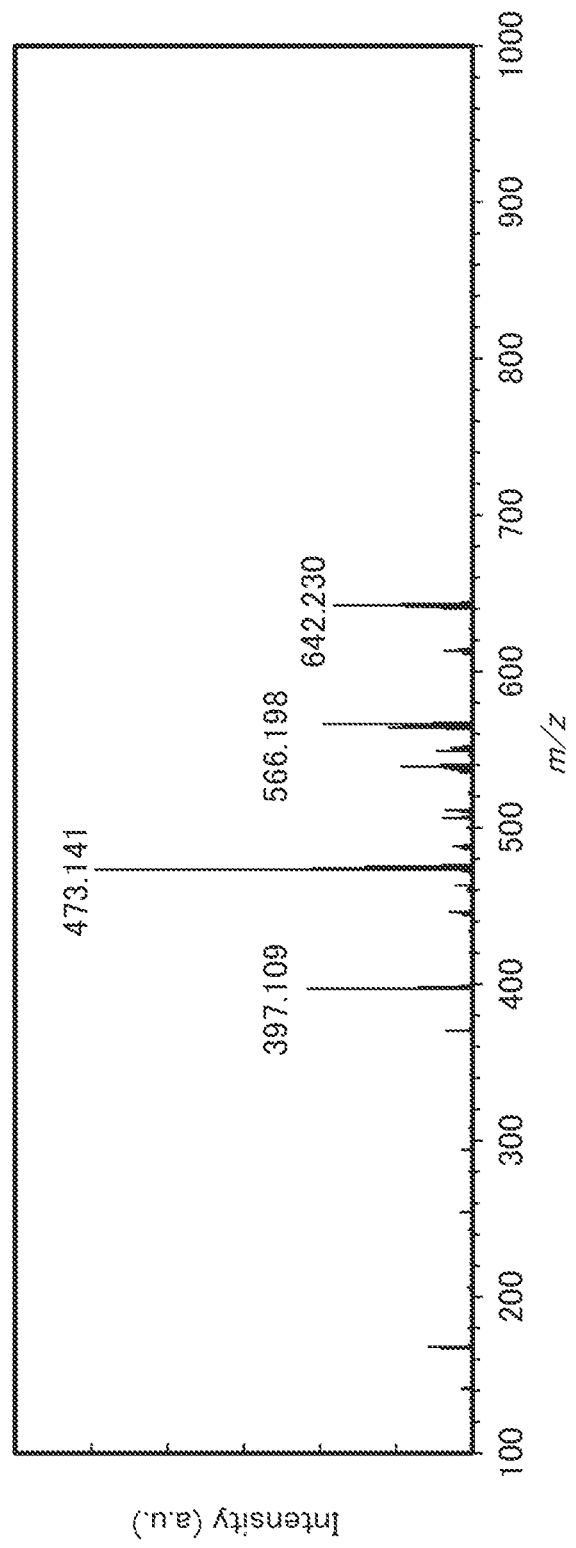
FIG. 22 shows an MS spectrum of 2,11DPhA2Nbf(II).

FIG. 22 shows that product ions of 2,11DPhA2Nbf(II) are mainly detected at m/z of around 566, 473, and 397. Note that the results in FIG. 22 show characteristics derived from 2,11DPhA2Nbf(II) and therefore can be regarded as important data for identifying 2,11DPhA2Nbf(II) contained in the mixture.

It can be presumed that the product ion around m/z=566 is a cation in a state where a phenyl group is eliminated from 2,11DPhA2Nbf(II). This suggests that 2,11DPhA2Nbf(II) contains a phenyl group. It can also be presumed that the product ion around m/z=473 is a cation in a state where a diphenylamino group is eliminated from 2,11DPhA2Nbf (II). This suggests that 2,11DPhA2Nbf(II) contains a diphenylamino group.

Example 2

Synthesis Example 2

In this example, a synthesis example of 3,10-bis(diphenylamino)naphtho[2,3-b;7,6-b']bisbenzofuran (abbreviation: 3,10DPhA2Nbf(II)), which is represented by Structural Formula (100) in Embodiment 1, will be described in detail. The structural formula of 3,10DPhA2Nbf(II) is shown below.

[Chemical Formula 85]

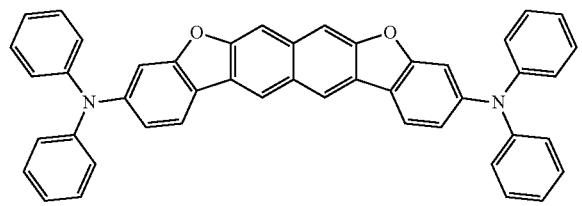

Step 1: Synthesis of 3,6-bis(4-chloro-2-fluorophenyl)-2,7-dimethoxynaphthalene

Into a 200-mL three-neck flask were put 3.0 g (8.7 mmol) of 3,6-dibromo-2,7-dimethoxynaphthalene, 3.3 g (19 mmol)

of 4-chloro-2-fluorophenylboronic acid, 5.8 g (42 mmol) of potassium carbonate, and 0.13 g (0.43 mmol) of tris(2-methylphenyl)phosphine. To this mixture was added 85 mL of toluene. The resulting mixture was degassed by being stirred while the pressure was reduced. To the mixture was added 19 mg (87 µmol) of palladium(II) acetate, and stirring was performed under a nitrogen stream at 60° C. for 14 hours and then at 120° C. for 11.5 hours. In the midstream of the stirring, 3.0 g (17 mmol) of 4-chloro-2-fluorophenylboronic acid and 4.8 g (35 mmol) of potassium carbonate were added to the resulting mixture.

After the stirring, toluene was added to the mixture, and the resulting mixture was suction-filtered through Florisil (manufactured by Wako Pure Chemical Industries, Ltd., Catalog No. 540-00135), Celite (manufactured by Wako Pure Chemical Industries, Ltd., Catalog No. 531-16855), and alumina to give a filtrate. The filtrate was concentrated to give an oily substance. The obtained oily substance was purified by silica gel column chromatography (as the developing solvent, toluene and hexane in a ratio of 1:2 were used). The resulting solid was purified by high performance liquid column chromatography. The high performance liquid column chromatography was performed using chloroform as a developing solvent. The obtained fractions were concentrated to obtain 5.8 g of a white solid which was an objective substance in a yield of 76%. A synthesis scheme of Step 1 is shown below.

[Chemical Formula 86]

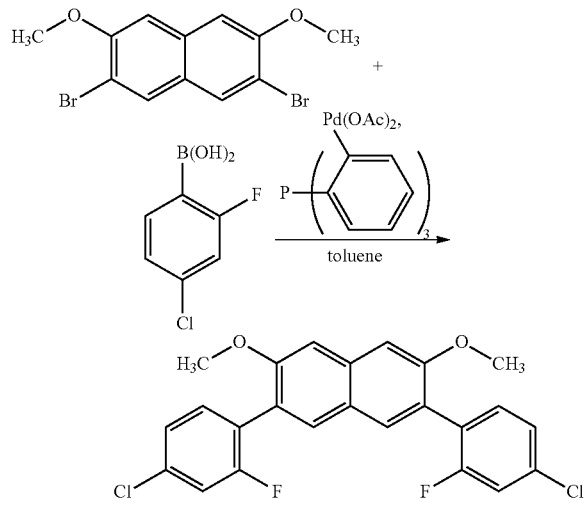

Figure 23A:
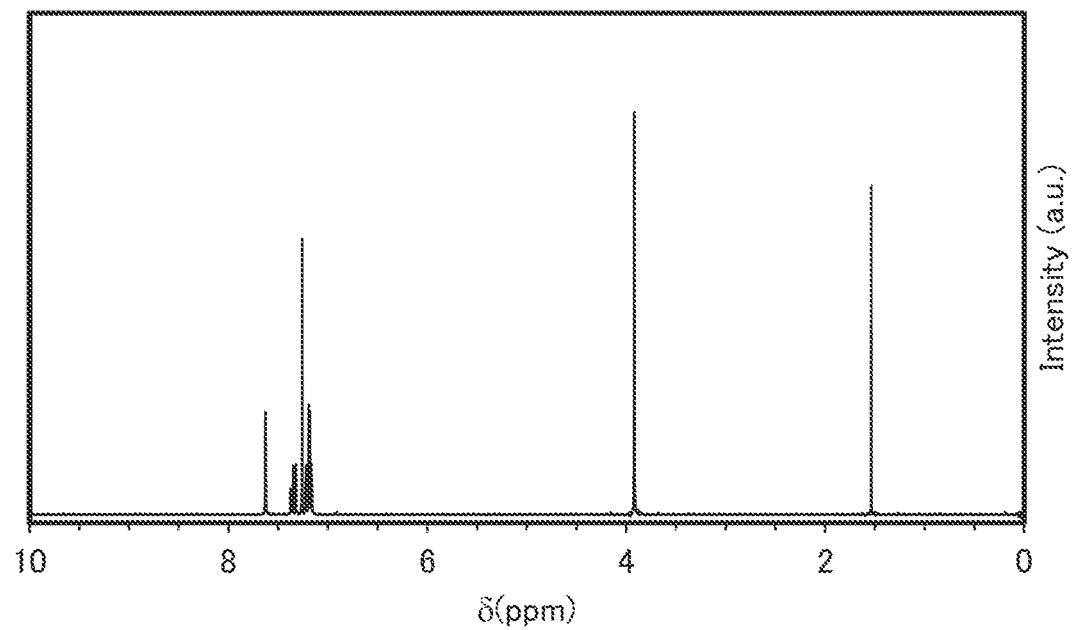
FIGS. 23A and 23B show ¹H NMR spectra of 3,6-bis(4-chloro-2-fluorophenyl)-2,7-dimethoxynaphthalene.
Figure 23B:
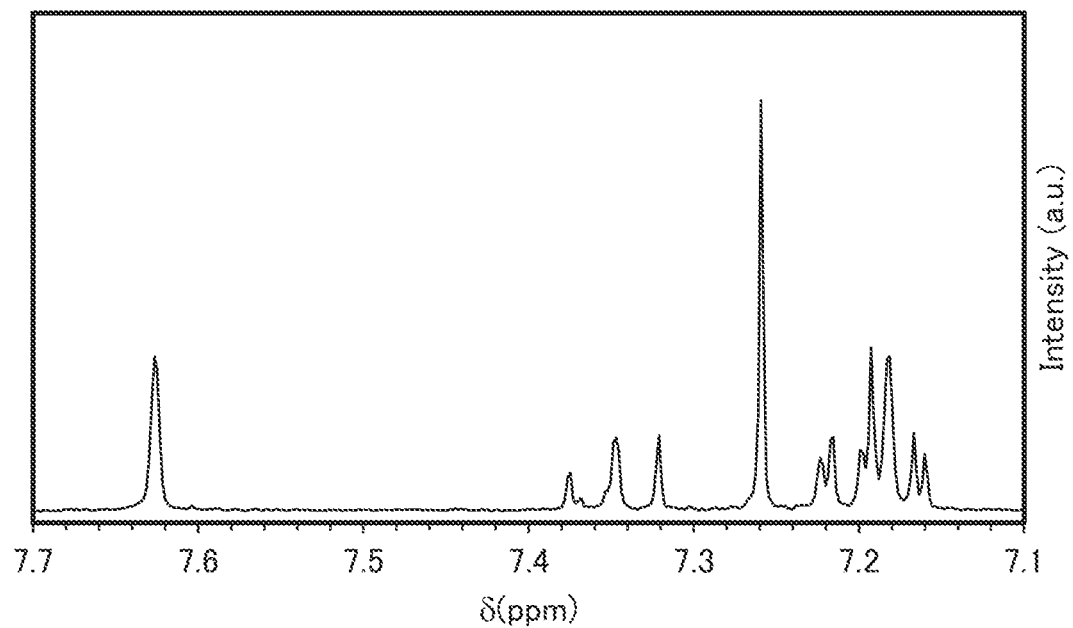

FIGS. 23A and 23B show $^1$H NMR charts of the resulting solid, whose numerical data is shown below. These indicate that 3,6-bis(4-chloro-2-fluorophenyl)-2,7-dimethoxynaphthalene was obtained in this synthesis example.

$^1$H NMR (CDCl$_3$, 300 MHz): δ=3.92 (s, 6H), 7.16-7.22 (m, 6H), 7.35 (t, J1=7.8 Hz, 2H), 7.63 (s, 2H).

Step 2: Synthesis of 3,6-bis(4-chloro-2-fluorophenyl)-2,7-dihydroxynaphthalene

Into a 200-mL three-neck flask was put 5.8 g (13 mmol) of 3,6-bis(4-chloro-2-fluorophenyl)-2,7-dimethoxynaphthalene. The air in the flask was replaced with nitrogen. Into the flask was additionally put 33 mL of dichloromethane. To the solution were dripped 29 mL of boron tribromide (approximately 1.0 mol/L dichloromethane solution) and 40 mL of dichloromethane. After the dripping, the resulting solution was stirred at room temperature. After that, approximately 20 mL of water was added to this solution under cooling with ice, and the solution was stirred. Then, the aqueous layer of this mixture was subjected to extraction with dichloromethane, and the extracted solution and the organic layer were combined and washed with water and a saturated aqueous solution of sodium hydrogen carbonate. Then, magnesium sulfate was added to the obtained organic layer to adsorb moisture, and the resulting mixture was subjected to gravity filtration. The obtained filtrate was concentrated to give 5.7 g of a white solid. A synthesis scheme of Step 2 is shown below.

[Chemical Formula 87]

Figure 24A:
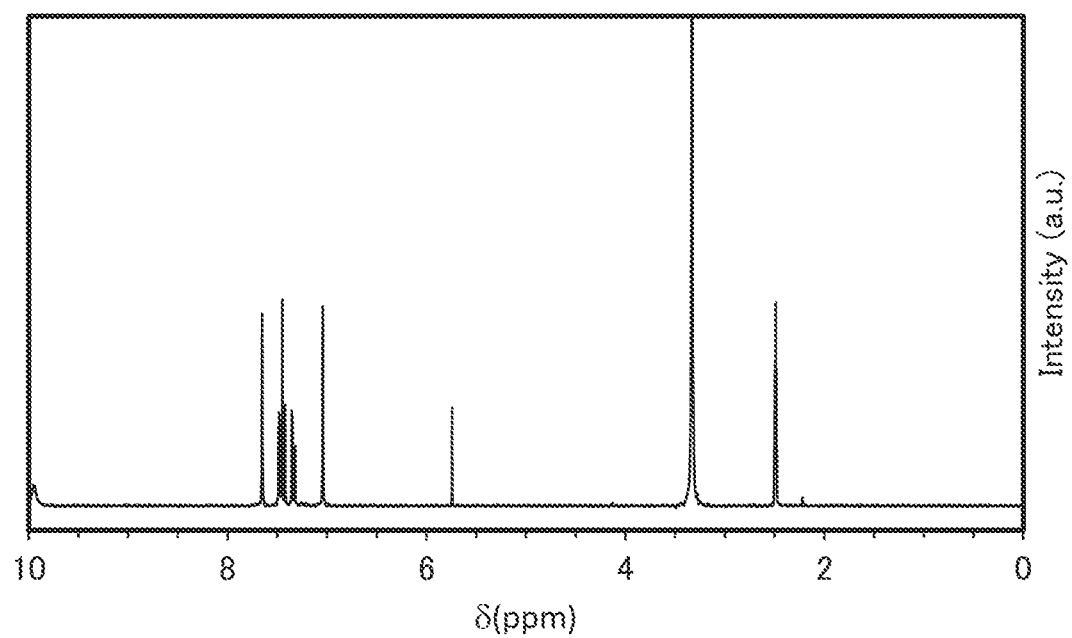
FIGS. 24A and 24B show ¹H NMR spectra of 3,6-bis(4-chloro-2-fluorophenyl)-2,7-dihydroxynaphthalene.
Figure 24B:
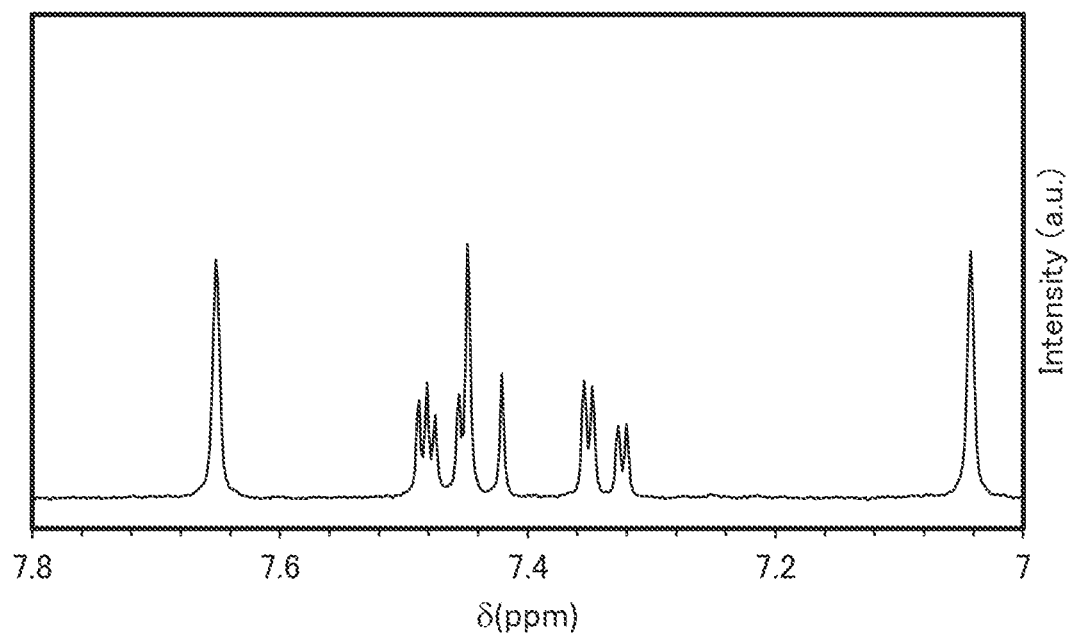

FIGS. 24A and 24B show $^1$H NMR charts of the obtained solid, whose numerical data is shown below. These indicate that 3,6-bis(4-chloro-2-fluorophenyl)-2,7-dihydroxynaphthalene was obtained in this synthesis example.

$^1$H NMR (DMSO-d$_6$, 300 MHz): δ=7.04 (s, 2H), 7.34 (dd, J1=8.4 Hz, J2=2.1 Hz, 2H), 7.42-7.49 (m, 4H), 7.65 (s, 2H), 9.95 (s, 2H).

Step 3: Synthesis of 3,10-dichloronaphtho[2,3-b;7,6-b']bisbenzofuran

Into a 200-mL three-neck flask were put 2.5 g (5.7 mmol) of 3,6-bis(4-chloro-2-fluorophenyl)-2,7-dihydroxynaphthalene and 7.6 g (55 mmol) of potassium carbonate. To this mixture was added 137 mL of N-methyl-2-pyrrolidone. The resulting mixture was degassed by being stirred while the pressure was reduced. After that, this mixture was stirred under a nitrogen stream at 120° C. for 6 hours. After that, water was added to the mixture, and a precipitated solid was collected by filtration. The obtained solid was washed with water and ethanol. Ethanol was added to the resulting solid, heating and stirring were performed, and then the resulting mixture was filtered to give a solid. The obtained solid was recrystallized with toluene to give 4.4 g of a white solid in a yield of 86%. A synthesis scheme of Step 3 is shown below.

[Chemical Formula 88]

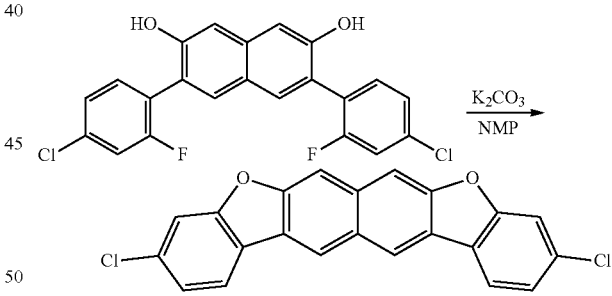

Figure 25A:
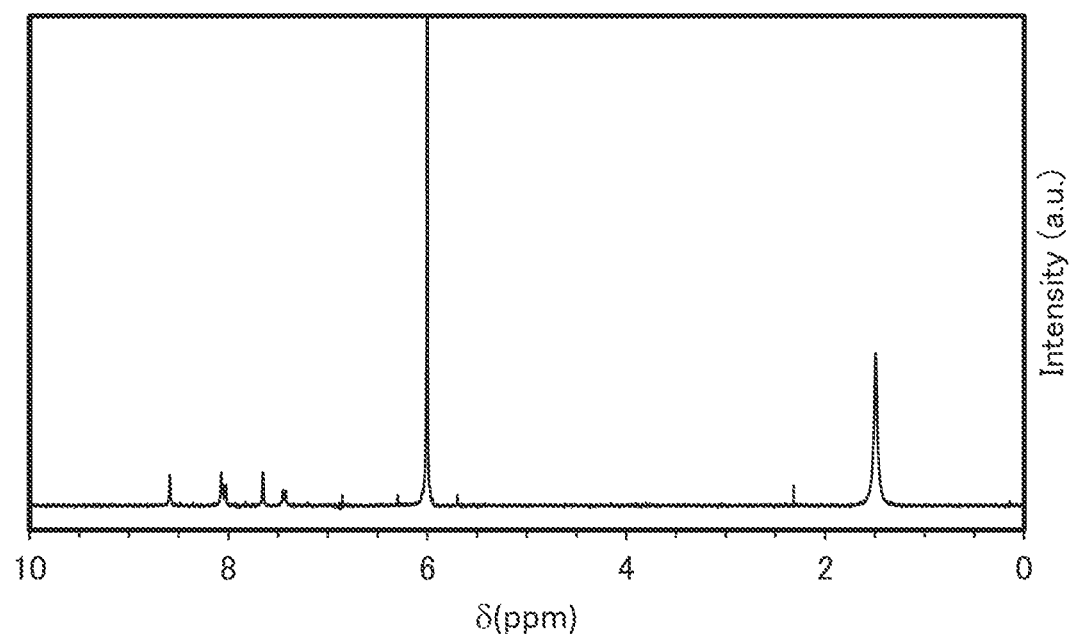
FIGS. 25A and 25B show ¹H NMR spectra of 3,10-dichloronaphtho[2,3-b;7,6-b']bisbenzofuran.
Figure 25B:
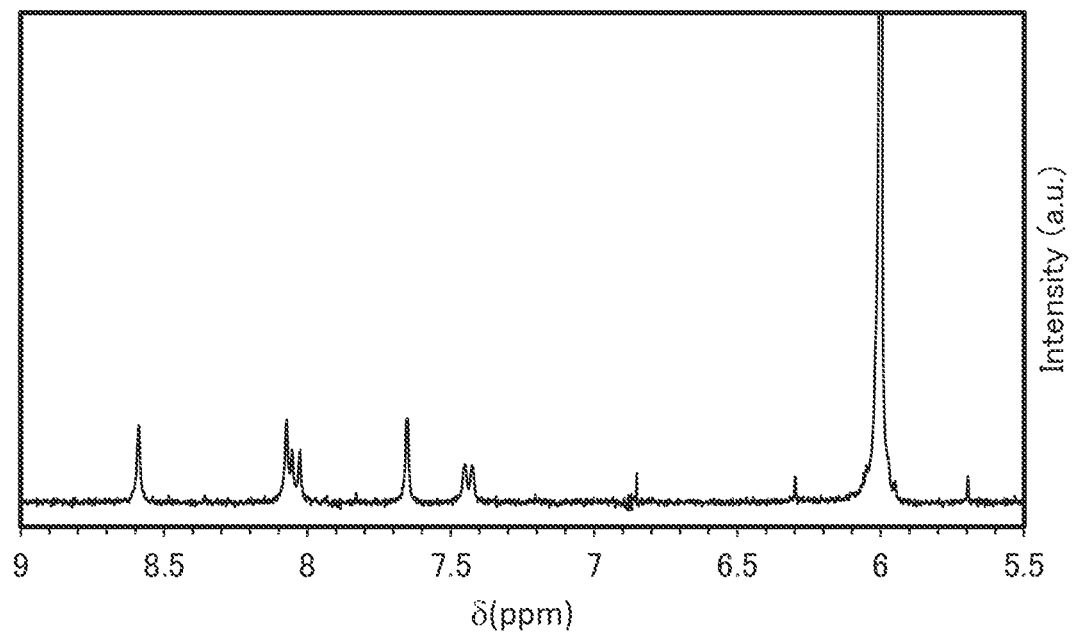

FIGS. 25A and 25B show $^1$H NMR charts of the resulting solid, whose numerical data is shown below. These indicate that 3,10-dichloro naphtho[2,3-b;7,6-b']bisbenzofuran was obtained in this synthesis example.

$^1$H NMR (1,1,2,2-Tetrachloroethane-D2, 300 MHz): δ=7.44 (d, J1=7.8 Hz, 2H), 7.65 (s, 2H), 8.04 (d, J1=8.4 Hz, 2H), 8.07 (s, 2H), 8.59 (s, 2H).

Step 4: Synthesis of 3,10-bis(diphenylamino)naphtho[2,3-b;7,6-b']bisbenzofuran (Abbreviation: 3,10DPhA2Nbf(II))

Into a 200-mL three-neck flask were put 1.5 g (3.9 mmol) of 3,10-dichloronaphtho[2,3-b;7,6-b']bisbenzofuran, 2.0 g (12 mmol) of diphenylamine, 0.14 g (0.39 mmol) of di(1-adamantyl)-n-butylphosphine, and 2.2 g (23 mmol) of sodium tert-butoxide. To the mixture was added 40 mL of xylene. The resulting mixture was degassed by being stirred while the pressure was reduced. To this mixture was added 45 mg (78 μmol) of bis(dibenzylideneacetone)palladium(0), and stirring was performed under a nitrogen stream at 150° C. for 14 hours. After the stirring, toluene was added to the mixture, and the resulting mixture was suction-filtered through Florisil (manufactured by Wako Pure Chemical Industries, Ltd., Catalog No. 540-00135), Celite (manufactured by Wako Pure Chemical Industries, Ltd., Catalog No. 531-16855), and alumina to give a filtrate. The obtained filtrate was concentrated to give a solid. This solid was purified by silica gel column chromatography (as the developing solvent, a mixed solvent of toluene and hexane in a ratio of 1:3 was used) to give a solid. The resulting solid was recrystallized with a mixed solvent of toluene and ethanol to give 2.0 g of a pale yellow solid in a yield of 81%. A synthesis scheme of Step 4 is shown below.

[Chemical Formula 89]

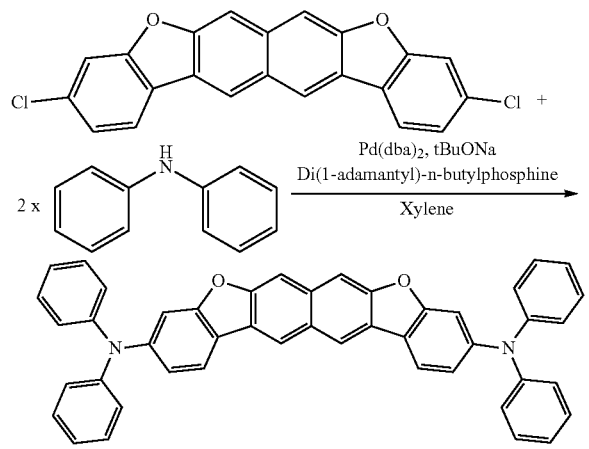

Figure 26A:
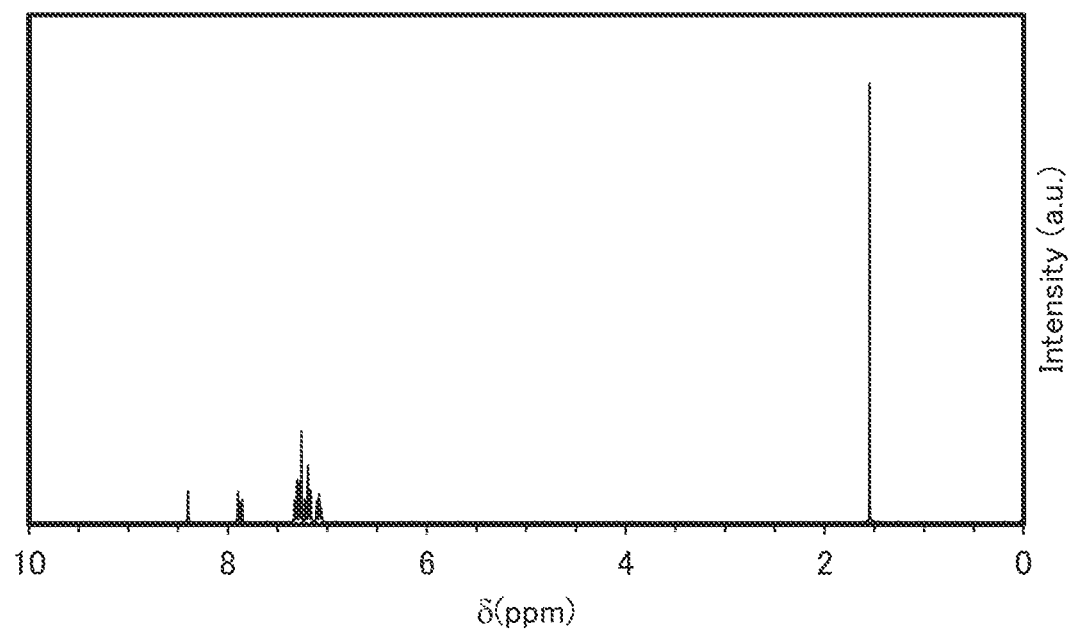
FIGS. 26A and 26B show ¹H NMR spectra of 3,10-bis(diphenylamino)naphtho[2,3-b;7,6-b']bisbenzofuran (abbreviation: 3,10DPhA2Nbf(II)).
Figure 26B:
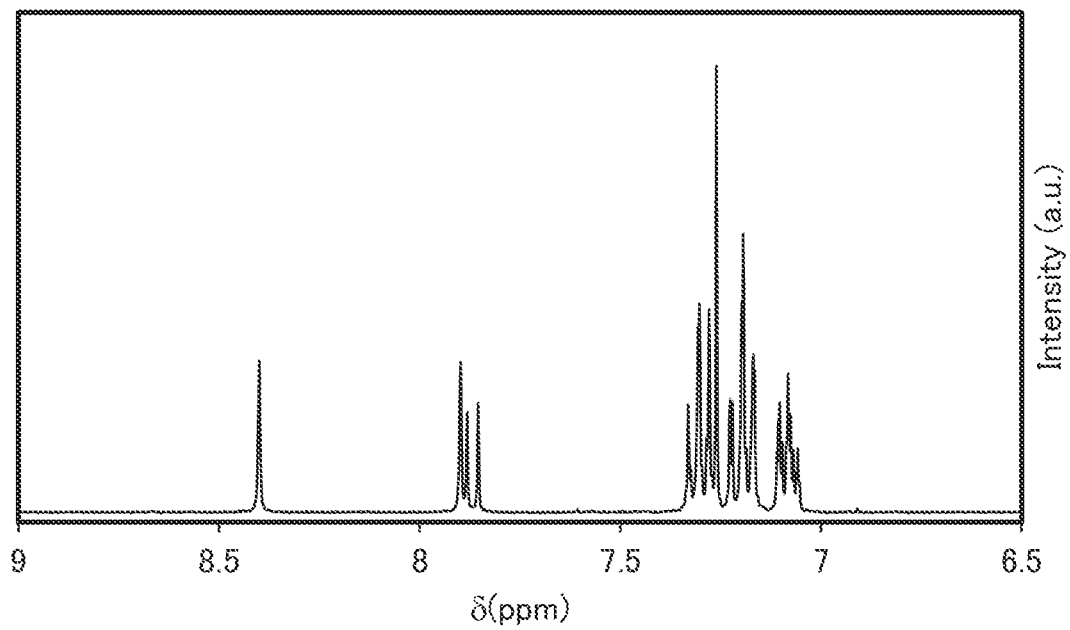

FIGS. 26A and 26B show $^1$H NMR charts of the resulting solid, whose numerical data is shown below. These indicate that 3,10DPhA2Nbf(II), which is an organic compound of one embodiment of the present invention, was obtained in this synthesis example.

$^1$H NMR (CDCl$_3$, 300 MHz): δ=7.05-7.11 (m, 6H), 7.17-7.20 (m, 8H), 7.22 (d, J1=2.1 Hz, 2H), 7.27-7.33 (m, 8H), 7.87 (d, J1=8.4 Hz, 2H), 7.90 (s, 2H), 8.40 (s, 2H).

Then, 2.0 g of the resulting solid was purified by a train sublimation method under a pressure of 4.1 Pa with an argon flow rate of 15 mL/min at 300° C. After the purification by sublimation, 1.7 g of an yellow solid was obtained at a collection rate of 86%.

Figure 27:
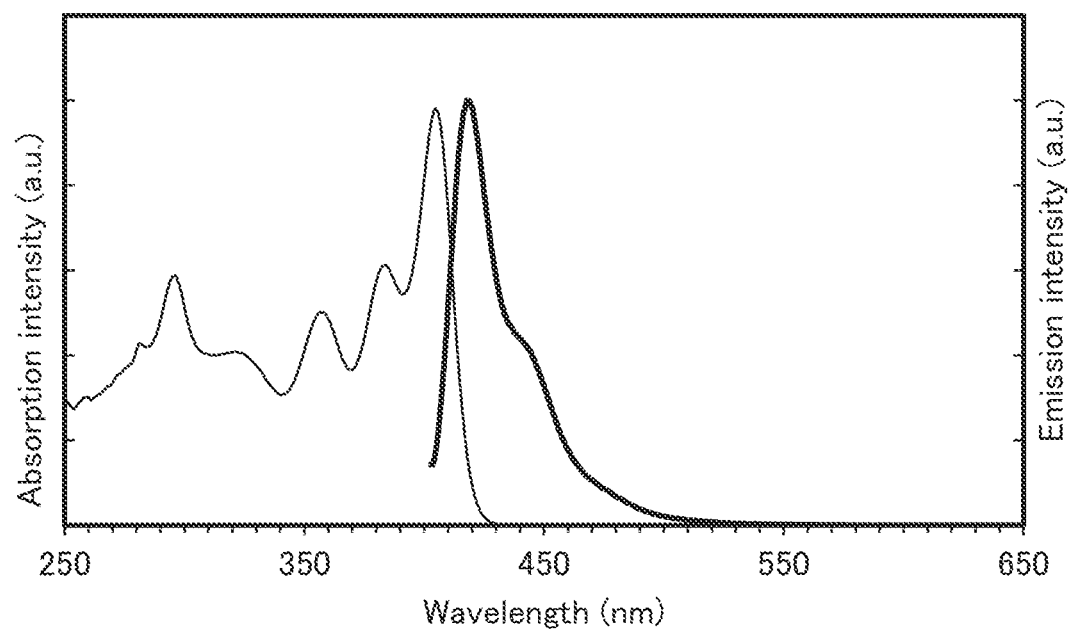
FIG. 27 shows an absorption spectrum and an emission spectrum of 3,10DPhA2Nbf(II) in a toluene solution.
Figure 28:
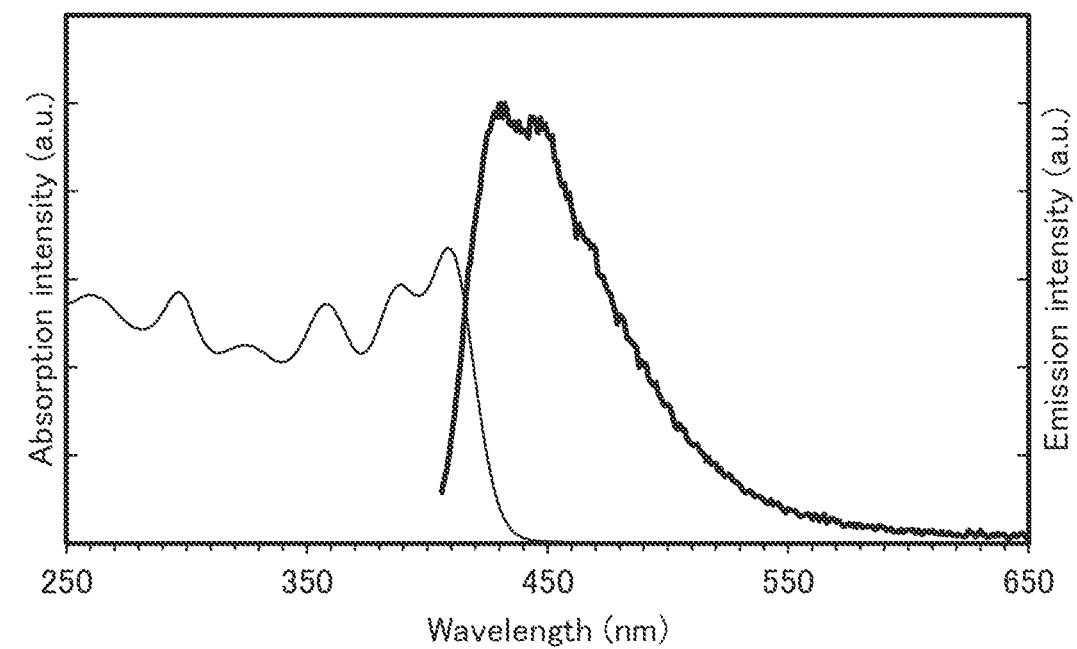
FIG. 28 shows an absorption spectrum and an emission spectrum of a thin film of 3,10DPhA2Nbf(II).

Next, FIG. 27 shows the measurement results of the absorption and emission spectra of 3,10DPhA2Nbf(II) in a toluene solution. FIG. 28 shows the absorption and emission spectra of a thin film of 3,10DPhA2Nbf(II). The solid thin film was formed over a quartz substrate by a vacuum evaporation method. The absorption spectrum of the toluene solution was measured with an ultraviolet-visible light spectrophotometer (V550, manufactured by JASCO Corporation), and FIG. 27 shows a spectrum obtained by subtracting the spectrum of toluene from the spectrum of 3,10DPhA2Nbf(II) in the toluene solution. The absorption spectrum of the thin film was measured with a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.). Quantum yields were measured using an absolute PL quantum yield measurement system (Quantaurus-QY, manufactured by Hamamatsu Photonics K. K.).

As shown in FIG. 27, 3,10DPhA2Nbf(II) in the toluene solution has absorption peaks at around 403 nm, 383 nm, 357 nm, 322 nm, and 296 nm, and emission wavelength peaks at 419 nm and 442 nm (excitation wavelength: 383 nm). As shown in FIG. 28, the thin film of 3,10DPhA2Nbf (II) has absorption peaks at around 411 nm, 389 nm, 359 nm, 325 nm, 298 nm, 261 nm, and 225 nm, and emission wavelength peaks at around 430 nm and 447 nm (excitation wavelength: 400 nm). These results indicate that 3,10DPhA2Nbf(II) emits blue light and can be used as a host for a light-emitting substance or a substance which emits fluorescence in the visible region.

The measured quantum yield of 3,10DPhA2Nbf(II) in the toluene solution was as high as 87%, which indicates that 3,10DPhA2Nbf(II) is suitable for a light-emitting material.

From the above results, it was found that the quantum yield of the compound of one embodiment of the present invention in which diarylamine is bonded to the 3-position and the 10-position of a naphtho[2,3-b;7,6-b']bisbenzofuran skeleton is noticeably high. The compound also exhibited a sharp emission spectrum, which means that it has high color purity. Thus, the compound is suitable for a light-emitting material for displays.

Next, 3,10DPhA2Nbf(II) obtained in this example was analyzed by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving 3,10DPhA2Nbf(II) in an organic solvent at a given concentration, and the injection amount was 5.0 μL.

A component with m/z of 642.23, which is an ion derived from 3,10DPhA2Nbf(II), was subjected to the MS$^2$ analysis by a Targeted-MS$^2$ method. For setting of the Targeted-MS$^2$, the mass range of a target ion was set to m/z=642.23±2.0 (isolation window=4) and detection was performed in a positive mode. The analysis was performed with energy (normalized collision energy: NCE) for accelerating a target ion in a collision cell set to 60. The obtained MS spectrum is shown in FIG. 29.

Figure 29:
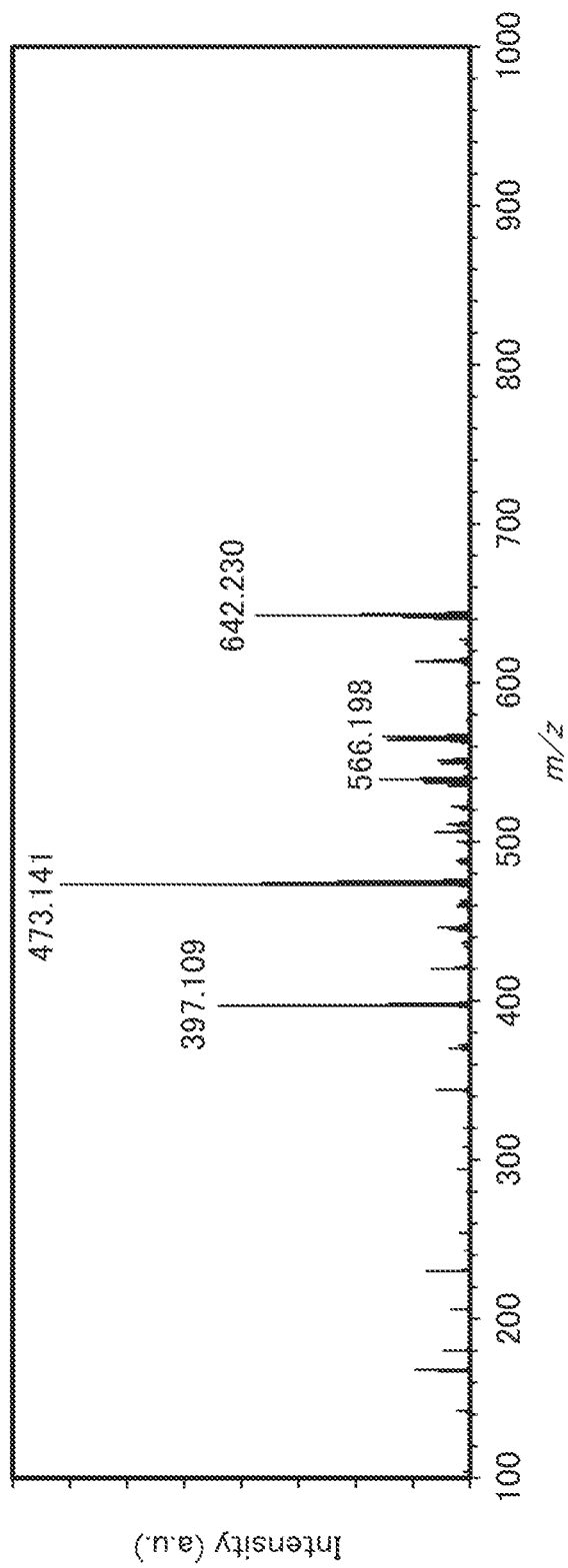
FIG. 29 shows an MS spectrum of 3,10DPhA2Nbf(II).

FIG. 29 shows that product ions of 3,10DPhA2Nbf(II) are mainly detected at m/z of around 566, 473, and 397. Note that the results in FIG. 29 show characteristics derived from 3,10DPhA2Nbf(II) and therefore can be regarded as important data for identifying 3,10DPhA2Nbf(II) contained in the mixture.

It can be presumed that the product ion around m/z=566 is a cation in a state where a phenyl group is eliminated from 3,10DPhA2Nbf(II). This suggests that 3,10DPhA2Nbf(II) contains a phenyl group. It can also be presumed that the product ion around m/z=473 is a cation in a state where a diphenylamino group is eliminated from 3,10DPhA2Nbf (II). This suggests that 3,10DPhA2Nbf(II) contains a diphenylamino group.

Example 3

Synthesis Example 3

In this example, a synthesis example of 3,10-bis[N-(4-biphenyl)-N-(9,9-dimethyl-9H-fluoren-2-yl)amino]naphtho [2,3-b;7,6-b']bisbenzofuran (abbreviation: 3,10FBi2Nbf (II)), which is the organic compound of one embodiment of the present invention represented by Structural Formula (109) in Embodiment 1, will be described. The structural formula of 3,10FBi2Nbf(II) is shown below.

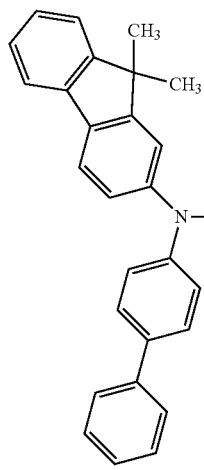
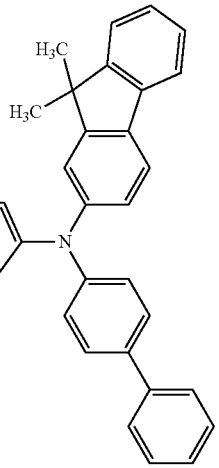

[Chemical Formula 90]

Step 1: Synthesis of 3,6-bis(4-chloro-2-fluorophenyl)-2,7-dimethoxynaphthalene

As in Step 1 in Synthesis Example 2, 3,6-bis(4-chloro-2-fluorophenyl)-2,7-dimethoxynaphthalene was synthesized.

Step 2: Synthesis of 3,6-bis(4-chloro-2-fluorophenyl)-2,7-dihydroxynaphthalene

As in Step 2 in Synthesis Example 2, 3,6-bis(4-chloro-2-fluorophenyl)-2,7-dimethoxynaphthalene was synthesized.

Step 3: Synthesis of 3,10-dichloronaphtho[2,3-b;7,6-b']bisbenzofuran

As in Step 3 in Synthesis Example 2, 3,10-dichloronaphtho[2,3-b;7,6-b']bisbenzofuran was synthesized.

Step 4: Synthesis of 3,10-bis[N-(4-biphenyl)-N-(9,9-dimethyl-9H-fluoren-2-yl)amino]naphtho[2,3-b;7,6-b']bisbenzofuran (Abbreviation: 3,10FBi2Nbf(II))

Into a 200-mL three-neck flask were put 0.73 g (2.0 mmol) of 3,10-dichloronaphtho[2,3-b;7,6-b']bisbenzofuran, 2.1 g (5.9 mmol) of N-(4-biphenyl)-(9,9-dimethylfluoren-2-yl)amine, 70 mg (0.20 mmol) of di(1-adamantyl)-n-butylphosphine, and 1.1 g (12 mmol) of sodium tert-butoxide. To the mixture was added 20 mL of xylene. The resulting mixture was degassed by being stirred while the pressure was reduced. To this mixture was added 22 mg (39 μmol) of bis(dibenzylideneacetone)palladium(0), and stirring was performed under a nitrogen stream at 150° C. for 15 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (as the developing solvent, first, toluene and hexane in a ratio of 1:3 were used, and then toluene and hexane in a ratio of 1:1 were used) to give a solid. The resulting solid was recrystallized with a mixed solvent of toluene and ethanol to give 1.7 g of a pale yellow solid in a yield of 86%. A synthesis scheme of Step 4 is shown below.

[Chemical Formula 91]

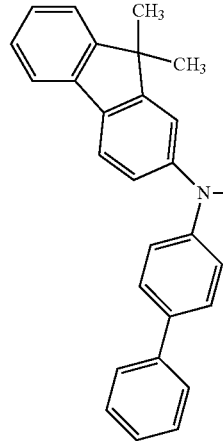
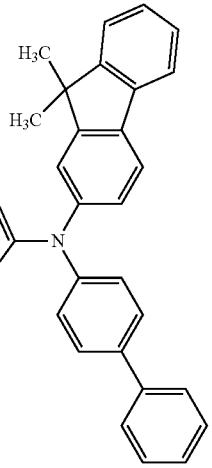

Figure 30A:
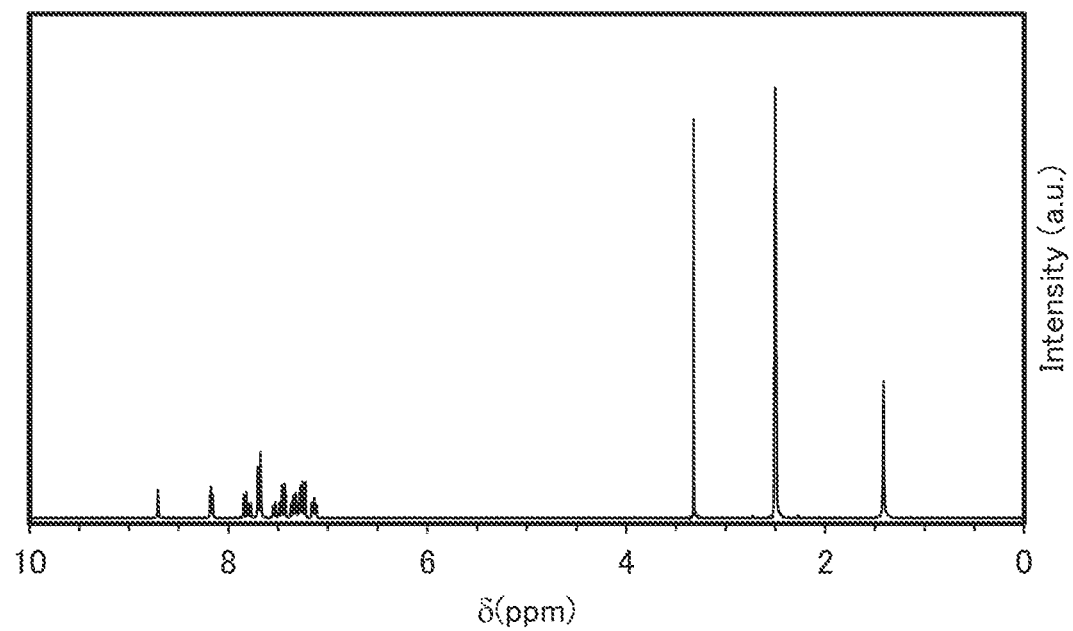
FIGS. 30A and 30B show ¹H NMR spectra of 3,10-bis[N-(4-biphenyl)-N-(9,9-dimethyl-9H-fluoren-2-yl)amino]naphtho[2,3-b;7,6-b']bisbenzofuran (abbreviation: 3,10FBi2Nbf(II)).
Figure 30B:
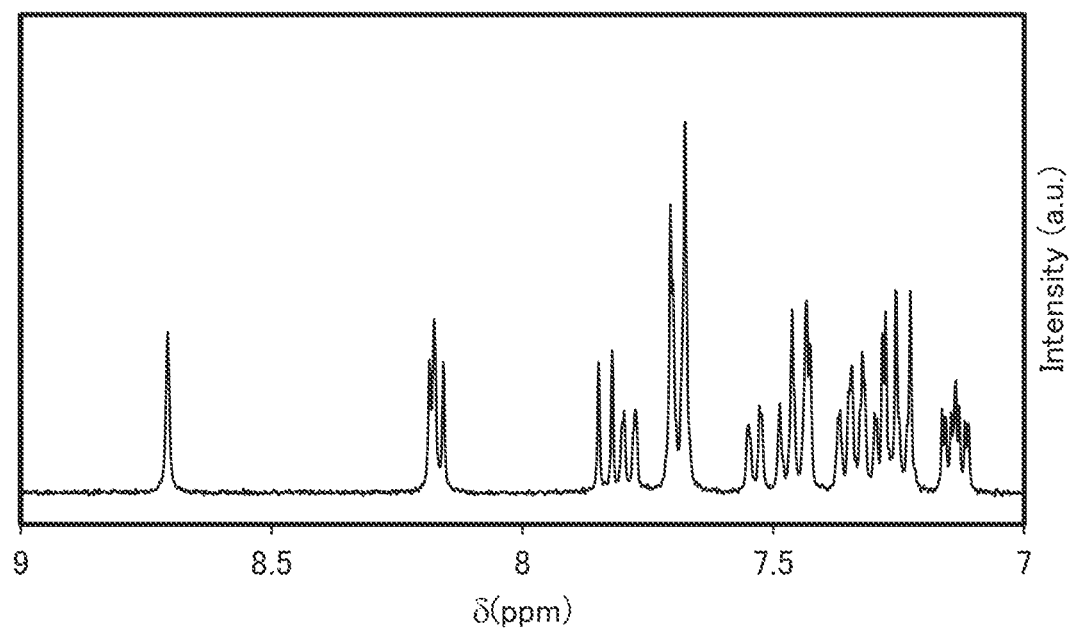

FIGS. 30A and 30B show ¹H NMR charts of the resulting solid, whose numerical data is shown below. These indicate that 3,10FBi2Nbf(II), which is an organic compound of one embodiment of the present invention, was obtained in this synthesis example.

¹H NMR (DMSO-d₆, 300 MHz): δ=1.41 (s, 12H), 7.11-7.16 (m, 4H), 7.23-7.37 (m, 12H), 7.43-7.49 (m, 6H), 7.54 (d, J1=7.8 Hz, 2H), 7.68-7.70 (m, 8H), 7.79 (d, J1=6.9 Hz, 2H), 7.83 (d, J1=7.8 Hz, 2H), 8.16-8.19 (m, 4H), 8.71 (s, 2H).

Figure 31:
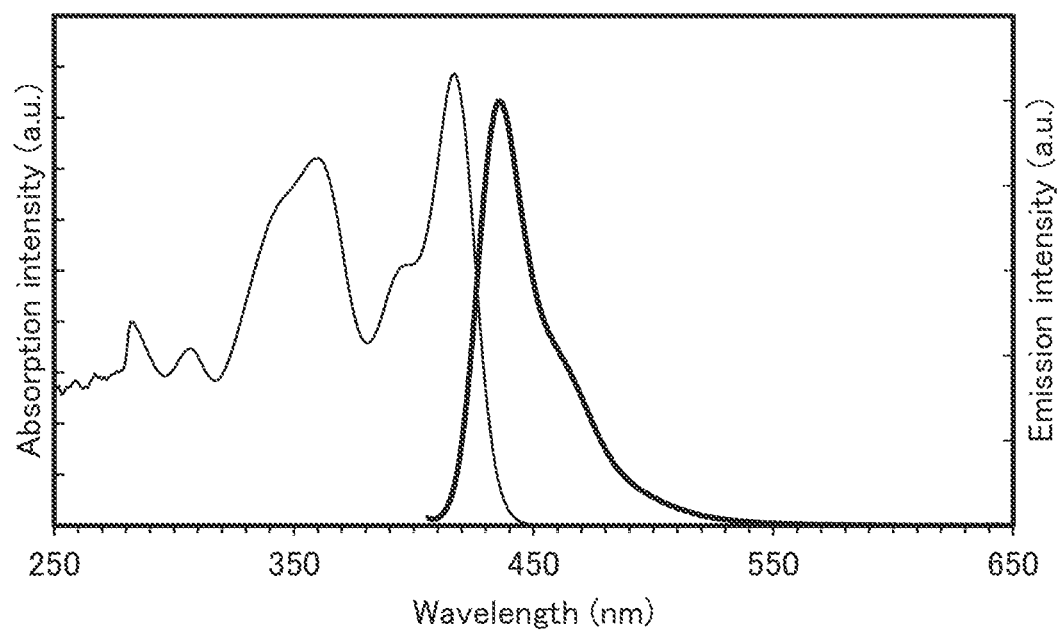
FIG. 31 shows an absorption spectrum and an emission spectrum of 3,10FBi2Nbf(II) in a toluene solution.
Figure 32:
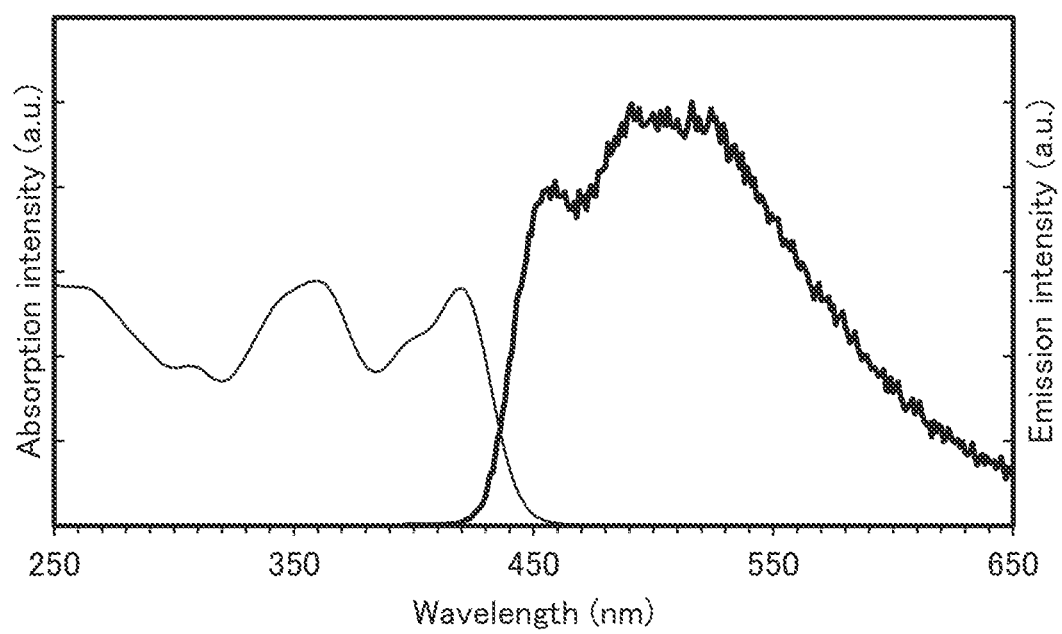
FIG. 32 shows an absorption spectrum and an emission spectrum of a thin film of 3,10FBi2Nbf(II).

Next, FIG. 31 shows the measurement results of the absorption and emission spectra of 3,10FBi2Nbf(II) in a toluene solution. FIG. 32 shows the absorption and emission spectra of a thin film of 3,10FBi2Nbf(II). The solid thin film was formed over a quartz substrate by a vacuum evaporation method. The absorption spectrum of the toluene solution was measured with an ultraviolet-visible light spectrophotometer (V550, manufactured by JASCO Corporation), and FIG. 31 shows a spectrum obtained by subtracting the spectrum of toluene from the spectrum of 3,10FBi2Nbf(II) in the toluene solution. The absorption spectrum of the thin film was measured with a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.). Quantum yields were measured using an absolute PL quantum yield measurement system (Quantaurus-QY, manufactured by Hamamatsu Photonics K. K.).

As shown in FIG. 31, 3,10FBi2Nbf(II) in the toluene solution has absorption peaks at around 417 nm, 395 nm, 360 nm, 307 nm, and 282 nm, and an emission wavelength peak at 436 nm (excitation wavelength: 400 nm). As shown in FIG. 32, the thin film of 3,10FBi2Nbf(II) has absorption peaks at around 420 nm, 398 nm, 358 nm, 348 nm, 308 nm, 263 nm, 248 nm, and 207 nm, and emission wavelength peaks at around 458 nm and 505 nm (excitation wavelength: 390 nm). These results indicate that 3,10FBi2Nbf(II) emits blue light and can be used as a host for a light-emitting substance or a substance which emits fluorescence in the visible region.

The measured quantum yield of 3,10FBi2Nbf(II) in the toluene solution was as high as 76%. This implies that 3,10FBi2Nbf(II) is suitable for a light-emitting material.

Next, 3,10FBi2Nbf(II) obtained in this example was analyzed by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving 3,10FBi2Nbf(II) in an organic solvent at a given concentration, and the injection amount was 5.0 µL.

A component with m/z of 1026.42, which is an ion derived from 3,10FBi2Nbf(II), was subjected to the MS² analysis by a Targeted-MS² method. For setting of the Targeted-MS², the mass range of a target ion was set to m/z=1026.42±2.0 (isolation window=4) and detection was performed in a positive mode. The analysis was performed with energy (normalized collision energy: NCE) for accelerating a target ion in a collision cell set to 50. The obtained MS spectrum is shown in FIG. 33.

Figure 33:
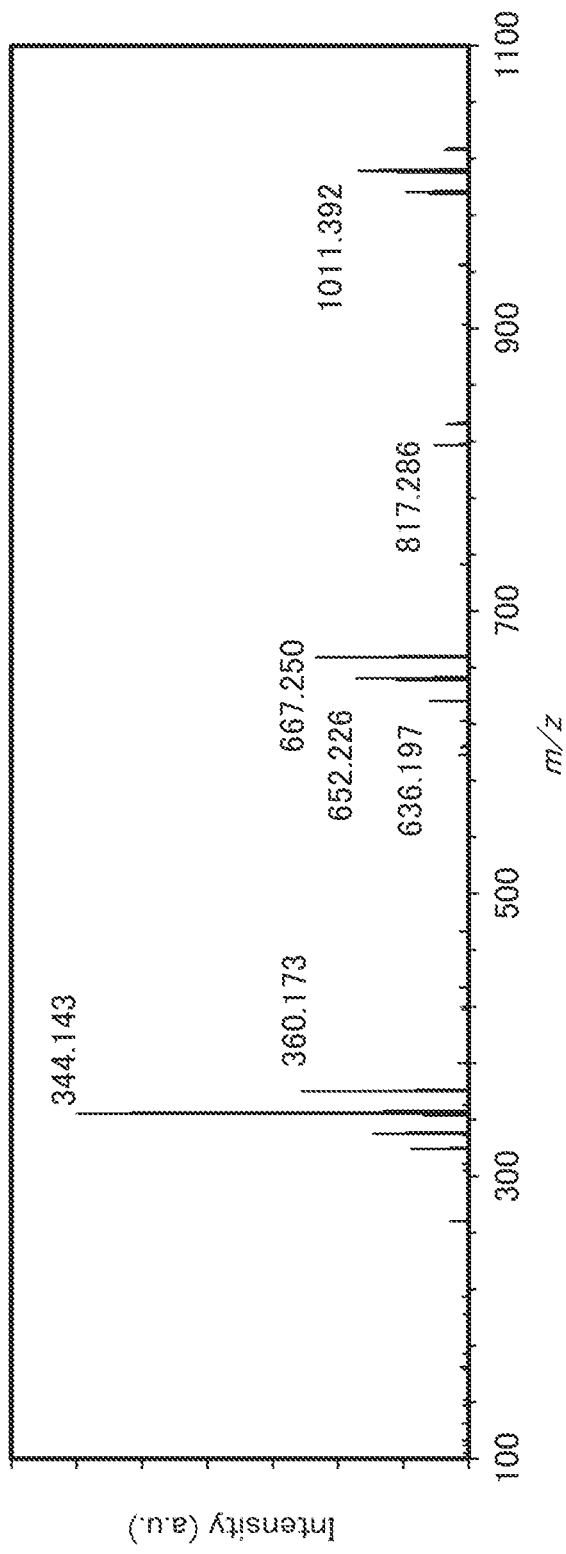
FIG. 33 shows an MS spectrum of 3,10FBi2Nbf(II).

FIG. 33 shows that product ions of 3,10FBi2Nbf(II) are mainly detected at m/z of around 1011, 995, 817, 667, 652, 636, 360, 344, and 330. Note that the results in FIG. 33 show characteristics derived from 3,10FBi2Nbf(II) and therefore can be regarded as important data for identifying 3,10FBi2Nbf(II) contained in the mixture.

It can be presumed that the product ion around m/z=1011 is a cation in a state where a methyl group is eliminated from 3,10FBi2Nbf(II). This suggests that 3,10FBi2Nbf(II) contains a methyl group. It can also be presumed that the product ion around m/z=817 is a cation in a state where a methyl group and a 9,9-dimethylfluorenyl group are eliminated from 3,10FBi2Nbf(II). This suggests that 3,10FBi2Nbf(II) contains a methyl group and a 9,9-dimethylfluorenyl group. It can also be presumed that the product ion around m/z=667 is a cation in a state where an N-(4-biphenyl)-(9,9-dimethylfluoren-2-yl)amino group is eliminated from 3,10FBi2Nbf(II). This suggests that 3,10FBi2Nbf(II) contains an N-(4-biphenyl)-(9,9-dimethylfluoren-2-yl)amino group.

Example 4

Synthesis Example 4

In this example, a synthesis example of 3,10-bis(3,3'-dimethyldiphenylamino)naphtho[2,3-b;7,6-b']bisbenzofuran (abbreviation: 3,10mMeDPhA2Nbf(II)), which is the organic compound of one embodiment of the present invention represented by Structural Formula (102) in Embodiment 1, will be described. The structural formula of 3,10mMeDPhA2Nbf(II) is shown below.

[Chemical Formula 92]

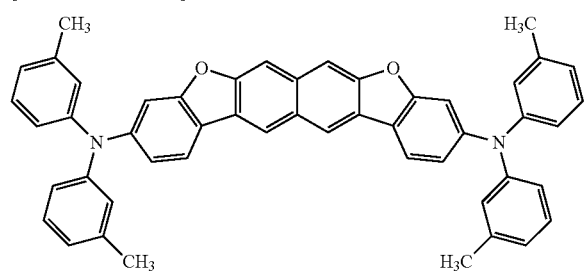

Step 1: Synthesis of 3,6-bis(4-chloro-2-fluorophenyl)-2,7-dimethoxynaphthalene

As in Step 1 in Synthesis Example 2, 3,6-bis(4-chloro-2-fluorophenyl)-2,7-dimethoxynaphthalene was synthesized.

Step 2: Synthesis of 3,6-bis(4-chloro-2-fluorophenyl)-2,7-dihydroxynaphthalene

As in Step 2 in Synthesis Example 2, 3,6-bis(4-chloro-2-fluorophenyl)-2,7-dihydroxynaphthalene was synthesized.

Step 3: Synthesis of 3,10-dichloronaphtho[2,3-b;7,6-b']bisbenzofuran

As in Step 3 in Synthesis Example 2, 3,10-dichloronaphtho[2,3-b;7,6-b']bisbenzofuran was synthesized.

Step 4: Synthesis of 3,10-bis(3,3'-dimethyldiphenylamino)naphtho[2,3-b;7,6-b']bisbenzofuran (Abbreviation: 3,10mMeDPhA2Nbf(II))

Into a 200-mL three-neck flask were put 1.0 g (2.7 mmol) of 3,10-dichloronaphtho[2,3-b;7,6-b']bisbenzofuran, 1.7 g (8.6 mmol) of m,m'-ditolylamine, 0.10 g (0.29 mmol) of di(1-adamantyl)-n-butylphosphine, and 1.7 g (17 mmol) of sodium tert-butoxide. To the mixture was added 30 mL of xylene. The resulting mixture was degassed by being stirred while the pressure was reduced. To this mixture was added 33 mg (57 μmol) of bis(dibenzylideneacetone)palladium(0), and stirring was performed under a nitrogen stream at 150° C. for 6.5 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (as the developing solvent, toluene and hexane in a ratio of 1:3 were used) to give a solid. The resulting solid was recrystallized with a mixed solvent of toluene and ethyl acetate to give 1.3 g of a pale yellow solid in a yield of 63%. A synthesis scheme of Step 4 is shown below.

[Chemical Formula 93]

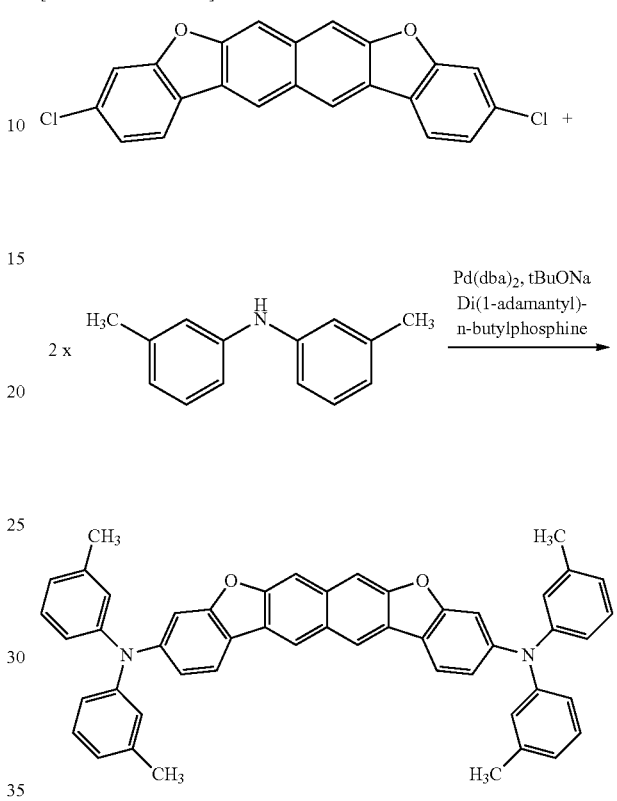

Then, 1.3 g of the resulting solid was purified by a train sublimation method under a pressure of $7.0 \times 10^{-3}$ Pa with an argon flow rate of 0 mL/min at 300° C. After the purification by sublimation, 1.0 g of a pale yellow solid was obtained at a collection rate of 82%.

Figure 34A:
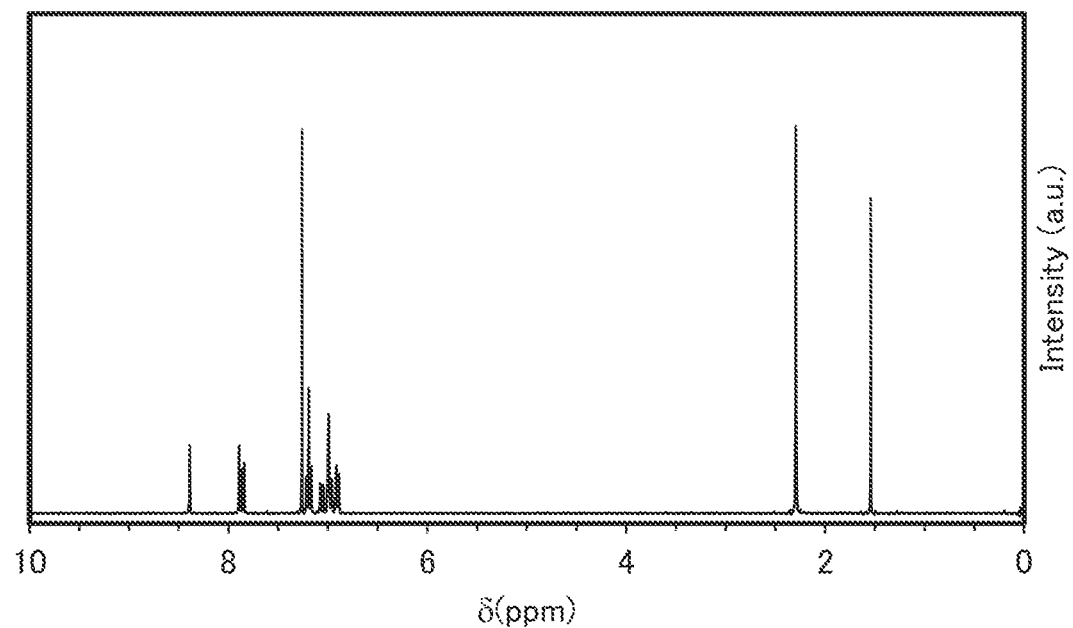
FIGS. 34A and 34B show $^1$H NMR spectra of 3,10-bis (3,3'-dimethyldiphenylamino)naphtho[2,3-b;7,6-b']bisbenzofuran (abbreviation: 3,10mMeDPhA2Nbf(II)).
Figure 34B:
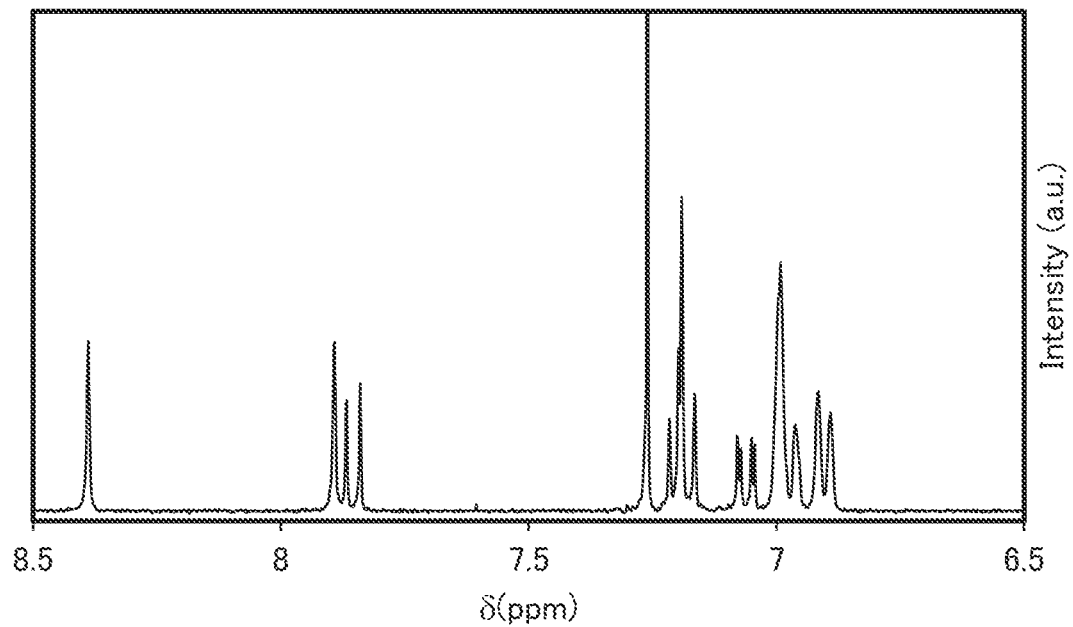

FIGS. 34A and 34B show $^1$H NMR charts of the resulting solid, whose numerical data is shown below. These indicate that 3,10mMeDPhA2Nbf(II), which is an organic compound of one embodiment of the present invention, was obtained in this synthesis example.

$^1$H NMR (CDCl$_3$, 300 MHz): δ=2.23 (s, 12H), 6.90 (d, J1=7.5 Hz, 4H), 6.96-6.99 (m, 8H), 7.06 (dd, J1=2.1 Hz, J2=8.7 Hz, 2H), 7.17-7.22 (m, 6H), 7.85 (d, J1=8.4 Hz, 2H), 7.89 (s, 2H), 8.39 (s, 2H).

Figure 35:
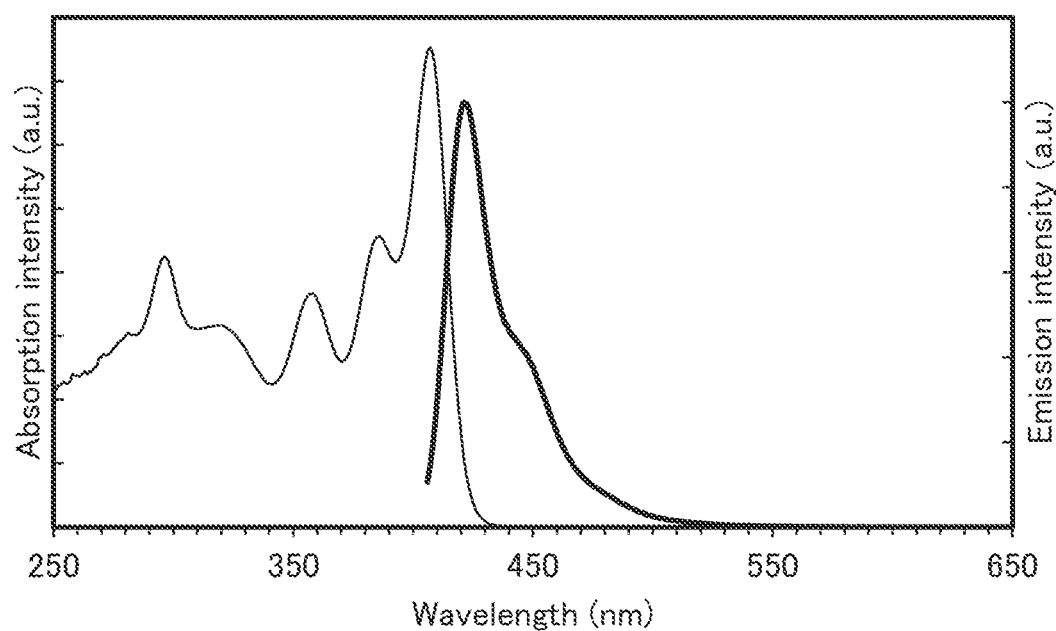
FIG. 35 shows an absorption spectrum and an emission spectrum of 3,10mMeDPhA2Nbf(II) in a toluene solution.
Figure 36:
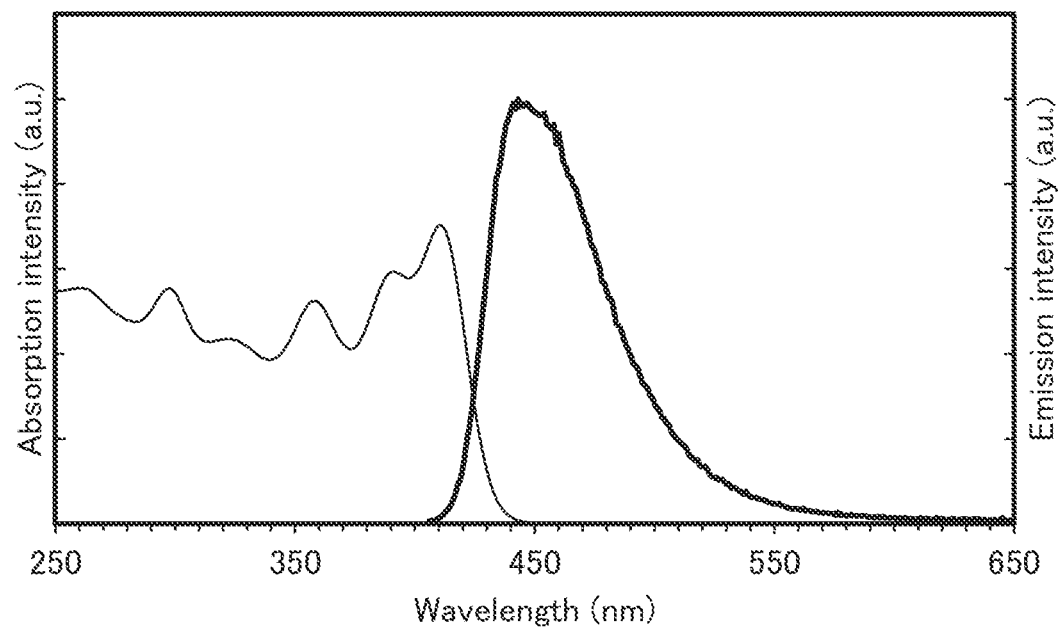
FIG. 36 shows an absorption spectrum and an emission spectrum of a thin film of 3,10mMeDPhA2Nbf(II).

Next, FIG. 35 shows the measurement results of the absorption and emission spectra of 3,10mMeDPhA2Nbf(II) in a toluene solution. FIG. 36 shows the absorption and emission spectra of a thin film of 3,10mMeDPhA2Nbf(II). The solid thin film was formed over a quartz substrate by a vacuum evaporation method. The absorption spectrum of the toluene solution was measured with an ultraviolet-visible light spectrophotometer (V550, manufactured by JASCO Corporation), and FIG. 35 shows a spectrum obtained by subtracting the spectrum of toluene from the spectrum of 3,10mMeDPhA2Nbf(II) in the toluene solution. The absorption spectrum of the thin film was measured with a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.). Quantum yields were measured using an absolute PL quantum yield measurement system (Quantaurus-QY, manufactured by Hamamatsu Photonics K. K.).

As shown in FIG. 35, 3,10mMeDPhA2Nbf(II) in the toluene solution has absorption peaks at around 407 nm, 386 nm, 358 nm, 319 nm, and 296 nm, and emission wavelength peaks at 420 nm and 445 nm (excitation wavelength: 400 nm). As shown in FIG. 36, the thin film of 3,10mMeDPhA2Nbf(II) has absorption peaks at around 412 nm, 392 nm, 359 nm, 323 nm, 298 nm, 262 nm, and 215 nm, and an emission wavelength peak at around 445 nm (excitation wavelength: 400 nm). These results indicate that 3,10mMeDPhA2Nbf(II) emits blue light and can be used as a host for a light-emitting substance or a substance which emits fluorescence in the visible region.

The measured quantum yield of 3,10mMeDPhA2Nbf(II) in the toluene solution was as high as 87%. This implies that 3,10mMeDPhA2Nbf(II) is suitable for a light-emitting material.

Next, 3,10mMeDPhA2Nbf(II) obtained in this example was analyzed by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving 3,10mMeDPhA2Nbf(II) in an organic solvent at a given concentration, and the injection amount was 5.0 µL.

A component with m/z of 698.29, which is an ion derived from 3,10 OmMeDPhA2Nbf(II), was subjected to the MS$^2$ analysis by a Targeted-MS$^2$ method. For setting of the Targeted-MS$^2$, the mass range of a target ion was set to m/z=698.29±2.0 (isolation window=4) and detection was performed in a positive mode. The analysis was performed with energy (normalized collision energy: NCE) for accelerating a target ion in a collision cell set to 60. The obtained MS spectrum is shown in FIG. 37.

Figure 37:
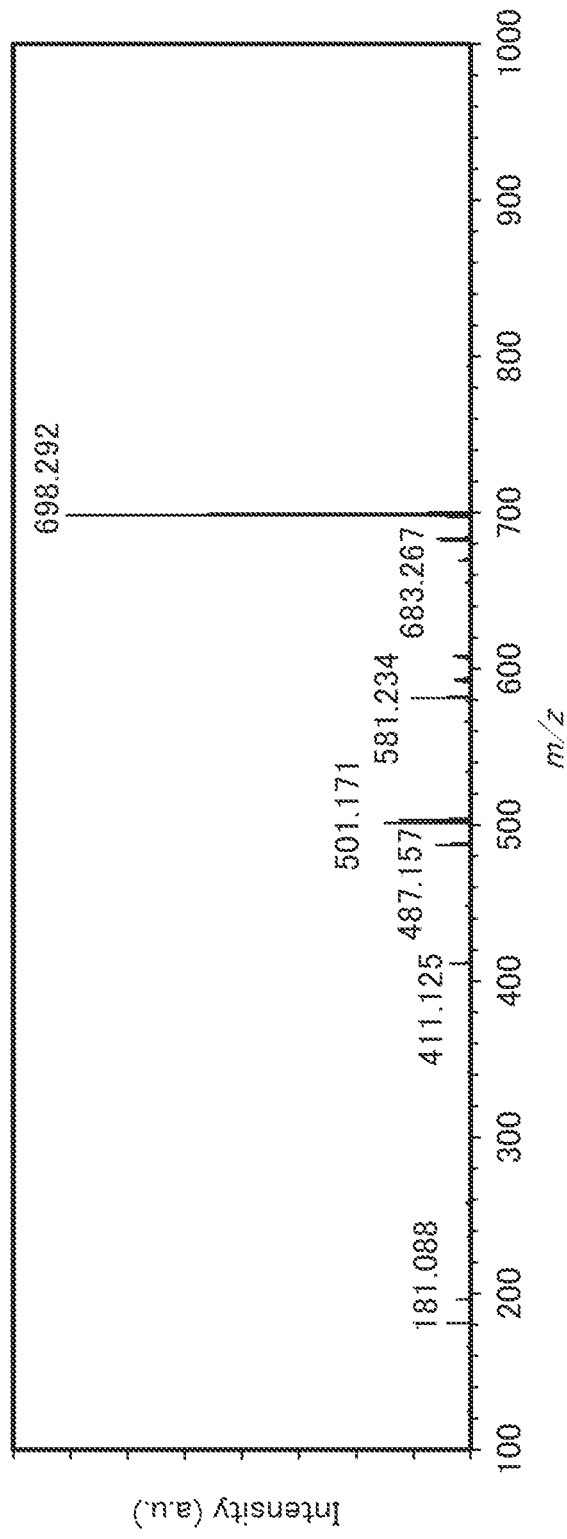
FIG. 37 shows an MS spectrum of 3,10mMeDPhA2Nbf (II).

FIG. 37 shows that product ions of 3,10mMeDPhA2Nbf (II) are mainly detected at m/z of around 682, 501, 487, 411, 196, and 181. Note that the results in FIG. 37 show characteristics derived from 3,10mMeDPhA2Nbf(II) and therefore can be regarded as important data for identifying 3,10mMeDPhA2Nbf(II) contained in the mixture.

It can be presumed that the product ion around m/z=682 is a cation in a state where a methyl group is eliminated from 3,10mMeDPhA2Nbf(II). This suggests that 3,10mMeDPhA2Nbf(II) contains a methyl group. It can also be presumed that the product ion around m/z=501 is a cation in a state where a bis(3-dimethylphenyl)amino group is eliminated from 3,10mMeDPhA2Nbf(II). This suggests that 3,10mMeDPhA2Nbf(II) contains a bis(3-dimethylphenyl) amino group.

Example 5

Synthesis Example 5

In this example, a synthesis example of 3,10-bis(10-phenyl-9-anthryl)naphtho[2,3-b;7,6-b']bisbenzofuran (abbreviation: 3,10PhA2Nbf(II)), which is the organic compound of one embodiment of the present invention represented by Structural Formula (118) in Embodiment 1, will be described. The structural formula of 3,10PhA2Nbf (II) is shown below.

[Chemical Formula 94]

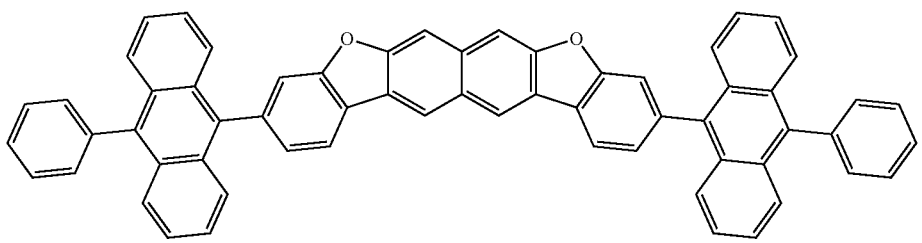

Step 1: Synthesis of 3,6-bis(4-chloro-2-fluorophenyl)-2,7-dimethoxynaphthalene

As in Step 1 in Synthesis Example 2, 3,6-bis(4-chloro-2-fluorophenyl)-2,7-dimethoxynaphthalene was synthesized.

Step 2: Synthesis of 3,6-bis(4-chloro-2-fluorophenyl)-2,7-dihydroxynaphthalene

As in Step 2 in Synthesis Example 2, 3,6-bis(4-chloro-2-fluorophenyl)-2,7-dihydroxynaphthalene was synthesized.

Step 3: Synthesis of 3,10-dichloronaphtho[2,3-b;7,6-b']bisbenzofuran

As in Step 3 in Synthesis Example 2, 3,10-dichloronaphtho[2,3-b;7,6-b']bisbenzofuran was synthesized.

Step 4: Synthesis of 3,10-bis(10-phenyl-9-anthryl) naphtho[2,3-b;7,6-b']bisbenzofuran (Abbreviation: 3,10PhA2Nbf(II)

Into a 200-mL three-neck flask were put 1.2 g (3.1 mmol) of 3,10-dichloronaphtho[2,3-b;7,6-b']bisbenzofuran, 2.4 g (8.1 mmol) of 10-phenyl-9-anthraceneboronic acid, and 2.2 g (16 mmol) of potassium carbonate. To the mixture was added 30 mL of xylene. The resulting mixture was degassed by being stirred while the pressure was reduced. To this mixture was added 71 mg (61 µmol) of tetrakis(triphenylphosphine)palladium(0), and stirring was performed at 150° C. under a nitrogen stream for 19 hours. After the stirring, 1.8 g (6.2 mmol) of 10-phenyl-9-anthraceneboronic acid, 1.7 g (12 mmol) of potassium carbonate, 64 mg (0.18 mmol) of di(1-adamantyl)-n-butylphosphine, 8 mg (36 µmol) of palladium(II) acetate, and 30 mL of diethylene glycol dimethyl ether were added to the resulting mixture, and stirring was performed at 150° C. under a nitrogen stream for 28 hours. After the stirring, ethanol was added to the mixture, and the resulting mixture was irradiated with ultrasonic waves and then suction-filtered to give a solid. The obtained solid was washed with water and ethanol. Ethyl acetate was added to the solid, and the resulting solid was irradiated with ultrasonic waves and then suction-filtered to give a solid. This solid was purified by silica gel column chromatography (as the developing solvent, toluene was used) to give a solid. Toluene was added to the resulting solid, heating and stirring were performed, and then the obtained solid was collected. This process was performed twice to give 0.52 g of a pale yellow solid in a yield of 21%. A synthesis scheme of Step 4 is shown below.

Corporation). The emission spectra were measured using a fluorescence spectrophotometer (FS920 manufactured by Hamamatsu Photonics K.K.).

Figure 39:
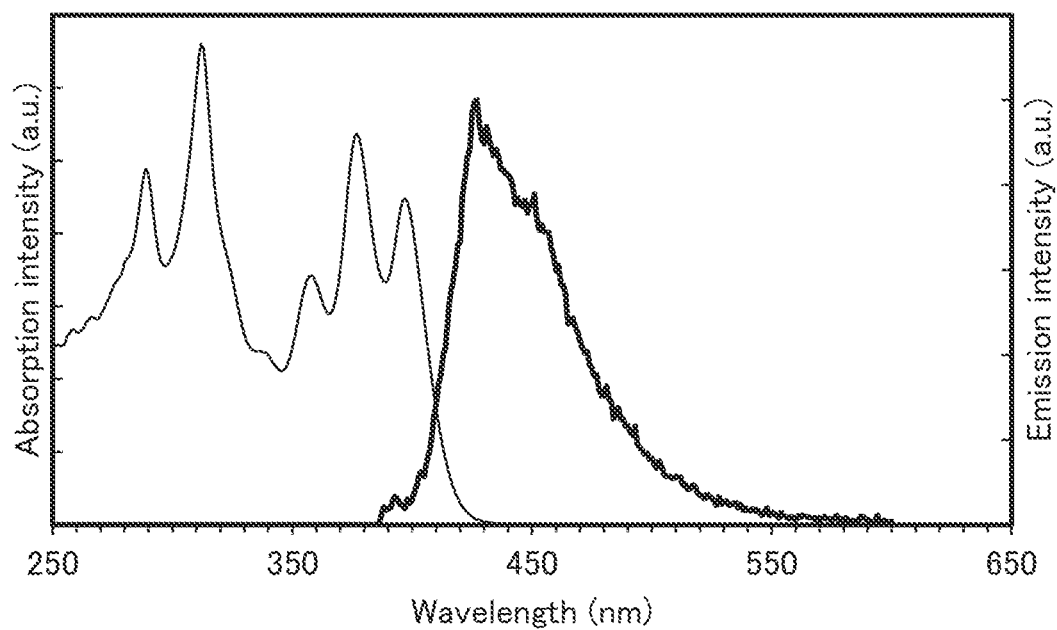
FIG. 39 shows an absorption spectrum and an emission spectrum of 3,10PhA2Nbf(II) in a toluene solution.
Figure 40:
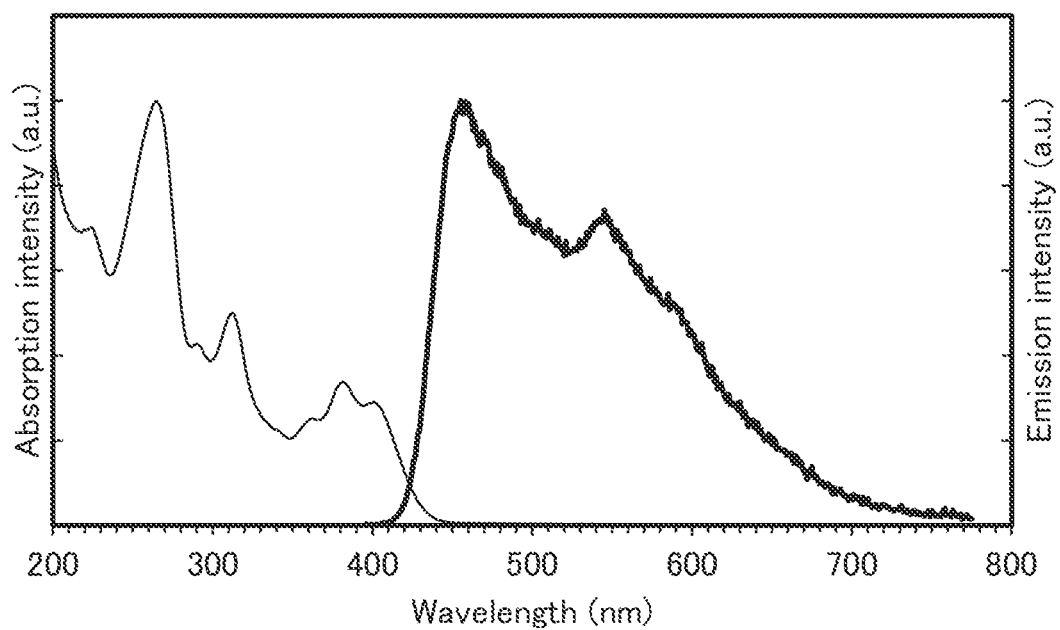
FIG. 40 shows an absorption spectrum and an emission spectrum of a thin film of 3,10PhA2Nbf(II).

As shown in FIG. 39, 3,10PhA2Nbf(II) in the toluene solution has absorption peaks at around 397 nm, 377 nm, 358 nm, 338 nm, 312 nm, and 289 nm, and emission wavelength peaks at 427 nm and 450 nm (excitation wavelength: 397 nm). As shown in FIG. 40, the thin film of 3,10PhA2Nbf(II) has absorption peaks at around 401 nm, 382 nm, 363 nm, 340 nm, 314 nm, 290 nm, 266 nm, and 224 nm, and emission wavelength peaks at around 455 nm, 545 nm, and 590 nm (excitation wavelength: 390 nm). These results indicate that 3,10PhA2Nbf(II) emits blue light and can be used as a host for a light-emitting substance or a substance which emits fluorescence in the visible region.

[Chemical Formula 95]

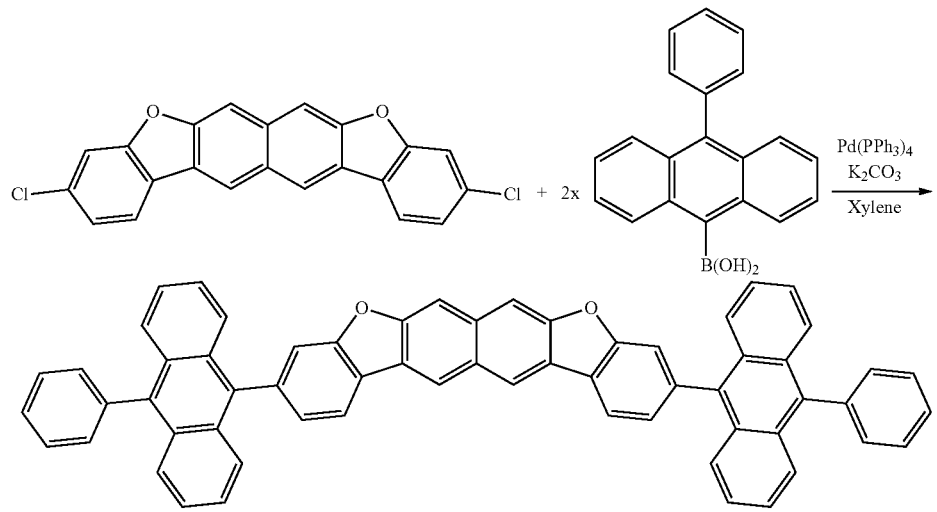

Figure 38A:
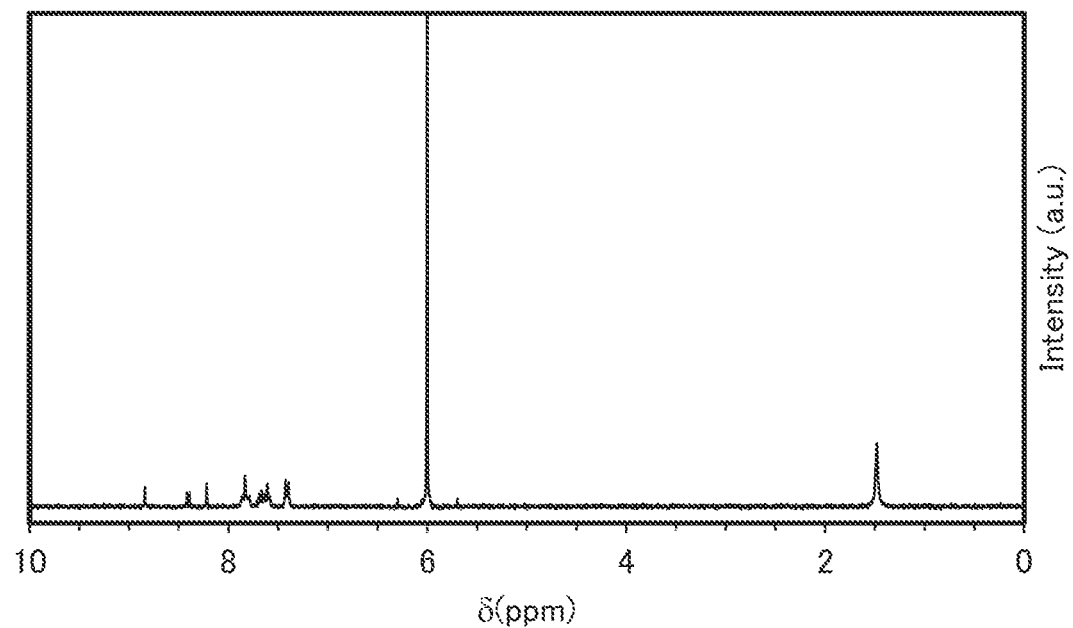
FIGS. 38A and 38B show $^1$H NMR spectra of 3,10-bis (10-phenyl-9-anthryl)naphtho[2,3-b;7,6-b']bisbenzofuran (abbreviation: 3,10PhA2Nbf(II)).
Figure 38B:
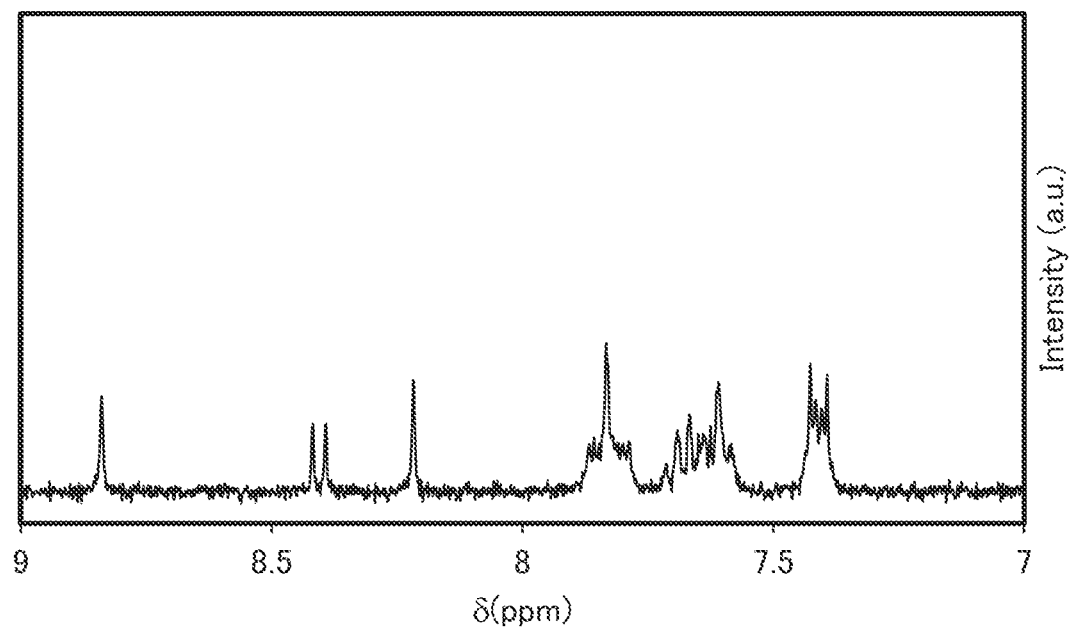

FIGS. 38A and 38B show $^1$H NMR charts of the resulting solid, whose numerical data is shown below. These indicate that 3,10PhA2Nbf(II), which is an organic compound of one embodiment of the present invention, was obtained in this synthesis example.

$^1$H NMR (1,1,2,2-Tetrachloroethane-D2, 300 MHz): δ=7.39-7.43 (m, 8H), 7.58-7.71 (m, 12H), 7.79-7.87 (m, 10H), 8.21 (s, 2H), 8.40 (d, J1=7.8 Hz, 2H), 8.84 (s, 2H).

Then, 0.52 g of the resulting solid was purified by a train sublimation method under a pressure of 1.2 k×10$^{-2}$ Pa with an argon flow rate of 0 mL/min at 380° C. After the purification by sublimation, 0.42 g of an yellow solid was obtained at a collection rate of 80%.

Next, FIG. 39 shows the measurement results of the absorption and emission spectra of 3,10PhA2Nbf(II) in a toluene solution. FIG. 40 shows the absorption and emission spectra of a thin film of 3,10PhA2Nbf(II). The solid thin film was formed over a quartz substrate by a vacuum evaporation method. The absorption spectrum of the toluene solution was measured with an ultraviolet-visible light spectrophotometer (V550, manufactured by JASCO Corporation), and FIG. 39 shows a spectrum obtained by subtracting the spectrum of toluene from the spectrum of 3,10PhA2Nbf(II) in the toluene solution. The absorption spectrum of the thin film was measured with a spectrophotometer (U-4100 Spectrophotometer, manufactured by Hitachi High-Technologies Next, 3,10PhA2Nbf(II) obtained in this example was analyzed by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving 3,10PhA2Nbf(II) in an organic solvent at a given concentration, and the injection amount was 5.0 µL.

A component with m/z of 812.27, which is an ion derived from 3,10PhA2Nbf(II), was subjected to the MS$^2$ analysis by a Targeted-MS$^2$ method. For setting of the Targeted-MS$^2$, the mass range of a target ion was set to m/z=812.27±2.0 (isolation window=4) and detection was performed in a positive mode. The analysis was performed with energy (normalized collision energy: NCE) for accelerating a target ion in a collision cell set to 50. The obtained MS spectrum is shown in FIG. 41.

A component with m/z of 812.27, which is an ion derived from 3,10PhA2Nbf(II), was subjected to the MS$^2$ analysis by a Targeted-MS$^2$ method. For setting of the Targeted-MS$^2$, the mass range of a target ion was set to m/z=812.27±2.0

(isolation window=4) and detection was performed in a positive mode. The analysis was performed with energy (normalized collision energy: NCE) for accelerating a target ion in a collision cell set to 70. The obtained MS spectrum is shown in FIG. 42.

Figure 41:
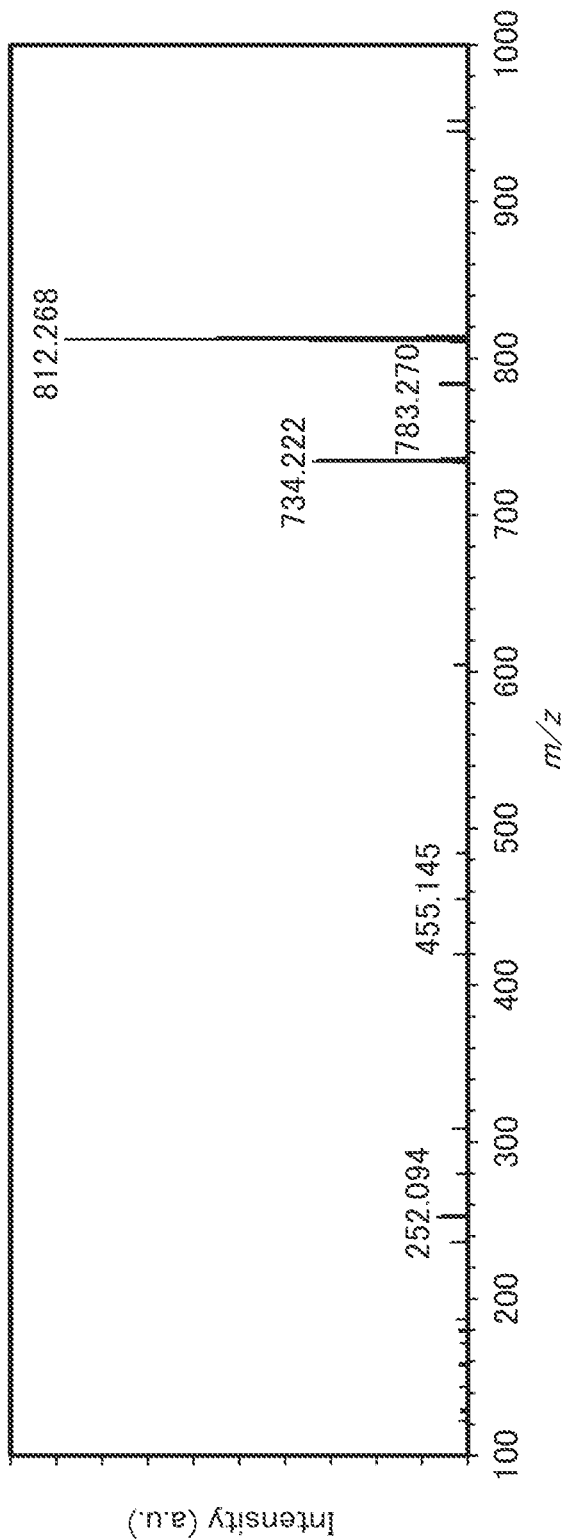
FIG. 41 shows an MS spectrum of 3,10PhA2Nbf(II).
Figure 42:
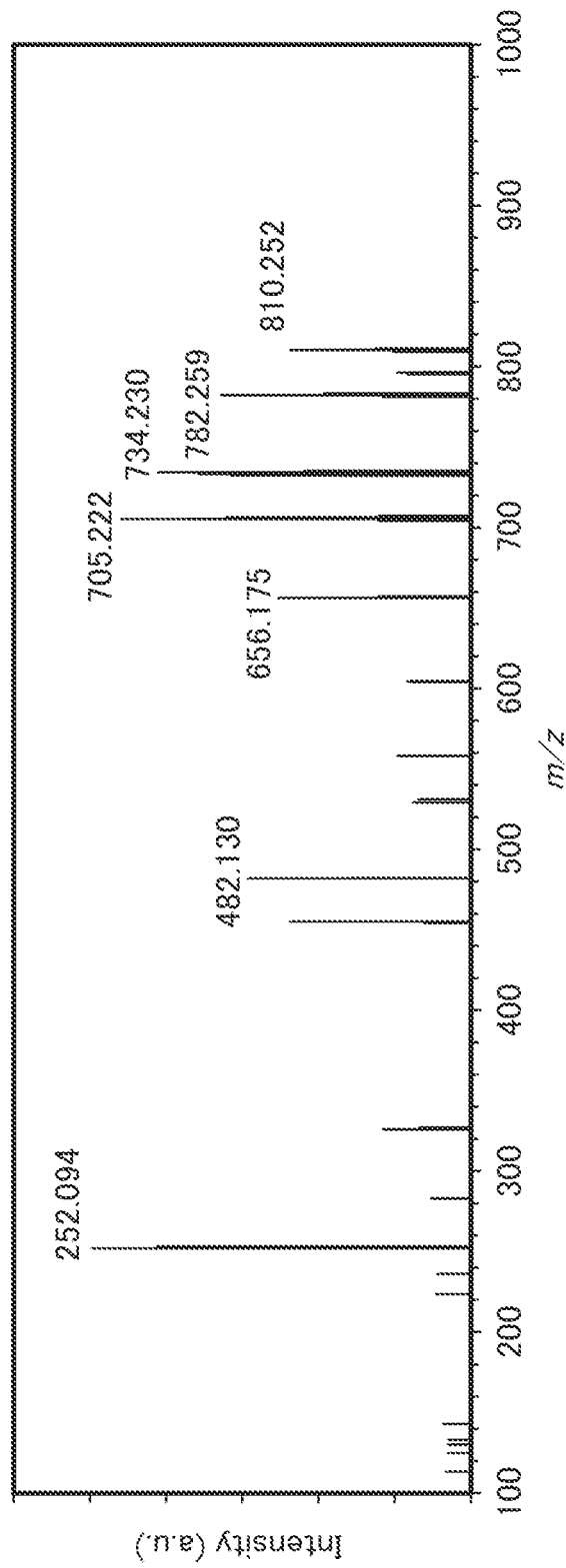
FIG. 42 shows an MS spectrum of 3,10PhA2Nbf(II).

FIGS. 41 and 42 show that product ions of 3,10PhA2Nbf (II) are mainly detected at m/z of around 734, 656, 482, and 252. Note that the results in FIGS. 41 and 42 show characteristics derived from 3,10PhA2Nbf(II) and therefore can be regarded as important data for identifying 3,10PhA2Nbf(II) contained in the mixture.

It can be presumed that the product ion around m/z=734 is a cation in a state where a phenyl group is eliminated from 3,10PhA2Nbf(II). This suggests that 3,10PhA2Nbf(II) contains a phenyl group. It can also be presumed that the product ion around m/z=482 is a cation in a state where a phenyl group and a 9-phenylanthryl group are eliminated from 3,10PhA2Nbf(II). This suggests that 3,10PhA2Nbf(II) contains a phenyl group and a 9-phenylanthryl group.

Example 6

Synthesis Example 6

In this example, a synthesis example of 3-(10-phenyl-9-anthryl)naphtho[2,3-b;7,6-b']bisbenzofuran (abbreviation: Nbf(II)PhA), which is the organic compound of one embodiment of the present invention represented by Structural Formula (112) in Embodiment 1, will be described. The structural formula of Nbf(II)PhA is shown below.

[Chemical Formula 96]

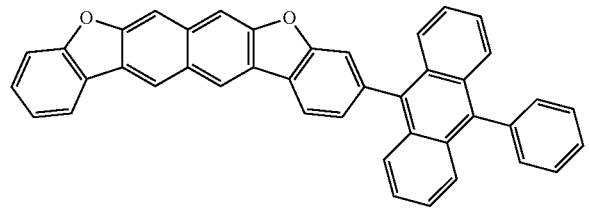

Step 1: Synthesis of 3-bromo-6-(2-fluorophenyl)-2,7-dimethoxynaphthalene

Into a 200-mL three-neck flask were put 3.0 g (8.7 mmol) of 3,6-dibromo-2,7-dimethoxynaphthalene, 1.2 g (8.7 mmol) of 2-fluorophenylboronic acid, 2.4 g (17 mmol) of potassium carbonate, and 0.13 g (0.43 mmol) of tris(2-methylphenyl)phosphine. To this mixture was added 90 mL of toluene. The resulting mixture was degassed by being stirred while the pressure was reduced. To the mixture was added 19 mg (87 µmol) of palladium(II) acetate, and stirring was performed under a nitrogen stream at 110° C. for 7 hours. After the stirring, toluene was added to the mixture, and the resulting mixture was suction-filtered through Florisil (manufactured by Wako Pure Chemical Industries, Ltd., Catalog No. 540-00135), Celite (manufactured by Wako Pure Chemical Industries, Ltd., Catalog No. 531-16855), and alumina to give a filtrate. The filtrate was concentrated to give a solid. This solid was purified by silica gel column chromatography (as the developing solvent, first, toluene and hexane in a ratio of 1:2 were used, and then toluene and hexane in a ratio of 1:1 were used) to give 1.1 g of a white solid which was an objective substance in a yield of 34%. A synthesis scheme of Step 1 is shown below.

[Chemical Formula 97]

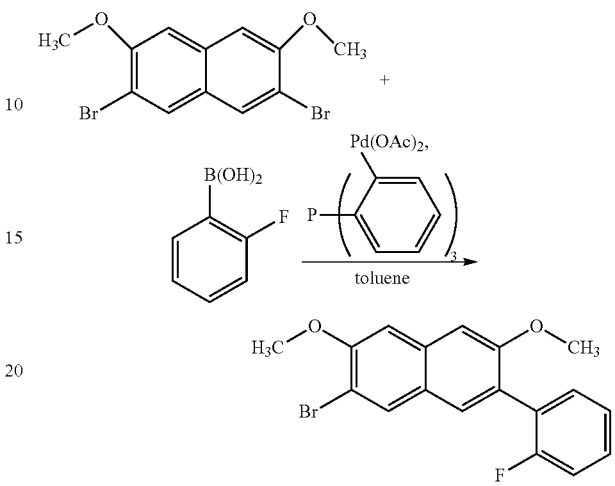

Figure 43A:
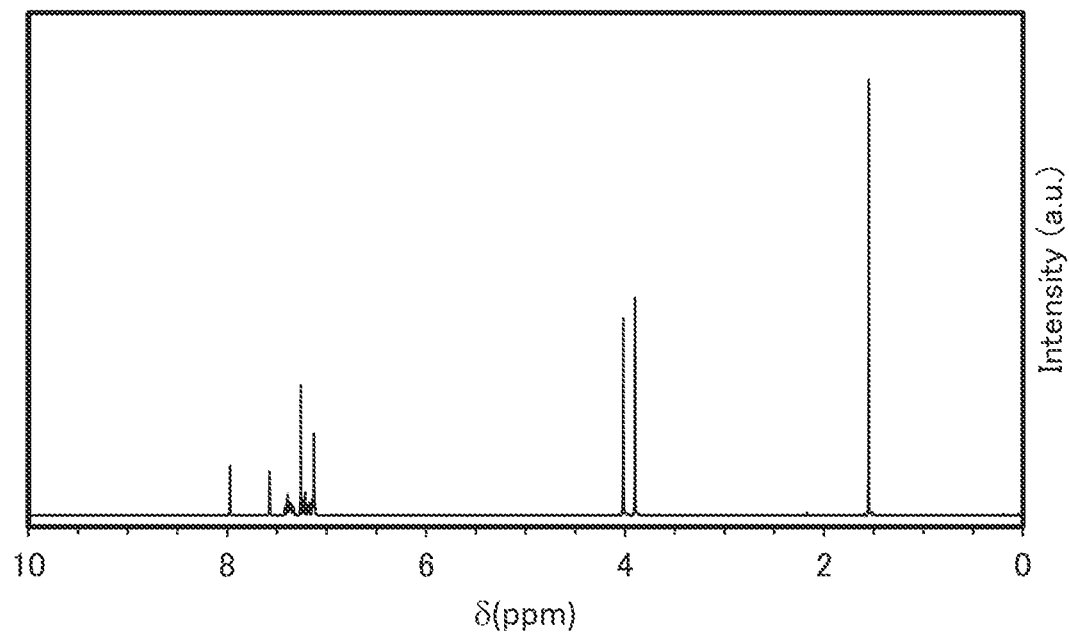
FIGS. 43A and 43B show $^1$H NMR spectra of 3-bromo-6-(2-fluorophenyl)-2,7-dimethoxynaphthalene.
Figure 43B:
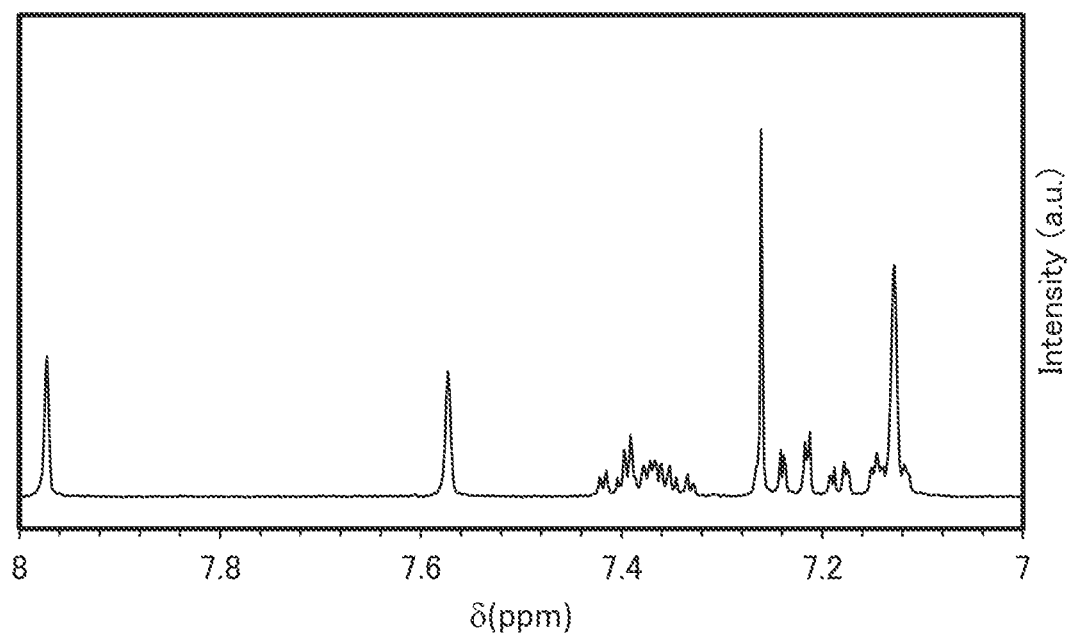

FIGS. 43A and 43B show $^1$H NMR charts of the resulting solid, whose numerical data is shown below. These indicate that 3-bromo-6-(2-fluorophenyl)-2,7-dimethoxynaphthalene was obtained in this synthesis example.

$^1$H NMR (CDCl$_3$, 300 MHz): δ=3.90 (s, 3H), 4.02 (s, 3H), 7.12-7.18 (m, 3H), 7.21 (td, J1=7.8 Hz, J2=0.9 Hz, 1H), 7.33-7.42 (m, 2H), 7.57 (s, 1H), 7.97 (s, 1H).

Step 2: Synthesis of 3-(2-fluorophenyl)-6-(2-fluoro-4-chlorophenyl)-2,7-dimethoxynaphthalene Into a 200-mL three-neck flask were put 2.2 g (6.0 mmol) of 3-bromo-6-(2-fluorophenyl)-2,7-dimethoxynaphthalene, 1.3 g (7.2 mmol) of 4-chloro-2-fluorophenylboronic acid, 2.0 g (14 mmol) of potassium carbonate, and 92 mg (0.30 mmol) of tris(2-methylphenyl)phosphine. To the mixture was added 30 mL of toluene. The resulting mixture was degassed by being stirred while the pressure was reduced. To the mixture was added 14 mg (60 µmol) of palladium(II) acetate, and stirring was performed under a nitrogen stream at 110° C. for 7 hours. After the stirring, toluene was added to the mixture, and the resulting mixture was suction-filtered through Florisil, Celite, and alumina to give a filtrate. The filtrate was concentrated to give a solid. This solid was purified by silica gel column chromatography (as the developing solvent, toluene and hexane in a ratio of 1:1 were used) to give 2.4 g of an objective substance in a yield of 95%. A synthesis scheme of Step 2 is shown below.

[Chemical Formula 98]

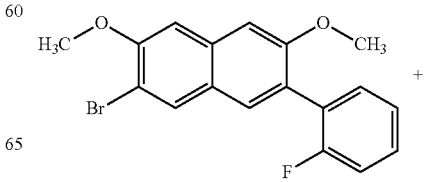

-continued

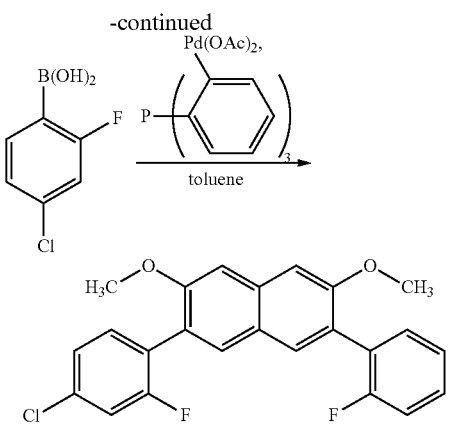

Figure 44A:
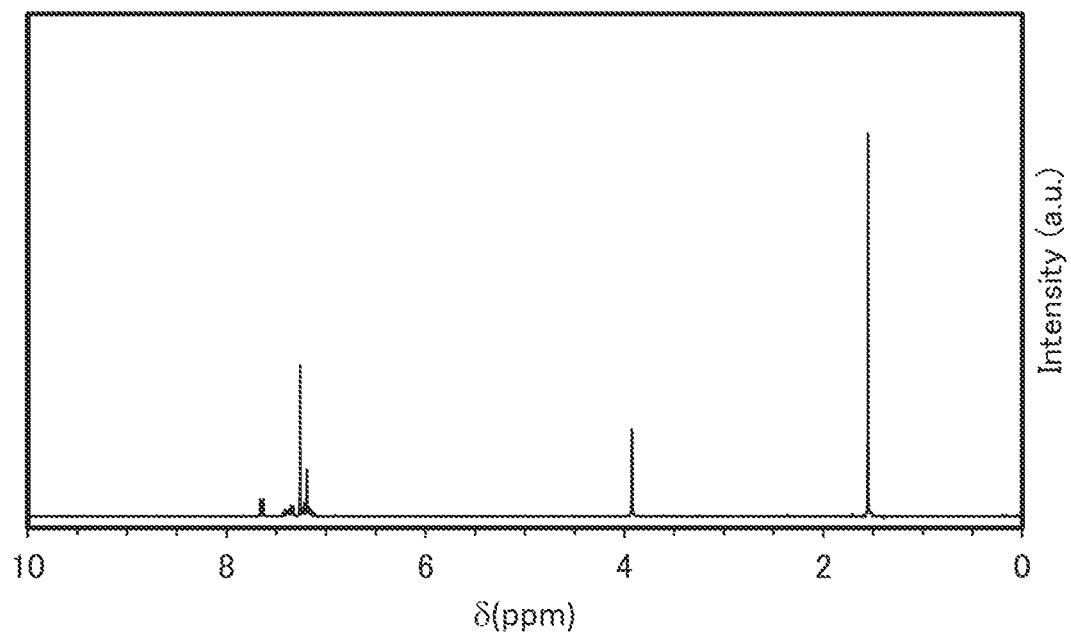
FIGS. 44A and 44B show $^1$H NMR spectra of 3-(2-fluorophenyl)-6-(2-fluoro-4-chlorophenyl)-2,7-dimethoxynaphthalene.
Figure 44B:
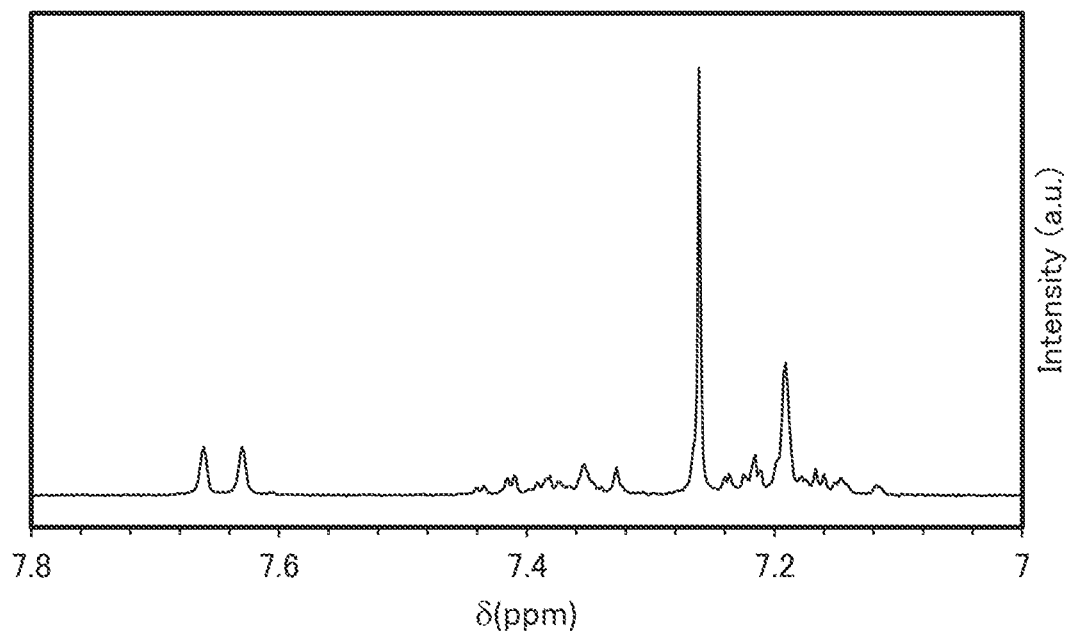

FIGS. 44A and 44B show ¹H NMR charts of the resulting solid, whose numerical data is shown below. These indicate that 3-(2-fluorophenyl)-6-(2-fluoro-4-chlorophenyl)-2,7-dimethoxynaphthalene was obtained in this synthesis example.

¹H NMR (CDCl₃, 300 MHz): δ=3.92-3.93 (m, 6H), 7.12-7.24 (m, 6H), 7.33-7.44 (m, 3H), 7.63 (s, 1H), 7.66 (s, 1H).

Step 3: Synthesis of 3-(2-fluorophenyl)-6-(2-fluoro-4-chlorophenyl)-2,7-dihydroxynaphthalene Into a 200-mL three-neck flask was put 2.3 g (5.6 mmol) of 3-(2-fluorophenyl)-6-(2-fluoro-4-chlorophenyl)-2,7-dimethoxynaphthalene. The air in the flask was replaced with nitrogen. Into the flask was additionally put 15 mL of dichloromethane. To the solution were dripped 12 mL (12 mmol) of boron tribromide (approximately 1.0 mol/L dichloromethane solution) and 15 mL of dichloromethane. After the dripping, the resulting solution was stirred at room temperature. After that, approximately 20 mL of water was added to this solution under cooling with ice, and the solution was stirred. After that, an aqueous layer and an organic layer of this mixture were separated, and the aqueous layer was subjected to extraction with dichloromethane. The extracted solution and the organic layer were combined and washed with water and a saturated aqueous solution of sodium hydrogen carbonate. The organic layer was dried with magnesium sulfate, and then this mixture was gravity filtered. The obtained filtrate was concentrated to give 2.1 g of a white solid. A synthesis scheme of Step 3 is shown below.

[Chemical Formula 99]

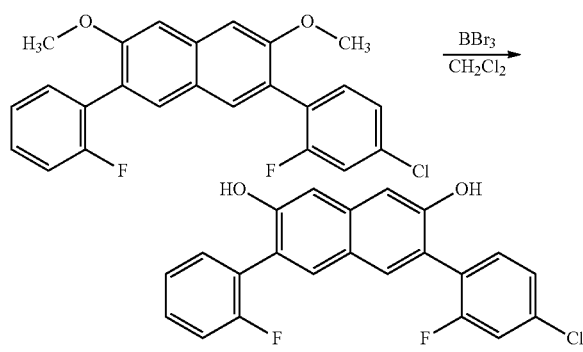

Figure 45A:
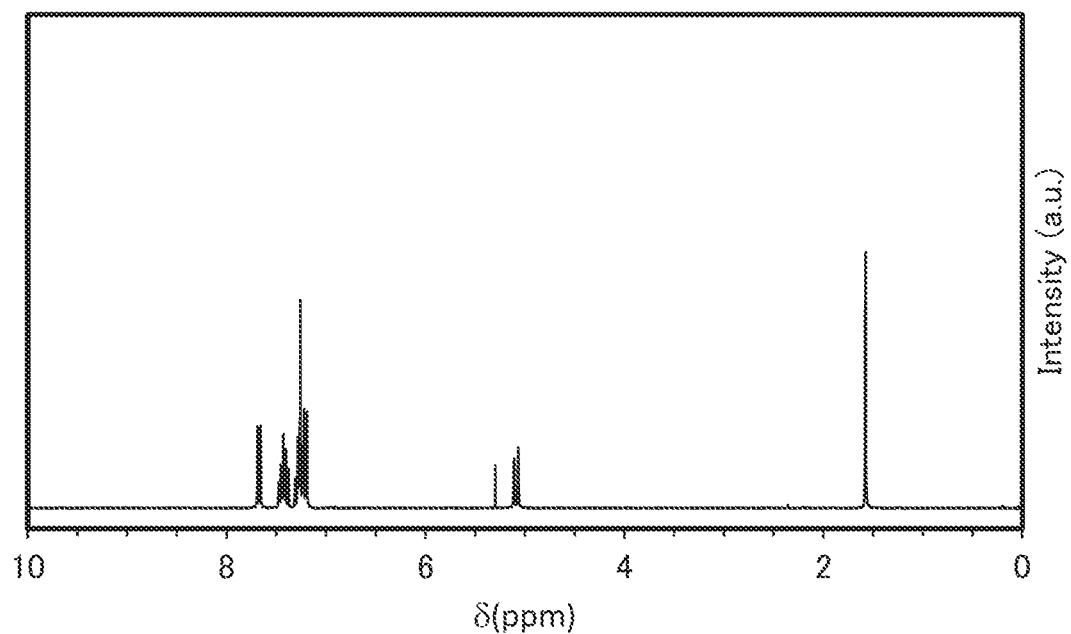
FIGS. 45A and 45B show $^1$H NMR spectra of 3-(2-fluorophenyl)-6-(2-fluoro-4-chlorophenyl)-2,7-dihydroxynaphthalene.
Figure 45B:
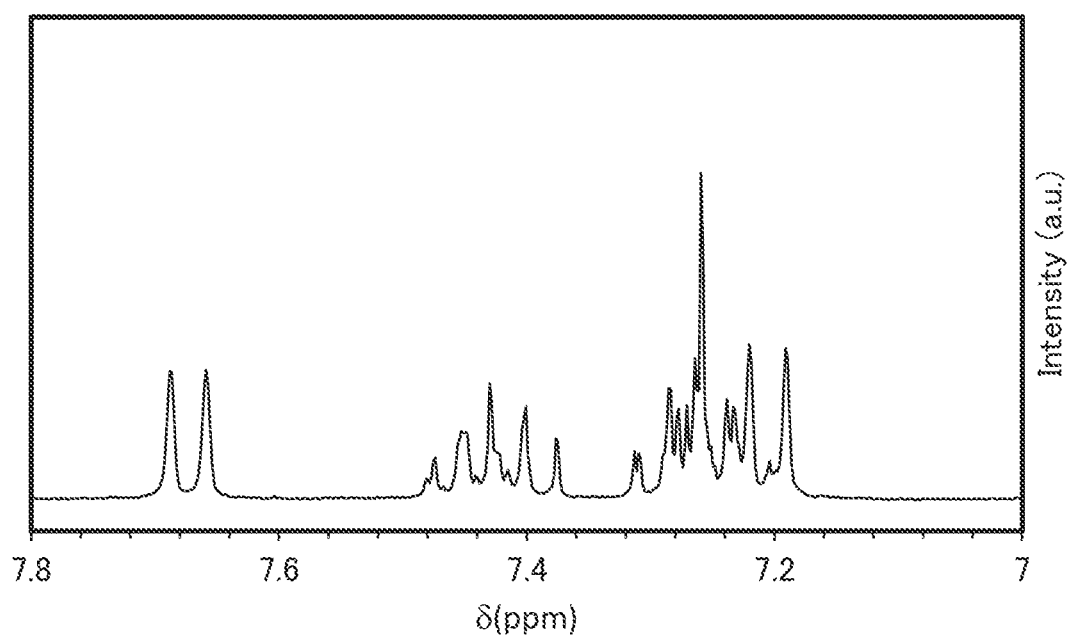

FIGS. 45A and 45B show ¹H NMR charts of the resulting solid, whose numerical data is shown below. These indicate that 3-(2-fluorophenyl)-6-(2-fluoro-4-chlorophenyl)-2,7-dihydroxynaphthalene was obtained in this synthesis example.

¹H NMR (CDCl₃, 300 MHz): δ=5.07 (s, 1H), 5.11 (s, 1H), 7.19-7.31 (m, 6H), 7.38-7.48 (m, 3H), 7.66 (s, 1H), 7.69 (s, 1H).

Step 4: Synthesis of 2-chloronaphtho[2,3-b;7,6-b'] bisbenzofuran

Into a 200-mL three-neck flask were put 2.1 g (5.6 mmol) of 3-(2-fluorophenyl)-6-(2-fluoro-4-chlorophenyl)-2,7-dihydroxynaphthalene and 3.1 g (22 mmol) of potassium carbonate. To this mixture was added 60 mL of N-methyl-2-pyrrolidone. The resulting mixture was degassed by being stirred while the pressure was reduced. After that, this mixture was stirred under a nitrogen stream at 120° C. for 13.5 hours. After that, water was added to the mixture, and a precipitated solid was collected by filtration. The obtained solid was washed with water and ethanol. Ethanol was added to the resulting solid, heating and stirring were performed, and then the resulting mixture was filtered to give a solid. This solid was purified by silica gel column chromatography (as the developing solvent, toluene was used). The resulting solid was recrystallized with toluene to give 1.6 g of a white solid in a yield of 85%. A synthesis scheme of Step 4 is shown below.

[Chemical Formula 100]

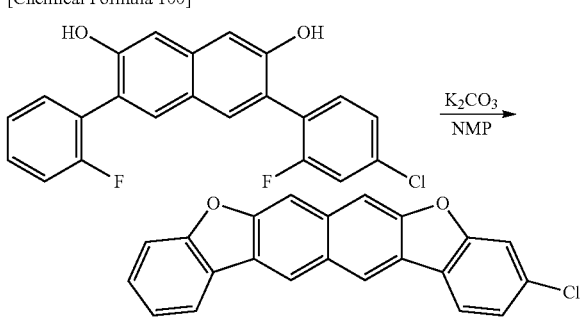

Figure 46A:
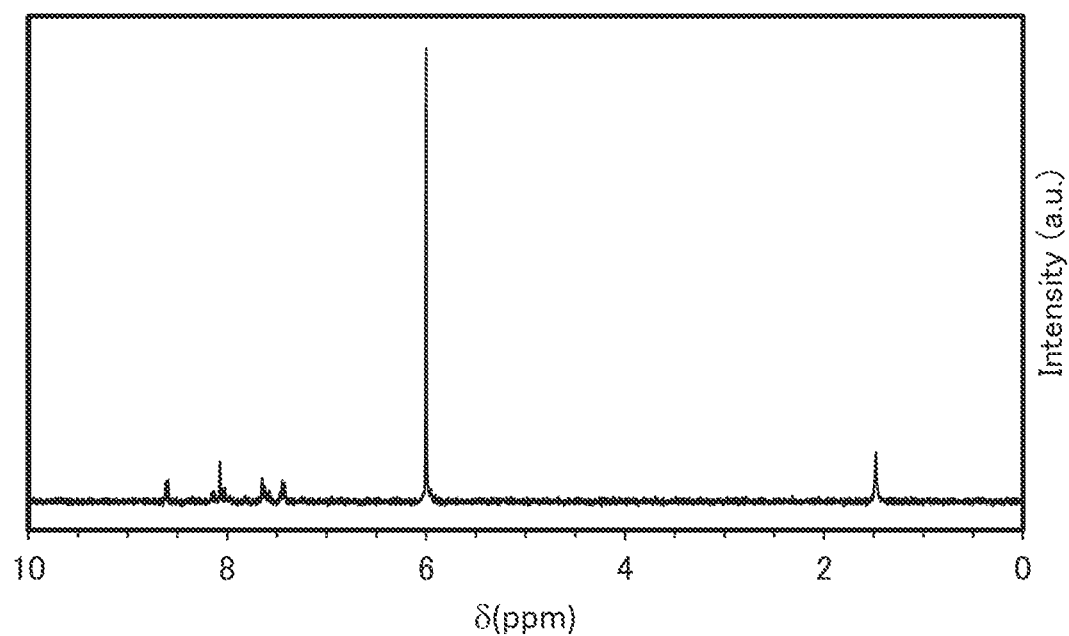
FIGS. 46A and 46B show $^1$H NMR spectra of 2-chloronaphtho[2,3-b;7,6-b']bisbenzofuran.
Figure 46B:
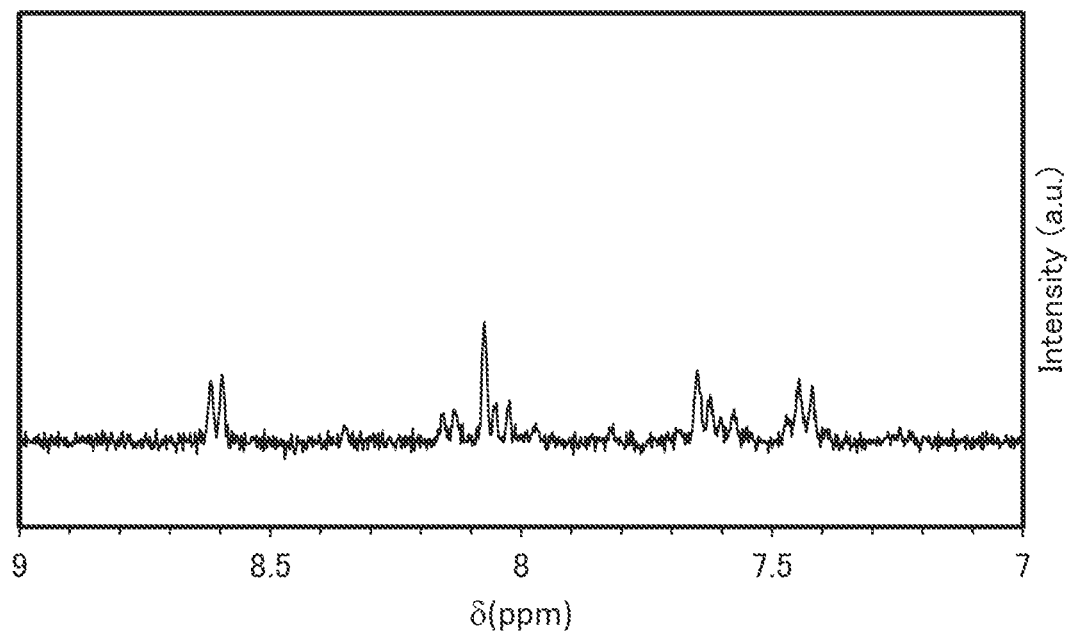

FIGS. 46A and 46B show ¹H NMR charts of the resulting solid, whose numerical data is shown below. These indicate that 3-chloronaphtho[2,3-b;7,6-b']bisbenzofuran was obtained in this synthesis example.

¹H NMR (1,1,2,2-Tetrachloroethane-D2, 300 MHz): δ=7.42-7.47 (m, 2H), 7.57-7.65 (m, 3H), 8.02-8.07 (m, 3H), 8.14 (d, J1=6.9 Hz, 1H), 8.60 (s, 1H), 8.62 (s, 1H).

Step 5: Synthesis of 3-(10-phenyl-9-anthryl)naphtho[2,3-b;7,6-b']bisbenzofuran (Abbreviation: Nbf(II)PhA)

Into a 200-mL three-neck flask were put 1.2 g (3.6 mmol) of 3-chloronaphtho[2,3-b;7,6-b']bisbenzofuran, 1.3 g (4.5 mmol) of 10-phenyl-9-anthraceneboronic acid, and 1.3 g (9.0 mmol) of potassium carbonate. To the mixture was added 20 mL of diethylene glycol dimethyl ether. The resulting mixture was degassed by being stirred while the pressure was reduced. To this mixture was added 41 mg (36 μmol) of tetrakis(triphenylphosphine)palladium(0), and stirring was performed at 150° C. under a nitrogen stream for 18 hours. After the stirring, 20 mL of xylene, 1.3 g (4.5 mmol) of 10-phenyl-9-anthraceneboronic acid, 1.3 g (9.0 mmol) of potassium carbonate, 64 mg (0.18 mmol) of di(1-adamantyl)-n-butylphosphine, and 8 mg (36 µmol) of palladium(II) acetate were added to the resulting mixture, and stirring was performed at 150° C. under a nitrogen stream for 42 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (as the developing solvent, toluene was used). The resulting solid was recrystallized with toluene to give 0.53 g of a pale yellow solid (crude). A synthesis scheme of Step 5 is shown below.

[Chemical Formula 101]

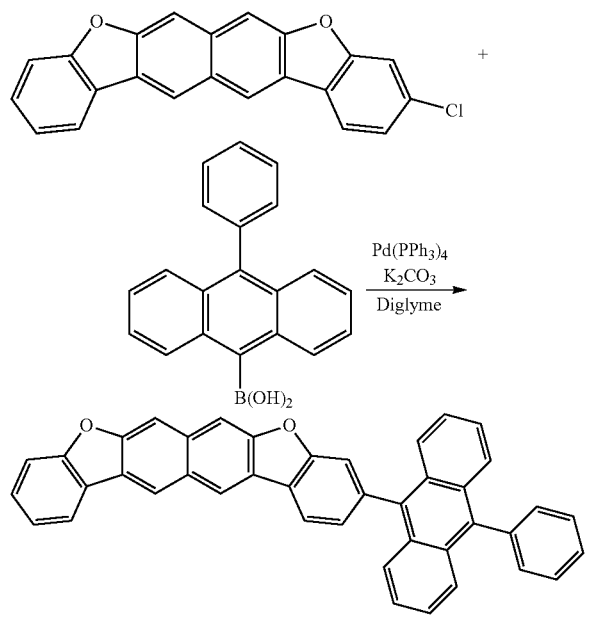

Figure 47A:
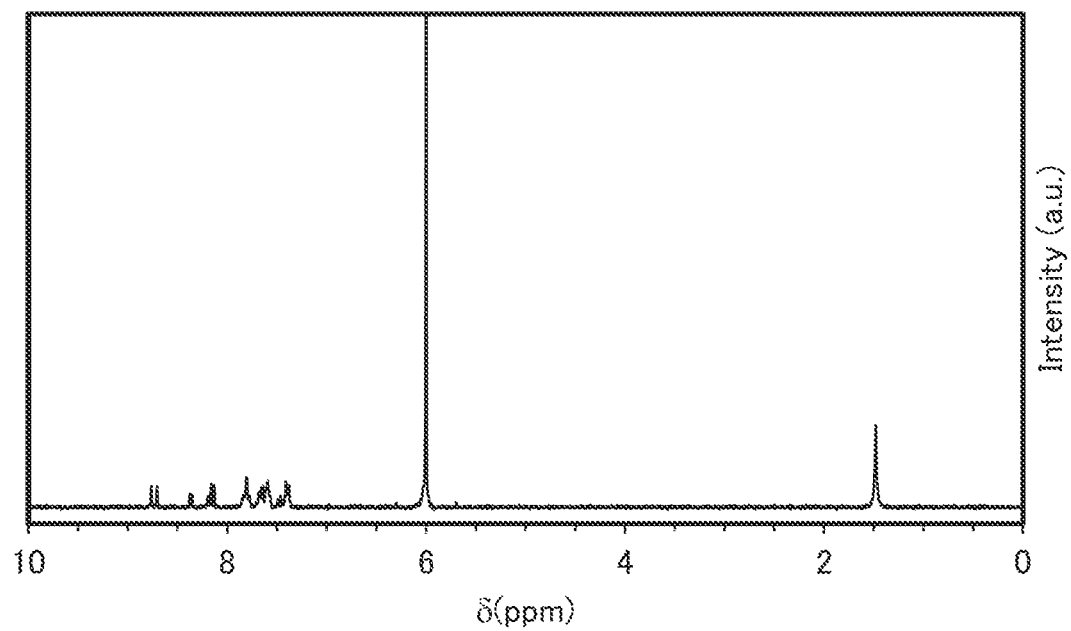
FIGS. 47A and 47B show $^1$H NMR spectra of 3-(10-phenyl-9-anthryl)naphtho[2,3-b;7,6-b']bisbenzofuran (abbreviation: Nbf(II)PhA).
Figure 47B:
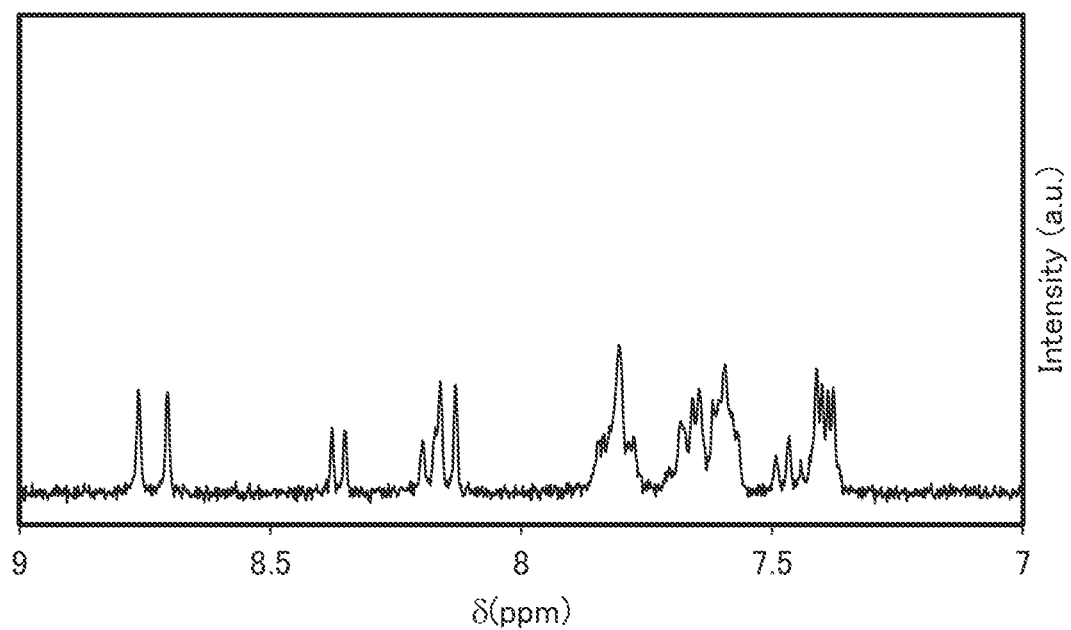

FIGS. 47A and 47B show $^1$H NMR charts of the resulting solid, whose numerical data is shown below. These indicate that Nbf(II)PhA, which is an organic compound of one embodiment of the present invention, was obtained in this synthesis example.

$^1$H NMR (1,1,2,2-Tetrachloroethane-D2, 300 MHz): δ=7.40 (dd, J1=3.3 Hz, J2=6.9 Hz, 4H), 7.47 (t, J1=7.8 Hz, 1H), 7.57-7.68 (m, 9H), 7.77-7.85 (m, 5H), 8.13-8.20 (m, 3H), 8.37 (d, J1=7.2 Hz, 1H), 8.71 (s, 1H), 8.76 (s, 1H).

Then, 0.52 g of the resulting solid was purified by a train sublimation method under a pressure of 1.6 k×10$^{-2}$ Pa with an argon flow rate of 0 mL/min at 290° C. After the purification by sublimation, 0.33 g of a pale yellow solid was obtained at a collection rate of 63%.

Figure 48:
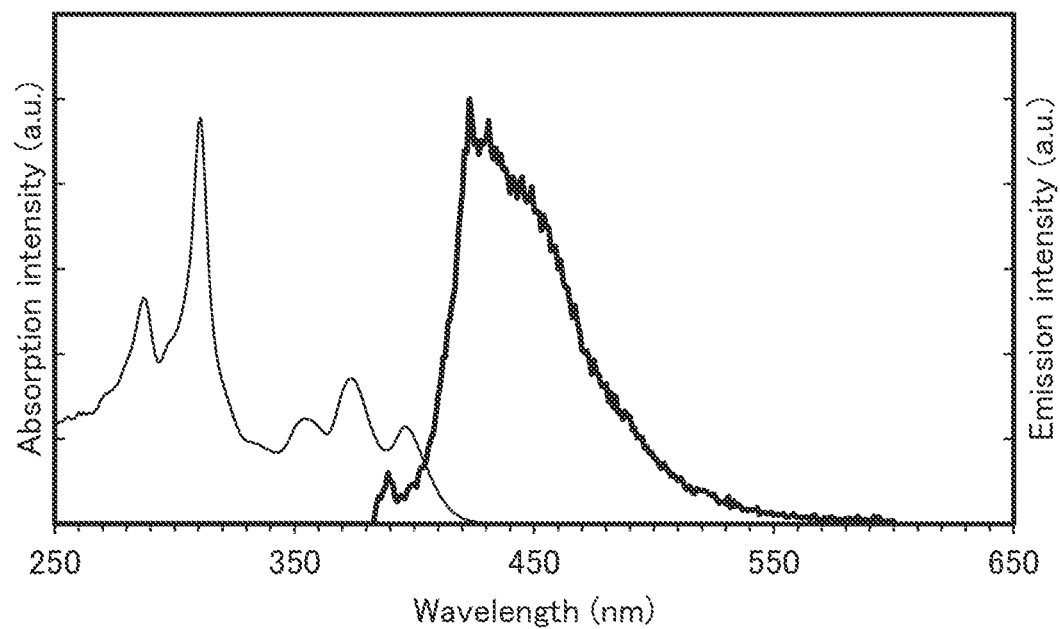
FIG. 48 shows an absorption spectrum and an emission spectrum of Nbf(II)PhA in a toluene solution.
Figure 49:
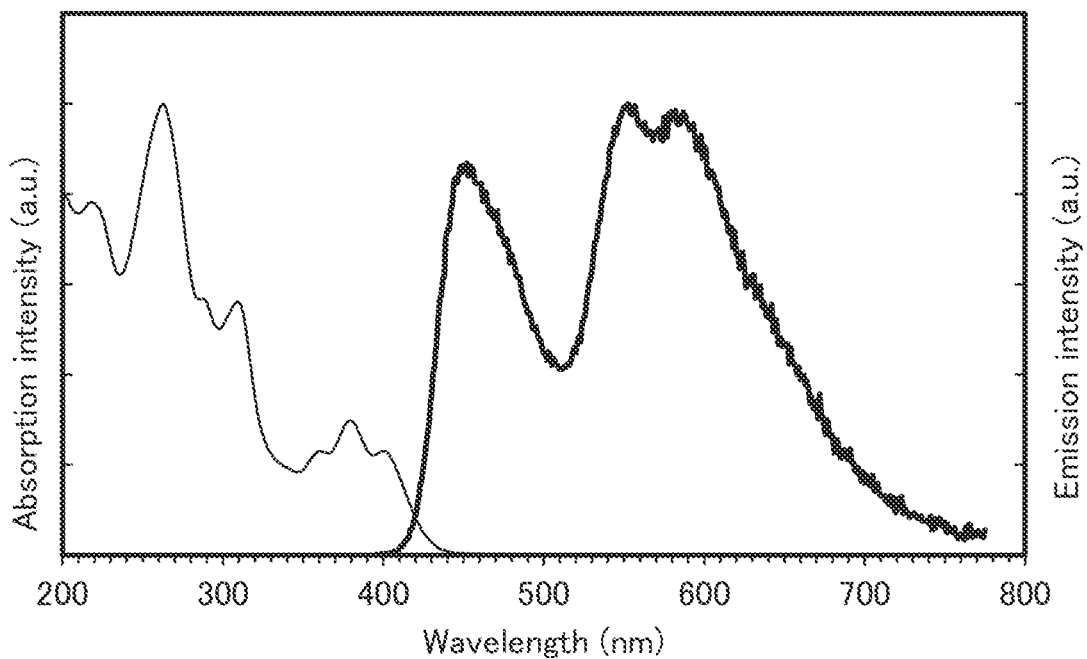
FIG. 49 shows an absorption spectrum and an emission spectrum of a thin film of Nbf(II)PhA.

Next, FIG. 48 shows the measurement results of the absorption and emission spectra of Nbf(II)PhA in a toluene solution. FIG. 49 shows the absorption and emission spectra of a thin film of Nbf(II)PhA. The solid thin film was formed over a quartz substrate by a vacuum evaporation method. The absorption spectrum of the toluene solution was measured with an ultraviolet-visible light spectrophotometer (V550, manufactured by JASCO Corporation), and FIG. 48 shows a spectrum obtained by subtracting the spectrum of toluene from the spectrum of Nbf(II)PhA in the toluene solution. The absorption spectrum of the thin film was measured with a spectrophotometer (U-4100 Spectrophotometer, manufactured by Hitachi High-Technologies Corporation). The emission spectra were measured using a fluorescence spectrophotometer (FS920 manufactured by Hamamatsu Photonics K.K.).

As shown in FIG. 48, Nbf(II)PhA in the toluene solution has absorption peaks at around 397 nm, 374 nm, 356 nm, 336 nm, 311 nm, and 290 nm, and emission wavelength peaks at 424 nm and 430 nm (excitation wavelength: 374 nm). As shown in FIG. 49, the thin film of Nbf(II)PhA has absorption peaks at around 401 nm, 381 nm, 358 nm, 335 nm, 311 nm, 289 nm, 264 nm, and 222 nm, and emission wavelength peaks at around 451 nm, 552 nm, and 585 nm (excitation wavelength: 390 nm). These results indicate that Nbf(II)PhA emits blue light and can be used as a host for a light-emitting substance or a substance which emits fluorescence in the visible region.

Next, Nbf(II)PhA obtained in this example was analyzed by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving Nbf(II)PhA in an organic solvent at a given concentration, and the injection amount was 5.0 µL.

A component with m/z of 560.18, which is an ion derived from Nbf(II)PhA, was subjected to the MS$^2$ analysis by a Targeted-MS$^2$ method. For setting of the Targeted-MS$^2$, the mass range of a target ion was set to m/z=560.18±2.0 (isolation window=4) and detection was performed in a positive mode. The analysis was performed with energy (normalized collision energy: NCE) for accelerating a target ion in a collision cell set to 50. The obtained MS spectrum is shown in FIG. 50.

Figure 50:
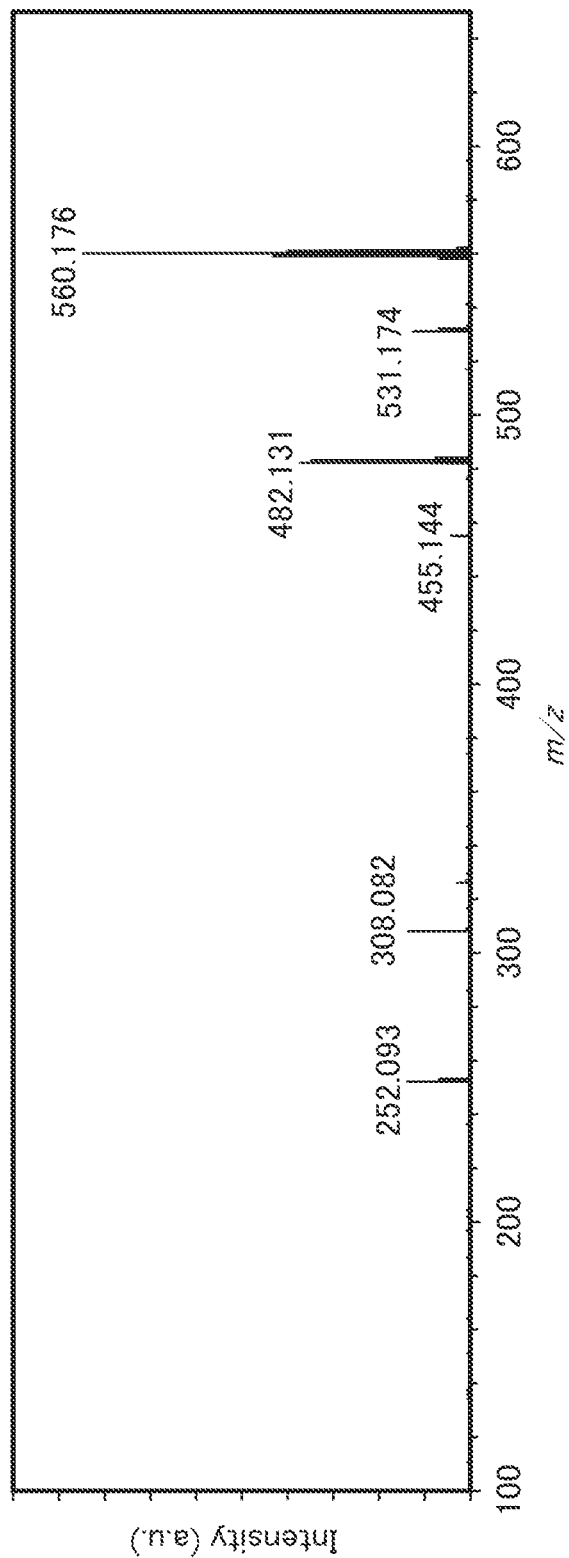
FIG. 50 shows an MS spectrum of Nbf(II)PhA.

FIG. 50 shows that product ions of Nbf(II)PhA are mainly detected at m/z of around 482, 308, and 252. Note that the results in FIG. 50 show characteristics derived from Nbf(II)PhA and therefore can be regarded as important data for identifying Nbf(II)PhA contained in the mixture.

It can be presumed that the product ion around m/z=482 is a cation in a state where a phenyl group is eliminated from Nbf(II)PhA. This suggests that Nbf(II)PhA contains a phenyl group. It can also be presumed that the product ion around m/z=308 is a cation in a state where a 9-phenylanthryl group is eliminated from Nbf(II)PhA. This suggests that Nbf(II)PhA contains a 9-phenylanthryl group. It can also be presumed that the product ion around m/z=252 is a cation in a state where naphtho[2,3-b;7,6-b']bisbenzofuran is eliminated from Nbf(II)PhA. This suggests that Nbf(II)PhA contains naphtho[2,3-b;7,6-b']bisbenzofuran.

Example 7

In this example, Light-emitting Element 1, which corresponds to the light-emitting element of one embodiment of the present invention described in the above embodiment, will be described in detail. The structural formulae of organic compounds used for Light-emitting Element 1 are shown below.

[Chemical Formul 102]

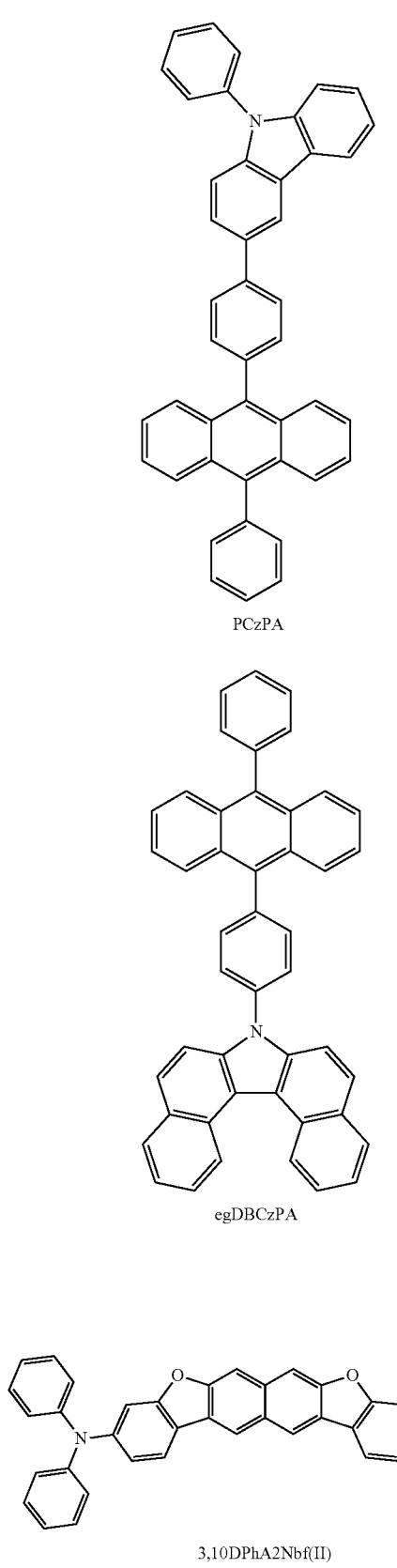

(i) PCzPA (ii) egDBCzPA (iii) 3,10DPhA2Nbf(II)

(iv) BPhen (Method for Fabricating Light-Emitting Element 1)

First, indium tin oxide containing silicon oxide (ITSO) was deposited on a glass substrate by a sputtering method to form the anode 101. The thickness of the anode 101 is 70 nm, and the electrode area is 4 mm² (2 mm×2 mm).

Next, in pretreatment for forming the light-emitting element over a substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 45 minutes.

Next, the substrate provided with the anode 101 was fixed to a substrate holder provided in the vacuum evaporation apparatus such that the side on which the anode 101 was formed faced downward. Then, 9-phenyl-3-[4-(10-phenyl-9-anthryl)phenyl]-9H-carbazole (abbreviation: PCzPA) represented by Structural Formula (i) and molybdenum(VI) oxide were co-evaporated on the anode 101 to a thickness of 10 nm by an evaporation method using resistance heating such that the weight ratio of PCzPA to molybdenum oxide was 4:2, whereby the hole-injection layer 111 was formed.

Subsequently, on the hole-injection layer 111, PCzPA was deposited to a thickness of 30 nm by evaporation to form the hole-transport layer 112.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by Structural Formula (ii) and 3,10-bis(diphenylamino)naphtho[2,3-b;7,6-b']bisbenzofuran (abbreviation: 3,10DPhA2Nbf(II)) represented by Structural Formula (iii) in a weight ratio of 1:0.03 (=cgDBCzPA:3,10DPhA2Nbf(II)).

After that, on the light-emitting layer 113, cgDBCzPA was deposited to a thickness of 10 nm by evaporation, and then, bathophenanthroline (abbreviation: BPhen) represented by Structural Formula (iv) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, Light-emitting Element 1 of this example was fabricated.

The element structure of Light-emitting Element 1 is shown in the following table.

TABLE 1

| | Hole-injection layer | Hole-transport layer | Light-emitting layer | Electron-transport layer | | Electron-injection layer |
|---|---|---|---|---|---|---|
| | 10 nm | 30 nm | 25 nm | 10 nm | 15 nm | 1 nm |
| Light-emitting Element 1 | PCzPA:MoOx (4:2) | PCzPA | cgDBCzPA:3,10DPhA2Nbf(II) (1:0.03) | cgDBCzPA | BPhen | LiF |

The Light-emitting Element 1 was sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, the initial characteristics of the light-emitting element were measured. Note that the measurement was performed at room temperature.

Figure 51:
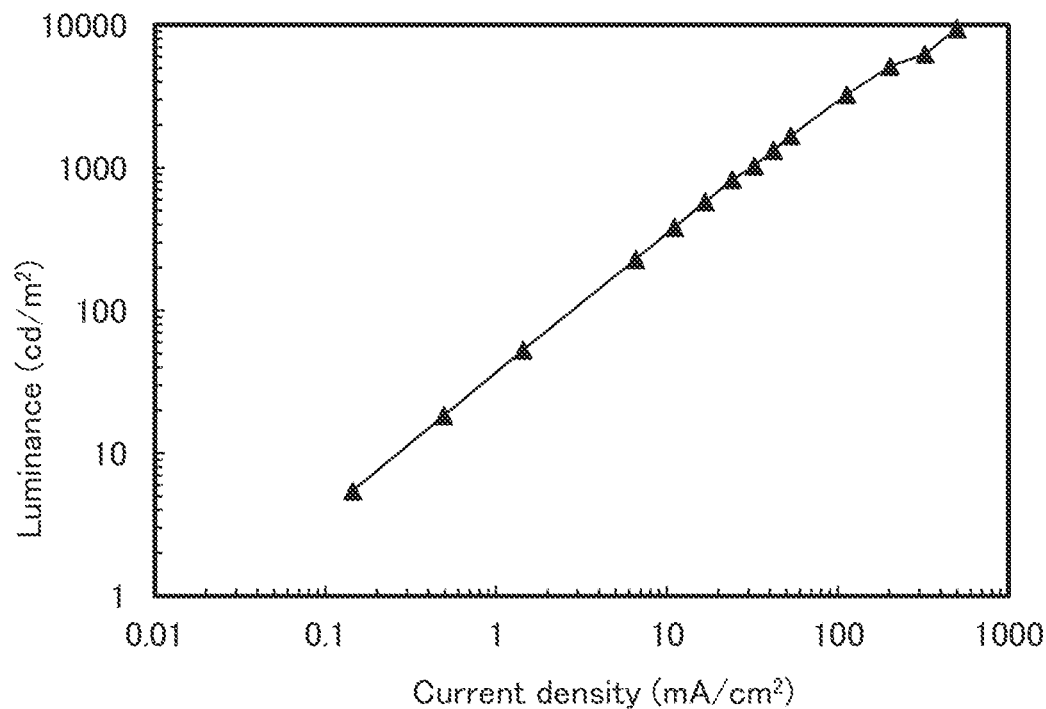
FIG. 51 shows the luminance-current density characteristics of Light-emitting Element 1.
Figure 52:
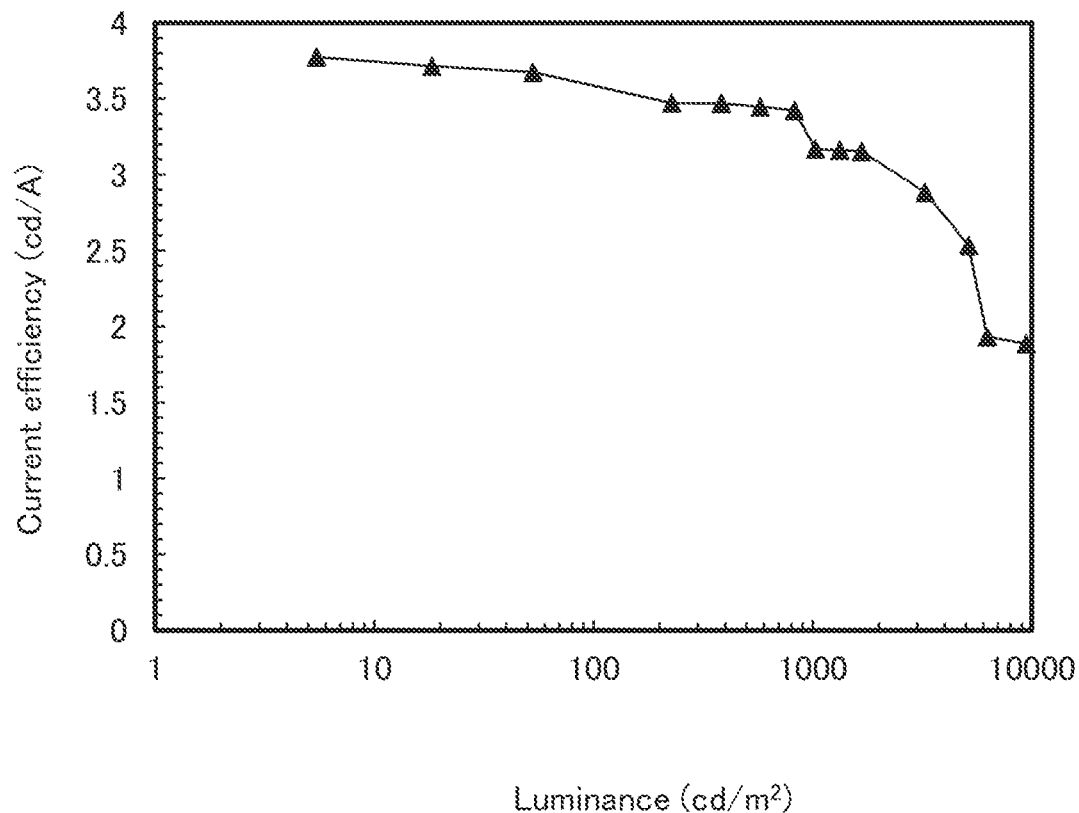
FIG. 52 shows the current efficiency-luminance characteristics of Light-emitting Element 1.
Figure 53:
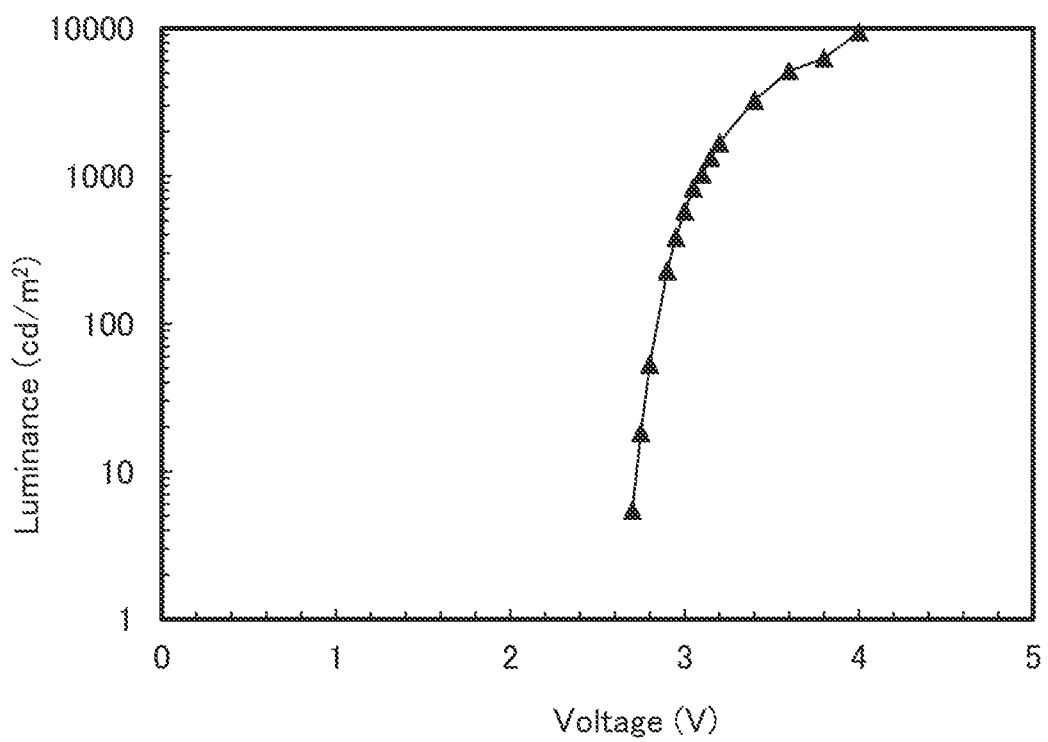
FIG. 53 shows the luminance-voltage characteristics of Light-emitting Element 1.
Figure 54:
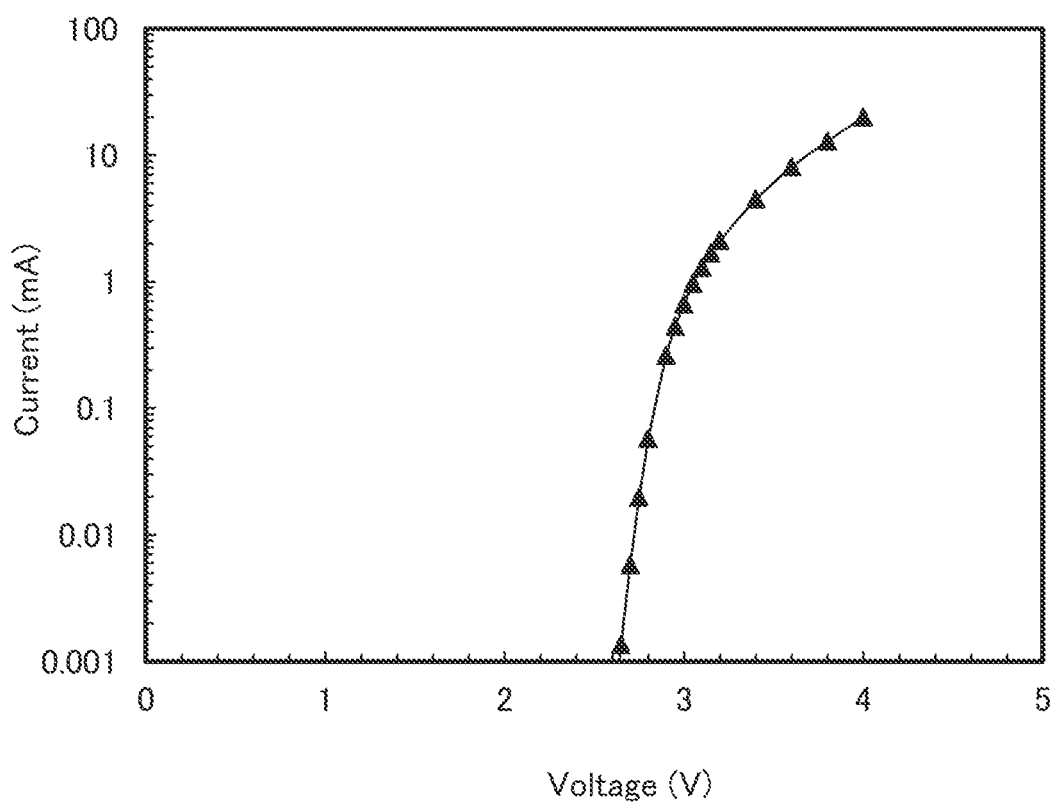
FIG. 54 shows the current-voltage characteristics of Light-emitting Element 1.
Figure 55:
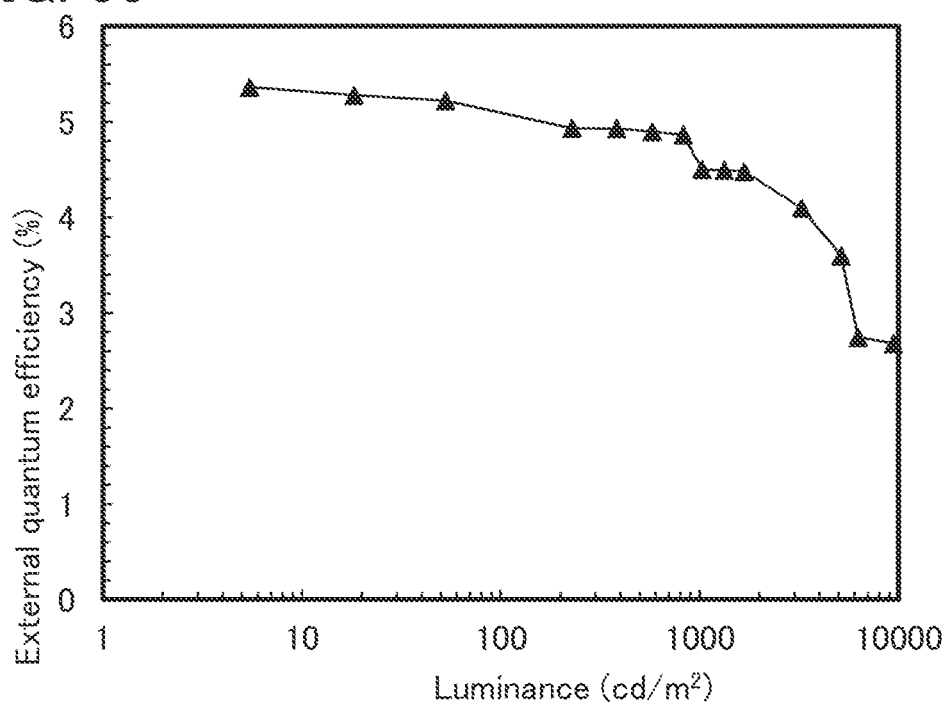
FIG. 55 shows the external quantum efficiency-luminance characteristics of Light-emitting Element 1.
Figure 56:
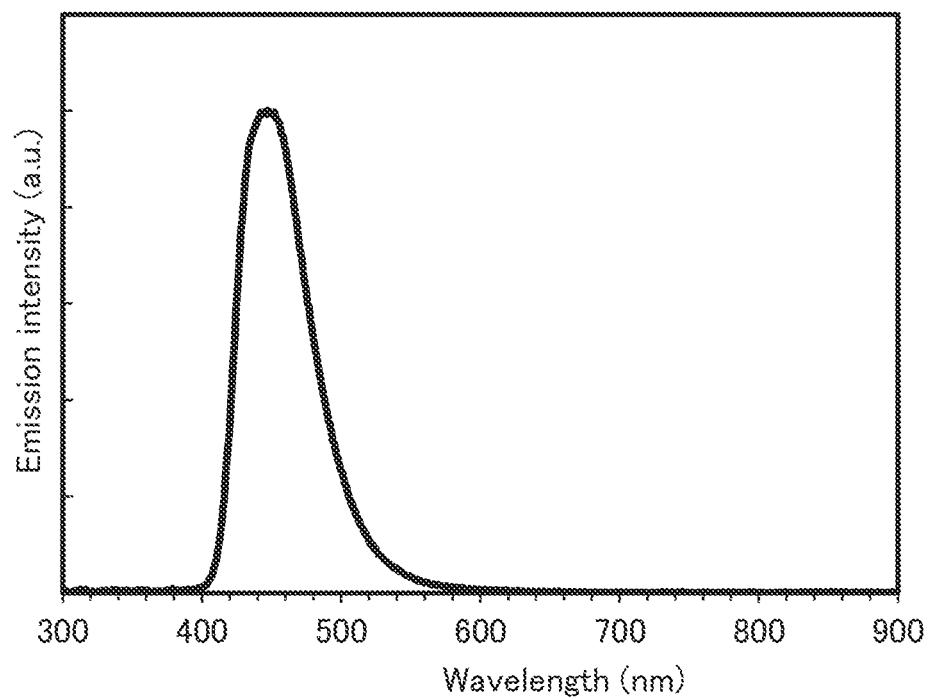
FIG. 56 shows the emission spectrum of Light-emitting Element 1.

FIG. 51 shows the luminance-current density characteristics of Light-emitting Element 1. FIG. 52 shows the current efficiency-luminance characteristics thereof. FIG. 53 shows the luminance-voltage characteristics thereof. FIG. 54 shows the current-voltage characteristics thereof. FIG. 55 shows the external quantum efficiency-luminance characteristics thereof. FIG. 56 shows the emission spectrum thereof.

TABLE 2

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting Element 1 | 3.1 | 1.30 | 32.5 | 0.14 | 0.07 | 3.2 | 4.5 |

According to FIGS. 51 to 55 and Table 2, Light-emitting Element 1 has a high external quantum efficiency of 4.5% at 1000 cd/m$^2$.

Figure 57:
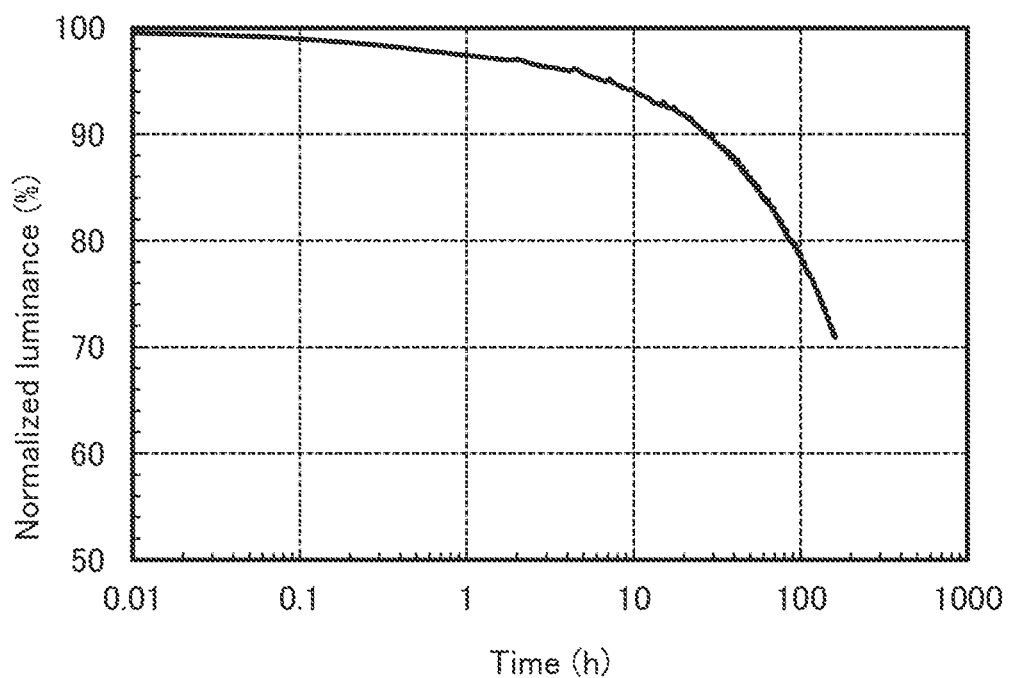
FIG. 57 shows the time dependence of normalized luminance of Light-emitting Element 1.

FIG. 57 is a graph showing driving time-dependent change in luminance under the conditions where the current value is 2 mA and the current density is constant. As shown in FIG. 57, Light-emitting Element 1 maintained 75% or more of the initial luminance after 100-hour-driving and was found to be a long-life light-emitting element.

The above results imply that the use of the organic compound in which a naphtho[2,3-b;7,6-b']bisbenzofuran skeleton or a naphtho[2,3-b;7,6-b']bisbenzothiophene skeleton has a diarylamino group as a substituent, as a light-emitting material of a light-emitting element, allows the light-emitting element to have favorable characteristics such as high external quantum efficiency. In particular, the compound in which diarylamino groups are bonded to the 3-position and the 10-position of any of the skeletons was found to have high reliability.

Example 8

In this example, Light-emitting Element 2, which corresponds to the light-emitting element of one embodiment of the present invention described in the above embodiment, will be described in detail. The structural formulae of organic compounds used for Light-emitting Element 2 are shown below.

[Chemical Formula 103]

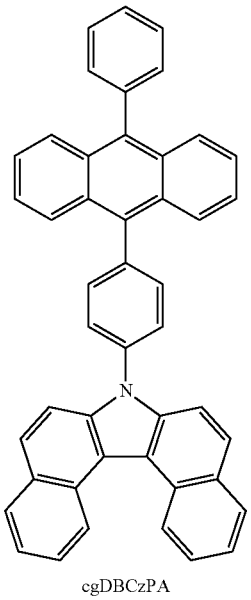

cgDBCzPA (ii)

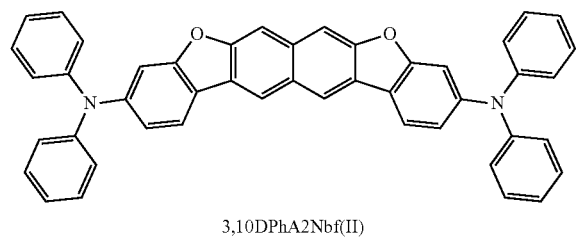

3,10DPhA2Nbf(II) (iii)

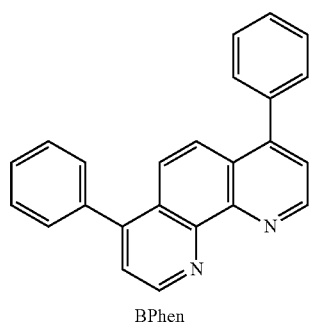

BPhen (iv)

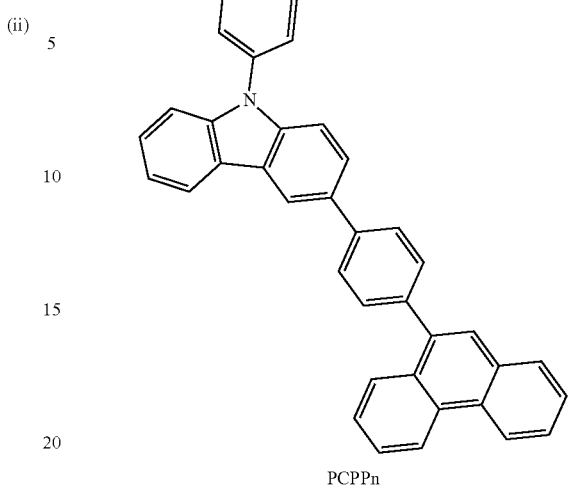

PCPPn (v)

(Method for Fabricating Light-Emitting Element 2)

First, indium tin oxide containing silicon oxide (ITSO) was deposited on a glass substrate by a sputtering method to form the anode 101. The thickness of the anode 101 is 70 nm, and the electrode area is 4 mm² (2 mm×2 mm).

Next, in pretreatment for forming the light-emitting element over a substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 30 minutes.

Next, the substrate provided with the anode 101 was fixed to a substrate holder provided in the vacuum evaporation apparatus such that the side on which the anode 101 was formed faced downward. Then, 3-[4-(9-phenanthryl)-phenyl]-9-phenyl-9H-carbazole (abbreviation: PCPPn) represented by Structural Formula (v) and molybdenum(VI) oxide were co-evaporated on the anode 101 to a thickness of 10 nm by an evaporation method using resistance heating such that the weight ratio of PCPPn to molybdenum oxide was 4:2, whereby the hole-injection layer 111 was formed.

Subsequently, on the hole-injection layer 111, PCPPn was deposited to a thickness of 30 nm by evaporation to form the hole-transport layer 112.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by Structural Formula (ii) and 3,10-bis(diphenylamino)naphtho[2,3-b;7,6-b']bisbenzofuran (abbreviation: 3,10DPhA2Nbf(II)) represented by Structural Formula (iii) in a weight ratio of 1:0.03 (=cgDBCzPA:3,10DPhA2Nbf(II)).

After that, on the light-emitting layer 113, cgDBCzPA was deposited to a thickness of 10 nm by evaporation, and bathophenanthroline (abbreviation: BPhen) represented by Structural Formula (iv) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, Light-emitting Element 2 of this example was fabricated.

The element structure of Light-emitting Element 2 is shown in the following table.

TABLE 3

| | Hole-injection layer | Hole-transport layer | Light-emitting layer | Electron-transport layer | | Electron-injection layer |
|---|---|---|---|---|---|---|
| | 10 nm | 30 nm | 25 nm | 10 nm | 15 nm | 1 nm |
| Light-emitting Element 2 | PCPPn:MoOx (4:2) | PCPPn | cgDBCzPA: 3,10DPhA2Nbf(II) (1:0.03) | cgDBCzPA | BPhen | LiF |

Light-emitting Element 2 was sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, the initial characteristics of the light-emitting element were measured. Note that the measurement was performed at room temperature.

Figure 58:
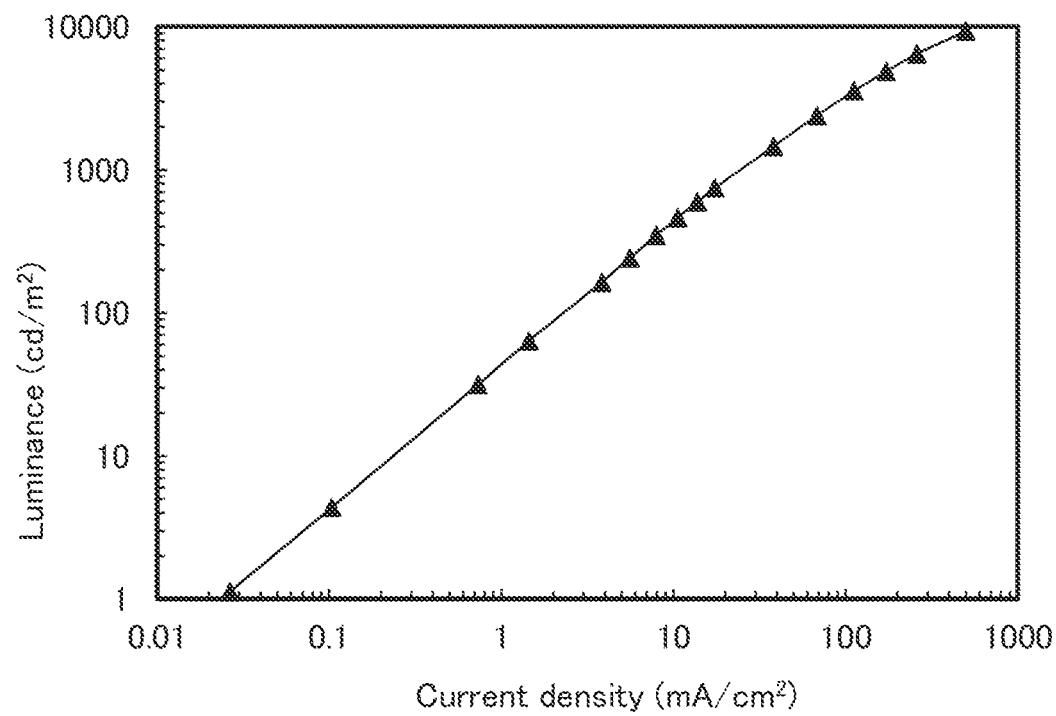
FIG. 58 shows the luminance-current density characteristics of Light-emitting Element 2.
Figure 59:
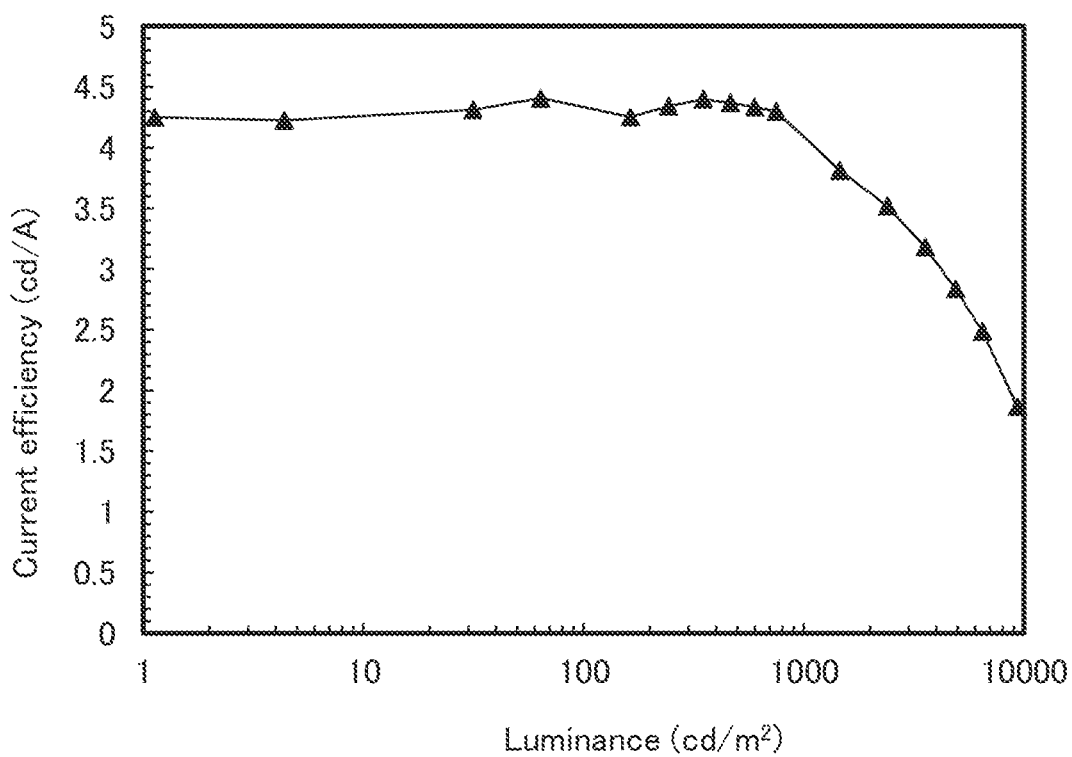
FIG. 59 shows the current efficiency-luminance characteristics of Light-emitting Element 2.
Figure 60:
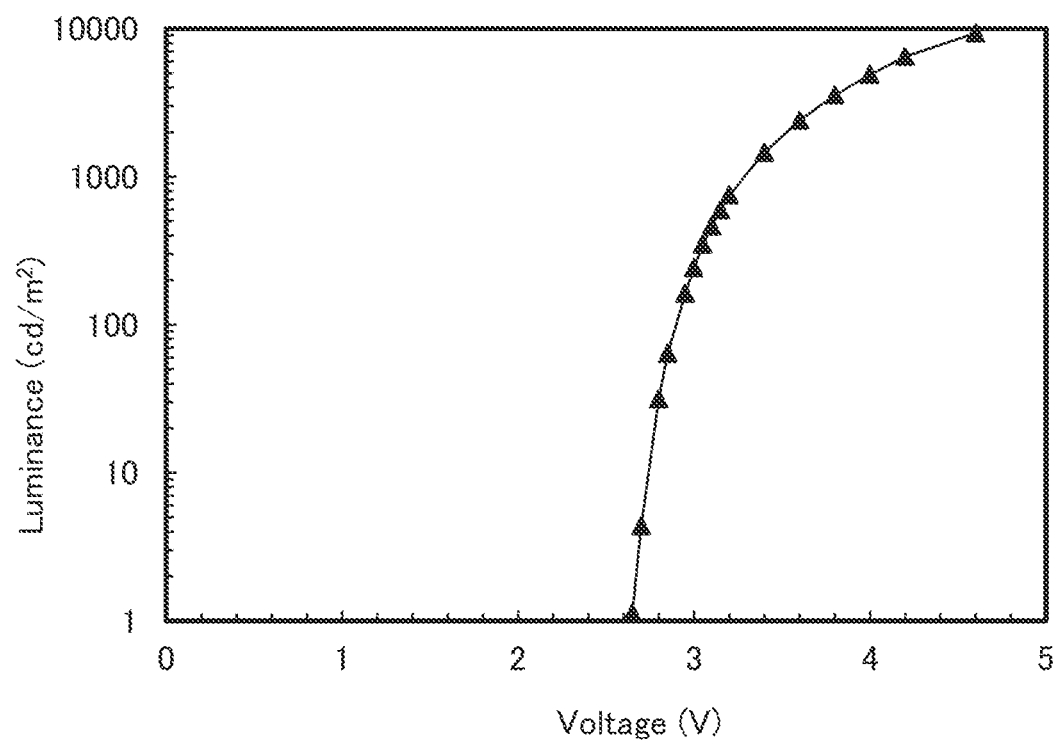
FIG. 60 shows the luminance-voltage characteristics of Light-emitting Element 2.
Figure 61:
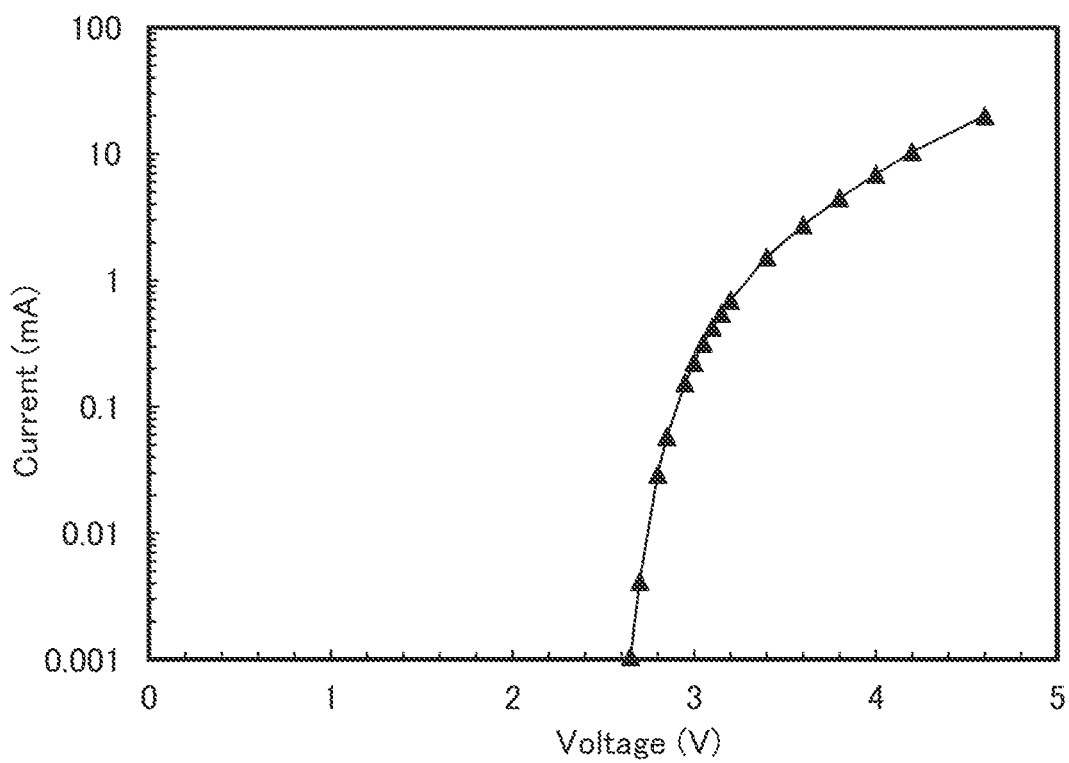
FIG. 61 shows the current-voltage characteristics of Light-emitting Element 2.
Figure 62:
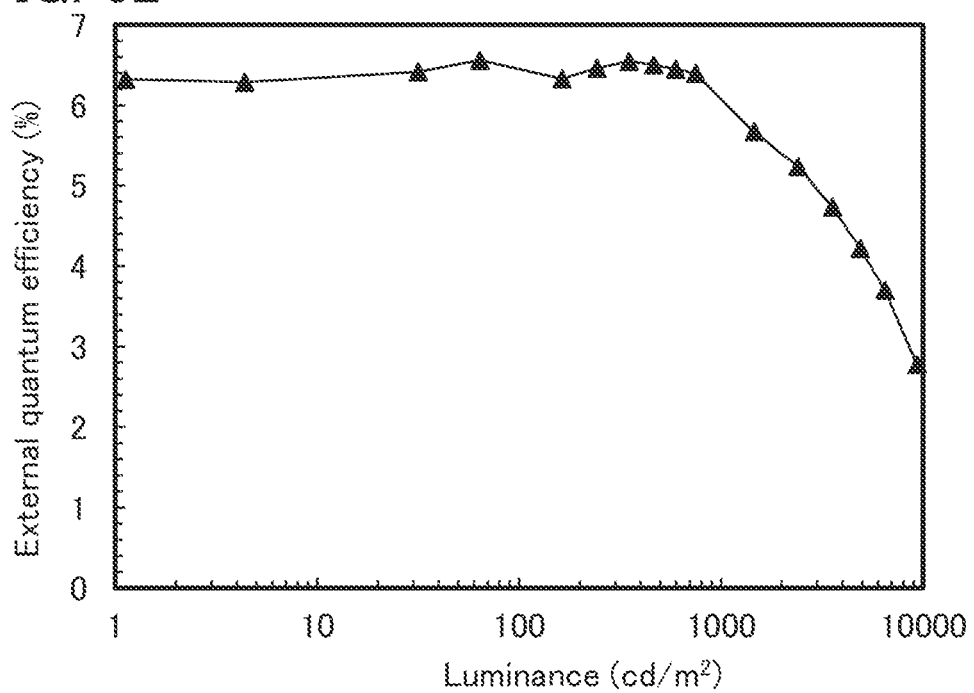
FIG. 62 shows the external quantum efficiency-luminance characteristics of Light-emitting Element 2.
Figure 63:
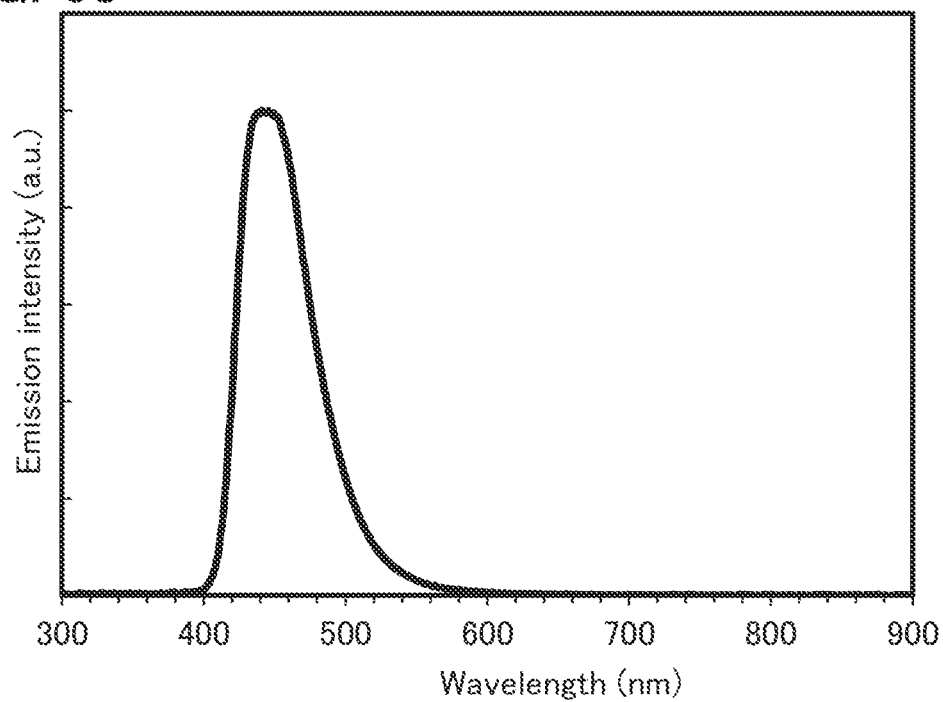
FIG. 63 shows the emission spectrum of Light-emitting Element 2.

FIG. 58 shows the luminance-current density characteristics of Light-emitting Element 2. FIG. 59 shows the current efficiency-luminance characteristics thereof. FIG. 60 shows the luminance-voltage characteristics thereof. FIG. 61 shows the current-voltage characteristics thereof. FIG. 62 shows the external quantum efficiency-luminance characteristics thereof. FIG. 63 shows the emission spectrum thereof.

TABLE 4

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting Element 2 | 3.2 | 0.70 | 17.4 | 0.14 | 0.07 | 4.3 | 6.4 |

According to FIGS. 58 to 62 and Table 4, Light-emitting Element 2 has high external quantum efficiency of 6.4% at 1000 cd/m$^2$.

Figure 64:
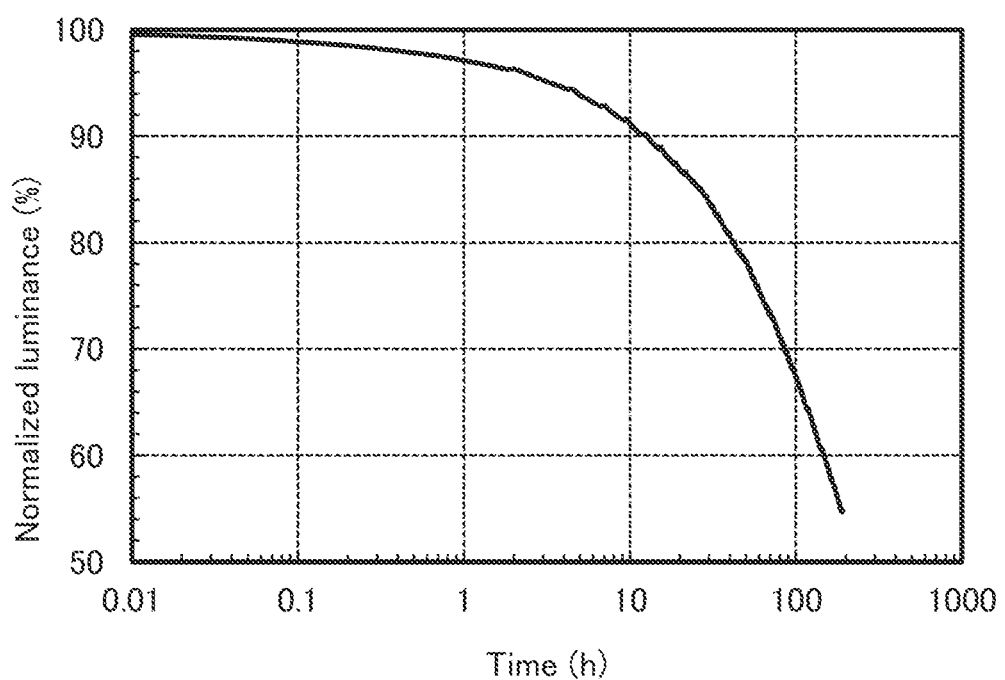
FIG. 64 shows the time dependence of normalized luminance of Light-emitting Element 2.

FIG. 64 is a graph showing driving time-dependent change in luminance under the conditions where the current value is 2 mA and the current density is constant. As shown in FIG. 64, Light-emitting Element 2 maintained 65% or more of the initial luminance after 100-hour-driving and was found to be a long-life light-emitting element.

The above results imply that the use of the organic compound in which a naphtho[2,3-b;7,6-b']bisbenzofuran skeleton or a naphtho[2,3-b;7,6-b']bisbenzothiophene skeleton has a diarylamino group as a substituent, as a light-emitting material of a light-emitting element, allows the light-emitting element to have favorable characteristics such as high external quantum efficiency. In particular, the use of a material with a high LUMO level for a hole-transport layer appears to lead to high efficiency.

Example 9

In this example, Light-emitting Element 3, which corresponds to the light-emitting element of one embodiment of the present invention described in the above embodiment, will be described. The structural formulae of organic compounds used for Light-emitting Element 3 are shown below.

[Chemical Formula 104]

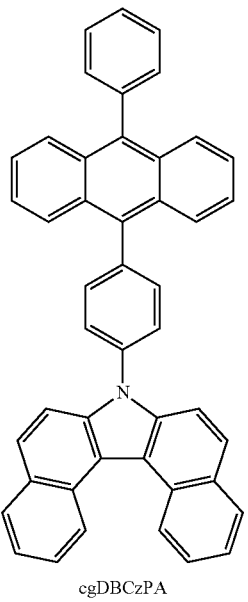

cgDBCzPA

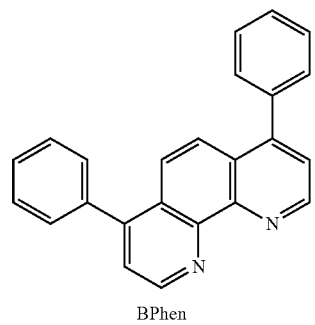

BPhen

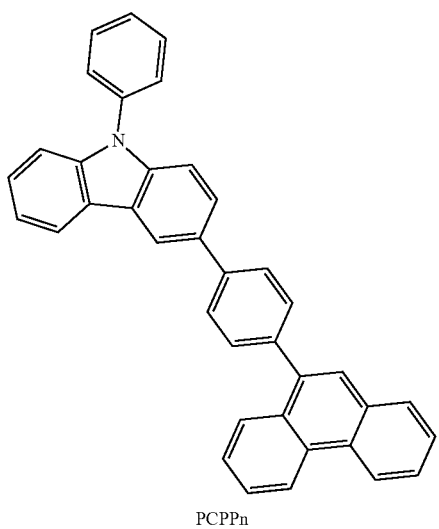

PCPPn

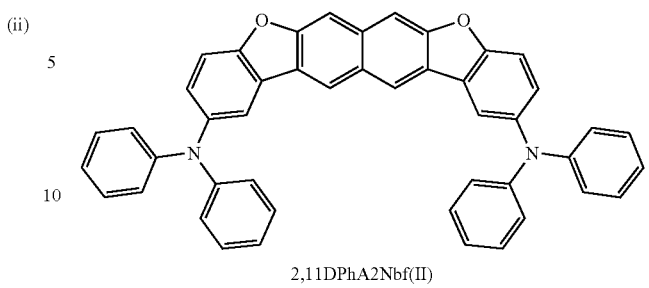

2,11DPhA2Nbf(II)

(Method for Fabricating Light-Emitting Element 3)

First, indium tin oxide containing silicon oxide (ITSO) was deposited on a glass substrate by a sputtering method to form the anode 101. The thickness of the anode 101 is 70 nm, and the electrode area is 4 mm² (2 mm×2 mm).

Next, in pretreatment for forming the light-emitting element over a substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 45 minutes.

Next, the substrate provided with the anode 101 was fixed to a substrate holder provided in the vacuum evaporation apparatus such that the side on which the anode 101 was formed faced downward. Then, 3-[4-(9-phenanthryl)-phenyl]-9-phenyl-9H-carbazole (abbreviation: PCPPn) represented by Structural Formula (v) and molybdenum(VI) oxide were co-evaporated on the anode 101 to a thickness of 10 nm by an evaporation method using resistance heating such that the weight ratio of PCPPn to molybdenum oxide was 4:2, whereby the hole-injection layer 111 was formed.

Subsequently, PCPPn was deposited by evaporation to a thickness of 30 nm on the hole-injection layer 111 to form the hole-transport layer 112.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by Structural Formula (ii) and 2,11-bis(diphenylamino)naphtho[2,3-b;7,6-b']bisbenzofuran (abbreviation: 2,11DPhA2Nbf(II)) represented by Structural Formula (vi) in a weight ratio of 1:0.03 (=cgDBCzPA:2,11DPhA2Nbf(II)).

After that, on the light-emitting layer 113, cgDBCzPA was deposited to a thickness of 10 nm by evaporation, and then, bathophenanthroline (abbreviation: BPhen) represented by Structural Formula (iv) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, Light-emitting Element 3 of this example was fabricated.

The element structure of Light-emitting Element 3 is shown in the following table.

TABLE 5

| | Hole-injection layer | Hole-transport layer | Light-emitting layer | Electron-transport layer | | Electron-injection layer |
|---|---|---|---|---|---|---|
| | 10 nm | 30 nm | 25 nm | 10 nm | 15 nm | 1 nm |
| Light-emitting Element 3 | MoOx (4:2) | PCPPn | 2,11DPhA2Nbf(II) (1:0.03) | cgDBCzPA | BPhen | LiF |

Light-emitting Element 3 was sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, the initial characteristics of the light-emitting element were measured. Note that the measurement was performed at room temperature.

Figure 65:
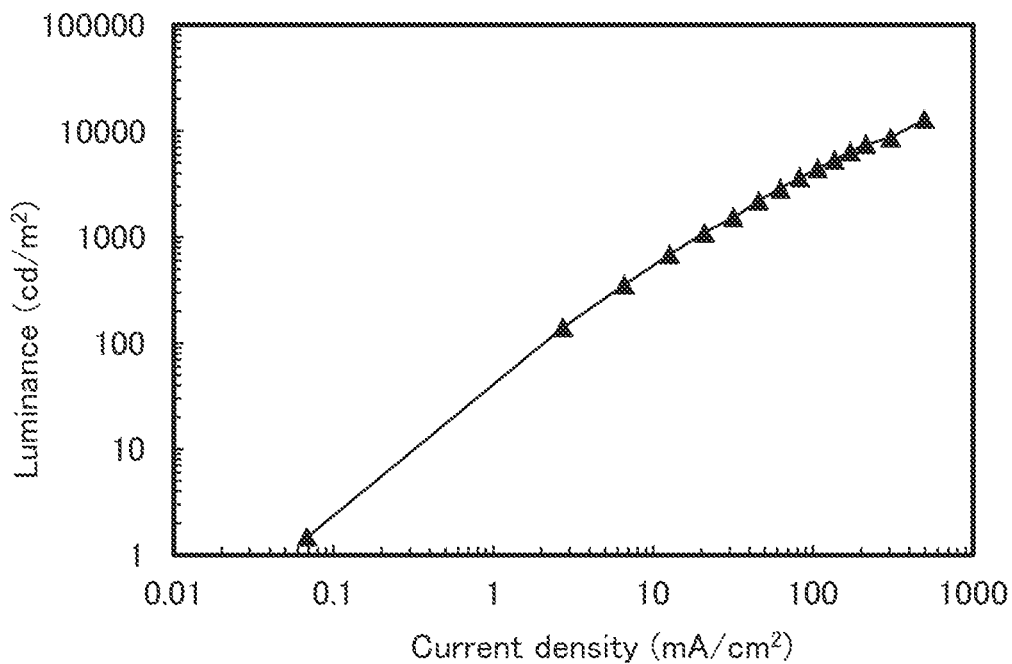
FIG. 65 shows the luminance-current density characteristics of Light-emitting Element 3.
Figure 66:
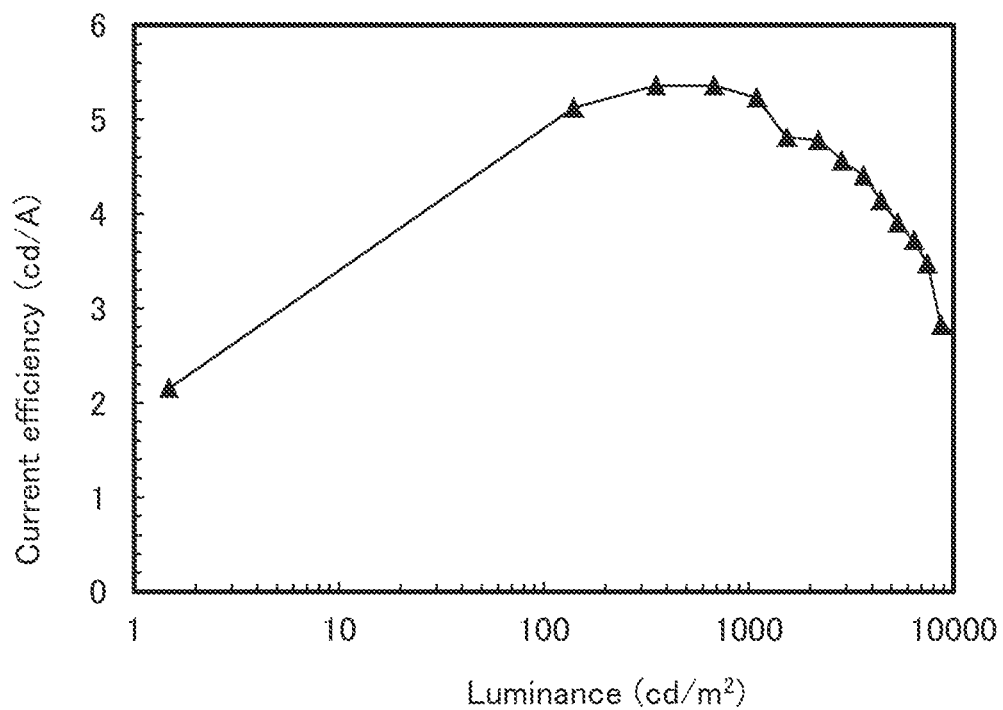
FIG. 66 shows the current efficiency-luminance characteristics of Light-emitting Element 3.
Figure 67:
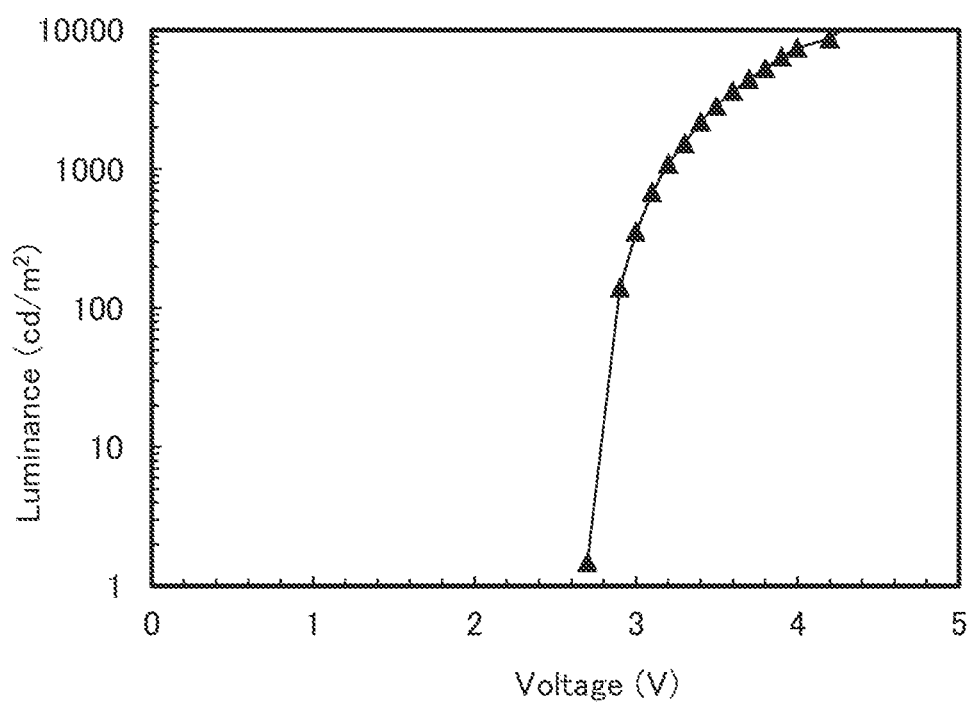
FIG. 67 shows the luminance-voltage characteristics of Light-emitting Element 3.
Figure 68:
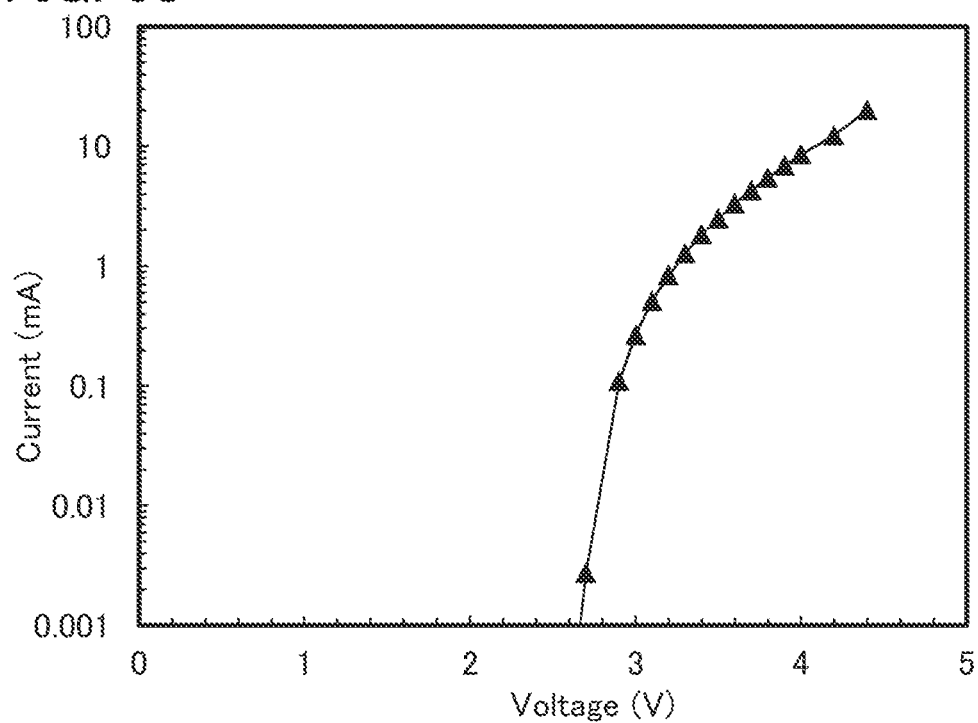
FIG. 68 shows the current-voltage characteristics of Light-emitting Element 3.
Figure 69:
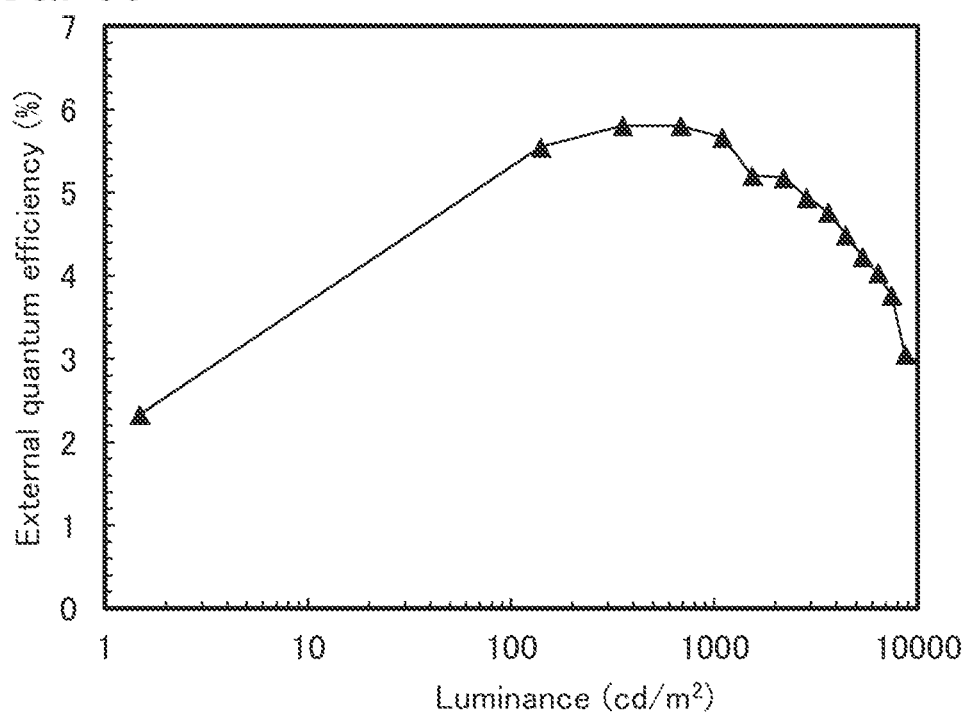
FIG. 69 shows the external quantum efficiency-luminance characteristics of Light-emitting Element 3.
Figure 70:
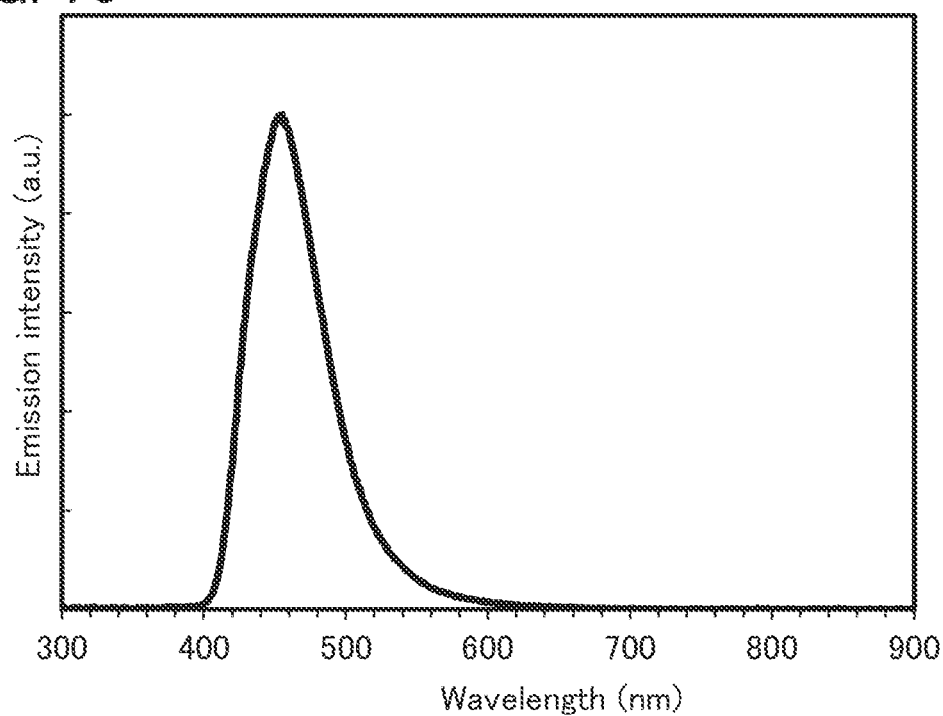
FIG. 70 shows the emission spectrum of Light-emitting Element 3.

FIG. 65 shows the luminance-current density characteristics of Light-emitting Element 3. FIG. 66 shows the current efficiency-luminance characteristics thereof. FIG. 67 shows the luminance-voltage characteristics thereof. FIG. 68 shows the current-voltage characteristics thereof. FIG. 69 shows the external quantum efficiency-luminance characteristics thereof. FIG. 70 shows the emission spectrum thereof.

TABLE 6

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting Element 3 | 3.2 | 0.84 | 21.0 | 0.15 | 0.10 | 5.2 | 5.7 |

According to FIGS. 65 to 69 and Table 6, Light-emitting Element 3 has very high external quantum efficiency of 5.7% at 1000 cd/m$^2$.

The above results imply that the use of the organic compound in which a naphtho[2,3-b;7,6-b']bisbenzofuran skeleton or a naphtho[2,3-b;7,6-b']bisbenzothiophene skeleton has a diarylamino group as a substituent, as a light-emitting material of a light-emitting element, allows the light-emitting element to have favorable characteristics such as high external quantum efficiency. In particular, the use of the compound in which diarylamino groups are bonded to the 2-position and the 11-position of any of the skeletons appears to lead to high current efficiency.

Example 10

In this example, Light-emitting Element 4, which corresponds to the light-emitting element of one embodiment of the present invention described in the above embodiment, will be described in detail. The structural formulae of organic compounds used for Light-emitting Element 4 are shown below.

[Chemical Formula 105]

(ii)

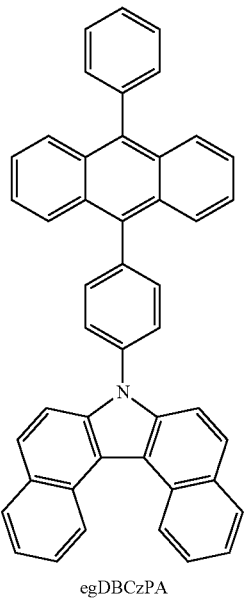

egDBCzPA (vii)

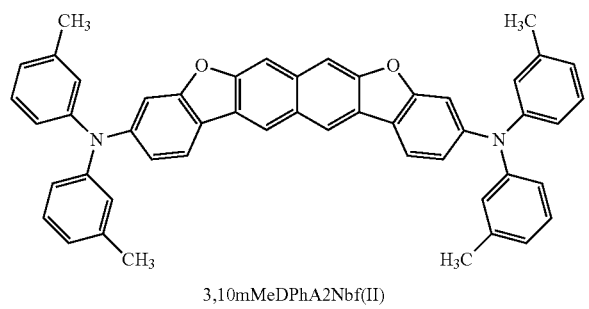

3,10mMeDPhA2Nbf(II)

(v)

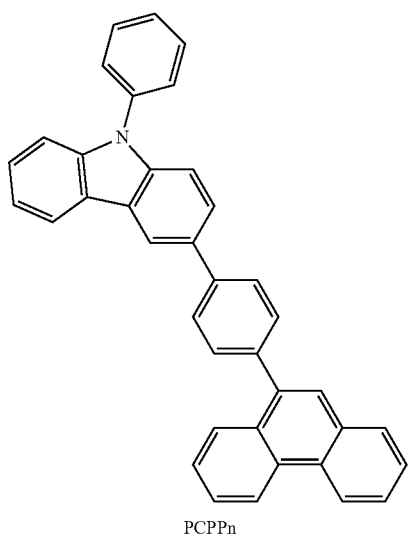

PCPPn (iv)

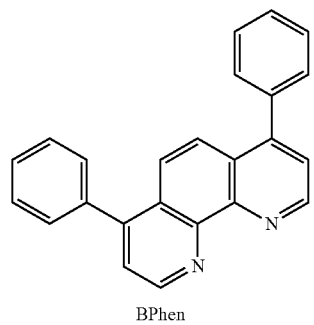

BPhen (Method for Fabricating Light-Emitting Element 4)

First, indium tin oxide containing silicon oxide (ITSO) was deposited on a glass substrate by a sputtering method to form the anode 101. The thickness of the anode 101 is 70 nm, and the electrode area is 4 mm² (2 mm×2 mm).

Next, in pretreatment for forming the light-emitting element over a substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 45 minutes.

Next, the substrate provided with the anode 101 was fixed to a substrate holder provided in the vacuum evaporation apparatus such that the side on which the anode 101 was formed faced downward. Then, 3-[4-(9-phenanthryl)-phenyl]-9-phenyl-9H-carbazole (abbreviation: PCPPn) represented by Structural Formula (v) and molybdenum(VI) oxide were co-evaporated on the anode 101 to a thickness of 10 nm by an evaporation method using resistance heating such that the weight ratio of PCPPn to molybdenum oxide was 4:2, whereby the hole-injection layer 111 was formed.

Subsequently, PCPPn was deposited by evaporation to a thickness of 30 nm on the hole-injection layer 111 to form the hole-transport layer 112.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by Structural Formula (ii) and 3,10-bis(3,3'-dimethyldiphenylamino)naphtho[2,3-b;7,6-b'] bisbenzofuran (abbreviation: 3,10mMeDPhA2Nbf(II)) represented by Structural Formula (vii) in a weight ratio of 1:0.03 (=cgDBCzPA:3,10mMeDPhA2Nbf(II)).

After that, on the light-emitting layer 113, cgDBCzPA was deposited to a thickness of 10 nm by evaporation, and then, bathophenanthroline (abbreviation: BPhen) represented by Structural Formula (iv) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, Light-emitting Element 4 of this example was fabricated.

The element structure of Light-emitting Element 4 is shown in the following table.

TABLE 7

|  | Hole-injection layer 10 nm | Hole-transport layer 30 nm | Light-emitting layer 25 nm | Electron-transport layer | | Electron-injection layer 1 nm |
| --- | --- | --- | --- | --- | --- | --- |
|  |  |  |  | 10 nm | 15 nm |  |
| Light-emitting Element 4 | PCPPn: MoOx (4:2) | PCPPn | cgDBCzPA: 3,10mMeDPhA2Nbf(II) | cgDBCzPA | BPhen | LiF |

The Light-emitting Element 4 was sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, the initial characteristics of the light-emitting element were measured. Note that the measurement was performed at room temperature.

Figure 71:
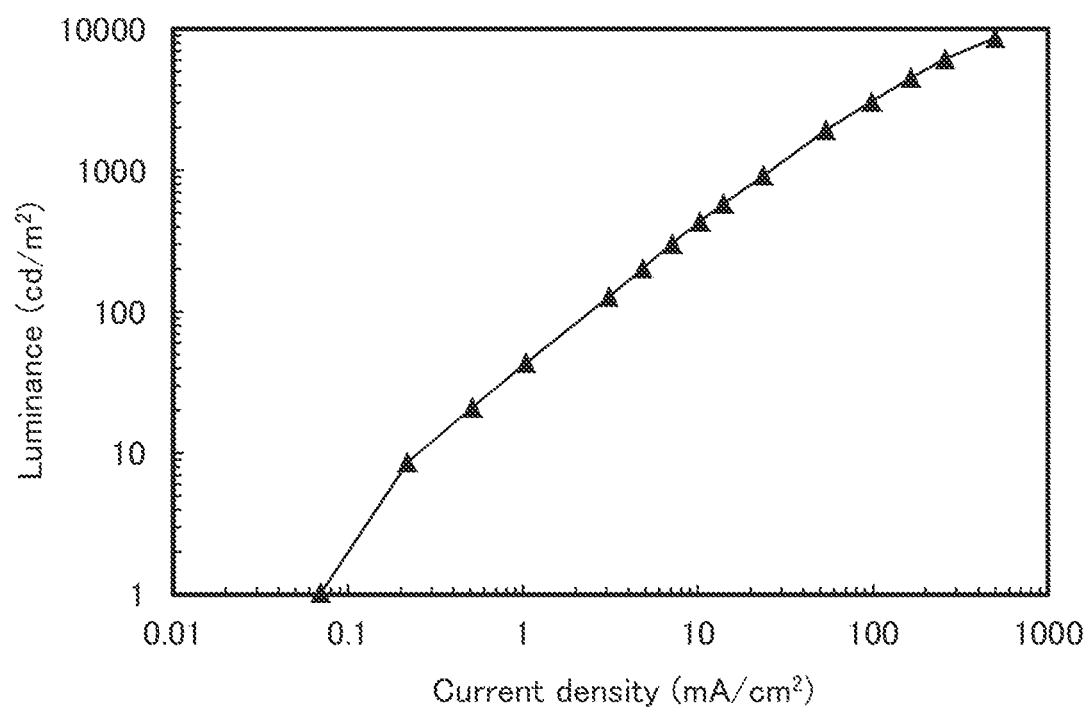
FIG. 71 shows the luminance-current density characteristics of Light-emitting Element 4.
Figure 72:
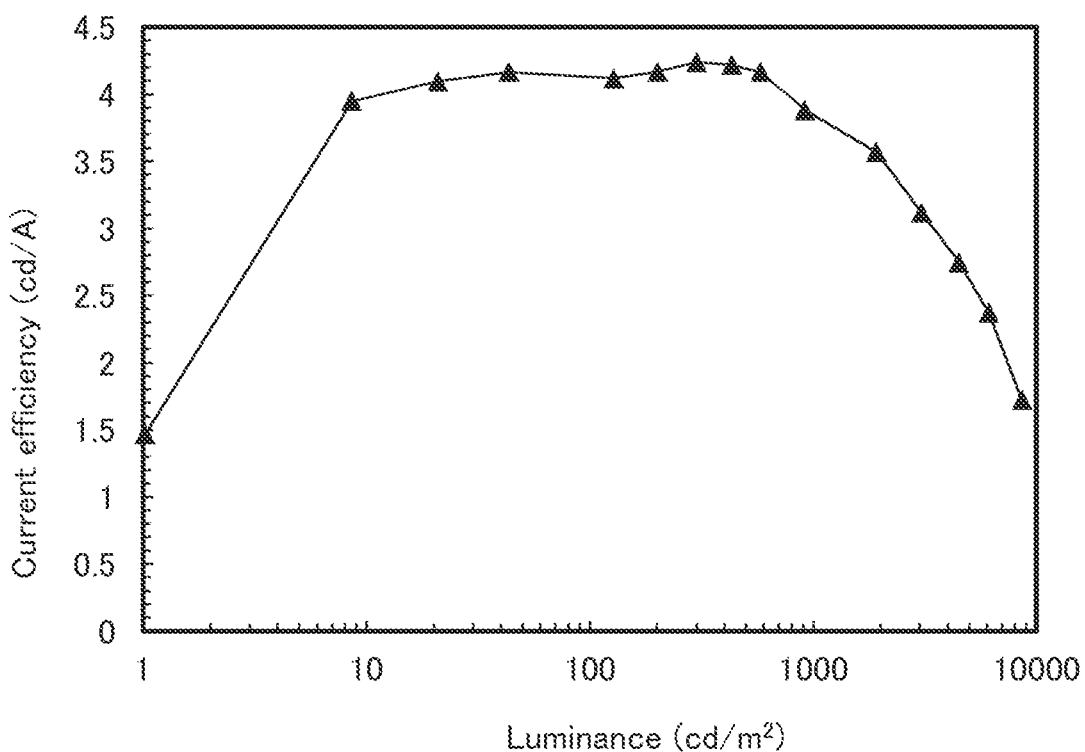
FIG. 72 shows the current efficiency-luminance characteristics of Light-emitting Element 4.
Figure 73:
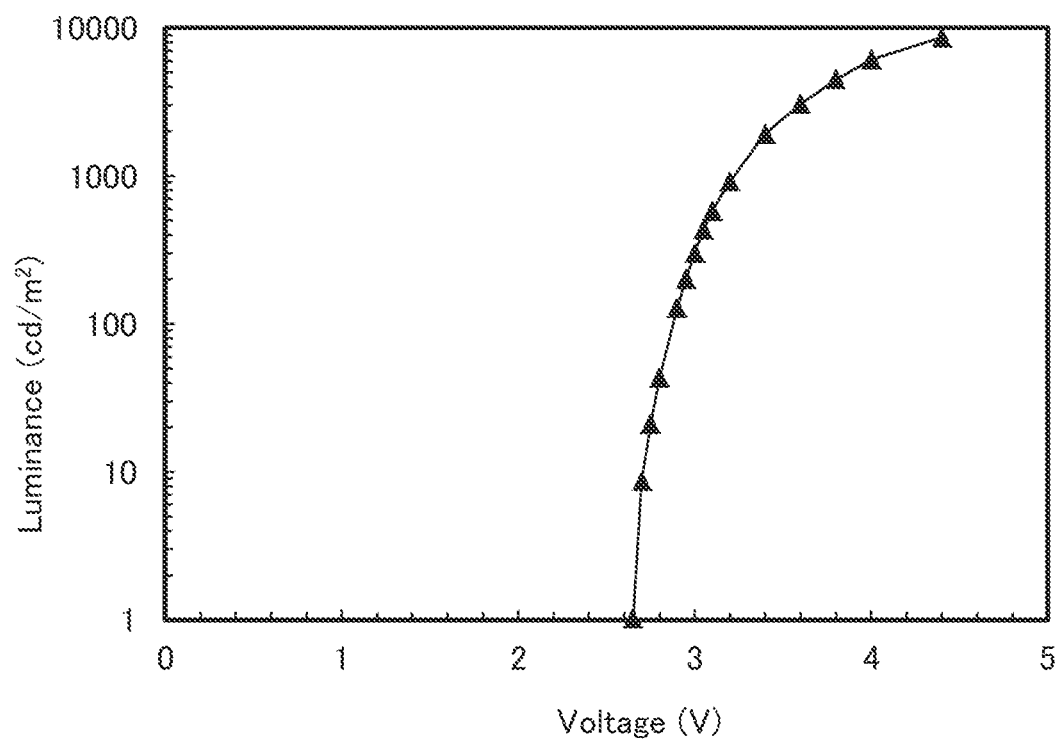
FIG. 73 shows the luminance-voltage characteristics of Light-emitting Element 4.
Figure 74:
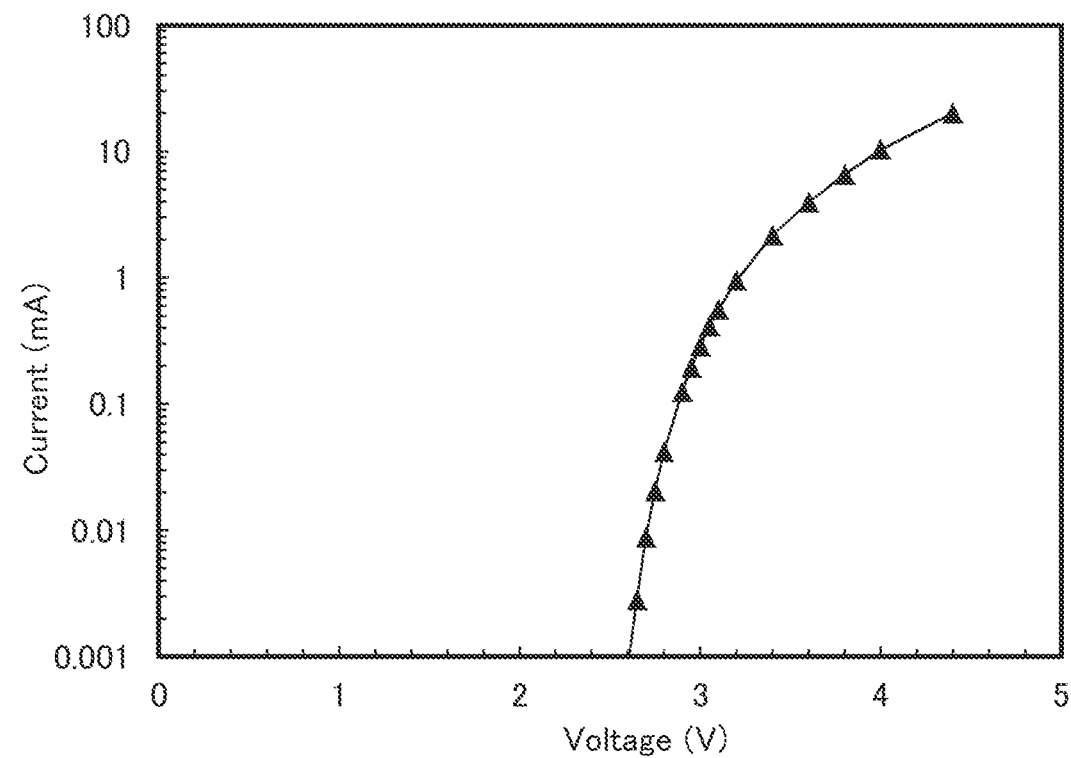
FIG. 74 shows the current-voltage characteristics of Light-emitting Element 4.
Figure 75:
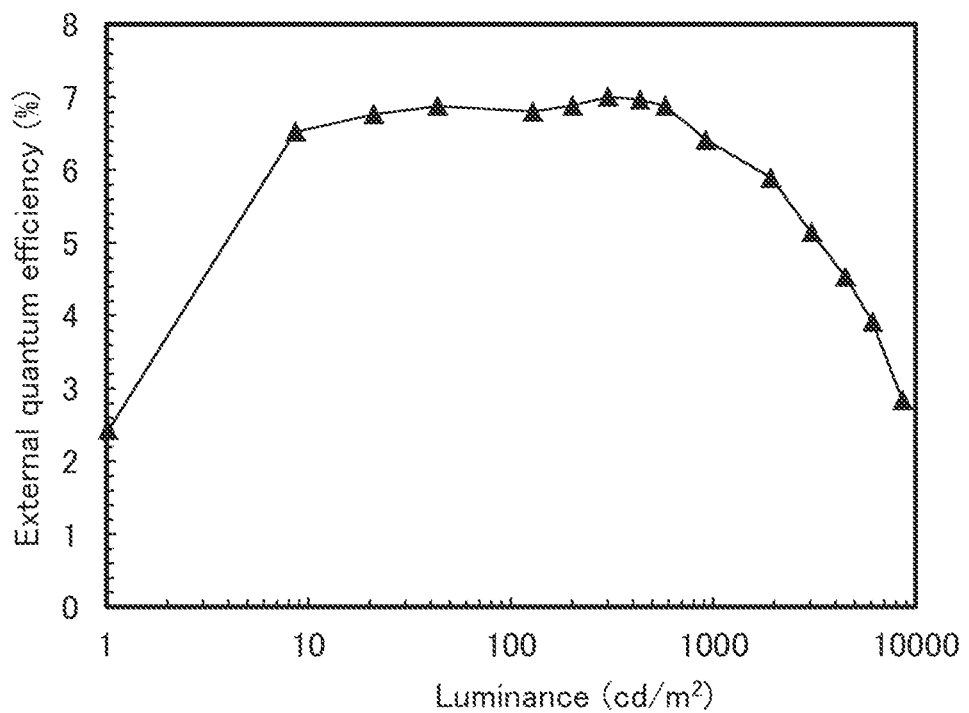
FIG. 75 shows the external quantum efficiency-luminance characteristics of Light-emitting Element 4.
Figure 76:
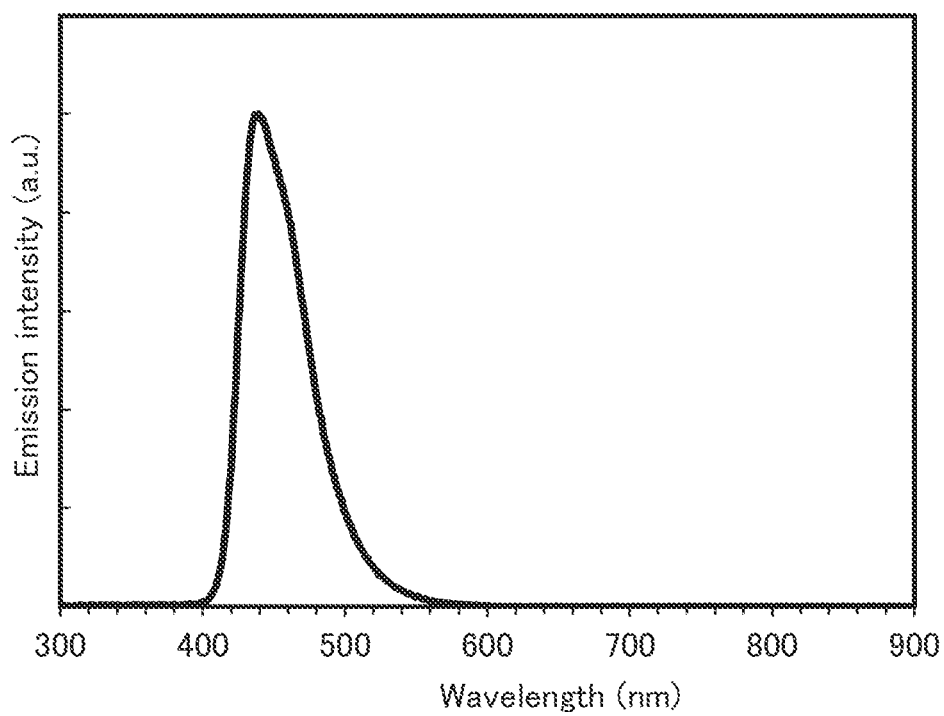
FIG. 76 shows the emission spectrum of Light-emitting Element 4.

FIG. 71 shows the luminance-current density characteristics of Light-emitting Element 4. FIG. 72 shows the current efficiency-luminance characteristics thereof. FIG. 73 shows the luminance-voltage characteristics thereof. FIG. 74 shows the current-voltage characteristics thereof. FIG. 75 shows the external quantum efficiency-luminance characteristics thereof. FIG. 76 shows the emission spectrum thereof.

TABLE 8

|  | Voltage (V) | Current (mA) | Current density (mA/cm$^2$) | Chromaticity x | Chromaticity y | Current efficiency (cd/A) | External quantum efficiency (%) |
| --- | --- | --- | --- | --- | --- | --- | --- |
| Light-emitting Element 4 | 3.2 | 0.95 | 23.6 | 0.14 | 0.06 | 3.9 | 6.4 |

According to FIGS. 71 to 75 and Table 8, Light-emitting Element 4 has very high external quantum efficiency of 6.4% at 1000 cd/m$^2$.

Figure 77:
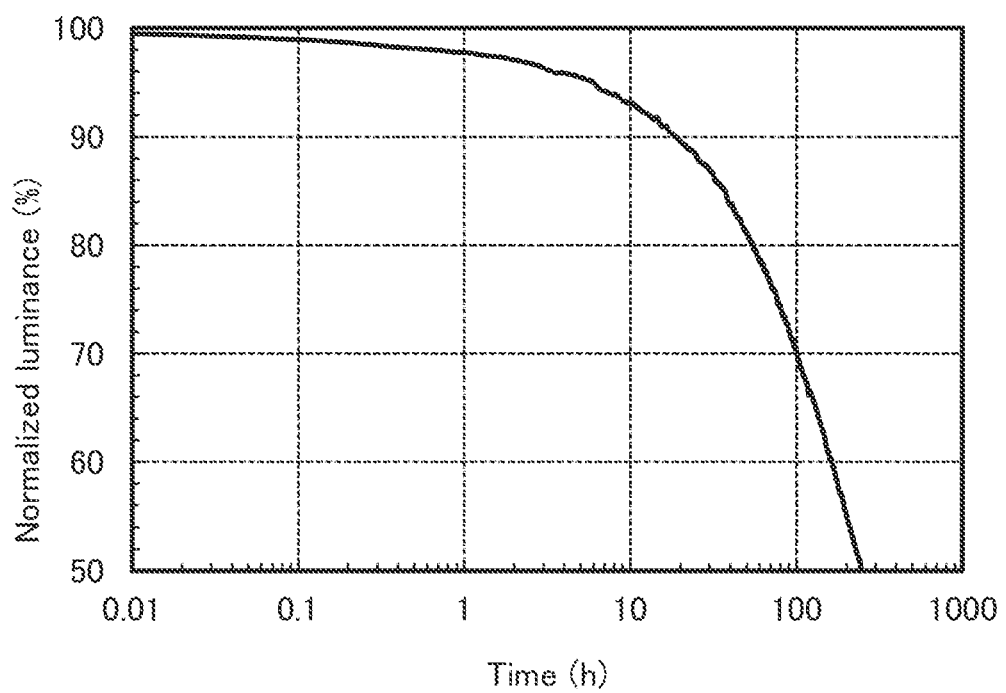
FIG. 77 shows the time dependence of normalized luminance of Light-emitting Element 4.

FIG. 77 is a graph showing driving time-dependent change in the luminance under the conditions where the current value was 2 mA and the current density was constant. As shown in FIG. 77, Light-emitting Element 4 maintains 70% or more of the initial luminance after 100-hour-driving and was found to be a long-life light-emitting element.

Example 11

In this example, Light-emitting Element 5, which corresponds to the light-emitting element of one embodiment of the present invention described in the above embodiment, will be described in detail. The structural formulae of organic compounds used for Light-emitting Element 5 are shown below.

[Chemical Formula 106]
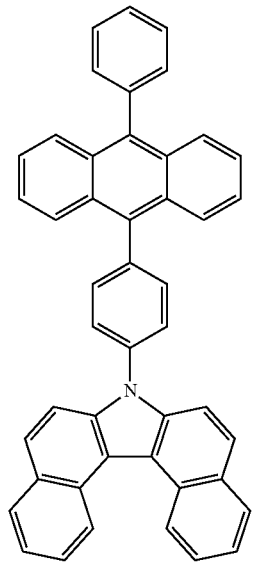
egDBCzPA
(ii)
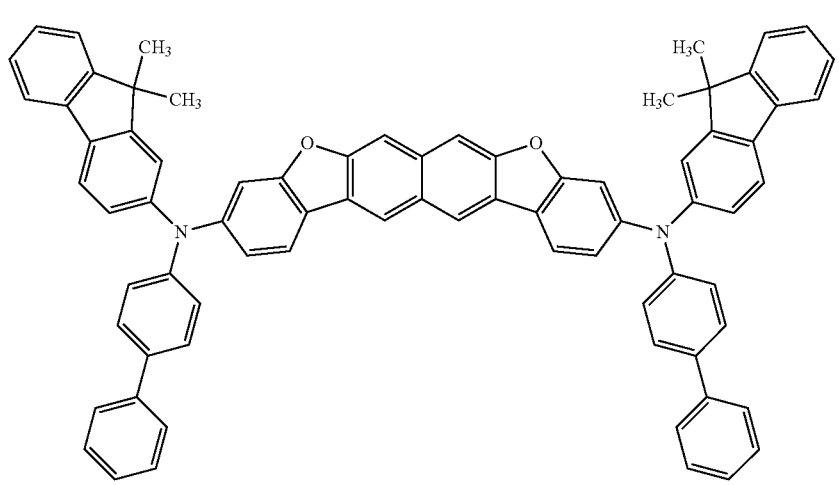
3,10FBi2Nbf(II)
(viii)

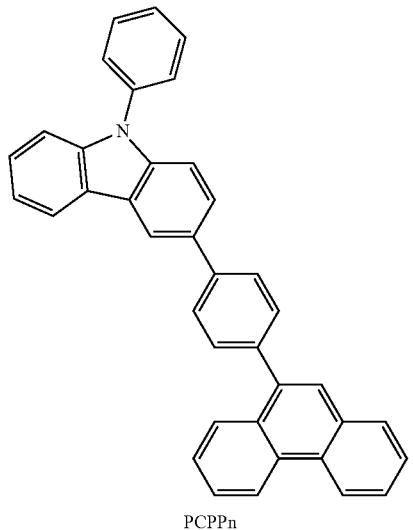

PCPPn
(v)

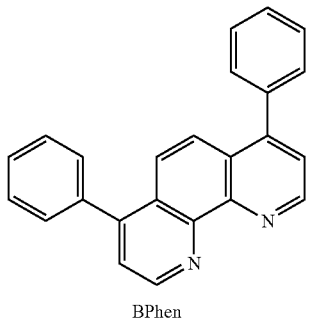

BPhen
(iv)

(Method for Fabricating Light-Emitting Element 5)

First, indium tin oxide containing silicon oxide (ITSO) was deposited on a glass substrate by a sputtering method to form the anode 101. The thickness of the anode 101 is 70 nm, and the electrode area is 4 mm² (2 mm×2 mm).

Next, in pretreatment for forming the light-emitting element over a substrate, a surface of the substrate was washed with water and baked at 200° C. for 1 hour, and then, UV ozone treatment was performed for 370 seconds.

After that, the substrate was transferred into a vacuum evaporation apparatus in which the pressure was reduced to approximately $10^{-4}$ Pa, vacuum baking was performed at 170° C. for 30 minutes in a heating chamber of the vacuum evaporation apparatus, and then, the substrate was cooled down for approximately 45 minutes.

Next, the substrate provided with the anode 101 was fixed to a substrate holder provided in the vacuum evaporation apparatus such that the side on which the anode 101 was formed faced downward. Then, 3-[4-(9-phenanthryl)-phenyl]-9-phenyl-9H-carbazole (abbreviation: PCPPn) represented by Structural Formula (v) and molybdenum(VI) oxide were co-evaporated on the anode 101 to a thickness of 10 nm by an evaporation method using resistance heating such that the weight ratio of PCPPn to molybdenum oxide was 4:2, whereby the hole-injection layer 111 was formed.

Subsequently, PCPPn was deposited by evaporation to a thickness of 30 nm on the hole-injection layer 111 to form the hole-transport layer 112.

Then, the light-emitting layer 113 was formed to a thickness of 25 nm by co-evaporation of 7-[4-(10-phenyl-9-anthryl)phenyl]-7H-dibenzo[c,g]carbazole (abbreviation: cgDBCzPA) represented by Structural Formula (ii) and 3,10-bis[N-(4-biphenyl)-N-(9,9-dimethyl-9H-fluoren-2-yl)amino]naphtho[2,3-b;7,6-b']bisbenzofuran (abbreviation: 3,10FBi2Nbf(II)) represented by Structural Formula (viii) in a weight ratio of 1:0.03 (=cgDBCzPA:3,10FBi2Nbf(II)).

After that, on the light-emitting layer 113, cgDBCzPA was deposited to a thickness of 10 nm by evaporation, and then, bathophenanthroline (abbreviation: BPhen) represented by Structural Formula (iv) was deposited to a thickness of 15 nm by evaporation, whereby the electron-transport layer 114 was formed.

After the formation of the electron-transport layer 114, lithium fluoride (LiF) was deposited to a thickness of 1 nm by evaporation to form the electron-injection layer 115. Then, aluminum was deposited to a thickness of 200 nm by evaporation to form the cathode 102. Thus, Light-emitting Element 5 of this example was fabricated.

The element structure of Light-emitting Element 5 is shown in the following table.

TABLE 9

| | Hole-injection layer | Hole-transport layer | Light-emitting layer | Electron-transport layer | | Electron-injection layer |
|---|---|---|---|---|---|---|
| | 10 nm | 30 nm | 25 nm | 10 nm | 15 nm | 1 nm |
| Light-emitting Element 5 | PCPPn: MoOx (4:2) | PCPPn | cgDBCzPA: 3,10FBi2Nbf(II) (1:0.03) | cgDBCzPA | BPhen | LiF |

The Light-emitting Element 5 was sealed using a glass substrate in a glove box containing a nitrogen atmosphere so as not to be exposed to the air (specifically, a sealant was applied to surround the element, and UV treatment and 1-hour heat treatment at 80° C. were performed for sealing). Then, the initial characteristics of the light-emitting element were measured. Note that the measurement was performed at room temperature.

Figure 78:
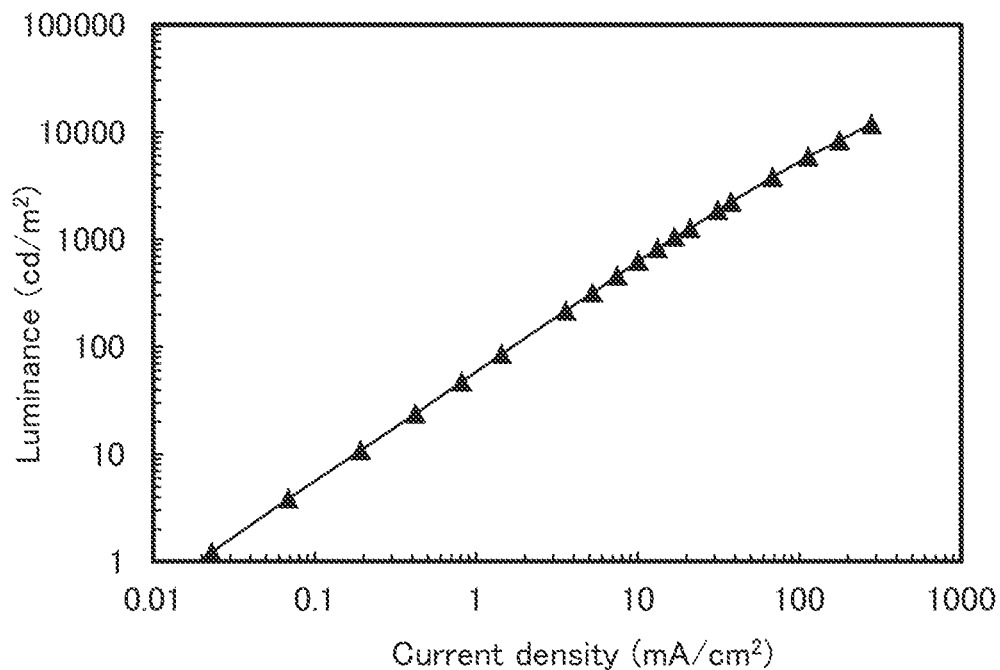
FIG. 78 shows the luminance-current density characteristics of Light-emitting Element 5.
Figure 79:
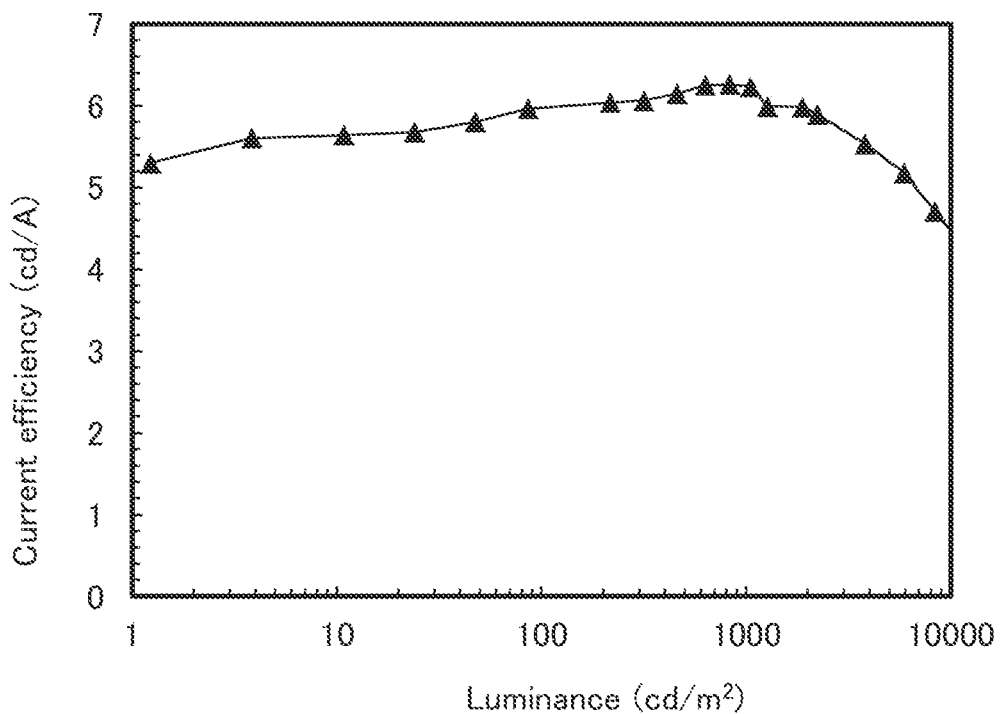
FIG. 79 shows the current efficiency-luminance characteristics of Light-emitting Element 5.
Figure 80:
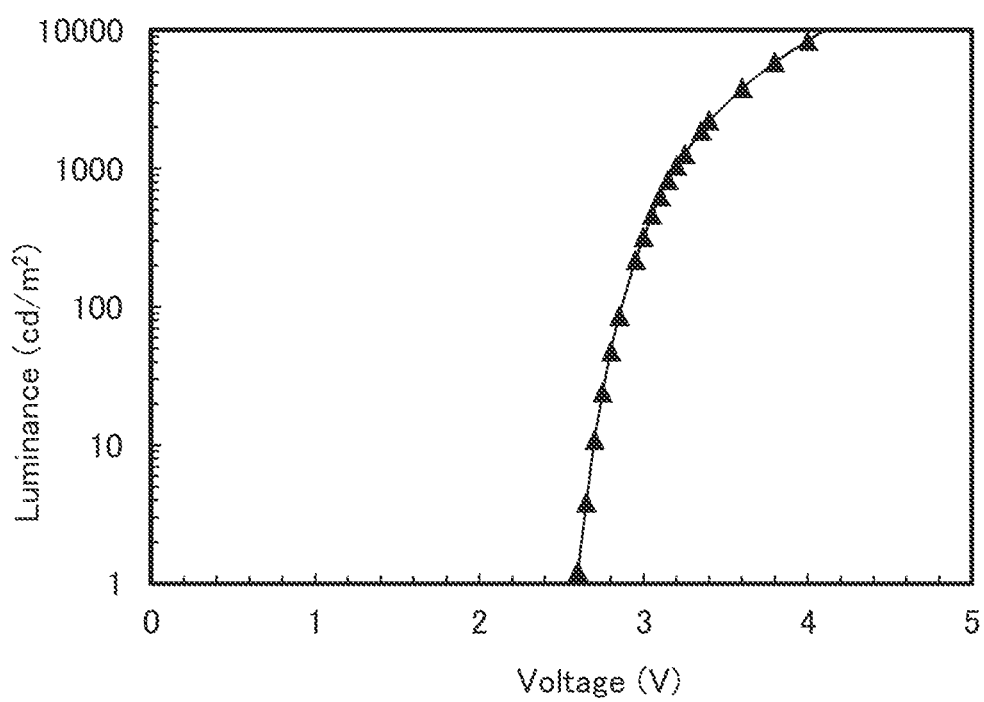
FIG. 80 shows the luminance-voltage characteristics of Light-emitting Element 5.
Figure 81:
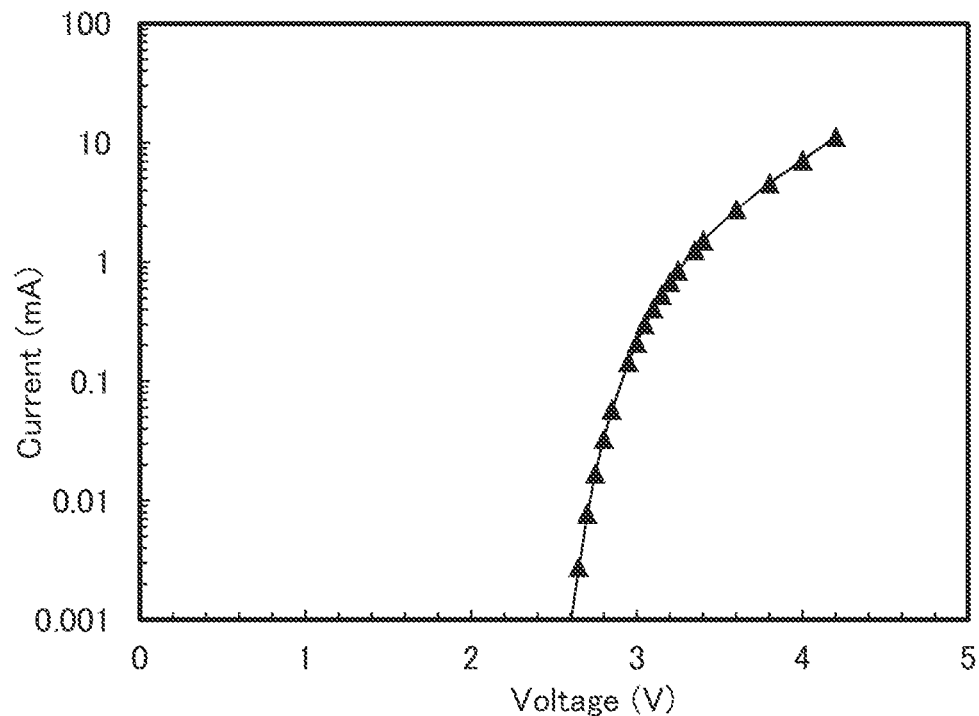
FIG. 81 shows the current-voltage characteristics of Light-emitting Element 5.
Figure 82:
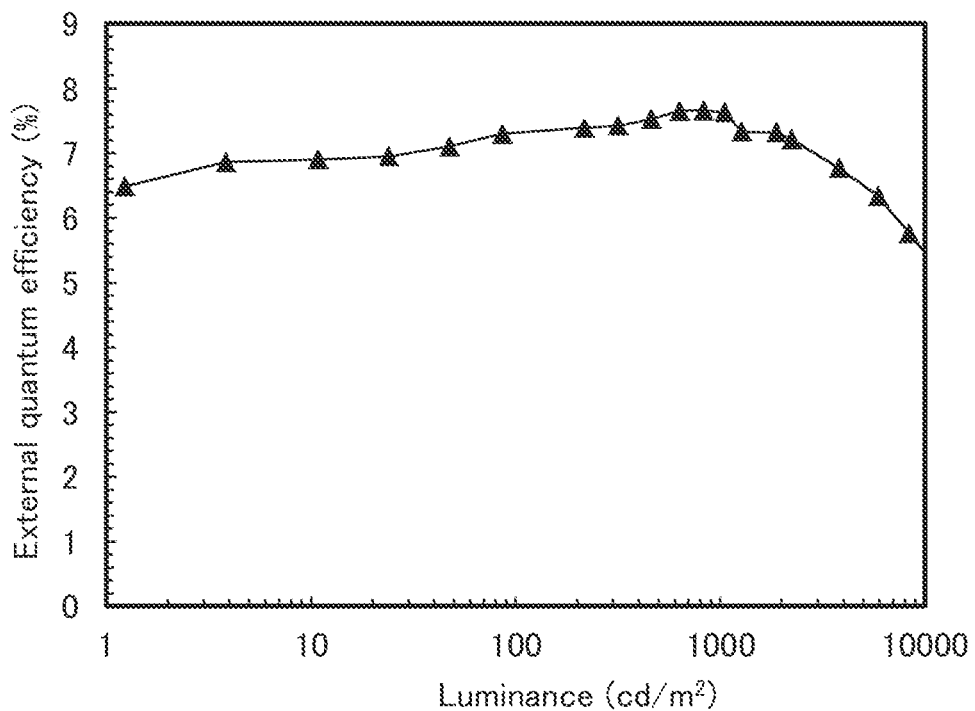
FIG. 82 shows the external quantum efficiency-luminance characteristics of Light-emitting Element 5.
Figure 83:
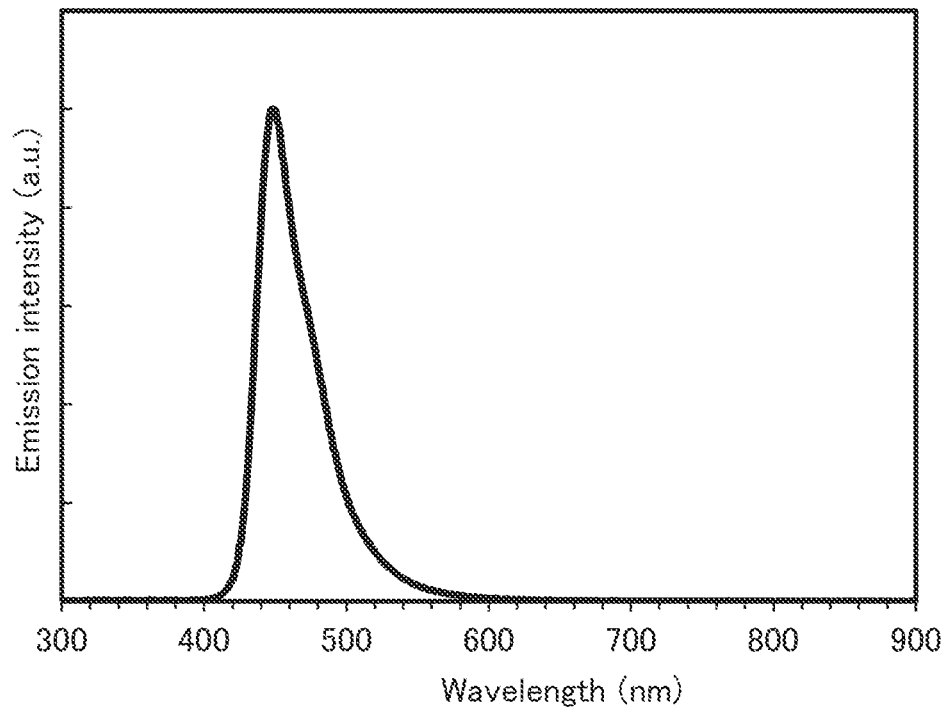
FIG. 83 shows the emission spectrum of Light-emitting Element 5.

FIG. 78 shows the luminance-current density characteristics of Light-emitting Element 5. FIG. 79 shows the current efficiency-luminance characteristics thereof. FIG. 80 shows the luminance-voltage characteristics thereof. FIG. 81 shows the current-voltage characteristics thereof. FIG. 82 shows the external quantum efficiency-luminance characteristics thereof. FIG. 83 shows the emission spectrum thereof.

TABLE 10

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting Element 5 | 3.2 | 0.68 | 16.9 | 0.15 | 0.09 | 6.2 | 7.6 |

According to FIGS. 78 to 82 and Table 10, Light-emitting Element 5 has very high external quantum efficiency of 7.6% at 1000 cd/m$^2$.

The above results imply that the use of the organic compound having a fluorenylamino group or a biphenylamino group as a substituent, which is one embodiment of the present invention, as a light-emitting material of a light-emitting element, allows the light-emitting element to have particularly favorable characteristics such as a sharp emission spectrum, high current efficiency, and high external quantum efficiency.

EXPLANATION OF REFERENCE

101: anode, 102: cathode, 103: EL layer, 111: hole-injection layer, 112: hole-transport layer, 113: light-emitting layer, 114: electron-transport layer, 115: electron-injection layer, 116: charge-generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: first electrode, 502: second electrode, 503: EL layer, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: flexible printed circuit (FPC), 610: element substrate, 611: switching FET, 612: current controlling FET, 613: first electrode, 614: insulator, 616: EL layer, 617: second electrode, 618: light-emitting element, 623: n-channel FET, 624: p-channel FET, 730: insulating film, 770: planarization insulating film, 772: conductive film, 782: light-emitting element, 783: droplet discharge apparatus, 784: droplet, 785: layer, 786: layer containing light-emitting substance, 788: conductive film, 901: housing, 902: liquid crystal layer, 903: backlight unit, 904: housing, 905: driver IC, 906: terminal, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode of light-emitting element, 1024R: first electrode of light-emitting element, 1024G: first electrode of light-emitting element, 1024B: first electrode of light-emitting element, 1025: partition, 1028: EL layer, 1029: cathode, 1031: sealing substrate, 1032: sealant, 1033: transparent base material, 1034R: red coloring layer, 1034G: green coloring layer, 1034B: blue coloring layer, 1035: black layer (black matrix), 1036: overcoat layer, 1037: third interlayer insulating film, 1040: pixel portion, 1041: driver circuit portion, 1042: peripheral portion, 1400: droplet discharge apparatus, 1402: substrate, 1403: droplet discharge means, 1404: imaging means, 1405: head, 1406: dotted line, 1407: control means, 1408: storage medium, 1409: image processing means, 1410: computer, 1411: marker, 1412: head, 1413: material supply source, 1414: material supply source, 1415: material supply source, 1416: head, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 9033: clasp, 9034: switch, 9035: power switch, 9036: switch, 9038: control switch, 9310: portable information terminal, 9311: display panel, 9312: display region, 9313: hinge, 9315: housing, 9630: housing, 9631: display portion, 9631a: display portion, 9631b: display portion, 9632a: touch panel region, 9632b: touch panel region, 9633: solar cell, 9634: charge and discharge control circuit, 9635: battery, 9636: DCDC converter, 9637: operation key, 9638: converter, 9639: button This application is based on Japanese Patent Application Serial No. 2017-053054 filed with Japan Patent Office on Mar. 17, 2017, the entire contents of which are hereby incorporated by reference.

The invention claimed is:

1. A light-emitting element comprising:

a pair of electrodes; and a light-emitting layer between the pair of electrodes, the light-emitting layer comprising a light-emitting substance and a host material, wherein the light-emitting substance comprises an organic compound having a molecular weight of less than or equal to 5000 and represented by General Formula (G1):

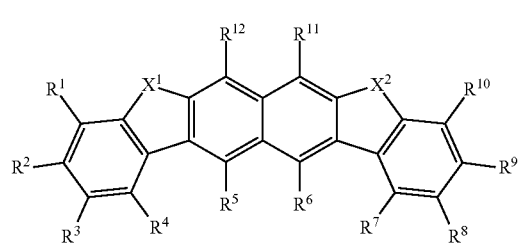

(G1)

wherein $X^1$ and $X^2$ independently represent an oxygen atom or a sulfur atom, wherein at least one of $R^1$ to $R^{12}$ represents a substituent having 6 to 100 carbon atoms, wherein the others of $R^1$ to $R^{12}$ independently represent hydrogen or a substituent having 1 to 25 carbon atoms, wherein the substituent having 6 to 100 carbon atoms is a substituent represented by General Formula (g2):

(g2)

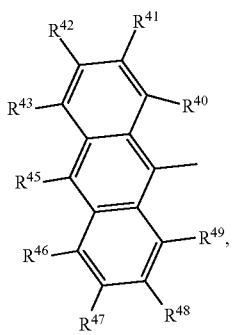

and wherein $R^{40}$ to $R^{43}$ and $R^{45}$ to $R^{49}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

2. The light-emitting element according to claim 1, wherein the organic compound is represented by General Formula (G4):

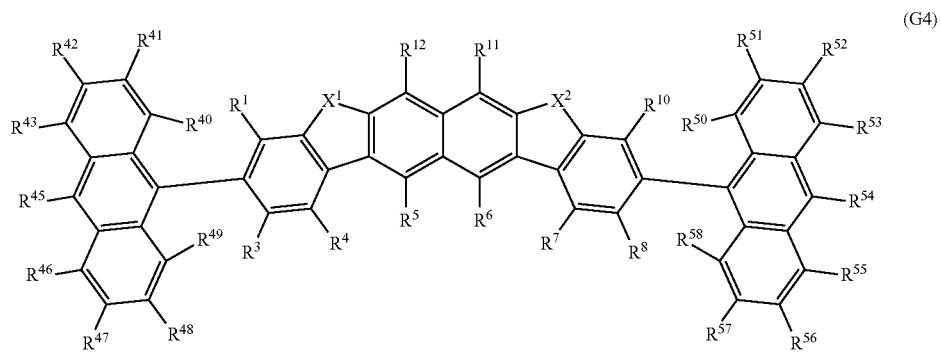

(G4)

wherein $X^1$ and $X^2$ independently represent an oxygen atom or a sulfur atom, and wherein $R^1$, $R^3$ to $R^8$, $R^{10}$ to $R^{12}$, $R^{40}$ to $R^{43}$, $R^{45}$ to $R^{49}$, and $R^{50}$ to $R^{58}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

3. The light-emitting element according to claim 1, wherein the organic compound emits blue light.

4. The light-emitting element according to claim 1, wherein one or both of $R^2$ and $R^9$ independently represent the substituent having 6 to 100 carbon atoms, and wherein $R^1$, $R^3$ to $R^8$, and $R^{10}$, to $R^{12}$ independently represent hydrogen or a substituent having 1 to 25 carbon atoms.

5. The light-emitting element according to claim 1, wherein the substituent having 1 to 25 carbon atoms is a substituted or unsubstituted aliphatic hydrocarbon group, a substituted or unsubstituted alicyclic hydrocarbon group, a substituted or unsubstituted aromatic hydrocarbon group, or a substituted or unsubstituted heterocyclic group.

6. The light-emitting element according to claim 1, wherein $X^1$ and $X^2$ are oxygen atoms.

7. The light-emitting element according to claim 1, wherein the organic compound is represented by Formula (118):

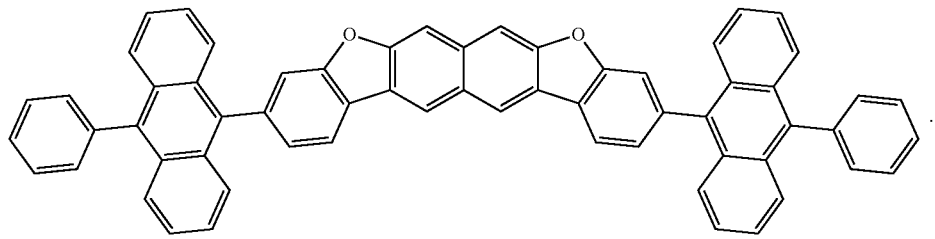

(118)

8. A light-emitting element comprising:
a pair of electrodes; and
a light-emitting layer between the pair of electrodes, the light-emitting layer comprising a light-emitting substance and a host material,
wherein the light-emitting substance comprises an organic compound having a molecular weight of less than or equal to 5000 and represented by General Formula (G4):

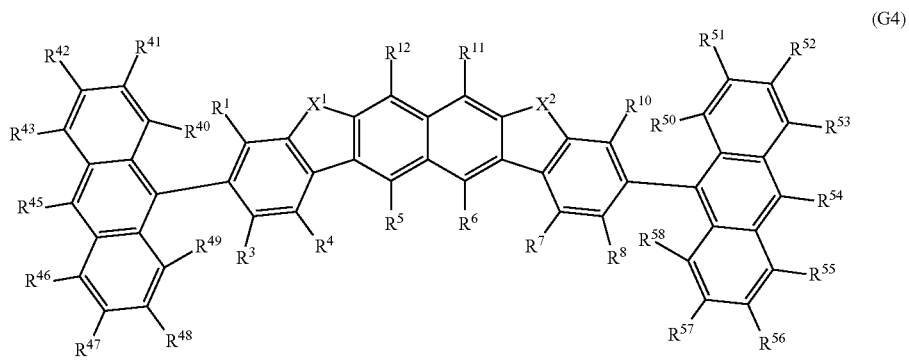

(G4)

wherein $X^1$ and $X^2$ independently represent an oxygen atom or a sulfur atom, and
wherein $R^1$, $R^3$ to $R^8$, $R^{10}$ to $R^{12}$, $R^{40}$ to $R^{43}$, $R^{45}$ to $R^{49}$, and $R^{50}$ to $R^{58}$ independently represent hydrogen, an aliphatic hydrocarbon group having 1 to 10 carbon atoms, an alicyclic hydrocarbon group having 3 to 20 carbon atoms, an aromatic hydrocarbon group having 6 to 25 carbon atoms, or a heterocyclic group having 1 to 25 carbon atoms.

9. The light-emitting element according to claim 8, wherein the organic compound is represented by Formula (118):

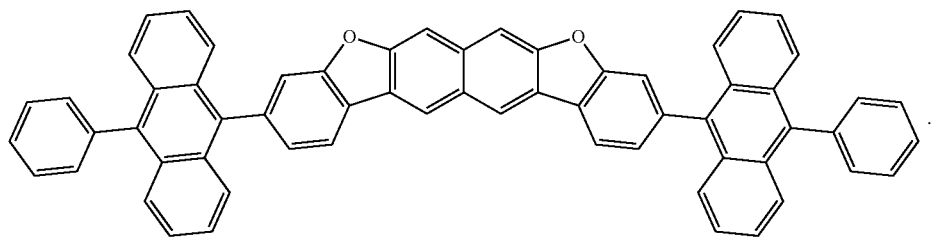

(118)

\* \* \* \* \*